US009719117B2

(12) United States Patent
Schaffer et al.

(10) Patent No.: US 9,719,117 B2
(45) Date of Patent: Aug. 1, 2017

(54) PRODUCTION OF OMEGA-AMINO FATTY ACIDS

(71) Applicants: Steffen Schaffer, Herten (DE); Jasmin Gielen, Bochum (DE); Mirja Wessel, Bochum (DE); Hans-Georg Hennemann, Marl (DE); Harald Haeger, Luedinghausen (DE); Thomas Haas, Muenster (DE); Wilfried Bluemke, Schoeneck (DE)

(72) Inventors: Steffen Schaffer, Herten (DE); Jasmin Gielen, Bochum (DE); Mirja Wessel, Bochum (DE); Hans-Georg Hennemann, Marl (DE); Harald Haeger, Luedinghausen (DE); Thomas Haas, Muenster (DE); Wilfried Bluemke, Schoeneck (DE)

(73) Assignee: Evonik Degussa, Essen (DE)

( * ) Notice: Subject to any disclaimer, the term of this patent is extended or adjusted under 35 U.S.C. 154(b) by 0 days.

(21) Appl. No.: 14/132,473

(22) Filed: Dec. 18, 2013

(65) Prior Publication Data
US 2014/0178948 A1 Jun. 26, 2014

(30) Foreign Application Priority Data

Dec. 21, 2012 (EP) .................................... 12199024

(51) Int. Cl.
C12P 13/00 (2006.01)
C12N 9/12 (2006.01)
C12N 9/02 (2006.01)
C12N 9/06 (2006.01)
C12N 9/10 (2006.01)

(52) U.S. Cl.
CPC .......... *C12P 13/001* (2013.01); *C12N 9/0008* (2013.01); *C12N 9/0016* (2013.01); *C12N 9/0069* (2013.01); *C12N 9/1096* (2013.01); *C12N 9/1288* (2013.01); *C12P 13/005* (2013.01); *Y02P 20/582* (2015.11)

(58) Field of Classification Search
CPC ............................ C12P 7/6409; C12P 13/001
See application file for complete search history.

(56) References Cited

U.S. PATENT DOCUMENTS

| 6,620,970 | B2 | 9/2003 | Schiffer et al. |
| 6,639,108 | B2 | 10/2003 | Schiffer et al. |
| 6,764,671 | B2 | 7/2004 | Haas et al. |
| 6,861,540 | B2 | 3/2005 | Herwig et al. |
| 6,878,836 | B2 | 4/2005 | Haas et al. |
| 7,005,528 | B2 | 2/2006 | Haas et al. |
| 7,030,052 | B2 | 4/2006 | Stochniol et al. |
| 7,049,450 | B2 | 5/2006 | Hofen et al. |
| 7,091,384 | B2 | 8/2006 | Jaeger et al. |
| 7,195,748 | B2 | 3/2007 | Jaeger et al. |
| 7,507,862 | B2 | 3/2009 | Stochniol et al. |
| 7,608,738 | B2 | 10/2009 | Herwig et al. |
| 7,879,938 | B2 | 2/2011 | Häger et al. |
| 7,923,225 | B2 | 4/2011 | Mueller et al. |
| 8,022,201 | B2 | 9/2011 | Roos et al. |
| 8,158,391 | B2 * | 4/2012 | Gross .................. C12N 9/0006 435/134 |
| 8,168,841 | B2 | 5/2012 | Herwig et al. |
| 8,232,333 | B2 | 7/2012 | Haeger et al. |
| 8,241,879 | B2 * | 8/2012 | Picataggio ........... C12N 9/0006 435/145 |
| 8,343,752 | B2 * | 1/2013 | Picataggio ............. C12N 9/001 435/142 |
| 8,349,596 | B2 | 1/2013 | Mueller et al. |

(Continued)

FOREIGN PATENT DOCUMENTS

WO WO 2008/148640 A1 12/2008
WO WO 2013/024111 A1 2/2013
(Continued)

OTHER PUBLICATIONS

Nunn, W. D., et al., 1996, "Transport of long-chain fatty acids in *Escherichia coli*: Evidence for role of fadL gene product as long-chain fatty acid receptor", The Journal of Biological Chemistry, vol. 261, No. 1, pp. 167-171.*
DiRusso, C. C., et al., 1999, "Molecular inroads into the regulation and metabolism of fatty acids, lessons from bacteria", Progress in Lipid Research, vol. 38, No. 2, pp. 129-197.*
Sanishvilia, R., et al., 2003, Integrating structure, bioinformatics, and enzymology to discover function: BioH, a new carboxylesterase from *Escherichia coli*, The Journal of Biological Chemistry, vol. 378, No. 18, pp. 26039-26045.*
Copp, J.N., et al., 2006, "The phosphopantetheinyl transferase superfamily: Phylogenetic analysis and functional implications in cyanobacteria", Applied and Environmental Microbiology, vol. 72, No. 4, pp. 2298-2305.*
Hong, H., et al., 2006, "The outer membrane protein OmpW forms an eight-stranded β-barrel with a hydrophobic channel", The Journal of Biological Chemistry, vol. 281, No. 11, pp. 7568-7577.*

(Continued)

*Primary Examiner* — Anand Desai
(74) *Attorney, Agent, or Firm* — Oblon, McClelland, Maier & Neustadt, L.L.P.

(57) ABSTRACT

The invention provides a whole cell catalyst which expresses a recombinant α-dioxygenase or the combination of a recombinant fatty acid reductase and a phosphopantetheinyl transferase phosphopantetheinylating the fatty acid reductase, and which in addition to the α-dioxygenase and/or the combination of fatty acid reductase and phosphopantetheinyl transferase expresses a transaminase, characterized in that the phosphopantetheinyl transferase and/or transaminase is preferably recombinant; and a method for the conversion of a fatty acid, ω-hydroxy fatty acid, ω-oxo fatty acid or a monoester thereof to an amine, comprising oxidation of the fatty acid, ω-hydroxy fatty acid, ω-oxo fatty acid or the monoester thereof to an oxidation product by contacting with an alkane hydroxylase and/or alcohol dehydrogenase, contacting the oxidation product with a phosphopantetheinylated fatty acid reductase or a α-dioxygenase to give an aldehyde, and contacting the aldehyde with a transaminase.

19 Claims, No Drawings

(56) References Cited

U.S. PATENT DOCUMENTS

| | | | |
|---|---|---|---|
| 8,378,127 B2 | 2/2013 | Dingerdissen et al. | |
| 8,399,658 B2 | 3/2013 | Hengstermann et al. | |
| 8,404,470 B2 | 3/2013 | Thum et al. | |
| 8,445,720 B2 | 5/2013 | Hannen et al. | |
| 8,597,923 B2 * | 12/2013 | Ness | C12N 9/0006 435/134 |
| 8,703,993 B2 | 4/2014 | Hannen et al. | |
| 8,728,798 B2 * | 5/2014 | Picataggio | C12N 9/001 435/142 |
| 8,778,658 B2 * | 7/2014 | Picataggio | C12N 9/0006 435/145 |
| 8,809,576 B2 | 8/2014 | Schraven et al. | |
| 8,835,691 B2 | 9/2014 | Klasovsky et al. | |
| 8,871,862 B2 | 10/2014 | Pawlik et al. | |
| 8,927,773 B2 | 1/2015 | Klasovsky et al. | |
| 8,946,463 B2 | 2/2015 | Klasovsky et al. | |
| 8,981,159 B2 | 3/2015 | Klasovsky et al. | |
| 9,000,223 B2 | 4/2015 | Micoine et al. | |
| 2002/0087036 A1 | 7/2002 | Haas et al. | |
| 2003/0212298 A1 | 11/2003 | Brasse et al. | |
| 2005/0063896 A1 | 3/2005 | Jaeger et al. | |
| 2006/0199254 A1 * | 9/2006 | Rosazza et al. | 435/147 |
| 2010/0035314 A1 | 2/2010 | Mueller et al. | |
| 2010/0105963 A1 * | 4/2010 | Hu | 568/840 |
| 2010/0266518 A1 | 10/2010 | Springer et al. | |
| 2010/0285545 A1 * | 11/2010 | Gross | C12N 9/0006 435/134 |
| 2010/0291644 A1 | 11/2010 | Marx et al. | |
| 2010/0291653 A1 * | 11/2010 | Ness | C12N 9/0006 435/171 |
| 2010/0298612 A1 * | 11/2010 | Behrouzian et al. | 568/840 |
| 2010/0317069 A1 * | 12/2010 | Burk et al. | 435/121 |
| 2010/0324257 A1 | 12/2010 | Karau et al. | |
| 2011/0015267 A1 * | 1/2011 | Nelson | A61K 9/0095 514/546 |
| 2011/0118433 A1 | 5/2011 | Pötter et al. | |
| 2011/0118504 A1 | 5/2011 | Haas et al. | |
| 2011/0165640 A1 | 7/2011 | Mueller et al. | |
| 2011/0171702 A1 | 7/2011 | Reinecke et al. | |
| 2011/0189742 A1 | 8/2011 | Haas et al. | |
| 2011/0250663 A1 * | 10/2011 | Schirmer et al. | 435/157 |
| 2011/0251399 A1 | 10/2011 | Dingerdissen et al. | |
| 2012/0034665 A1 | 2/2012 | Haas et al. | |
| 2012/0077237 A1 * | 3/2012 | Picataggio | C12N 9/001 435/142 |
| 2012/0077252 A1 * | 3/2012 | Picataggio | C12N 9/001 435/254.22 |
| 2012/0156761 A1 * | 6/2012 | Picataggio | C12N 9/0006 435/254.22 |
| 2012/0264877 A1 | 10/2012 | Häger et al. | |
| 2012/0315366 A1 | 12/2012 | Zehnacker et al. | |
| 2013/0035513 A1 * | 2/2013 | Hu et al. | 568/448 |
| 2013/0052700 A1 | 2/2013 | Poetter et al. | |
| 2013/0092232 A1 | 4/2013 | Pawlik et al. | |
| 2013/0092233 A1 | 4/2013 | Pawlik et al. | |
| 2013/0149756 A1 * | 6/2013 | Sporleder | C12N 9/0069 435/147 |
| 2013/0157343 A1 * | 6/2013 | Picataggio | C12N 9/0006 435/254.22 |
| 2013/0164797 A1 | 6/2013 | Gielen et al. | |
| 2013/0165685 A1 | 6/2013 | Hannen et al. | |
| 2013/0171388 A1 | 7/2013 | Pawlik et al. | |
| 2013/0183725 A1 | 7/2013 | Poetter et al. | |
| 2013/0207050 A1 | 8/2013 | Hermasch et al. | |
| 2013/0217081 A1 * | 8/2013 | Pearlman et al. | 435/129 |
| 2013/0224807 A1 * | 8/2013 | Pearlman et al. | 435/121 |
| 2013/0240799 A1 | 9/2013 | Haeger et al. | |
| 2013/0252300 A1 * | 9/2013 | Green et al. | 435/161 |
| 2013/0267012 A1 * | 10/2013 | Steen | C12P 7/40 435/254.21 |
| 2013/0299750 A1 | 11/2013 | Hermasch et al. | |
| 2014/0039071 A1 | 2/2014 | Thum et al. | |
| 2014/0039210 A1 | 2/2014 | Erhardt et al. | |
| 2014/0054224 A1 | 2/2014 | Erhardt et al. | |
| 2014/0120587 A1 | 5/2014 | Haas et al. | |
| 2014/0141478 A1 | 5/2014 | Schaffer et al. | |
| 2014/0178948 A1 | 6/2014 | Schaffer et al. | |
| 2014/0186902 A1 * | 7/2014 | Botes | C12P 13/001 435/121 |
| 2014/0186905 A1 | 7/2014 | Schaffer et al. | |
| 2014/0242646 A1 | 8/2014 | Pötter et al. | |
| 2014/0242655 A1 * | 8/2014 | Pearlman et al. | 435/142 |
| 2014/0256904 A1 * | 9/2014 | Schaffer | C12N 9/0006 528/310 |
| 2014/0308717 A1 | 10/2014 | Haas et al. | |
| 2015/0010968 A1 | 1/2015 | Engel et al. | |
| 2015/0055744 A1 | 2/2015 | Pfeffer et al. | |
| 2015/0057461 A1 * | 2/2015 | Park | C12N 15/52 554/219 |
| 2015/0099282 A1 | 4/2015 | Haas et al. | |
| 2015/0111253 A1 * | 4/2015 | Schaffer et al. | 435/71.1 |
| 2015/0111254 A1 * | 4/2015 | Hennemann et al. | 435/71.2 |

FOREIGN PATENT DOCUMENTS

| | | |
|---|---|---|
| WO | WO 2013/024114 A2 | 2/2013 |
| WO | WO 2013/083412 A1 | 6/2013 |
| WO | WO 2013/092426 A1 | 6/2013 |
| WO | WO 2013/110557 A1 | 8/2013 |
| WO | WO 2013/135650 A1 | 9/2013 |
| WO | WO 2013/156454 A1 | 10/2013 |

OTHER PUBLICATIONS

Steen, E.J., et al., 2010, "Microbial production of fatty-acid-derived fuels and chemicals from plant biomass", Nature, vol. 463, pp. 559-562, together with on-line "Methods" page.*

Lin S., et al., 2010, "Biotin synthesis begins by hijacking the fatty acid synthetic pathway", Nature Chemistry Biology, vol. 6, No. 9, pp. 682-688.*

Cronan, J.E., et al., 2011, "Synthesis of the α,ω-dicarboxylic acid precursor of biotin by the canonical fatty acid biosynthetic pathway", Current Opinion in Chemistry and Biology, vol. 15, pp. 407-413.*

Akhtar, M.K., et al., Jan. 2013, "Carboxylic acid reductase is a versatile enzyme for the conversion of fatty acids into fuels and chemical commodities", Proceedings of the National Academy of Sciences, U.S.A., vol. 110, No. 1, pp. 87-92.*

Hamberg, M., et al., 2006, "Synthesis of 3-oxalinolenic acid and β-oxidation-resistant 3-oxa-oxylipins", Lipids, vol. 41, No. 5, pp. 499-506.*

Kaehne, F., et al., 2011, "A recombinant a-dioxygenase from rice to produce fatty aldehydes using *E. coli*", Applied Microbiology and Biotechnology, vol. 90, No. 3, pp. 989-995.*

Huff, G.S., et al., 2011, "Experimental and computational investigations of oxygen reactivity in a heme and tyrosyl radical-containing fatty acid α-(di)oxygenase", Biochemistry, vol. 50, No. 34, pp. 7375-7389.*

Vicente, J., et al., 2012, "Role of 9-lipoxygenase and α-dioxygenase oxylipin pathways as modulators of local and systemic defense", Molecular Plant, vol. 5, No. 4, pp. 914-928.*

Eggink, G., et al., 1987, "Controlled and functional expression of the Pseudomonas oleovorans alkane utilizing system in Pseudomonas putida and *Escherichia coli*", The Journal of Biological Chemistry, vol. 262, No. 36, pp. 17712-17718.*

Hearn, E.M., et al., 2009, "Transmembrane passage of hydrophobic compounds through a protein channel wall", Nature, vol. 458, pp. 367-370.*

Lennen, R.M., et al., 2010, "A process for microbial hydrocarbon synthesis: Overproduction of fatty acids in *Escherichia coli* and catalytic conversion to alkanes", Biotechnology and Bioengineering, vol. 106, No. 2, pp. 193-202.*

Julsing, M.K., et al., 2012, "Outer membrane protein AlkL boosts biocatalytic oxyfunctionalization of hydrophobic substrates in *Escherichia coli*", Applied and Environmental Microbiology, vol. 78, No. 16, pp. 5724-5733.*

(56) References Cited

OTHER PUBLICATIONS

Koeduka, T., et al., 2002, "Catalytic properties of rice alpha-oxygenase", The Journal of Biological Chemistry, vol. 277, No. 25, pp. 22648-22655.*

Saffert, A., et al., 2000, "A dual function alpha-dioxygenase-peroxidase and NAO(+) oxidoreductase active enzyme from germinating pea rationalizing alpha-oxidation of fatty acids in plants", Plant Physiology. vol. 123, pp. 1545-1552.*

Steen, E.J., et al., 2010, "Microbial production of fatty-acid-derived fuels and chemicals from plant biomass", Nature, vol. 463, pp. 559-562 and Methods supplement (one page).*

Touw, D.S., et al., 2010, "The crystal structure of OprG from Pseudomonas aeruginosa, a potential channel for transport of hydrophobic molecules across the outer membrane", PLoS ONE, vol. 5, No. 11, e15016. doi:10.1371/journal.pone.0015016.*

U.S. Appl. No. 14/384,301, filed Sep. 10, 2014, Schaffer, et al.
U.S. Appl. No. 14/363,178, filed Jun. 5, 2014, Haas, et al.
U.S. Appl. No. 14/390,133, filed Oct. 2, 2014, Hennemann, et al.
U.S. Appl. No. 14/400,379, filed Nov. 11, 2014, Haas, et al.
U.S. Appl. No. 14/380,483, filed Aug. 22, 2014, Schiemann, et al.
U.S. Appl. No. 14/405,050, filed Dec. 2, 2014, Haas, et al.
U.S. Appl. No. 14/367,610, filed Jun. 20, 2014, Haas, et al.
U.S. Appl. No. 14/649,414, filed Jun. 3, 2015, Schaffer et al.
U.S. Appl. No. 14/763,378, filed Jul. 24, 2015, Haas, et al.
U.S. Appl. No. 14/419,580, filed Feb. 4, 2015, Erhardt, et al.
U.S. Appl. No. 14/425,180, filed Mar. 2, 2015, Ortelt, et al.

* cited by examiner

PRODUCTION OF OMEGA-AMINO FATTY ACIDS

CROSS REFERENCE TO RELATED APPLICATIONS

This application claims priority to European Application No. 12199024, filed Dec. 21, 2012, the disclosure of which is incorporated herein by reference in its entirety.

BACKGROUND OF THE INVENTION

The invention relates to a whole cell catalyst which expresses a recombinant α-dioxygenase or the combination of a recombinant fatty acid reductase and of a phosphopantetheinyl transferase phosphopantetheinylating the fatty acid reductase, and which additionally expresses a transaminase, characterized in that the phosphopantetheinyl transferase and/or transaminase is preferably recombinant; and a method for the conversion of a fatty acid, ω-hydroxy fatty acid, ω-oxo fatty acid or a monoester thereof to an amine, comprising the steps oxidation of the fatty acid, ω-hydroxy fatty acid, ω-oxo fatty acid or the monoester thereof to an oxidation product by contacting with an alkane hydroxylase and/or alcohol dehydrogenase, contacting the oxidation product with a phosphopantetheinylated fatty acid reductase or a α-dioxygenase to give an aldehyde, and contacting the aldehyde with a transaminase.

Polyamides are a class of polymer which are characterized by repeating amide groups. The term "polyamide" in contrast to the chemically related proteins, usually relates to synthetic, commercially available thermoplastic plastics. Polyamides are derived from primary amines or from secondary amines, which are conventionally obtained in the cracking of hydrocarbons. However, derivatives, more precisely aminocarboxylic acids, lactams and diamines, can also be used for polymer production. Also of interest are short-chain, gaseous alkanes as educts which can be obtained starting from renewable raw materials by biotechnological methods.

Many polyamides in great commercial demand are produced starting from lactams. For example "polyamide 6" can be obtained by polymerization of ϵ-caprolactam and "polyamide 12" by polymerization of laurolactam. Other commercially interesting products include copolymers of lactams, e.g. copolymers of ϵ-caprolactam and laurolactam.

The conventional industrial chemical production of amines is dependent on the supply of fossil raw materials, and inefficient, and in the process large quantities of undesired by-products are formed, in many steps of the synthesis up to 80%. One example of such a process is the production of laurolactam. Conventionally, laurolactam is obtained via a multistage process which not only gives a low yield, but at the same time necessitates the provision of a costly infrastructure.

In view of these disadvantages, methods have been developed for obtaining amines with the use of biocatalysts starting from renewable raw materials. Possible renewable raw materials are in particular sources of fatty acids, which can be obtained in the form of rape oil, great globe thistle oil, palm nut oil, coconut oil, sunflower oil and similar natural products from a multitude of biological sources, in particular from plants.

PCT/EP2008/067447 describes a biotechnological system for the production of chemically related products, more precisely ω-aminocarboxylic acids, with the use of a cell which has a range of suitable enzymatic activities and is capable of converting carboxylic acids to corresponding ω-aminocarboxylic acids. The process comprises a cascade of enzymatically catalysed reactions, in particular the oxidation of a fatty acid at the terminal carbon atom to the aldehyde, and subsequent amination with the use of a transaminase and an amino acid as amine donor, which can be regenerated via an amino acid dehydrogenase.

However, a known disadvantage of the AlkBGT oxidase system from *Pseudomonas putida* GPO1 used therein consists in that it is not capable of performing a selective oxidation of aliphatic alkanes to primary alcohols. Rather, a large number of oxidation products are formed, in particular the proportion of more highly oxidised products such as the corresponding aldehyde, ketone or the corresponding carboxylic acid increases with increasing reaction time (C. Grant, J. M. Woodley and F. Baganz (2011), *Enzyme and Microbial Technology* 48, 480-486), which correspondingly reduces the yield of desired amine.

The problem of the relatively unselective oxidation is worsened by the fact that the oxidation products which form are structurally very similar. This means that it is very difficult to separate them from the desired oxidation products efficiently and without significant loss of yield.

A further disadvantage of this method consists in that overoxidized by-products, for example the dicarboxylic acid of the fatty acid used as educt, the recycling of hydrophobic solvents and hydrophobic liquid cation exchangers, which according to PCT/EP2011/071491 are used for the separation of the product from the aqueous reaction mixture, are at the expense of the efficiency in resource utilization.

In this connection, it should be emphasized that the complexity of biotechnological systems with a cascade of reactions as described in PCT/EP2008/067447, each case reaction of which is catalyzed by one specific enzyme, renders the optimization of the reaction conditions difficult. Thus in the case of the essentially reactive ω-amino fatty acids as product, there is the possibility that beyond a certain critical concentration in the interior of the cell they will react with essential components of the organism and thus have a toxic effect. If that is the case, then the growth and synthetic ability of the organism is impaired even leading to the death of the cell, without the developer being able directly to recognize the toxicity or even to attribute it to a specific educt, intermediate or product. It is also not predictable which organism tolerates what concentration of a chemically reactive substance.

Also with reference to a product yield to be improved and formation of by-products to be decreased, those skilled in the art cannot routinely identify limiting and critical factors in a system such as that described in PCT/EP2008/067447. If the yield of product is too low, then this can be because one of the enzymes is present in too low a concentration, without it being known which of the possible enzymes this is, i.e. owing to insufficient synthetic capacity the educt is not converted in the predicted time periods or before degradation by competing enzymes. Alternatively, it is entirely possible that an enzyme is indeed detectable in the cell in the form of a polypeptide, but in this particular cell does not have the folding essential for the activity, or a cofactor hitherto unknown but essential for the activity is lacking. Likewise, as already mentioned, the metabolic product can be toxic to the cell, or be degraded. Finally, interfering interactions with endogenous enzymes, i.e. those naturally present in a cell used as a whole cell catalyst, must be reckoned with.

There is thus a need for processes for the production of ω-amino fatty acids from fatty acids, wherein the enzymatically catalyzed reactions proceed more selectively and the formation of undesired by-products is minimized.

Against this background, the problem on which the invention is based is to provide as efficient as possible a biotechnological process for the production of ω-amino fatty acids with regard to yield, carbon and/or nitrogen balance and/or purity.

A further problem on which the invention is based consists in providing as efficient as possible a biotechnological process for the conversion of carboxylic acid esters to aminated carboxylic acid esters with regard to yield, carbon and/or nitrogen balance, reusability of agents used and/or purity of the product. In this context, an efficient carbon and/or nitrogen balance is preferably understood to mean that as high as possible a proportion of the carbon and/or nitrogen fed to a cell for the conversion of a carboxylic acid ester in the form of suitable substrates is recovered in the desired end product, instead of for example being converted to products other than that desired.

A further problem on which the invention is based consists in improving the processability of a multiphase reaction mixture from the conversion of a carboxylic acid ester, particularly with regard to the reusability of the hydrophobic solvents and liquid cation exchangers used for the processing, and with regard to the phase formation and separation in a biphasic system comprising an aqueous phase, in which the conversion of the carboxylic acid ester proceeds, and an organic phase with organic solvents and/or liquid cation exchangers.

SUMMARY OF THE INVENTION

These and other problems are solved by the subject matter of the present application and in particular by the subject matter of the appended independent claims, wherein embodiments follow from the subclaims.

In a first aspect, the problem on which the invention is based is solved by a whole cell catalyst which expresses a recombinant α-dioxygenase or the combination of a recombinant fatty acid reductase and of a phosphopantetheinyl transferase phosphopantetheinylating the fatty acid reductase, and which additionally expresses a transaminase, wherein the phosphopantetheinyl transferase and/or transaminase is preferably recombinant.

In a first embodiment of the first aspect the problem is solved by a whole cell catalyst which additionally expresses an amino acid dehydrogenase which is preferably recombinant.

In a second embodiment, which is also an embodiment of the first embodiment, the problem is solved by a whole cell catalyst which additionally expresses an alkane hydroxylase which is preferably recombinant.

In a third embodiment, which is also an embodiment of the first to second embodiment, the problem is solved by a whole cell catalyst which additionally expresses a polypeptide of the AlkL family which is preferably recombinant.

In a fourth embodiment, which is also an embodiment of the first to third embodiment, the problem is solved by a whole cell catalyst which additionally expresses an alcohol dehydrogenase which is preferably recombinant.

In a fifth embodiment, which is also an embodiment of the first to fourth embodiment, the problem is solved by a whole cell catalyst wherein the activity of at least one enzyme involved in β-oxidation is decreased compared to the wild type of the whole cell catalyst.

In a sixth embodiment, which is also an embodiment of the first to fifth embodiment, the problem is solved by a whole cell catalyst wherein the activity of BioH or a variant thereof is decreased compared to the wild type of the whole cell catalyst.

In a seventh embodiment, which is also an embodiment of the first to sixth embodiment, the problem is solved by a whole cell catalyst wherein the activity of FadL or a variant thereof is increased compared to the wild type of the whole cell catalyst.

In a second aspect, the problem on which the invention is based is solved by a process for the conversion of a fatty acid, ω-hydroxy fatty acid, ω-oxo fatty acid or a monoester thereof to an amine, comprising:

a) oxidation of the fatty acid, ω-hydroxy fatty acid, ω-oxo fatty acid or the monoester thereof to an oxidation product by contacting with an alkane hydroxylase and/or alcohol dehydrogenase, b) contacting the oxidation product with a phosphopantetheinylated fatty acid reductase or an α-dioxygenase to give an aldehyde, and c) contacting the aldehyde with a transaminase.

In a second aspect, the problem on which the invention is based is solved by a process wherein in c) an amino acid dehydrogenase is present.

In a first embodiment of the second aspect, the problem is solved by a process wherein at least one enzyme from the group comprising phosphopantetheinylated fatty acid reductase, α-dioxygenase, transaminase, amino acid dehydrogenase and alkane hydroxylase, preferably all enzymes used from this group, are provided in the form of a whole cell catalyst according to the first aspect of the invention.

In a second embodiment, which is also an embodiment of the first embodiment, the problem is solved by a process wherein the fatty acid, ω-hydroxy fatty acid, ω-oxo fatty acid or the monoester thereof is a compound of the formula (I)

$$R^1\text{-A-COOR}^2 \qquad (I)$$

wherein $R^1$ is selected from the group which comprises —H, —CHO, —OH and COOR$^3$, wherein $R^2$ and $R^3$ each and independently of one another are selected from the group which comprises H, methyl, ethyl and propyl, with the proviso that at least one of the residues $R^2$ and $R^3$ is H, and wherein A represents an unbranched, branched, linear, cyclic, substituted or unsubstituted hydrocarbon group with at least four carbon atoms.

In a third embodiment, which is also an embodiment of the first to second embodiment, the problem is solved by a process wherein A has the formula —(CH$_2$)$_n$—, wherein n is at least 4, preferably at least 10.

In a third aspect, the problem on which the invention is based is solved by use of the whole cell catalyst according to the first aspect or of the process according to the second aspect for the amination of a fatty acid, ω-hydroxy fatty acid, ω-oxo fatty acid or a monoester thereof.

In a fourth aspect, the problem on which the invention is based is solved by a reaction mixture comprising the whole cell catalyst according to the first aspect in aqueous solution and a fatty acid, ω-hydroxy fatty acid, ω-oxo fatty acid or a monoester thereof of the formula (I)

$$R^1\text{-A-COOR}^2 \qquad (I),$$

wherein $R^1$ is selected from the group which comprises —H, —CHO, —OH and COOR$^3$, wherein $R^2$ and $R^3$ each and independently of one another are selected from the group which comprises H, methyl, ethyl and propyl, with the proviso that at least one of the residues $R^2$ and $R^3$ is H, and wherein A represents an unbranched, branched, linear, cyclic, substituted or unsubstituted hydrocarbon group with at least four carbon atoms, preferably the formula —$(CH_2)_n$—, wherein n is at least 4, particularly preferably at least 10.

DETAILED DESCRIPTION OF THE PREFERRED EMBODIMENTS

The present invention is based on the discovery of the inventors that a functionally coexpressed recombinant fatty acid reductase or α-dioxygenase in a whole cell catalyst which is used for the production of ω-amino fatty acids from fatty acids and has an appropriate enzyme composition, surprisingly increases the yield of ω-amino fatty acids.

Furthermore, the present invention is based on the discovery of the inventors that a functionally coexpressed recombinant fatty acid reductase or α-dioxygenase in a whole cell catalyst which is used for the production of ω-amino fatty acids from fatty acids and has an appropriate enzyme composition, surprisingly decreases the concentration of interfering by-products, in particular of overoxidized fatty acids in the form of dicarboxylic acids and esters thereof, in the product obtained.

Furthermore, the present invention is based on the discovery of the inventors that a functionally coexpressed recombinant fatty acid reductase or α-dioxygenase in a whole cell catalyst which is used for the production of ω-amino fatty acids from fatty acids and has an appropriate enzyme composition, improves the purity and reusability of liquid cation exchangers such as oleic acid, which are used for the removal of an ω-amino fatty acid from a fermentation solution containing the whole cell catalyst.

The present invention relates to an improved process for the conversion of a fatty acid, ω-hydroxy fatty acid, ω-oxo fatty acid or a monoester thereof to an amine, which is distinguished in that as well as the enzymes which catalyse the conversion of the fatty acid via its various oxidation stages to the amine, at least one fatty acid reductase or α-dioxygenase, or the combination of both enzymes, is also present, preferably, when a whole cell catalyst is used for performing the process. In a preferred embodiment, the term "fatty acid reductase", as used herein, is understood to mean, an enzyme which catalyses the conversion of an ω-carboxy acid, also described as dicarboxylic acid or ω-carboxy fatty acid, to the corresponding ω-oxo fatty acid with consumption of ATP and NAD(P)H. WO/2010/135624 describes fatty acid reductases for the production of ω-hydroxy fatty acids, but not as part of a system for production of ω-amino fatty acids. In a still more preferred embodiment, the fatty acid reductase is selected from the group of fatty acid reductases which contain the amino acid sequences YP_887275.1, ZP_11001941.1, ZP_06852401.1, NP_959974.1, YP_001070587.1, ZP_05217435.1, YP_882653.1, YP_639435.1, ZP_10800193.1, YP_006452763.1, YP_006730440.1, ZP_11196216.1, YP_005349252.1, ZP_05224908.1, YP_005338837.1, YP_006307000.1, YP_005343991.1, ZP_11001942.1, ZP_09979565.1, YP_005003162.1, YP_953393.1, YP_001850422.1, ZP_11011489.1, ZP_12689264.1, YP_905678.1, ZP_09976919.1, YP_004746059.1, NP_217106.1, YP_004525443.1, NP_337166.1, ZP_09685823.1, YP_978699.1, ZP_06437984.1, ZP_06514086.1, NP_856267.1, CAA19077.1, NP_301424.1, ZP_06522140.1, ZP_06518098.1, ZP_11008938.1, ZP_07432374.2, AAR91681.1, YP_006808747.1, YP_001851230.1, ZP_15327751.1, ZP_15455857.1, ZP_12874284.1, ZP_15332534.1, ZP_15512956.1, ZP_14244106.1, ZP_15470899.1, ZP_11439367.1, YP_001703694.1, ZP_15446742.1, YP_006808978.1, ZP_07964926.1, YP_006521379.1, WP_007769435.1, ZP_15512957.1, ZP_12874283.1, YP_005350955.1, ZP_14243341.1, YP_001705436.1, ZP_15329649.1, YP_006522325.1, YP_006732197.1, YP_003658971.1, ZP_05227804.1, YP_001703695.1, YP_006308707.1, ZP_15342047.1, YP_006521380.1, ZP_15327752.1, YP_005340557.1, ZP_11439578.1, ZP_15392943.1, ZP_15514789.1, ZP_12996178.1, ZP_09412214.1, ZP_06849686.1, YP_889972.1, YP_006570321.1, ZP_15375693.1, YP_006308219.1, YP_006521600.1, YP_005340029.1, YP_005350457.1, ZP_11439836.1, ZP_12994664.1, ZP_14240588.1, ZP_14236860.1, ZP_09410830.1, YP_006731697.1, YP_005264225.1, YP_001704097.1, ZP_15328186.1, ZP_09402885.1, ZP_12690463.1, AFO59871.1, ZP_07966879.1, YP_118225.1, YP_001828302.1, YP_006566873.1, YP_003660169.1, ZP_15337407.1, ZP_08240521.1, ZP_10456477.1, YP_001537947.1, YP_004016539.1, ZP_07664024.1, ZP_14244107.1, ZP_09794557.1, ZP_09274211.1, ZP_05224899.1, ZP_15484175.1, AAA17105.1, ZP_11437924.1, ZP_15446621.1, YP_003646340.1, ZP_15382134.1, ZP_14237669.1, ZP_09165547.1, YP_004019203.1, ZP_14240225.1, YP_001220863.1, CBA74242.1, ZP_12994240.1, EIE27140.1, ZP_15354547.1, ZP_15432557.1, ZP_15500132.1, ZP_15478632.1, ZP_06846978.1, AAA17108.1, ZP_15333767.1, ZP_05217205.1, AAD44234.1, YP_005348984.1, YP_006306749.1, ZP_05224611.1, YP_005343772.1, YP_006730188.1, YP_882425.1, ZP_10799956.1, ZP_05045132.1, NP_960176.1, ZP_12398880.1, ZP_11192735.1, ZP_11440091.1, ZP_05217203.1, ZP_06846979.1, ZP_10800936.1, ZP_06523596.1, YP_882421.1, YP_006306748.1, YP_006522017.1, ZP_15432556.1, ZP_15354095.1, ZP_05227781.1, ZP_09684639.1, YP_006730187.1, YP_005343770.1, YP_005338616.1, YP_005348983.1, ZP_15472813.1, ZP_15457007.1, ZP_15421152.1, ZP_15488933.1, ZP_14240030.1, YP_001704825.1, ZP_15328982.1, YP_005911512.1, ZP_09411638.1, ZP_12876400.1, ZP_12995435.1, ZP_07667680.1, YP_001281387.1, EIE21044.1, ZP_15375054.1, NP_334518.1, 4DQV_A, ZP_06435375.1, YP_003030020.1, YP_976237.1, ZP_04926822.1, YP_004998149.1, YP_004743589.1, YP_005907921.1, NP_214615.1, YP_001286047.1, ZP_06515541.1, ZP_05139482.1, YP_888016.1, ZP_06452908.1, ZP_06519578.1, YP_004721827.1, CAJ77696.1, ZP_09680854.1, ZP_09686453.1, YP_884815.1, YP_884815.1,
CAB55600.1, ZP_09081423.1, YP_006521568.1, ZP_11440626.1, ZP_15513309.1, ZP_09410778.1, ZP_15374248.1, ZP_15405954.1, YP_001704047.1, ZP_14236911.1, ZP_12873916.1, ZP_14242094.1, ZP_12994610.1, ZP_07664023.1, ZP_15446620.1, ZP_15484174.1, ZP_14240245.1, YP_005358845.1 and XP_002669159.1,
in particular YP_006731697.1, ZP_09839660.1, YP_001704097.1, YP_889972.1, ZP_05045132.1, NP_959974.1, ZP_10456477.1, YP_118225.1, YP_905678.1, YP_887275.1, ZP_11001941.1, WP_007769435.1 and YP_005349252.1 and variants thereof.

Fatty acid reductases are a group of enzymes which for their activity require a phosphopantetheinylation, i.e. the covalent binding of a phosphopantetheinyl cofactor on the enzymes. Accordingly, the fatty acid reductase used according to the invention is phosphopantetheinylated, and a whole cell catalyst expressing the fatty acid reductase expresses, either as part of its composition of endogenously expressed enzymes or in recombinant form, a phosphopantetheinyl transferase phosphopantetheinylating the fatty acid reductase. In a preferred embodiment, the term "phosphopantetheinyl transferase", as used herein, is understood to mean an enzyme which transfers a phosphopantetheinyl residue from a phosphopantetheinyl-CoA to an enzyme, preferably onto the fatty acid reductase. In a particularly preferred embodiment, the phosphopantetheinyl transferase is selected from the group of phosphopantetheinyl transferases which contain the amino acid sequences ABI83656.1, YP_006811024.1, YP_120266.1, YP_005265173.1, YP_004006671.1, ZP_08152482.1, ZP_11104141.1, ZP_14482198.1, YP_706581.1, ZP_10002626.1, ZP_09308410.1, YP_002783881.1, ZP_18276502.1, ZP_09271851.1, ZP_08204640.1, YP_002766085.1, ZP_09788717.1, ZP_09799863.1, ZP_10961877.1, YP_003273299.1, GAB86168.1, YP_006668875.1, ZP_08766535.1, ZP_09793386.1, ZP_09212827.1, ZP_09276344.1, ZP_09213870.1, ZP_09081490.1, ZP_10947586.1, YP_003658841.1, ZP_06852853.1, YP_953148.1, ZP_11011170.1, YP_639258.1, YP_886985.1, ZP_11194383.1, ZP_09681094.1, ZP_06455719.1, NP_337369.1, YP_004077819.1, NP_217310.1, YP_006452521.1, YP_005339056.1, ZP_05226335.1, ZP_07965127.1, ZP_07419314.2, NP_302077.1, YP_005003342.1, YP_005349465.1, ZP_10800435.1, ZP_06564430.1, YP_882860.1, YP_001135287.1, YP_001850220.1, ZP_05217634.1, YP_003646683.1, YP_004746246.1, ZP_15327906.1, ZP_09979035.1, YP_001703848.1, YP_906028.1, ZP_15395499.1, ZP_11438833.1, ZP_11005955.1, ZP_09410582.1, NP_961833.1, YP_001106197.1, ZP_14237113.1, YP_004085491.1, YP_003835595.1, ZP_12994399.1, YP_004523804.1, ZP_12690887.1, YP_003339468.1, ZP_06589331.1, YP_004801334.1, ZP_09974565.1, ZP_04608379.1, ZP_13037142.1, YP_712537.1, ZP_11236665.1, NP_630748.1, ZP_06527138.1, YP_003835167.1, CCH33620.1, ZP_10309401.1, ZP_08881396.1, YP_003102953.1, YP_003487252.1, ZP_08881565.1, YP_006263961.1, NP_822924.1, YP_004914569.1, ZP_09400366.1, AFV71333.1, ZP_07309518.1, ZP_09172171.1, ZP_06710898.1, CAN89630.1, ZP_06921116.1, ZP_08804003.1, ZP_19189663.1, ZP_10545589.1, YP_006248725.1, ZP_10455557.1, YP_004015869.1, ZP_08801530.1, ZP_10550999.1, YP_004492879.1, ZP_09958730.1, ZP_08286666.1, ZP_11212856.1, AAL15597.1, AAZ94407.1, ZP_19188802.1, AFF18625.1, ZP_06575404.1, AAK06801.1, ADC79635.1, YP_004080528.1, YP_004921314.1, ACY01405.1, YP_004584022.1, YP_003114157.1, YP_003203177.1, AFB69911.1, YP_006876460.1, ZP_08024798.1, YP_006269867.1, YP_006881814.1, CCK26150.1, ZP_07307765.1, ZP_07315112.1, YP_005466392.1, NP_824081.1, YP_003493882.1, ZP_06412387.1, ZP_10068239.1, ZP_08234258.1, YP_001822177.1, ZP_03979107.1, ZP_07979043.1, BAA22407.1, ZP_09402950.1, YP_003112617.1, NP_738483.1, YP_480609.1, EKX90208.1, BAE93744.1, BAB69186.1, ZP_04713061.1, YP_006881735.1, ZP_07274901.1, ZP_11379052.1, ZP_06581115.1, YP_006437406.1, ZP_12871839.1, NP_601186.1, ZP_08451808.1, YP_005057339.1, YP_005303909.1, ZP_07090824.1, YP_003783676.1, YP_004630011.1, ZP_06588772.1, AAX98203.1, AFK80329.1, ZP_08124665.1, ZP_03710365.1, AAB17877.1, ZP_07403633.1, ZP_11268660.1, ZP_07288841.1, ABV83217.1, ZP_16178576.1, AAG43513.1, ZP_09155938.1, YP_004605750.1, ZP_03918977.1, AAF71762.1, ZP_05007864.1, ZP_06836265.1, ZP_03934882.1, YP_001508477.1, ZP_06043756.1, ZP_05366306.1, YP_002835056.1, ZP_03933464.1, ZP_07469321.1, ZP_07713507.1, YP_005160553.1, NP_939820.1, AAU93794.1, ZP_14659796.1, ZP_14383679.1, YP_005058606.1, YP_001221073.1, ZP_08231568.1, YP_250920.1, ZP_11383249.1, YP_003916320.1, ZP_08681170.1, YP_001800249.1, YP_001157632.1, YP_166099.1, ZP_10088015.1, YP_004760065.1, ZP_07947675.1, YP_001603066.1, YP_003812683.1, YP_004403402.1, ZP_08292153.1, ZP_09471260.1, YP_004018108.1, ZP_05115352.1, AAD13565.1, ZP_09295321.1, YP_001535629.1, ZP_04607273.1, YP_006561753.1, ZP_00960958.1, YP_006571985.1, ZP_08862188.1, YP_002906426.1, CCK30433.1, ZP_13042493.1, ZP_09090153.1, YP_614397.1, ZP_11163860.1, YP_003983492.1, YP_004080668.1, ZP_09420475.1, ZP_05914565.1, ZP_01101149.1, ZP_14743088.1, YP_001239694.1, ZP_09127532.1, YP_003833873.1, ZP_08516197.1, ZP_10160483.1, ZP_01987188.1, ZP_01755304.1, ZP_08825027.1, ZP_05077116.1, YP_001444606.1, ZP_03392800.1, ZP_01057781.1, AFB69889.1, ZP_08815097.1 and AAO17175.1 and variants thereof. In a particularly preferred embodiment here, it is the phosphopantetheinyl transferase with the database code ABI83656.1 or a variant thereof.

Alternatively or in addition to the combination of fatty acid reductase and phosphopantetheinyl transferase, the whole cell catalyst can also contain an α-dioxygenase. In a preferred embodiment, the term "α-dioxygenase", as used herein, is understood to mean an enzyme which catalyses the conversion of a fatty acid with the consumption of one molecule of oxygen and with cleavage of one carbon dioxide molecule to a fatty acid shortened by one carbon atom at the terminal ω carbon atom compared to the fatty acid used as educt, and bearing an aldehyde group on the terminal ω carbon atom. In a particularly preferred embodiment, the α-dioxygenase is selected from the group of α-dioxygenases which contain the amino acid sequences NP_001066718.1, EAY82977.1, BAH79993.1, ABG22011.1, BAJ90503.1, AFD04418.1, AFD04417.1, BAJ87736.1, AFW75180.1, ABG22012.1, XP_002311389.1, CAH05011.1, XP_002279884.1, CBI34957.3, AAG59584.1, NP_001234414.1, NP_001234410.1, XP_003553942.1, XP_002275161.1, XP_003553937.1, CBI34960.3, CAA07589.1, XP_003543402.1, XP_002517402.1, XP_002882184.1, NP_186791.1, AAK85133.1, CAN77070.1, XP_002529555.1, CAH64542.1, NP_001234061.1, XP_002281357.1, ADM21465.1, XP_002318527.1, NP_177509.1, CAN74266.1, XP_002888940.1, NP_001185393.1, XP_003631072.1, BAJ33800.1, XP_002517377.1, XP_003530944.1, BAJ34623.1, ABG22013.1, ABP02610.1, XP_001773135.1, XP_002960339.1, ABK95279.1, ABD73303.1, ABD73304.1, YP_001805721.1, ZP_08971815.1, ZP_08430366.1, YP_823013.1, ZP_05026427.1, ZP_11003953.1, YP_007064484.1, YP_007113008.1, YP_633369.1, ZP_18906570.1, ZP_09251410.1, ZP_10050808.1, ZP_01306662.1, YP_001516886.1, ZP_05042862.1, AAC49625.1, ZP_09648375.1, ZP_09792714.1, ZP_09788527.1, XP_001728273.1, AAC83355.1, YP_890542.1, ZP_11000891.1, XP_002605323.1, EGO58341.1, YP_006249145.1, YP_001507004.1, YP_001704637.1, ZP_12876141.1, ZP_11150830.1, ZP_14236257.1, ZP_09411385.1, ZP_14243118.1, EKD16664.1, ZP_15416799.1, ZP_15338016.1, ZP_10080295.1, ZP_11438929.1, ZP_12995210.1, ZP_10946648.1, YP_003409541.1, XP_001637870.1, YP_005451221.1, XP_001212758.1, ZP_07290489.1, ZP_05781329.1, ZP_19187748.1, ZP_06574534.1, XP_002605322.1, NP_822950.1, YP_006366425.1, EJP63377.1, EKD21217.1, XP_001795927.1, XP_003042615.1, ZP_06566152.1, EGU88116.1, EFY94417.1, XP_388327.1, EKJ68934.1, ZP_07290463.1, CCC10458.1, YP_001107201.1, XP_003348248.1, T49753, CAD31840.1, XP_001229975.1, CBN77040.1, YP_004813753.1, XP_002513273.1, XP_001627136.1, AFG52858.1, AFG52857.1, AEW08450.1, NP_841291.1, YP_004512343.1, ACG75701.1 and ZP_03500906.1 and variants thereof. In a particularly preferred embodiment, it is the α-dioxygenase with the database code NP_001066718.1 or a variant thereof.

As well as the α-dioxygenase or the combination of fatty acid reductase and the phospho-pantetheinyl transferase, the whole cell catalyst according to the invention necessarily contains a transaminase which aminates the ω-oxo fatty acid. In a preferred embodiment, the term "transaminase", as used herein, is understood to mean an enzyme which catalyses the transfer of α amino groups from a donor molecule, preferably an amino acid, to an acceptor molecule, preferably an α-keto carboxylic acid. In a particularly preferred embodiment, the transaminase is selected from the group of transaminases which contain the amino acid sequences 3HMU_A, AAD41041.1, AAK15486.1, ABE03917.1, ADR60699.1, ADR61066.1, ADR62525.1, AEL07495.1, CAZ86955.1, EFW82310.1, EFW87681.1, EGC99983.1, EGD03176.1, EGE58369.1, EGH06681.1, EGH08331.1, EGH24301.1, EGH32343.1, EGH46412.1, EGH55033.1, EGH62152.1, EGH67339.1, EGH70821.1, EGH71404.1, EGH78772.1, EGH85312.1, EGH97105.1, EGP57596.1, NP_102850.1, NP_106560.1, NP_248912.1, NP_248909.1, NP_354026.2, NP_421926.1, NP_637699.1, NP_642792.1, NP_744329.1, NP_744732.1, NP_747283.1, NP_795039.1, NP_901695.1 (, XP_002943905.1, YP_001021095.1, YP_001059677.1, YP_001061726.1, YP_001066961.1, YP_001074671.1, YP_001120907.1, YP_001140117.1, YP_001170616.1, YP_001185848.1, YP_001188121.1, YP_001233688.1, YP_001268866.1, YP_001270391.1, YP_001345703.1, YP_001412573.1, YP_001417624.1, YP_001526058.1, YP_001579295.1, YP_001581170.1, YP_001668026.1, YP_001669478.1, YP_001671460.1, YP_001685569.1, YP_001747156.1, YP_001749732.1, YP_001765463.1, YP_001766294.1, YP_001790770.1, YP_001808775.1, YP_001809596.1, YP_001859758.1, YP_001888405.1, YP_001903233.1, YP_001977571.1, YP_002229759.1, YP_002231363.1, YP_002280472.1, YP_002297678.1, YP_002543874.1, YP_002549011.1, YP_002796201.1, YP_002801960.1, YP_002875335.1, YP_002897523.1, YP_002912290.1, YP_002974935.1, YP_003060891.1, YP_003264235.1, YP_003552364.1, YP_003578319.1, YP_003591946.1, YP_003607814.1, YP_003641922.1, YP_003674025.1, YP_003692877.1, YP_003755112.1, YP_003896973.1, YP_003907026.1, YP_003912421.1, YP_004086766.1, YP_004142571.1, YP_004147141.1, YP_004228105.1, YP_004278247.1, YP_004305252.1, YP_004356916.1, YP_004361407.1, YP_004378186.1, YP_004379856.1, YP_004390782.1, YP_004472442.1, YP_004590892.1, YP_004612414.1, YP_004676537.1, YP_004693233.1, YP_004701580.1, YP_004701637.1, YP_004704442.1, YP_108931.1, YP_110490.1, YP_168667.1, YP_237931.1, YP_260624.1, YP_262985.1, YP_271307.1, YP_276987.1, YP_334171.1, YP_337172.1, YP_350660.1, YP_351134.1, YP_364386.1, YP_366340.1, YP_369710.1, YP_370582.1, YP_426342.1, YP_440141.1, YP_442361.1, YP_468848.1, YP_521636.1, YP_554363.1, YP_608454.1, YP_610700.1, YP_614980.1, YP_622254.1, YP_625753.1, YP_680590.1, YP_751687.1, YP_767071.1, YP_774090.1, YP_774932.1, YP_788372.1, YP_858562.1, YP_928515.1, YP_983084.1, YP_995622.1, ZP_00948889.1, ZP_00954344.1, ZP_00959736.1, ZP_00998881.1, ZP_01011725.1, ZP_01037109.1, ZP_01058030.1, ZP_01076707.1, ZP_01103959.1, ZP_01167926.1, ZP_01224713.1, ZP_01442907.1, ZP_01446892.1, ZP_01550953.1, ZP_01625518.1, ZP_01745731.1, ZP_01750280.1, ZP_01754305.1, ZP_01763880.1, ZP_01769626.1, ZP_01865961.1, ZP_01881393.1, ZP_01901558.1, ZP_02145337.1, ZP_02151268.1, ZP_02152332.1, ZP_02167267.1, ZP_02190082.1, ZP_02242934.1, ZP_02360937.1, ZP_02367056.1, ZP_02385477.1, ZP_02456487.1, ZP_02883670.1, ZP_03263915.1, ZP_03263990.1, ZP_03400081.1, ZP_03452573.1, ZP_03456092.1, ZP_03517291.1, ZP_03529055.1, ZP_03571515.1, ZP_03572809.1, ZP_03587785.1, ZP_03588560.1, ZP_03697266.1, ZP_03697962.1, ZP_04521092.1, ZP_04590693.1, ZP_04890914.1, ZP_04891982.1, ZP_04893793.1, ZP_04902131.1, ZP_04905327.1, ZP_04941068.1, ZP_04944536.1, ZP_04945255.1, ZP_04959332.1, ZP_04964181.1, ZP_05053721.1, ZP_05063588.1, ZP_05073059.1, ZP_05077806.1, ZP_05082750.1, ZP_05091128.1, ZP_05095488.1, ZP_05101701.1, ZP_05116783.1, ZP_05121836.1, ZP_05127756.1, ZP_05637806.1, ZP_05742087.1, ZP_05783548.1, ZP_05786246.1, ZP_05843149.1, ZP_05945960.1, ZP_06459045.1, ZP_06487195.1, ZP_06492453.1, ZP_06493162.1, ZP_06703644.1, ZP_06731146.1, ZP_06839371.1, ZP_07007312.1, ZP_07266194.1, ZP_07374050.1, ZP_07662787.1, ZP_07778196.1, ZP_07797983.1, ZP_08099459.1, ZP_08138203.1, ZP_08141719.1, ZP_08142973.1, ZP_08177102.1, ZP_08185821.1, ZP_08186468.1, ZP_08208888.1, ZP_08266590.1, ZP_08402041.1, ZP_08406891.1, ZP_08522175.1, ZP_08527488.1, ZP_08631252.1, ZP_08636687 and variants thereof.

The fatty acid reductase used according to the invention and preferably also other enzymes used according to the invention may be recombinant enzymes. In a preferred embodiment, the term "recombinant", as used herein, is understood to mean that the nucleic acid molecule coding for the corresponding enzyme does not occur in the natural cell and/or it was produced with use of genetic engineering methods. In a preferred embodiment, the term recombinant protein is used when the corresponding polypeptide is encoded by a recombinant nucleic acid. In a preferred embodiment, a recombinant cell, as used herein, is understood to be a cell which contains at least one recombinant nucleic acid or one recombinant polypeptide. Suitable methods for the production of recombinant molecules or cells are known to those skilled in the art, for example those described in Sambrook/Fritsch/Maniatis (1989): Molecular Cloning: A Laboratory Manual, Cold Spring Harbor Laboratory Press, $2^{nd}$ edition. Recombinant enzymes are preferably overexpressed, for example with the use of pET or pGEX vector systems, which are known to those skilled in the art.

With regard to the choice of the organism, the whole cell catalyst usable according to the invention is subject to no restrictions, provided that it is culturable, stable and accessible if necessary to modifications introducible by genetic engineering, e.g. methods for the attenuation of enzyme activities, for example knockouts. Thus it can equally be a prokaryotic or a eukaryotic cell. In the case of a eukaryotic cell, unicellular eukaryotes may be particularly preferable, particularly yeasts such as *Saccharomyces cerevisiae*, *Candida tropicalis*, *Candida albicans* and *Pichia pastoris*. In the case of prokaryotic cells it can for example be a bacterium which is selected from the group which comprises *Magnetococcus, Mariprofundus, Acetobacter, Acetobacterium, Acidiphilium, Afipia, Ahrensia, Asticcacaulis, Aurantimonas, Azorhizobium, Azospirillum, Bacillus, Bartonella tribocorum, Beijerinckia, Bradyrhizobium, Brevundimonas subvibrioides, Brucella, Caulobacter, Chelativorans, Citreicella, Citromicrobium, Clostridium, Corynebacterium, Dinoroseobacter, Erythrobacter, Fulvimarina, Gluconacetobacter, Granulibacter, Hirschia, Hoeflea, Hyphomicrobium, Hyphomonas, Ketogulonicigenium, Labrenzia, Loktanella, Magnetospirillum, Maricaulis, Maritimibacter, Mesorhizobium, Methylobacterium, Methylocystis, Methylosinus, Nitrobacter, Novosphingobium, Oceanibulbus, Oceanicaulis, Oceanicola, Ochrobactrum, Octadecabacter, Oligotropha, Paracoccus, Parvibaculum, Parvularcula, Pelagibaca, Phaeobacter, Phenylobacterium, Polymorphum, Pseudovibrio, Rhodobacter, Rhodomicrobium, Rhodopseudomonas, Rhodospirillum, Roseibium, Roseobacter, Roseomonas, Roseovarius, Ruegeria, Sagittula, Silicibacter, Sphingobium, Sphingomonas, Sphingopyxis, Starkeya, Sulfitobacter, Thalassiobium, Xanthobacter, Zymomonas, Agrobacterium, Rhizobium, Sinorhizobium, Anaplasma, Ehrlichia, Neorickettsia, Orientia, Rickettsia, Wolbachia, Bordetella, Burkholderia, Cupriavidus, Taiwanensis, Lautropia, Limnobacter, Polynucleobacter, Ralstonia, Chromobacterium, Eikenella corrodens, Basfia, Kingella, Laribacter, Lutiella, Neisseria, Simonsiella, Achromobacter, Acidovorax, Alicycliphilus, Aromatoleum, Azoarcus, Comamonas, Dechloromonas, Delftia, Gallionella, Herbaspirillum, Herminiimonas, Hylemonella, Janthinobacterium, Leptothrix, Methylibium, Methylobacillus, Methylophilales, Methyloversatilis, Methylovorus, Nitrosomonas, Nitrosospira, Oxalobacter, Parasutterella, Polaromonas, Polaromonas, Pusillimonas, Rhodoferax, Rubrivivax, Sideroxydans, Sutterella wadsworthensis, Taylorella, Thauera, Thiobacillus, Thiomonas, Variovorax, Verminephrobacter, Anaeromyxobacter, Bdellovibrio bacteriovorus, Bilophila, Desulfarculus, Desulfatibacillum, Desulfobacca, Desulfobacterium, Desulfobulbus, Desulfococcus, Desulfohalobium, Desulfitobacterium, Desulfomicrobium, Desulfonatronospira, Desulfotalea, Desulfovibrio, Desulfuromonas, Geobacter, Haliangium, Hippea, Lawsonia, Myxococcus, Pelobacter, Plesiocystis, Sorangium, Stigmatella, Syntrophobacter, Syntrophus, Arcobacter, Caminibacter, Campylobacter, Helicobacter, Nitratifractor, Nitratiruptor, Sulfuricurvum, Sulfurimonas, Sulfurospirillum, Sulfurovum, Wolinella, Buchnera, Blochmannia, Hamiltonella, Regiella, Riesia, Citrobacter, Cronobacter, Dickeya, Edwardsiella, Enterobacter, Erwinia, Escherichia, Klebsiella, Pantoea, Pectobacterium, Proteus, Providencia, Rahnella, Salmonella, Serratia, Shigella, Sodalis, Wigglesworthia, Glossina, Xenorhabdus, Yersinia, Acidithiobacillus, Acinetobacter, Aeromonas, Alcanivorax, Alkalilimnicola, Allochromatium, Alteromonadales, Alteromonas, Baumannia, Beggiatoa, Bermanella, Carsonella, Ruthia, Vesicomyosocius, Cardiobacterium, Chromohalobacter, Colwellia, Congregibacter, Coxiella, Dichelobacter, Endoriftia, Enhydrobacter, Ferrimonas, Francisella, Glaciecola, Hahella, Halomonas, Halorhodospira, Halothiobacillus, Idiomarina, Kangiella, Legionella, Marinobacter, Marinomonas, Methylobacter, Methylococcus, Methylomicrobium, Methylophaga, Moraxella, Moritella, Neptuniibacter, Nitrococcus, Pseudoalteromonas, Psychrobacter, Psychromonas, Reinekea, Rickettsiella, Saccharophagus, Shewanella, Succinatimonas, Teredinibacter, Thioalkalimicrobium, Thioalkalivibrio, Thiomicrospira, Tolumonas, Vibrionales, Actinobacillus, Aggregatibacter, Gallibacterium, Haemophilus, Histophilus, Mannheimia, Pasteurella, Azotobacter, Cellvibrio, Pseudomonas, Aliivibrio, Grimontia, Photobacterium, Photobacterium, Vibrio, Pseudoxanthomonas, Stenotrophomonas, Xanthomonas, Xylella, Borrelia, Brachyspira, Leptospira, Spirochaeta, Treponema, Hodgkinia, Puniceispirillum, Liberibacter, Pelagibacter, Odyssella* and *Accumulibacter*, in particular *B. subtilis, B. megaterium, C. glutamicum, E. coli, Pseudomonas* sp., *Pseudomonas fluorescens, Pseudomonas putida, Pseudomonas stutzeri, Acinetobacter* sp., *Burkholderia* sp., *Burkholderia thailandensis*, cyanobacteria, *Klebsiella* sp., *Klebsiella oxytoca, Salmonella* sp., *Rhizobium* sp. and *Rhizobium meliloti*. In a particularly preferred embodiment the cell is an enterobacterium, most preferably *Escherichia coli*.

It is advantageous if the whole cell catalyst according to the invention, as well as the fatty acid reductase, phosphopantetheinyl transferase and the transaminase, also contains an alanine dehydrogenase in order to regenerate from inorganic nitrogen-containing molecules the alanine consumed by the transaminase during the amination of the ω-oxo fatty acid. In a preferred embodiment, the term "alanine dehydrogenase", as used herein, is understood to mean an enzyme which catalyses the conversion of L-alanine with consumption of water and $NAD^+$ to pyruvate, ammonia and NADH and the reverse reaction. In a particularly preferred embodiment, the alanine dehydrogenase is selected from the group of alanine dehydrogenases which include the amino acid sequence of the alanine dehydrogenase from *Bacillus subtilis* (database code L20916), *Rhizobium leguminosarum* (database code CP001622), *Vibrio proteolyticus* (database code AF070716), *Mycobacterium tuberculosis* (database code X63069), *Enterobacter aerogenes* (database code AB013821), EGR93259.1, YP_003654745.1, YP_003651439.1, YP_003637111.1, YP_003631815.1, YP_001327051.1, YP_001262560.1, YP_886996.1, YP_882850.1, YP_704410.1, YP_703508.1, ZP_08624689.1, YP_001230376.1, P17557.1, P17556.1, CCB94892.1, CCB73698.1, YP_001168635.1, YP_004668736.1, YP_004569425.1, YP_003513168.1, YP_004561169.1, ZP_08554945.1, YP_400777.1, ZP_08311476.1, ZP_08310170.1, ZP_08267322.1, ZP_08263846.1, ZP_07898723.1, YP_149301.1, YP_148605.1, YP_004340432.1, EFT09946.1, EFS80513.1, EFS51332.1, EFS42459.1, YP_003060895.1, YP_003059033.1, ZP_03305373.1, YP_847214.1, YP_004095847.1, YP_003338282.1, YP_003337256.1, YP_355846.1, YP_253131.1, ZP_08197563.1, ZP_08196283.1, ADW06447.1, YP_734091.1, NP_372233.1, NP_102173.1, ZP_08170259.1, EGD36706.1, EGD32748.1, ZP_08155540.1, YP_004142849.1, YP_002417649.1, YP_001301040.1, YP_002992892.1, YP_081348.1, YP_080482.1, YP_002476349.1, ZP_08115025.1, ZP_08114403.1, YP_003552869.1, YP_002358112.1, YP_575010.1, YP_477594.1, YP_474564.1, YP_130399.1, YP_129373.1, YP_123314.1, NP_810467.1, NP_646469.1, NP_626044.1, NP_391071.1, ZP_08086822.1, ZP_08084776.1, ZP_08083119.1, ZP_08020768.1, ZP_08013590.1, ZP_08011832.1, YP_003783744.1, YP_002781576.1, YP_002780533.1, ZP_02195873.1, NP_797482.1, ZP_07645051.1, ZP_07643260.1, ZP_06611917.1, AAT40119.1, ZP_07864946.1, YP_004068409.1, YP_002796203.1, YP_002774420.1, YP_003600348.1, YP_003599946.1, YP_003565624.1, YP_003565223.1, YP_335198.1, YP_423850.1, YP_155059.1, ZP_07843538.1, ZP_07841226.1, ZP_06928932.1, ZP_05692073.1, ZP_05687006.1, ZP_04867480.1, YP_775531.1, CBE70214.1, ZP_07721182.1, ZP_04302850.1, ZP_04298961.1, ZP_04287684.1, ZP_04277177.1, ZP_04248389.1, ZP_04235899.1, ZP_02159718.1, ZP_02152178.1, YP_003974610.1, YP_003546595.1, YP_002317127.1, ZP_07313778.1, ZP_07302778.1, ZP_07298850.1, CBK69442.1, YP_003413835.1, YP_003595089.1, ZP_06807811.1, YP_003582455.1, YP_003464731.1, YP_003496397.1, YP_003421918.1, CBL07274.1, CBK64956.1, YP_003508515.1, AAL87460.1, AAC23579.1, AAC23578.1, AAC23577.1, ACU78652.1, YP_003471439.1, YP_003452777.1, ZP_06384971.1, ACY25368.1, ABC26869.1, AAP44334.1, EEZ80018.1, ZP_05110458.1, 1PJB_A, ZP_04717201.1, ZP_04689103.1, CAO90307.1, CAM75354.1, CAA44791.1, BAA77513.1, EGR96638.1, EGL90046.1, YP_004510847.1, ZP_08450330.1, YP_003387804.1, YP_003058152.1, EFS74272.1, EFS67128.1, ZP_06844564.1, YP_826658.1, YP_001195249.1, YP_003095978.1, YP_469292.1, YP_004442054.1, YP_004461174.1, YP_004055616.1, YP_003576656.1, YP_003094537.1, YP_001295973.1, AEE71143.1, YP_004447480.1, YP_003761844.1, YP_040853.1, YP_003154888.1, YP_003142045.1, YP_002280953.1, NP_371963.1, NP_422368.1, EGC98966.1, EGC76398.1, YP_004263661.1, YP_004252039.1, YP_679036.1, YP_499973.1, ZP_08054972.1, ZP_08053009.1, ZP_04067276.1, ZP_03968868.1, ZP_03963857.1, ZP_03933079.1, ZP_03497046.1, ZP_06668924.1, ZP_06667106.1, ZP_06324464.1, ZP_06196777.1, ZP_05114159.1, ZP_05083968.1, ZP_05070370.1, ZP_05030022.1, ZP_04673064.1, ZP_03517011.1, ZP_03505783.1, XP_001310698.1, ABK27691.1 and CAB59281.2 and variants thereof. For the reaction catalysed by the alanine dehydrogenase, the presence not only of pyruvate, which is formed as part of the primary metabolism by any cell possible as a whole cell catalyst, but also of ammonium, is necessary. The latter is typically provided in the form of inorganic nitrogen salts, for example ammonium salts, nitrates or the like. Preferably, an ammonium salt, e.g. ammonium chloride, is added to the aqueous reaction medium.

Furthermore, it may be advantageous if the whole cell catalyst according to the invention expresses an alkane hydroxylase and optionally further enzymes essential for the activity of the alkane hydroxylase, in particular for the case that a fatty acid with an oxidation level at the terminal ω carbon atom which lies below the oxidation level of the aldehyde is used as substrate for the production of the ω-amino fatty acid. The alkane hydroxylase and/or an additionally expressed alcohol dehydrogenase then oxidize the terminal carbon atom to the aldehyde group, which may then be aminated by the transaminase. In a preferred embodiment, the term "alkane hydroxylase", as used herein, is understood to mean an enzyme which catalyses the hydroxylation of unsubstituted linear alkyl residues containing at least six, preferably twelve hydrocarbon residues.

As alkane hydroxylases, many oxidation systems may be suitable according to the invention, such as are inter alia described in PCT/EP2008/067447. In a preferred embodiment, the alkane hydroxylase may be a cytochrome P450 monooxygenase of the CYP153 family. In a preferred embodiment, the term "cytochrome P450 monooxygenase of the CYP153 family" is understood to mean a cytosolic oxidase which is part of a 3-component system which further contains a ferredoxin and a ferredoxin reductase, with an alkane binding site and the ability to hydroxylate alkanes. In a particularly preferred embodiment, it is an enzyme which has up to at least 80, preferably 90, most preferably 95 or 99 percent sequence identity to the cytochrome P450 monooxygenase of the CYP153 family from *Alcanivorax borkumensis* SK2 (database code YP_691921) or an enzyme, which contains a polypeptide sequence which has at least 80, preferably 90, most preferably 95 or 99 percent sequence identity to the cytochrome P450 monooxygenase of the CYP153 family from *Alcanivorax borkumensis* SK2 (database code YP_691921) and moreover has alkane hydroxylase activity. Here, as throughout in this application, the said database codes are based on the NCBI (National Center for Biotechnology Information, Bethesda, USA) databases, more precisely the version available online on 21 Nov. 2012. In a preferred embodiment, the term "cytochrome P450 mono-oxygenase of the CYP153 family" is understood to mean a non-membrane-bound oxidase which includes a binding site for alkanes, unsubstituted linear alkyl residues including at least five, preferably twelve hydrocarbon residues or singly hydroxylated alkanes and the polypeptide chain whereof contains the motif LL(I/L)(V/I)GGNDTTRN. In a preferred embodiment, a "cytochrome P450 monooxygenase of the CYP153 family", as used herein, is a cytochrome P450 monooxygenase of the CYP153 family from *Alcanivorax borkumensis* SK2 (database code YP_691921) or a variant thereof, which preferably has alkane hydroxylase activity.

For the optimal supply of the cytochrome P450 monooxygenase of the CYP153 family with electrons from the reducing agent, preferably NADH, it may be preferable that the cell expresses the monooxygenase together with ferredoxin reductase functionally interacting with it and ferredoxin functionally interacting with it. Here these may be isolated polypeptides or polypeptides co-expressed during the use of a whole cell catalyst or polypeptides N- or C-terminally fused with the cytochrome P450 monooxygenase of the CYP153 family. Whether a ferredoxin reductase or a ferredoxin with a given cytochrome P450 monooxygenase of the CYP153 family functionally interact with one another can easily be determined by those skilled in the art by whether the reducing agent is oxidized more efficiently in the presence of an alkane substrate and the three polypeptides than in the case where at least one of the three is lacking. Alternatively, the enzyme test described by Scheps, D., Malca, H., Hoffmann, B., Nestl, B. M., and Hauer, B. (2011) *Org. Biomol. Chem.,* 9, 6727 can be used, which in the case of functionally interacting polypeptides shows a marked increase in the reaction rate. In a particularly preferred embodiment, the cytochrome P450 monooxygenase of the CYP153 family, the ferredoxin and the ferredoxin reductase come from the same organism. In a particularly preferred embodiment, they may be the ferredoxin reductase from *Alcanivorax borkumensis* SK2 (database code YP_691923) or a variant thereof, the ferredoxin from *Alcanivorax borkumensis* SK2 (database code YP_691920) or a variant thereof and the cytochrome P450 monooxygenase of the CYP153 family from *Alcanivorax borkumensis* SK2 (database code YP_691921) or a variant thereof.

In a further preferred embodiment, the alkane hydroxylase may be an AlkB monooxygenase. AlkB is an oxidoreductase which first became known from the AlkBGT system from *Pseudomonas putida* Gpo1, which is dependent on two further polypeptides, AlkG and AlkT. AlkT is characterized as an FAD-dependent rubredoxin reductase, which passes electrons from NADH on to AlkG. AlkG is a rubredoxin, an iron-containing redox protein, which functions as a direct electron donor for AlkB. In a preferred embodiment, the term "AlkB monooxygenase" is understood to mean a polypeptide with a sequence homology of at least, stated in order of increasing preference, 75, 80, 85, 90, 92, 94, 96, 98 or 99% to the sequence of the AlkB from *Pseudomonas putida* Gpo1 (database code: CAB54050.1; like all others used in the application, this database code derives from the state of the art, namely from the NCBI Database, more precisely the release available online on 15 Oct. 2012) with the ability to oxidize alkanes. In a particularly preferred embodiment, the AlkB monooxygenase is an alkane-oxidizing oxidoreductase functionally interacting with the AlkG (CAB54052.1) and AlkT (CAB54063.1) polypeptides from *Pseudomonas putida* Gpo1. For the optimal supply of the AlkB alkane hydroxylase with electrons, it is preferable that the cell expresses the monooxygenase together with auxiliary proteins functionally interacting with it, preferably AlkG and/or AlkT or respective variants thereof, where in a particularly preferred embodiment these are once again AlkG (CAB54052.1) and AlkT (CAB54063.1) polypeptides from *Pseudomonas putida* Gpo1.

In the use of a whole cell catalyst, the problem can arise that a substrate must be brought into contact with an enzyme located within the cell, so that the desired reaction occurs. In the case of long-chain alkanes and derivatives thereof it is preferable that the whole cell catalyst contains a polypeptide of the AlkL family. AlkL is a membrane protein from *Pseudomonas putida*, which can import long-chain fatty acids and derivatives thereof into bacterial cells. In a preferred embodiment, a "polypeptide of the AlkL family", as used herein, is a polypeptide which over a length of 230 consecutive amino acids has at least 80, preferably 90, still more preferably 90% sequence identity to AlkL from *Pseudomonas putida* (database code CAB69081) or a variant of AlkL from *Pseudomonas putida* and preferably the ability to promote the importation of long-chain alkanes into the interior of a cell. In a further embodiment, a "polypeptide of the AlkL family", as used herein, is a polypeptide located in the outer membrane of a Gram-negative bacterium, which has the sequence motif DXWAPAXQ(V/A)GXR, wherein X represents a proteinogenic amino acid, and preferably additionally is AlkL from *Pseudomonas putida* (database code CAB69081) or a variant thereof. Examples of members of the AlkL family include AlkL from *Pseudomonas putida* (database code CAB69081), *Marinobacter aquaeolei* VT8 (database code YP_957722), *Oceanicaulis alexandrii* HTCC2633 (database code ZP_00953584), *Marinobacter manganoxydans* MnI7-9 (database code ZP_09158756), *Caulobacter* sp. K31 (database code YP_001672217), *Pseudomonas oleovorans* (database code Q00595) and variants thereof.

The present invention may be implemented not only with use of macromolecules with the exact amino acid or nucleic acid sequence, to which reference is made herein, or not only with use of a cell with decreased activity relative to the respective wild type of a polypeptide with the exact amino acid sequence to which reference is made herein, but also with use of a variant of such macromolecules or of a cell with a decreased activity, relative to the respective wild type of the respective cell, of a variant of the polypeptide, which can be obtained by deletion, addition or substitution of one or more than one amino acid or nucleic acid. In a preferred embodiment, the term "variant" of a nucleic acid sequence or amino acid sequence, used below equivalently and exchangeably with the term "homolog", as used herein, means another nucleic acid or amino acid sequence, which includes or is a sequence which with regard to the corresponding original wild type nucleic acid or amino acid sequence has a homology, here used equivalently with identity, of 70, 75, 80, 85, 90, 92, 94, 96, 98, 99% or more percent, wherein preferably amino acids other than those forming the catalytically active centre or essential for the structure or folding are deleted or substituted or such are only conservatively substituted, for example a glutamate instead of an aspartate or a leucine instead of a valine. Conventionally known algorithms which may be used to calculate the degree of homology of two sequences, e.g. Arthur Lesk (2008), Introduction to bioinformatics, $3^{rd}$ edition. In a further more preferred embodiment of the present invention, the variant of an amino acid or nucleic acid sequence, preferably in addition to the aforesaid sequence homology, essentially has the same enzymatic activity of the wild type molecule or of the original molecule. For example, a variant of a polypeptide enzymatically active as a protease has the same or essentially the same proteolytic activity as the polypeptide enzyme, i.e. the ability to catalyse the hydrolysis of a peptide bond. In a particular embodiment, the term "essentially the same enzymatic activity" means an activity with regard to the substrates of the wild type polypeptide, which lies markedly over the background activity or/and differs by less than 3, more preferably 2, still more preferably one order of magnitude from the $K_M$ and/or $k_{cat}$ values which the wild type polypeptide displays with regard to the same substrates. In a further preferred embodiment, the term "variant" of a nucleic acid or amino acid sequence comprises at least one active part or fragment of the nucleic acid or amino acid sequence. In a further preferred embodiment, the term "active part", as used herein, means an amino acid sequence or a nucleic acid sequence, which has less than the full length of the amino acid sequence or codes for less than the full length of the amino acid sequence, wherein the amino acid sequence or the encoded amino acid sequence with lesser length than the wild type amino acid sequence has essentially the same enzymatic activity as the wild type polypeptide or a variant thereof, for example as a protease. In a particular embodiment, the term "variant" of a nucleic acid includes a nucleic acid the complementary strand whereof binds to the wild type nucleic acid, preferably under stringent conditions. For those skilled in the art, the stringency of the hybridization reaction is easily determinable and generally depends on the length of the probe, the temperatures during the washing and the salt concentration. In general, longer probes require higher temperatures for the hybridization, whereas shorter probes work with lower temperatures. Whether hybridization takes place depends in general on the ability of the denatured DNA to anneal to complementary strands which are present in their vicinity, and this below the melting temperature. The stringency of hybridization reaction and corresponding conditions are described in more detail in F. M. Ausubel (1995), Current Protocols in Molecular Biology, John Wiley & Sons, Inc. Those skilled in the art find instructions for the identification of DNA sequences by hybridization inter alia in the manual "The DIG system User's Guide for Filter Hybridization" from the firm Boehringer Mannheim GmbH (Mannheim, Germany, 1993) and in Liebl et al. (International Journal of Systematic Bacteriology 41: 255-260 (1991)). In a preferred embodiment, the hybridization takes place under stringent conditions, that is, only hybrids wherein probe and target sequence, i.e. the polynucleotides treated with the probe, are at least 70% identical are formed. It is known that the stringency of the hybridization including the washing step is influenced or determined by variation of the buffer composition, the temperature and the salt concentration. In general, the hybridization reaction is performed at relatively low stringency in comparison to the washing steps (Hybaid Hybridisation Guide, Hybaid Limited, Teddington, UK, 1996). For example, a buffer corresponding to 5×SSC buffer at a temperature of ca. 50° C.-68° C. can be used for the hybridization reaction. During this, probes can also hybridize with polynucleotides which have less than 70% identity to the sequence of the probe. Such hybrids are less stable and are removed by washing under stringent conditions. This can for example be achieved by lowering the salt concentration to 2×SSC and if necessary subsequently 0.5×SSC (The DIG System User's Guide for Filter Hybridization, Boehringer Mannheim, Mannheim, Germany, 1995), wherein a temperature of increasing preference in the order ca. 50° C.-68° C., ca. 52° C.-68° C., ca. 54° C.-68° C., ca. 56° C.-68° C., ca. 58° C.-68° C., ca. 60° C.-68° C., ca. 62° C.-68° C., ca. 64° C.-68° C., ca. 66° C.-68° C. is established. Temperature ranges of ca. 64° C.-68° C. or ca. 66° C.-68° C. are preferred. It is also possible if necessary to lower the salt concentration to a concentration corresponding to 0.2×SSC or 0.1×SSC. By stepwise raising of the hybridization temperature in steps of ca. 1-2° C. from 50° C. to 68° C., polynucleotide fragments can be isolated which for example in order of increasing preference display at least 70% or at least 80% or at least 90%, at least 91%, at least 92%, at least 93%, at least 94%, at least 95%, at least 96%, at least 97%, at least 98% or at least 99% identity to the sequence of the nucleic acid molecule used. Further instructions on hybridization are obtainable on the market in the form of so-called kits (e.g. DIG Easy Hyb from the firm Roche Diagnostics GmbH, Mannheim, Germany, Catalogue No. 1603558). In a preferred embodiment, the term "variant" of a nucleic acid, as used herein, includes any nucleic acid sequence which in the context of the degeneracy of the genetic code codes for the same amino acid sequence as the original nucleic acid or a variant of this amino acid sequence.

In a preferred embodiment, the cell used according to the invention has activity of at least one enzyme which catalyses one of the reactions of the β-oxidation of fatty acids decreased compared to the wild type thereof, wherein this is preferably an enzyme from the group which comprises fatty acid-CoA ligase, Acyl-CoA dehydrogenase, 2,4-dienoyl-CoA reductase, enoyl-CoA hydratase and 3-ketoacyl-CoA thiolase, a fatty acid importer or variants thereof. The β-oxidation of fatty acids is a widespread metabolic route which allows prokaryotic and eukaryotic organisms alike to oxidize fatty acids and to make the chemical energy contained therein available to the metabolism. In the wider sense, it begins with the uptake of a fatty acid into the cell. There the fatty acid, insofar as the conditions require it, is firstly oxidized at the β position of the CoA fatty acid ester by an acyl-CoA dehydrogenase, in the case of E. coli FadE. Alternatively, a similar molecule can also be formed from a doubly unsaturated fatty acid by reduction by means of a 2,4-dienoyl-CoA reductase, in E. coli FadH. A multifunctional enzyme, enoyl-CoA hydratase/3-hydroxyacyl-CoA dehydrogenase, in E. coli FadB, then catalyses the hydration with formation of the secondary alcohol and its subsequent oxidation to the ketone. In the last step, a 3-ketoacyl-CoA thiolase, in the case of E. coli FadA, catalyses the cleavage of the ketoacyl-CoA with the result that acetyl-CoA and a CoA ester of the fatty acid shortened by two carbon atoms in comparison to the starting molecule are liberated. Provided that it is not also acetyl-CoA, the latter can be fed afresh into the β oxidation cycle and shortened by oxidation. Also involved in the regulation of the β oxidation of fatty acids is FadR, a regulator of the Fad operon, which comprises genes necessary for the degradation of fatty acids, without FadR catalyzing a reaction of the β oxidation. In a preferred embodiment, the term "enzyme which catalyses one of the reactions of the β oxidation of fatty acids" is understood to mean any enzyme which interacts directly with the fatty acid substrate or a molecule formed therefrom on the pathway to acetyl-CoA, preferably recognizes it as substrate, and catalyses its conversion to a metabolic product lying closer to acetyl-CoA on this degradation pathway, preferably including the fatty acid importer which effects the uptake of the fatty acid into the cell. For example, acyl-CoA dehydrogenase is among these enzymes according to the foregoing definition, since it interacts with the fatty acid CoA ester and catalyses its conversion to the enoyl-CoA, which lies closer to acetyl-CoA on the metabolic pathway of the β oxidation than the fatty acid CoA ester. In a particularly preferred embodiment, the term "enzyme which catalyses one of the reactions of the β oxidation of fatty acids", as used herein, is understood to mean any enzyme from the group which comprises the gene products FadA, FadB, FadD, FadL and FadE from E. coli and/or variants or homologues thereof from other organisms. The gene products FadA, FadB, FadD, FadL and FadE from E. coli, like also variants and homologues of many other biotechnologically usable organisms and their nucleic acid and polypeptide sequences, are described in the state of the art, for example FadA under access number AP009048.1, FadB under access number BAE77457.1, FadD under access number BAA15609.1, and FadE under access number BAA77891.2. The state of the art discloses many tests which are especially suitable for the measurement of the activity of enzymes which catalyse one of the reactions of the β oxidation of fatty acids, for example in K Kameda & W D Nunn (1981) J. Biol. Chem. 256, 5702-5707, H Marrakchi, W E DeWolf, C Quinn, J West, B J Polizzi, C Y So et al. (2003) Biochem. J. 370, 1055-1062, Lobo et al. (2001) and X Yu, T Liu, F Zhu, and C Khosla (2011) PNAS, electronic publication before printing.

For the effectiveness of the whole cell catalyst according to the invention it may be advantageous if the substrate to be converted, preferably the fatty acid, ω-hydroxy- or ω-oxo fatty acid, can easily come into contact with the enzymes necessary according to the invention, which are located in the interior of the whole cell catalyst. Hence it is critical that the substrate can reach the interior of the cell. In order to facilitate this, it is preferable that the whole cell catalyst expresses a fatty acid importer, in the case of a bacterial, in particular Gram-negative whole cell catalyst, particularly preferably the fatty acid importer FadL (database code: BAA16205.1, SEQ ID NO: 31) or a variant, preferably in a concentration and with an activity which is increased compared to the activity of the wild type of the corresponding whole cell catalyst. The raising of the activity of a polypeptide compared to the wild type of the cell may be achieved via various routes which are known to those skilled in the art, for example the incorporation of additional copies of the nucleotide sequence coding for the polypeptide functionally linked with a promoter, or the exchange of the natural promoter for a stronger one.

It has been found that the ω-amino fatty acids are produced according to the invention in higher yield and purity when the background of enzymes endogenously expressed in the whole cell catalyst is optimized such that the activity of endogenous enzymes which degrade the educts, intermediate products or products of the method according to the invention or with use of the cell according to the invention, preferably ω-amino fatty acids, on metabolic pathways or modify them in other ways, which lead away from the formation of the desired product, is decreased or switched off. Accordingly, it may be advantageous if the whole cell catalyst according to the invention is about one cell, which has decreased activity of the esterase BioH [Database code YP_492020.1, SEQ ID NO: 30] or a variant thereof compared to its wild type. Such cells with decreased BioH activity, their production and tests for activity determination are described in European patent application EP12007663.3.

The whole cell catalyst according to the invention can be used in a method for the conversion of a fatty acid, ω-hydroxy- or ω-oxo fatty acid to the corresponding amine, preferably an ω-amino fatty acid, wherein the fatty acid, ω-hydroxy fatty acid, ω-oxo fatty acid or the monoester thereof is a compound of the formula (I)

$$R^1\text{-A-COOR}^2 \tag{I}$$

wherein $R^1$ is selected from —H, —CHO, —OH and COOR$^3$, wherein $R^2$ and $R^3$ each and independently of one another are selected from H, methyl, ethyl and propyl, with the proviso that at least one of the residues $R^2$ and $R^3$ is H, and wherein A represents an unbranched, branched, linear, cyclic, substituted or unsubstituted hydrocarbon group with at least four carbon atoms. In a preferred embodiment, A may be a structure of the formula —(CH$_2$)$_n$—, wherein n is 4, 5, 6, 7, 8, 9, 10, 11, 12, 13, 14, 15, 16, 17, 18, 19, 20, 21, 22, 23, 24, 25, 26, 27, 28, 29 or 30. In a most preferred embodiment, the fatty acid, ω-hydroxy or ω-oxo fatty acid is lauric acid, ω-hydroxy- or ω-oxolauric acid. In a further most preferred embodiment, the fatty acid, ω-hydroxy or ω-oxo fatty acid is hexanoic acid, ω-hydroxy- or ω-oxo-hexanoic acid. In a further most preferred embodiment the fatty acid, ω-hydroxy or ω-oxo fatty acid is decanoic acid, ω-hydroxy- or ω-oxodecanoic acid.

With regard to the fatty acid as to every chemical compound described in this application, the respective formula stated includes all salts, protonated or deprotonated, of the respective compound. For example, lauric acid comprises not only the protonated form, but also the salt laurate with all cations, for example sodium laurate.

The process according to the invention requires that the enzymes used for the process according to the invention, optionally provided in the form of the whole cell catalyst according to the invention, are contacted with fatty acid, ω-hydroxy- or ω-oxo fatty acid in an aqueous solution. In a preferred embodiment, the term "contacting", as used herein, may be understood to mean that the particular enzyme comes into direct contact with its substrate, without physical barriers such as impermeable membranes or the like being inserted between. In the simplest case, the contacting takes place by addition of the substrate to an aqueous solution in which the enzyme or the whole catalyst is located.

The present invention further provides a reaction mixture comprising the whole cell catalyst according to the invention in aqueous solution and a fatty acid, ω-hydroxy fatty acid, ω-oxo fatty acid or a monoester thereof of the formula (I), wherein $R^1$ is selected from —H, —CHO, —OH and COOR$^3$, wherein $R^2$ and $R^3$ each and independently of one another are selected from H, methyl, ethyl and propyl, with the proviso that at least one of the residues $R^2$ and $R^3$ is H, wherein A represents an unbranched, branched, linear, cyclic, substituted or unsubstituted hydrocarbon group with at least four carbon atoms, preferably the formula —(CH$_2$)$_n$—, and wherein n is at least 4, particularly preferably at least 10. The aqueous solution here must, for example with regard to composition, pH and temperature, be constituted such that it at least for a time supports the viability or at least the catalytic ability of the whole cell catalyst. Many aqueous culture media suitable as the aqueous solution, which are suitable for the maintenance or culturing of cells, in particular biotechnologically important cells, are conventionally known. These include both complete media such as LB media, minimal media such as M9 media and selective media, for example those which contain a high salt concentration and hence only enable the growth of halophilic or at least halotolerant organisms. In a preferred embodiment, the term "aqueous culture medium", as used herein, is understood to mean a water-based reaction medium, which with regard to all relevant factors, in particular pH, salt content and temperature, is constituted such that it maintains or promotes the viability of cells contained therein, preferably microorganisms, and both aqueous culture medium and also hydrophobic organic phase are present in liquid form. The temperature demands of various biotechnologically important cells can be inferred from microbiology and molecular biology textbooks, e.g. Fuchs/Schlegl, 2008. In a preferred embodiment, the pH of the aqueous culture medium at the time of the contacting lies between 4 and 9, more preferably between 4.5 and 8.5, and most preferably between 6.5 and 7.5. In a further preferred embodiment, the temperature lies between 0 and 45° C., more preferably between 15 and 40° C., and most preferably between 20 and 37° C. The reaction mixture is typically contained in a fermenter. Any reaction vessel which can be sterilized, preferably autoclaved, and allows the culturing of the whole cell catalysts, aeration and control of the reaction conditions, for example the oxygen content and the temperature, may function as the fermenter.

In a preferred embodiment, the reaction mixture in addition to the aqueous solution includes a hydrophobic organic phase. This can comprise an organic solvent and/or a hydrophobic liquid cation exchanger for removal of the ω-amino fatty acid from the aqueous solution. Suitable solvents and cation exchangers are described in EP11191520.3.

The present invention is further illustrated by the following diagrams and non-limiting examples, from which further features, embodiments, aspects and advantages of the present invention can be inferred.

Example 1

Production of Expression Vectors for Co-Expression of Genes Coding for a Fatty Acid Reductase with npt from Nocardia sp.

For the production of vectors for the co-expression of the genes coding for a fatty acid reductase with npt (SEQ ID No.1, codes for ABI83656.1) from Nocardia sp., which codes for a phosphopantetheinyl transferase, the genes were codon-optimized for expression in Escherichia coli and synthesized together with a lacuv5 promoter (SEQ ID No.2)

and at the same time a restriction cleavage site was introduced upstream and downstream. The following fatty acid reductase genes were used:

MSMEG_2956 from *Mycobacterium smegmatis* (carA, SEQ ID No.3, codes for YP_887275.1)
MSMEG_5739 from *Mycobacterium smegmatis* (carB, SEQ ID No.4, codes for YP_889972.1)
FadD9 from *Mycobacterium intracellulare* MOTT-64 (car_Mint, SEQ ID No.5, codes for YP_005349252.1)
MFORT_07381 from *Mycobacterium fortuitum* subsp. *fortuitum* DSM 46621 (car_Mfort, SEQ ID No.6, codes for ZP_11001941.1)
FadD9 from *Mycobacterium avium* subsp. *paratuberculosis* K-10 (car_Mavi, SEQ ID No.7, codes for NP_959974.1)
CPCC7001_1320 from *Cyanobium* sp. PCC 7001 (car_Cs, SEQ ID No.8, codes for ZP_05045132.1)
MAB_3367 from *Mycobacterium abscessus* ATCC 19977 (car_Mab, SEQ ID No.9, codes for YP_001704097.1)
FadD9 from *Nocardia brasiliensis* ATCC 700358 (car_nbr, SEQ ID No.10, codes for ZP_09839660.1)
MIP_06852 from *Mycobacterium indicus pranii* MTCC 9506 (car_Mip, SEQ ID No.11, codes for YP_006731697.1)
nfa20150 from *Nocardia farcinica* IFM 10152 (car_nfa, SEQ ID No.12, codes for YP_118225.1)
MUL_1722 from *Mycobacterium ulcerans* Agy99 (car_Mul, SEQ ID No.13, codes for YP_905678.1)
Saci8_010100039603 from *Streptomyces acidiscabies* 84-104 (car_Sac, SEQ ID No.14, codes for ZP_10456477.1)
MCOL_V203220 from *Mycobacterium colombiense* CECT 3035 (car_Mcol, SEQ ID No.15, codes for WP_007769435.1)

The DNA fragment synthesized was digested with the restriction endonucleases NdeI and AvrII and ligated into the correspondingly cleaved vector pSC101 (SEQ ID No.16). The vector pSC101 is a very low copy vector, which mediates tetracycline resistance and has a low copy number of ca. 4 copies per cell. In this way, the following expression vectors were produced:

pSC101{Placuv5}[carA_Ms(co_Ec)-npt_Noc(co_Ec)] (SEQ ID No.17)
pSC101{Placuv5}[carB_Ms(co_Ec)-npt_Noc(co_Ec)] (SEQ ID No.18)
pSC101{Placuv5}[car_Mint(co_Ec)-npt_Noc(co_Ec)] (SEQ ID No.19)
pSC101{Placuv5}[car_Mfort(co_Ec)-npt_Noc(co_Ec)] (SEQ ID No.20)
pSC101{Placuv5}[car_Mavi(co_Ec)-npt_Noc(co_Ec)] (SEQ ID No.21)
pSC101{Placuv5}[car_Csp(co_Ec)-npt_Noc(co_Ec)] (SEQ ID No.22)
pSC101{Placuv5}[car_Mab(co_Ec)-npt_Noc(co_Ec)] (SEQ ID No.23)
pSC101{Placuv5}[car_nbr(co_Ec)-npt_Noc(co_Ec)] (SEQ ID No.24)
pSC101{Placuv5}[car_Mip(co_Ec)-npt_Noc(co_Ec)] (SEQ ID No.25)
pSC101{Placuv5}[car_nfa(co_Ec)-npt_Noc(co_Ec)] (SEQ ID No.26)
pSC101{Placuv5}[car_Mul(co_Ec)-npt_Noc(co_Ec)] (SEQ ID No.27)
pSC101{Placuv5}[car_Sac(co_Ec)-npt_Noc(co_Ec)] (SEQ ID No.28)
pSC101{Placuv5}[car_Mcol(co_Ec)-npt_Noc(co_Ec)] (SEQ ID No.29)

For the activation of the fatty acid reductase, the gene product npt transfers a phospho-pantetheinyl residue from coenzyme A to the fatty acid reductase enzyme.

Example 2

Production of *E. Coli* Strains with Deletion in the Gene bioH with Intensified Fatty Acid Reductase and Phosphopantetheinyl Transferase Activity for the Production of Aminolauric Acid Methyl Ester from Lauric Acid Methyl Ester For the creation of *E. coli* strains with deletion of the gene bioH, which codes for an esterase, and intensified fatty acid reductase activity for the production of aminolauric acid methyl ester, the strain *Escherichia coli* W3110 ΔbioH (production: see EP12007663) was transformed with the plasmids pBT10_alkL (sequence and production: compare example 1 of WO/2011/131420 and the Seq ID No.8 listed there), pJ294_alaDH_B.s._TA_C.v.(Ct) (compare example 1 of WO/2013/024114 and the SEQ ID No.17 listed there) and one of the vectors created in example 1 for the expression of a fatty acid reductase by electroporation and plated out onto LB agar plates containing kanamycin (50 μg/ml), ampicillin (100 μg/ml) and tetracycline (5 μg/ml). Transformants were tested for the presence of the correct plasmid by plasmid preparation and restriction analysis. The following strains were thus created:

*E. coli* W3110 ΔbioH pBT10_alkL/pJ294_alaDH_B.s._TA_C.v.(Ct)/pSC101{Placuv5}[carA_Ms(co_Ec)-npt_Noc(co_Ec)]
*E. coli* W3110 ΔbioH pBT10_alkL/pJ294_alaDH_B.s._TA_C.v.(Ct)/pSC101{Placuv5}[carB_Ms(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mint(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mfort(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mavi(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Csp(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mab(co_Ec)-npt_Noc(co_Ec)]
*E. coli* W3110 ΔbioH pBT10_alkL/pJ294_alaDH_B.s._TA_C.v.(Ct)/pSC101{Placuv5}[car_nbr(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mip(co_Ec)-npt_Noc(co_Ec)]
*E. coli* W3110 ΔbioH pBT10_alkL/pJ294_alaDH_B.s._TA_C.v.(Ct)/pSC101{Placuv5}[car_nfa(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mul(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Sac(co_Ec)-npt_Noc(co_Ec)]
*E. coli* W3110 ΔbioH pBT10_alkL/pJ294_alaDH_B.s._TA_C.v.(Ct)/pSC101{Placuv5}[car_Mcol(co_Ec)-npt_Noc(co_Ec)]

These strains were used in order to study their capacity for the production of aminolauric acid methyl ester starting from lauric acid methyl ester.

The expression vector pBT10_alkL contains the genes alkB, alkG, alkT, alkS and alkL from the alk operon of *Pseudomonas putida*. Through the gene products, the oxidation of the substrate lauric acid methyl ester via hydroxylauric acid methyl ester to oxolauric acid methyl ester was catalysed. The vector pJ294_alaDH_B.s._TA_C.v.(Ct) contains the genes ald from *Bacillus subtilis* (coding for an alanine dehydrogenase, NP_391071.1) and Cv_2505 from *Chromobacterium violaceum* (coding for an ω-transaminase, NP_901695.1). The gene product Cv_2505 is capable of converting oxolauric acid methyl ester to aminolauric acid methyl ester, and the amino donor alanine needed for this is made available by the gene product aid from pyruvate. On the basis of an additionally expressed fatty acid reductase, which was activated by the likewise overexpressed phosphopantetheinyl transferase npt, by-products arising in the production of aminolauric acid methyl ester, in particular dodecanedioic acid methyl ester, should be reduced in order to increase the ratio of aminolauric acid methyl ester to dodecanedioic acid methyl ester.

Example 3

Production of *E. Coli* Strains with Increased Fatty Acid Reductase and Phosphopantetheinyl Transferase Activity for the Production of Aminolauric Acid Methyl Ester from Lauric Acid Methyl Ester The host strain *E. coli* W3110 used was transformed with the expression vectors pBT10_alkL (sequence and production: compare example 1 of WO/2011/131420 and the Seq ID No.8 listed there), pJ294_alaDH_B.s._TA_C.v.(Ct) (compare example 1 of WO/2013/024114 and the SEQ ID No.17 listed there) and pSC101{Placuv5}[carB_Ms (co_Ec)-npt_Noc(co_Ec)] or pSC101, empty vector, by electroporation and plated out onto LB agar plates containing kanamycin (50 µg/ml), ampicillin (100 µg/ml) and tetracycline (5 µg/ml). Transformants were tested for the presence of the correct plasmid by plasmid preparation and restriction analysis. Thus the strains: *E. coli* W3110 pBT10_alkL/pJ294_alaDH_B.s._TA_C.v.(Ct)/ pSC101{Placuv5}[carB_Ms(co_Ec)-npt_Noc(co_Ec)] and *E. coli* W3110 pBT10_alkL/pJ294_alaDH_B.s._TA_C.v. (Ct)/pSC101 were created.

Example 4

Production of Aminolauric Acid by *E. Coli* Strains with an Expression Vector for a Fatty Acid Reductase Gene and the Gene Npt from *Nocardia* Sp. and Expression Vectors for the Genes ald from *Bacillus subtilis*, Cv_2025 from *Chromobacterium violaceum* in Combination with an Expression Vector for the Genes alkB, alkG, alkT and alkL from the alk Operon of *Pseudomonas putida*.

The strains created in example 2 and 3 were used in order to investigate their capacity for the production of aminolauric acid methyl ester.

The biotransformation of lauric acid methyl ester to aminolauric acid methyl ester was carried out in the 8-fold parallel fermentation system of DASGIP. The procedure for this was as follows:

For the fermentation, 1 L reactors were used. The pH probes were calibrated by a two-point calibration with standard solutions of pH 4.0 and pH 7.0. The reactors were filled with 300 mL drinking water and autoclaved for 20 mins at 121° C. in order to ensure sterility. Next, the pO2 probes were polarized overnight (for at least 6 hrs) on the DASGIP system. On the next morning, the water was removed under the Clean Bench and replaced by 300 mL high cell density medium containing 100 mg/L ampicillin, 50 mg/L kanamycin and 5 mg/L tetracycline. Subsequently, the pO2 probes were calibrated with a one-point calibration (stirrer: 400 rpm/aeration: 10 sL/hr air) and the feed, correction medium and induction medium lines cleaned by means of Clean-in-Place. For this the tubes were flushed with 70% ethanol, then with 1 M NaOH, then with sterile demineralized water and finally filled with the respective media. The ALS and ALSME producing *E. coli* strains were firstly grown up from the respective cryocultures in LB medium (25 mL in a 100 mL baffle flask) containing 100 mg/L ampicillin overnight at 37° C. and 200 rpm for ca. 18 hrs. Next, 2 mL of each of the cultures were inoculated into high density cell medium (glucose 15 g/L (30 mL/L of a separately autoclaved 500 g/L stock solution containing 1% $MgSO_4 \cdot 7H_2O$ and 2.2% $NH_4Cl$), $(NH_4)_2SO_4$ 1.76 g/L, $K_2HPO_4$ 19.08 g/L, $KH_2PO_4$ 12.5 g/L, yeast extract 6.66 g/L, trisodium citrate dihydrate 2.24 g/L, Ammonium iron citrate solution 17 mL/L of a separately autoclaved 1% stock solution, trace element solution 5 mL/L separately autoclaved stock solution (HCl (37%) 36.50 g/L, $MnCl_2 \cdot 4H_2O$ 1.91 g/L, $ZnSO_4 \cdot 7H_2O$ 1.87 g/L, ethylenediaminetetraacetic acid dihydrate 0.84 g/L, $H_3BO_3$ 0.30 g/L, $Na_2MoO_4 \cdot 2H_2O$ 0.25 g/L, $CaCl_2 \cdot 2H_2O$ 4.70 g/L, $FeSO_4 \cdot 7H_2O$ 17.80 g/L, $CuCl_2 \cdot 2H_2O$ 0.15 g/L)) (25 mL per strain in a 100 mL baffle flask) containing 100 mg/L ampicillin, 50 mg/L kanamycin and 5 mg/L tetracycline and incubated at 37° C./200 rpm for a further 5.5 hrs.

The reactors were inoculated with an optical density of 0.1 by drawing up an appropriate volume of the preculture into a 5 mL syringe (under sterile conditions) and inoculating the reactors via cannulae through a septum coated with 70% ethanol.

The following standard program was used:

| | DO Regulator | | | | pH Regulator | | |
|---|---|---|---|---|---|---|---|
| Preset | 0% | | | Preset | | 0 ml/h | |
| P | 0.1 | | | P | | 5 | |
| Ti | 300 s | | | Ti | | 200 s | |
| Min | 0% | | | Min | | 0 mL/hr | |
| Max | 100% | | | Max | | 40 mL/hr | |

| N (Rotation) | from | to | XO2 (gas mixture) | from | to | F (Gas flow) | from | to |
|---|---|---|---|---|---|---|---|---|
| Growth and biotransformation | 0% 400 rpm | 30% 1500 rpm | Growth and biotransformation | 0% 21% | 100% 21% | Growth and biotransformation | 15% 6 sL/hr | 80% 72 sL/hr |

-continued

| Script | |
|---|---|
| Trigger exactly | 31% DO (1/60 hr) |
| Induction IPTG | 2 hrs after feed start |
| Feed trigger | 50% DO |
| Feed rate | 3 [mL/hr] |

The experiment performed can be subdivided into two phases, growth, in which the cells should reach a defined optical density, and the subsequent biotransformation, in which after addition of the substrate lauric acid methyl ester a conversion to aminolauric acid ester by enzymes formed during expression should take place. The pH values were regulated one-sidedly with ammonia (12.5%) to pH 6.8. During growth and biotransformation, the dissolved oxygen (DO) in the culture was regulated at 30% via stirrer rotation rate and aeration rate. The fermentation was carried out as fed-batch, wherein the feed start, 5 g/Lhr glucose feed (500 g/L glucose with 1% $MgSO_4*7H_2O$ and 2.2% $NH_4Cl$) was triggered via a DO peak. At feed start, the temperature was also lowered from 37° C. previously to 30° C. The expression of the transaminase, alanine dehydrogenase and fatty acid reductase was induced 2 hrs after feed start by the automatic addition of IPTG (1 mM). The induction of the alk genes was effected by the manual addition of DCPK (0.025% v/v) 10 hrs after feed start. Before the start of the biotransformation, the optical density of the culture broths was determined.

The start of the biotransformation phase took place 14 hrs after feed start. For this, 150 mL of a mixture of lauric acid methyl ester and the ion exchanger oleic acid (techn. 90%) were added as a batch to the fermentation broth. In order to make an amino group donor available for the transaminase, half an hour before biotransformation start 5 mL of a 3M ammonium sulphate solution was added to the fermentation broth. For sampling, 2 mL of fermentation broth were withdrawn from the vessel and a portion thereof diluted 1/20 in an acetone-HCl mixture (c(HCl)=0.1 mol/L) and extracted. Samples were taken from all reactors at 1 hr, 2 hrs, 3 hrs, 4 hrs, 5 hrs, 7.5 hrs, 10.5 hrs, 19.5 hrs and 21 hrs after the start of the biotransformation. The conversion rates for oxygen (OTR=oxygen transfer rate) and carbon (CTR=carbon transfer rate) were determined during the fermentation via the exhaust gas analysis on the DASGIP systems. The fermentation was ended 21 hrs after the start of the biotransformation. The stirrer, the aeration, the temperature regulation and pH regulation were switched off and the vessel allowed to stand undisturbed for 5-10 minutes.

For the quantification of DDS (C12-dicarboxylic acid), DDSME (C12-dicarboxylic acid methyl ester), LS (lauric acid), LSME (lauric acid methyl ester), HLS (omega-hydroxy lauric acid), HLSME (omega-hydroxy lauric acid methyl ester), OLS (omega-oxo lauric acid), OLSME OLS (omega-oxo lauric acid methyl ester), ALS (omega-amino lauric acid) and ALSME (omega-amino lauric acid methyl ester) in fermentation samples, samples were withdrawn during the culturing. These samples were prepared for the analysis (see LC-ESI/$MS^2$-based quantification of products).

LC-ESI/$MS^2$-Based Quantification of Products

The quantification of ALS, ALSME, DDS, DDSME, LS, LSME, HLS, HLSME, OLS and OLSME in fermentation samples was effected by LC-ESI/$MS^2$ on the basis of an external calibration for all analytes (0.1-50 mg/L) and with use of the internal standards aminoundecanoic acid (AUD for HLS, DDS, OLS, HLSME, OLSME), d4-ALSME (for ALSME), $^{13}$C-DDSME (for DDSME), d3-LS (for LS) and d3-LSME (for LSME).

In this, the following instruments were used:

HPLC System 1260 (Agilent; Böblingen) with autosampler (G1367E), binary pump (G1312B) and column oven (G1316A)

Mass spectrometer TripelQuad 6410 (Agilent; Böblingen) with ESI source

HPLC column: Kinetex C18, 100×2.1 mm, particle size: 2.6 µm, pore size 100 Å (Phenomenex; Aschaffenburg)

Precolumn: KrudKatcher Ultra HPLC In-Line Filter; 0.5 µm filter depth and 0.004 mm internal diameter (Phenomenex; Aschaffenburg)

The samples were prepared by pipetting 1900 µL solvent (80% (v/v) ACN, 20% bidist. $H_2O$ (v/v), +0.1% formic acid) and 100 µL of sample into a 2 mL reaction vessel. The mixture was vortexed for 10 seconds and then centrifuged at ca. 13000 rpm for 5 mins. The clear supernatant was withdrawn with a pipette and analysed after appropriate dilution with diluent (80% (v/v) ACN, 20% bidist. $H_2O$ (v/v), +0.1% formic acid). 100 µL ISTD were pipetted into each 900 µL sample (10 µL with a sample volume of 90 µL).

The HPLC separation was effected with the aforesaid column and precolumn. The injection volume is 0.7 µL, the column temperature 50° C., and the flow rate 0.6 mL/min. The mobile phase consists of eluent A (0.1% (v/v) aqueous formic acid) and eluent B (acetonitrile with 0.1% (v/v) formic acid). The following gradient profile was used:

| Time [mins] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

The ESI-$MS^2$ analysis was effected in positive mode with the following ESI source parameters:

Gas temperature 280° C.

Gas flow rate 11 L/min

Nebulizer pressure 50 psi

Capillary voltage 4000 V

The detection and quantification of the compounds ALS, ALSME, DDS, DDSME, HLS, HLSME, OLS, OLSME was effected with the following MRM parameters, wherein in each case one product ion was used as Qualifier and one as Quantifier:

| Analyte | Precursor Ion [m/z] | Product Ion [m/z] | Residence time [ms] | Collision energy [eV] |
|---|---|---|---|---|
| DDSME | 245.2 | 167.1 | 25 | 6 |
| DDSME | 245.2 | 149.1 | 50 | 8 |
| HLSME | 231.3 | 181.2 | 15 | 2 |
| HLSME | 231.3 | 163.2 | 25 | 5 |
| DDS | 231.2 | 213.2 | 50 | 0 |
| DDS | 231.2 | 149.1 | 25 | 9 |
| ALSME | 230.3 | 198.1 | 25 | 10 |
| ALSME | 230.3 | 163.2 | 15 | 10 |
| OLSME | 229.2 | 197.2 | 50 | 0 |
| OLSME | 229.2 | 161.1 | 25 | 5 |
| HLS | 217.2 | 181.2 | 35 | 0 |
| HLS | 217.2 | 163.1 | 20 | 4 |
| OLS | 215.2 | 161.2 | 25 | 0 |
| OLS | 215.2 | 95.2 | 60 | 13 |

The analytes LS and LSME were detected in SIM mode (m/z 201 and 215).

It was shown that the strains are capable of producing aminolauric acid methyl ester from lauric acid methyl ester via the intermediate stages hydroxylauric acid methyl ester and oxolauric acid methyl ester and at the same time of reducing by-products formed such as dodecanedioic acid methyl ester and dodecanedioic acid with the aid of a fatty acid reductase activity and thus again introducing them into the metabolism for the formation of aminolauric acid methyl ester (Tab. 1 and 2). It was further shown that through the introduction of the various fatty acid reductases the ratio of desired products (aminolauric acid methyl ester and aminolauric acid) to by-products (dodecanedioic acid methyl ester and dodecanedioic acid) was increased (Tab. 1 and 2). It was also shown that through the introduction of the various fatty acid reductases, the final product concentration of aminolauric acid methyl ester was increased (Tab. 1 and 2). Finally it was shown that through the introduction of a fatty acid reductase the space-time yield of the aminolauric acid methyl ester formation (measured between 1 and 19 hrs after the start of the biotransformation) was increased and the related product-specific glucose consumption decreased (Tab. 2).

TABLE 1

Product and by-product formation of the strains generated in example 2 with overexpressed fatty acid reductase and the gene npt from *Nocardia* sp. relative to the strain without fatty acid reductase activity.

| Strain | Relative ALSME formation [%] | Relative DDSME formation [%] | ALSME/ DDSME ratio |
|---|---|---|---|
| E. coli W3110 ΔbioH pBT10_alkL/ pJ294_alaDH_B.s._TA_C.v.(Ct) | 100 | 100 | 4.5 |
| E. coli W3110 ΔbioH pBT10_alkL/ pJ294_alaDH_B.s._TA_C.v.(Ct)/ pSC101{Placuv5}[carA_Ms(co_Ec)-npt_Noc(co_Ec)] | 103 | 12 | 38.8 |
| E. coli W3110 ΔbioH pBT10_alkL/ pJ294_alaDH_B.s._TA_C.v.(Ct)/ pSC101{Placuv5}[carB_Ms(co_Ec)-npt_Noc(co_Ec)] | 105 | 26 | 18.9 |
| E. coli W3110 ΔbioH pBT10_alkL/ pJ294_alaDH_B.s._TA_C.v.(Ct)/ pSC101{Placuv5}[car_Mint(co_Ec)-npt_Noc(co_Ec)] | 106 | 27 | 17.7 |
| E. coli W3110 ΔbioH pBT10_alkL/ pJ294_alaDH_B.s._TA_C.v.(Ct)/ pSC101{Placuv5}[car_Mfort(co_Ec)-npt_Noc(co_Ec)] | 103 | 37 | 12.3 |
| E. coli W3110 ΔbioH pBT10_alkL/ pJ294_alaDH_B.s._TA_C.v.(Ct)/ pSC101{Placuv5}[car_Mavi(co_Ec)-npt_Noc(co_Ec)] | 112 | 21 | 23.3 |
| E. coli W3110 ΔbioH pBT10_alkL/ pJ294_alaDH_B.s._TA_C.v.(Ct)/ pSC101{Placuv5}[car_Csp(co_Ec)-npt_Noc(co_Ec)] | 101 | 87 | 5.2 |
| E. coli W3110 ΔbioH pBT10_alkL/ pJ294_alaDH_B.s._TA_C.v.(Ct)/ pSC101{Placuv5}[car_Mab(co_Ec)-npt_Noc(co_Ec)] | 111 | 20 | 24.9 |
| E. coli W3110 ΔbioH pBT10_alkL/ pJ294_alaDH_B.s._TA_C.v.(Ct)/ pSC101{Placuv5}[car_nbr(co_Ec)-npt_Noc(co_Ec)] | 109 | 24 | 20.4 |
| E. coli W3110 ΔbioH pBT10_alkL/ pJ294_alaDH_B.s._TA_C.v.(Ct)/ pSC101{Placuv5}[car_Mip(co_Ec)-npt_Noc(co_Ec)] | 101 | 66 | 6.8 |
| E. coli W3110 ΔbioH pBT10_alkL/ pJ294_alaDH_B.s._TA_C.v.(Ct)/ pSC101{Placuv5}[car_nfa(co_Ec)-npt_Noc(co_Ec)] | 110 | 25 | 19.6 |
| E. coli W3110 ΔbioH pBT10_alkL/ pJ294_alaDH_B.s._TA_C.v.(Ct)/ pSC101{Placuv5}[car_Mul(co_Ec)-npt_Noc(co_Ec)] | 107 | 35 | 13.6 |
| E. coli W3110 ΔbioH pBT10_alkL/ pJ294_alaDH_B.s._TA_C.v.(Ct)/ pSC101{Placuv5}[car_Sac(co_Ec)-npt_Noc(co_Ec)] | 102 | 87 | 5.3 |
| E. coli W3110 ΔbioH pBT10_alkL/ pJ294_alaDH_B.s._TA_C.v.(Ct)/ pSC101{Placuv5}[car_Mcol(co_Ec)-npt_Noc(co_Ec)] | 107 | 31 | 15.4 |

TABLE 2

Product and by-product formation, product formation rate and yield by the strain generated in example 3, which overexpresses a fatty acid reductase and the gene npt from *Nocardia* sp. relative to the strain without fatty acid reductase activity.

| Strain | Relative ALS(ME) formation [%] | Relative DDS(ME) formation [%] | ALS(ME)/ DDS(ME) ratio | Relative space-time yield [%] | Relative yield ALS(ME)/ Glucose [%] |
|---|---|---|---|---|---|
| *E. coli* W3110 pBT10_alkL/ pJ294_alaDH_B.s._TA_C.v.(Ct)/ pSC101{Placuv5}[carB_Ms(co_Ec)-npt_Noc(co_Ec)] | 121 | 40 | 37.02 | 133 | 123 |
| *E. coli* W3110 pBT10_alkL/ pJ294_alaDH_B.s._TA_C.v.(Ct)/ pSC101 | 100 | 100 | 12.15 | 100 | 100 |

The invention claimed is:

1. A whole cell catalyst which comprises a transaminase and one selected from the group consisting of
   1) an α-dioxygenase and
   2) a combination of 2a) a recombinant fatty acid reductase and 2b) a phosphopantetheinyl transferase,
   wherein:
   the phosphopantetheinyl transferase phospho-pantetheinylates the fatty acid reductase, thereby forming a phosphopantetheinylated fatty acid reductase,
   the fatty acid reductase catalyzes the conversion of an ω-carboxy acid to a corresponding ω-oxo fatty acid,
   at least one of the phosphopantetheinyl transferase and transaminase is recombinant,
   when the catalyst comprises the transaminase and the α-dioxygenase, the transaminase is overexpressed, and
   when the catalyst comprises the transaminase and the combination of 2a) a recombinant fatty acid reductase and 2b) a phosphopantetheinyl transferase, the transaminase and/or the phosphopantetheinyl transferase is overexpressed.

2. The whole cell catalyst according to claim 1, wherein the whole cell catalyst additionally comprises a recombinant amino acid dehydrogenase.

3. The whole cell catalyst according to claim 1, wherein the whole cell catalyst additionally comprises an alkane hydroxylase.

4. The whole cell catalyst according to claim 1, wherein the whole cell catalyst additionally comprises a polypeptide of the AlkL family.

5. The whole cell catalyst according to claim 1, wherein the whole cell catalyst additionally comprises an alcohol dehydrogenase.

6. The whole cell catalyst according to claim 1, wherein an activity of at least one enzyme of the cell involved in β-oxidation, selected from the group consisting of a fatty acid-CoA ligase, an acyl-CoA dehydrogenase, a 2,4-dienoyl-CoA reductase, an enoyl-CoA hydratase, a 3-ketoacyl-CoA thiolase, and a fatty acid importer, is decreased compared to a wild type of the whole cell of the catalyst.

7. The whole cell catalyst according to claim 1, wherein an esterase activity of BioH, or a variant of BioH having at least 70% amino acid sequence identity to SEQ ID NO: 30 and essentially the same esterase activity as BioH, in the whole cell is decreased compared to a wild type of the whole cell of the catalyst.

8. The whole cell catalyst according to claim 1, wherein a fatty acid importing activity of FadL, or a variant of FadL having at least 70% amino acid sequence identity to SEQ ID NO: 31 and essentially the same fatty acid importing activity as FadL, is increased in the whole cell of the catalyst compared to a wild type of the whole cell of the catalyst.

9. A method for preparing an amine, the method comprising:
   a) oxidizing a starting material comprising a fatty acid, ω-hydroxy fatty acid, ω-oxo fatty acid or monoester thereof by contacting the starting material with an alkane hydroxylase, an alcohol dehydrogenase, or a mixture thereof to obtain an oxidation product;
   b) contacting the oxidation product with a phosphopantetheinylated fatty acid reductase or an α-dioxygenase to obtain an aldehyde; and
   c) contacting the aldehyde with a transaminase to obtain the amine,
   wherein the phosphopantetheinylated fatty acid reductase or the α-dioxygenase in addition to the transaminase is provided in the form of the whole cell catalyst according to claim 1.

10. The method according to claim 9, wherein in c) an amino acid acts as an amine donor, and an amino acid dehydrogenase regenerates the amino acid after a transamination reaction.

11. The method according to claim 9, wherein the fatty acid, ω-hydroxy fatty acid, ω-oxo fatty acid or the monoester thereof is a compound of formula (I)

$$R^1\text{-A-COOR}^2 \qquad (I)$$

wherein
$R^1$ is —H, —CHO, —OH or $COOR^3$,
$R^2$ and $R^3$ are each independently H, methyl, ethyl or propyl, with the proviso that at least one of the residues $R^2$ and $R^3$ is H, and
A is an unbranched, branched, linear, cyclic, substituted or unsubstituted hydrocarbon group with at least four carbon atoms.

12. The method according to claim 11, wherein
A is —$(CH_2)_n$—, and n is at least 4.

13. A method for preparing an amine, the method comprising:
   a) oxidizing a starting material comprising a fatty acid, ω-hydroxy fatty acid, ω-oxo fatty acid or monoester thereof by contacting the starting material with an alkane hydroxylase, an alcohol dehydrogenase, or a mixture thereof to obtain an oxidation product;
   b) contacting the oxidation product with a phosphopantetheinylated fatty acid reductase or an α-dioxygenase to obtain an aldehyde; and
   c) contacting the aldehyde with a transaminase to obtain the amine;
   wherein at least one enzyme of a), b) and c) is present in the form of the whole cell catalyst according to claim 1.

14. The method according to claim 13, wherein in c) an amino acid acts as an amine donor, and an amino acid dehydrogenase regenerates the amino acid after a transamination reaction.

15. The method according to claim 13, wherein the fatty acid, ω-hydroxy fatty acid, ω-oxo fatty acid or the monoester thereof is a compound of formula (I)

$$R^1\text{-A-COOR}^2 \qquad (I)$$

wherein $R^1$ is —H, —CHO, —OH or $COOR^3$, $R^2$ and $R^3$ are each independently H, methyl, ethyl or propyl, with the proviso that at least one of the residues $R^2$ and $R^3$ is H, and A is an unbranched, branched, linear, cyclic, substituted or unsubstituted hydrocarbon group with at least four carbon atoms.

16. The method according to claim 15, wherein A is —$(CH_2)_n$—, and n is at least 4.

17. A reaction mixture comprising:

water;

the whole cell catalyst according to claim 1; and a fatty acid, ω-hydroxy fatty acid, ω-oxo fatty acid or a monoester thereof of the formula (I)

$$R^1\text{-A-}COOR^2 \qquad (I),$$

wherein $R^1$ is —H, —CHO, —OH or $COOR^3$, $R^2$ and $R^3$ are each independently H, methyl, ethyl or propyl, with the proviso that at least one of the residues $R^2$ and $R^3$ is H, and A is an unbranched, branched, linear, cyclic, substituted or unsubstituted hydrocarbon group with at least four carbon atoms.

18. The whole cell catalyst according to claim 1, comprising the transaminase and 1) the α-dioxygenase.

19. The whole cell catalyst according to claim 1, comprising the transaminase and 2) the combination of 2a) a recombinant fatty acid reductase and 2b) a phosphopantetheinyl transferase.

* * * * *

SEQUENCE LISTING

```
<160> NUMBER OF SEQ ID NOS: 31

<210> SEQ ID NO 1
<211> LENGTH: 669
<212> TYPE: DNA
<213> ORGANISM: Artificial Sequence
<220> FEATURE:
<223> OTHER INFORMATION: synthetic gene

<400> SEQUENCE: 1
atgattgaaa ccatcttacc agccggcgtc gaatcagcag agttacttga gtaccctgaa        60
gatctgaagg cgcatccggc tgaagagcat ctgatcgcaa agagcgtaga gaagcgtcgt       120
cgcgacttca ttggcgcacg tcattgcgcc cgtctggcac tggcggagct gggtgaaccg       180
ccggttgcga ttggcaaggg tgaacgtggt gcgccgattt ggccgcgtgg tgtcgtgggc       240
tctctgaccc attgcgatgg ctatcgcgca gcggcggttg ctcacaaaat gcgttttcgc       300
agcatcggca tcgacgccga accgcacgcg accctgccgg aaggtgtcct ggattcggtt       360
agcctgccgc ctgagcgtga gtggctgaaa accaccgaca gcgcactgca cctggaccgt       420
ttgctgtttt gtgcgaaaga agcaacttac aaagcgtggt ggccgctgac ggcacgttgg       480
ctgggtttcg aagaagcgca cattaccttc gaaatcgagg atggtagcgc cgactctggt       540
aatggcacgt ttcacagcga actgctggtg ccgggtcaga ccaatgacgg tggtaccccg       600
ctgctgtctt cgacggtcg ctggctgatc gctgatggct tcatcctgac ggcgattgca       660
tacgcatga                                                              669

<210> SEQ ID NO 2
<211> LENGTH: 153
<212> TYPE: DNA
<213> ORGANISM: Artificial Sequence
<220> FEATURE:
<223> OTHER INFORMATION: promoter

<400> SEQUENCE: 2
ggcagtgagc gcaacgcaat taatgtaagt tagctcactc attaggcacc ccaggcttga        60
cactttatgc ttccggctcg tataatgtgt ggaattgtga gcggataaca ataacaattt       120
cacacaggat ctaggaacca aggagagtgg cat                                    153

<210> SEQ ID NO 3
<211> LENGTH: 3507
```

<212> TYPE: DNA
<213> ORGANISM: Artificial Sequence
<220> FEATURE:
<223> OTHER INFORMATION: synthetic gene

<400> SEQUENCE: 3

| | | | | | |
|---|---|---|---|---|---|
| atgacaattg | aaacgcgcga | agatagattt | aacagacgta | ttgatcacct | ttttgaaaca | 60 |
| gacccgcagt | tcgcagcggc | acgtccggac | gaagctatta | gcgctgcagc | agccgatccg | 120 |
| gagctgcgcc | tgccagccgc | agtcaagcag | attctggccg | ttatgcgga | ccgtccggcc | 180 |
| ctgggtaagc | gtgctgtgga | gttcgttacg | gacgaagaag | gccgtaccac | cgcaaagttg | 240 |
| ctgccgcgtt | tcgatacgat | cacctaccgt | caattggcag | gtcgtattca | ggcggtgact | 300 |
| aacgcgtggc | acaatcaccc | ggtgaatgcg | ggtgaccgtg | tcgcaatttt | gggcttcacg | 360 |
| agcgttgact | atacgaccat | cgatatcgca | ctgctggaaa | ctgggtgctgt | tagcgttccg | 420 |
| ttgcaaacgt | ctgctccggt | tgcgcagctg | caaccgattg | tggccgaaac | cgagccgaag | 480 |
| gtcattgcga | gcagcgtcga | tttcctggca | gatgcgtcg | cactggttga | gagcggtcca | 540 |
| gccccgagcc | gtctggtcgt | ttttgattat | agccacgagg | tcgacgatca | gcgtgaggcc | 600 |
| ttcgaagcgg | ccaagggtaa | actggcgggt | accggtgttg | tggtgaaaac | gattacggat | 660 |
| gtcttggatc | gcggtcgcag | cctggctgat | gcgccgctgt | atgtcccaga | cgaaacggac | 720 |
| ccgctgaccc | tgctgatcta | taccagcggt | agcaccggta | cgccgaaggg | tgctatgtat | 780 |
| ccggaatcca | agaccgcgac | gatgtggcaa | gctggtagca | aggcgcgttg | ggatgaaacc | 840 |
| ctgggcgtta | tgccgagcat | caccctgaac | ttcatgccaa | tgtcccacgt | gatgggtcgc | 900 |
| ggcatcctgt | gtagcaccct | ggcgagcggc | ggtactgcgt | attttgccgc | acgtagcgac | 960 |
| ttgtctacct | ttctggagga | cctggcgttg | gtccgcccga | cccaactgaa | tttcgtccct | 1020 |
| cgcatctggg | atatgctgtt | ccaagagtat | cagagccgtc | tggacaatcg | tcgtgccgag | 1080 |
| ggtagcgagg | atcgcgcgga | agcggccgta | ctggaagagg | ttcgtaccca | attgctgggc | 1140 |
| ggtcgtttcg | tttccgctct | gaccggtagc | gctccaatca | gcgcggaaat | gaaaagctgg | 1200 |
| gtcgaggacc | tgctggacat | gcatttgctg | gaaggttacg | gttccaccga | ggcgggtgcc | 1260 |
| gtgttcattg | acggtcaaat | ccaacgtcca | cctgttatcg | attacaaact | ggttgatgtt | 1320 |
| ccggacttgg | gttactttgc | gaccgatcgt | ccatacccct | cgcggcgagct | gctggtgaag | 1380 |
| agcgagcaga | tgttcccggg | ctactataag | cgtccggaga | ttacggcgga | gatgtttgac | 1440 |
| gaggacggtt | attaccgtac | cggcgacatc | gtggccgaac | tgggtccgga | tcatctggag | 1500 |
| tatctggacc | gccgtaacaa | cgtcctgaag | ctgagccagg | gtgagtttgt | taccgtttcc | 1560 |
| aaactggaag | cggtctttgg | cgatagccca | ctggtgcgcc | agatttatgt | ctacggtaac | 1620 |
| tctgcacgca | gctatctgct | ggcggttgtc | gttccgaccg | aagaggcact | gagccgctgg | 1680 |
| gacggcgatg | aactgaagag | ccgcatcagc | gacagcttgc | aagatgcggc | acgtgccgca | 1740 |
| ggtttgcaaa | gctatgagat | cccgcgtgac | tttctggttg | aaaccacgcc | gttcacgttg | 1800 |
| gagaacggtc | tgctgaccgg | cattcgcaaa | ctggcgcgtc | gaagctgaa | agcgcattat | 1860 |
| ggcgaacgtc | tggaacaact | gtacacggat | ctggctgaag | gccaagccaa | tgagctgcgt | 1920 |
| gaactgcgcc | gtaatggtgc | ggatcgtccg | gttgttgaaa | cggtttcgcg | tgccgcggtc | 1980 |
| gccttgctgg | gtgcgtctgt | gacggacctg | cgttctgacg | cccactttac | ggacctgggc | 2040 |
| ggtgattccc | tgagcgccct | gagcttcagc | aacctgctgc | acgagatttt | tgacgtcgat | 2100 |
| gtcccggtgg | gcgtgattgt | cagcccggca | accgacctgg | ccggtgttgc | cgcctatatt | 2160 |

```
gagggtgagc tgcgtggtag caaacgtccg acctacgcaa gcgtccacgg tcgtgacgca    2220
accgaggtgc gtgctcgcga tctggcgctg ggcaaattca tcgacgcaaa aacgctgagc    2280
gcagcaccgg gtctgccgcg ctccggtacg gagatccgta cggtgctgct gacgggtgcg    2340
accggttttc tgggtcgcta cttggccttg gagtggctgg aacgtatgga cctggttgac    2400
ggcaaggtga tctgtttggt tcgtgcgcgt agcgacgacg aagcacgtgc gcgtctggac    2460
gcaaccttcg ataccggcga tgctaccttg ctggagcact accgtgccct ggcggctgac    2520
catctggaag ttattgcggg tgataagggt gaagccgact gggcctgga tcacgatacc     2580 tggcagcgtc tggcagatac ggtcgacctg atcgttgacc cggctgcgct ggttaaccac    2640
gttttgccgt acagccagat gttcggccca aacgctctgg gcactgcaga gctgattcgc    2700
attgcactga ccaccaccat taaaccgtac gtctacgtga gcaccattgg tgttggtcag    2760
ggcatcagcc cagaagcctt tgttgaagat gcggacatcc gcgaaatcag cgccacgcgt    2820
cgcgttgacg acagctacgc gaatggttat ggtaacagca atgggcagg tgaggttctg      2880 ctgcgcgaag cgcacgactg gtgcggcctg ccggtgagcg tgtttcgttg tgacatgatc    2940
ttggccgaca ccaccactc cggccagctg aatctgccgg atatgttcac ccgtctgatg     3000
ttgagcctgg tggcaactgg catcgcaccg ggcagctttt atgagctgga cgcggacggt    3060
aatcgtcaac gtgcacatta tgatggtctg ccggtggagt ttatcgcgga agcaatcagc    3120
acgatcggct ctcaagtgac tgacggtttc gaaacgttcc atgtcatgaa tccttatgat    3180
gatggtatcg gcctggacga gtacgtcgac tggctgattg aggctggcta cccggttcac    3240
cgtgttgatg attatgcgac gtggttgagc cgttttgaaa ccgccttgcg tgcgctgccg    3300
gagcgtcaac gtcaggcatc cctgctgccg ctgttgcaca actaccagca gccttctccg    3360
ccggtttgcg gtgctatggc tcctaccgac cgtttccgtg cagctgtcca ggacgccaaa    3420
attggcccag ataaagacat cccacatgta acggcggacg tgatcgtgaa atacattagc    3480
aacttgcaga tgctgggtct gctgtaa                                        3507

<210> SEQ ID NO 4
<211> LENGTH: 3525
<212> TYPE: DNA
<213> ORGANISM: Artificial Sequence
<220> FEATURE:
<223> OTHER INFORMATION: synthetic gene

<400> SEQUENCE: 4
atgactagcg atgtacatga cgcgactgac ggtgtgacag agacagcatt agatgacgag     60
caaagcaccc gtcgcattgc ggaactgtat gcaacggatc cggagtttgc agctgccgca    120
ccgctgccgg ctgttgtcga cgctgcacat aaaccgggtc tgcgtctggc ggagattctg    180
cagaccctgt ttaccggtta cggcgatcgt ccggccctgg gctaccgtgc tcgtgaactg    240
gcgacggatg agggtggccg taccgtgacc cgtttgttgc cgcgttttga cacgctgacg    300
tacgcgcaag tctggagccg tgtccaggct gtggcagcag cgctgcgcca taacttcgcg    360
cagcctatct atccaggtga cgcggttgcg accatcggct ttgcaagccc agactatctg    420
acgctggatc tggtctgcgc gtatttgggc ctggtcagcg tgccactgca gcacaacgct    480
cctgtgagcc gttttggcgcc gattctggcc gaggttgagc gcgtatcct gacggtcagc    540 gccgaatacc tggacctggc ggtcgagagc gtgcgtgatg tgaattctgt ctcgcaattg    600
gtcgttttcg accaccaccc ggaagtcgat gaccaccgcg atgcgctggc acgcgcacgt    660
gaacagctgg ccggtaaagg tattgccgtt acgactctgg acgcgattgc ggacgaaggc    720
```

```
gctggtctgc cagcggagcc gatctatacc gccgatcacg atcaacgcct ggcgatgatc    780
ctgtacacca gcggttctac cggcgctccg aagggtgcga tgtatactga ggccatgctg    840
gcgcgtctgt ggaccatgtc ctttatcacc ggcgacccga ctcctgtgat taatgtgaac    900
tttatgccgc tgaatcacct gggtggtcgt attccgatta gcaccgcggt ccagaacggc    960
ggtacgagct acttcgttcc ggagagcgac atgtctaccc tgtttgagga cctggccttg   1020
gttcgcccga cggaactggg tctggttccg cgtgtggcgg acatgttgta ccagcatcac   1080
ctggcaactg ttgaccgtct ggttacccag ggcgcagacg agctgaccgc agagaagcag   1140
gcaggcgcag aactgcgtga acaggtgctg ggcggtcgtg tgattaccgg cttcgtgagc   1200
acggcgccac tggcggctga gatgcgtgcc ttcctggata tcacgctggg tgcccacatc   1260
gttgatggtt acgttttgac cgaaaccggt gcggtgacgc gtgatggcgt tatcgtccgt   1320
ccgccggtca ttgattacaa gctgattgat gttccagagc tgggctactt cagcaccgat   1380
aaaccgtacc cacgtggcga actgttggtt cgtagccaaa cgttgacccc gggttactat   1440
aaacgtccgg aagttaccgc atcggtgttt gatcgcgacg gctattacca taccggtgac   1500
gttatggcag aaaccgctcc agatcacctg gtatatgtgg accgccgcaa taacgttctg   1560
aaactggcgc agggtgaatt tgtcgcagtc gcaaacctgg aagccgtttt cagcggtgcc   1620
gcgctggttc gccaaatctt cgtgtacggc aacagcgagc gcagcttcct gttggcggtg   1680
gtggtgccga cgccagaagc cctggaacaa tacgatccgg cagccctgaa ggcggccttg   1740
gcagatagcc tgcagcgcac ggctcgtgat cgggagctgc aatcgtatga agttccggcc   1800
gatttcattg tggaaaccga ccgttcagc gccgcaaatg gtctgttgag cggtgtcggc   1860
aagttgctgc gtccgaacct gaaagatcgt tatggtcaac gtctggagca aatgtatgcc   1920
gatattgccg cgacccaggc gaatcagctg cgcgagctgc gtcgtgccgc agccacccag   1980
ccggtgattg atacccctgac gcaggctgct gcgacgattt tgggtaccgg tagcgaagtg   2040
gcgtctgatg cccactttac ggatctgggt ggcgacagcc tgtccgctct gaccttgtcc   2100
aatttgctga gcgatttctt tggttttgag gttccggttg gtaccattgt taacccggcg   2160
actaatctgg cgcagctggc acagcacatc gaagcacagc gcaccgccgg tgaccgccgt   2220
ccgagcttta ccacggtgca tggtgcggac gcgacggaaa ttcgtgcgag cgaactgacc   2280
ctggataagt ttattgacgc agaaaccctg caggcagcac caggcctgcc gaaggtgacc   2340
accgagccgc gcaccgtcct gctgagcggt gccaatggtt ggttgggtcg cttcctgacc   2400
ctgcaatggc tggaacgtct ggcgcctgtt ggtggtacgc tgatcaccat tgtccgcggt   2460
cgtgacgacg ctgcggctcg tgctcgcctg acccaagctt acgacaccga cccagagttg   2520
tctcgccgct tcgcagaact ggcggaccgc catctgcgtg ttgtagcagg cgatatcggt   2580
gatccgaatc tgggcctgac cccagaaatc tggcaccgtc tggctgctga ggtggatttg   2640
gttgtgcatc agcggcgtt ggtgaaccac gtcttgccgt atcgtcagct gttcggcccg   2700
aacgtcgtgg gcaccgccga agtgattaag ctggcgctga cggagcgcat caagccagtt   2760
acctacctga gcaccgtcag cgttgcaatg ggtatcccgg actttgaaga ggatggtgat   2820
atccgtaccg tttcccctgt tcgtccgctg acggcggct atgctaatgg ctacggcaac   2880
tctaagtggg ctggtgaggt cctgctgcgt gaggcccacg acctgtgtgg cctgccggtg   2940
gccacgttcc gtagcgacat gattttggca cacccgcgct accgtggtca ggttaatgtg   3000
ccggatatgt tcactcgtct gttgttgtcg ctgctgatca ctggcgtggc tccgcgctct   3060
```

```
ttctacattg gtgatggtga acgtcctcgt gcgcattatc cgggtctgac tgtcgacttt    3120
gtggccgagg ccgtgacgac cctgggtgca cagcagcgtg aaggctacgt tagctacgat    3180
gtcatgaacc cgcatgacga tggcatcagc ctggatgttt tcgtggactg gctgatccgc    3240
gcaggccatc cgattgaccg tgtggacgat tacgacgatt gggtgcgtcg cttcgagact    3300
gcactgacgg cgctgccgga aaaacgtcgc gcacaaaccg ttctgccgtt gctgcacgcg    3360
ttccgtgccc cgcaagcgcc gctgcgtggt gccccggagc caaccgaggt tttccatgcg    3420
gcggttcgta ccgcaaaagt cggtccaggc gacattccgc acttggatga agcgctgatt    3480
gataagtaca tccgtgatct gcgtgagttt ggcctgatct aataa                   3525
```

<210> SEQ ID NO 5
<211> LENGTH: 3525
<212> TYPE: DNA
<213> ORGANISM: Artificial Sequence
<220> FEATURE:
<223> OTHER INFORMATION: synthetic gene

<400> SEQUENCE: 5

```
atgagcactg caattcacga tgaacacttg gatcgccgca ttgaagaact gattgcaaac      60
gatccgcaat cgctgcggc acgcccgac ccggcgatta ccgcagcgac cgaggcccca     120
ggtctgcgtc tgccgcagat catccgtacg gtcctggacg ttatgccga tcgtccggcg     180 ctggcgcaaa cgctggttga attcgttacc gacgccaaaa ccggtcgtac caccgcagag     240
ttgctgccac gttttgaaac catcacgtac ggtgagctgg gtgagcgtgt gagcgcactg     300
ggtcgcgcat gggccggtga cgccgtgcgc cctggcgacc gcgtttgcgt cctgggtttc     360
aactccgtgg attacgcgac gattgacatc gcgctgggta ccatcggtgc ggtgagcgtg     420
ccgctgcaaa ccagcgcagc gattagcagc ctgcagccga ttgtggcgga aaccgagccg     480
agcctgattg cgagcagcgt gaatcagctg ccggacgccg tcgagctgat tctggcaggt     540
gaccatgttc cgggtaagct ggtcgtattt gattatcaac cgcaagttga tgaccagcgt     600
gaggcggttg aggcagcggc tgcgcgcctg gcagacagcg gcgtcgcagt ggaagcgctg     660
gcggatgttc tgcgtcgtgg taaagacctg ccggcagttg aaccgccagc gtccgatgag     720
gatagcctgg ctctgttgat ttacacctct ggcagcaccg gtgcgccgaa gggcgcgatg     780
tacccgcaga gcaacgtggg taaaatgtgg cgtcgcggta gcaagaactg gtttggtgag     840
agcgccgcaa gcatcaccct gaatttcatg ccgatgagcc atgttatggg tcgcggtatt     900
ttgtatggca cgttgggtaa cggcggcacc gcgtatttcg cggctcgtag cgatttgtct     960
acgctgctgg aagatctgga gttggtgcgc cctacggaga tgaattttgt cccgcgtatt    1020
tgggaaacgc tgtatggtga gttccagcgt caggtggagc ccgtctggc ggacggtgac    1080 gctggcccgg aagcccgtga aaccgtcgag gcggcagtgc tggaagagca gcgtcaatat    1140
ctgctgggtg gccgttttat cttcgccatg accggctctg cgccgacgag cccggagctg    1200
aaagcatggg cggagagctt gctgcaaatg cacctgatgg acggttacgg cagcaccgag    1260
gcgggcatgg tgctgttcga cggtgagatc cagcgtccgc cggtcatcga ttacaaactg    1320
gtggatgtcc cggatctggg ttactttttcg acgaccgtc cgcatccgcg tggtgagctg    1380
ttgctgcgta ccgagaacat gttcccgggt tactataaac gcgcggaaac caccgcaaat    1440
gttttcgacg aggatggtta ctaccgcacc ggcgatgtgt cgcggagat cgcaccggac    1500 cgtttggttt acgtcgatcg tcgcaataac gtccttgaaac tggcccaggg tgagtttgta    1560
accctggcca aactggaagc ggttttcggt aactcgccgc tgatccgcca gatctacgtg    1620
```

```
tacggcaaca gcagccagcc gtacctgctg gcggtggtgg tcccgaccga agaggcgctg    1680
gccgataatg acttggaaag cttgaagccg aaaatcgcag actccctgca aaaagttgca    1740
aaagaaactg gcctgcagtc ctatgaggtt ccgcgtgatt tcatcatcga gactacgccg    1800
ttcaccctgg agaacggttt gctgaccggc attcgtaagc tggcgtggcc taagctgaag    1860
gcccactatg gcgatcgtct ggagcaaatg tacgctgagc tggctgcggg tcaggcgaat    1920
gagctggcgg agctgcgccg tagcggtgcg gcagcgccgg tggcccagac cgtgtcccgc    1980
gcagcagcgg cgctgctggg cgctgctgct ggtgatctga gcgcggatgc ccactttact    2040
gacctgggtg gtgattccct gtccgcactg acctttggta acctgctgcg tgagattttt    2100
gacgtcgatg ttccggttgg cgttattgtc tcccctgcta acgacttggc gggcattgcc    2160
gcatacattg aagcagagcg tcaaggtagc aaacgtccga cgttcgcagc agtgcatggt    2220
cgcggtgcca cgatggtgca tgcgagcgac ttgactctgg ataagtttct ggacgaagcc    2280
accctggcag cagccccaag cctgccgaaa ccggcgacgg aagttcgtac ggttctgctg    2340
accggtgcga cgggttttct gggccgttat ctggcactgg actggctgga gcgcatggat    2400
atggttgacg gcaaagttat tgcgctggtc cgtgcgcgca ccgatgaaga gcgcgtgcg    2460 cgtttggaca agacgtttga cagcggcgac ccgaaactgc tggctcacta ccaacgtctg    2520
gcagcggacc acttggaagt tatcgcgggt gacaaaggtg aggctaatct gggcttggac    2580
ccgcaaacct ggcagcgtct ggccgaagaa gtggacgtga tcgttgaccc ggcagcgctg    2640
gtgaaccatg tcctgccgta ctctgaattg tttggcccga acgcactggg cacggccgaa    2700
ctgatccgca tcgcgctgac ctctaagcaa aaaccgtata cgtatgttag caccattggt    2760
gttggcgatc agattcaacc gggcgagttc gttgaaaatg ctgatatccg tcagatcagc    2820
gcgacgcgtg agatcaacga tggctacgct aatggttatg caatagcaa gtgggcgggt    2880 gaggttctgc tgcgcgaggc gcacgacctg tgtggcctgc cggtcaccgt gttccgttgc    2940
gatatgatcc tggctgacac cacgtacgct ggccagctga atctgccgga catgtttacc    3000
cgtttgatgc tgagcctggt cgcgaccggt atcgcaccgg gcagctttta cgaactggac    3060
acggatggca atcgccagcg tgtccactat gatggtctgc cagtcgagtt cattgctgcg    3120
gccatcagca ccctgggcac ccaaatcacg gatagcgaca ccggtttcca gacttatcat    3180
gtaatgaatc catacgatga cggtattggt ctggatgagt acattgactg gctgattgag    3240
gctggttaca gcatcgaacg tattgcggac tatagcgaat ggctgcgtcg cttcgaaacg    3300
tcgctgcgtg ccctgcctga ccgtcaacgc cagtattcgc tgctgccgct gttgcacaat    3360
tatcaaaagc cggagaagcc gattaacggt agcatggcgc caactgatgt ctttcgtgca    3420
gccgttcaag aagcgaagat cggtccggat aaggacattc cgcacgtctc tgcgccggtg    3480
attgtcaagt acatcaccga cctggagctg ctgggtttgc tgtaa              3525
```

<210> SEQ ID NO 6  
<211> LENGTH: 3471  
<212> TYPE: DNA  
<213> ORGANISM: Artificial Sequence  
<220> FEATURE:  
<223> OTHER INFORMATION: synthetic gene

<400> SEQUENCE: 6

```
atgacgaccg aaaccagaga agatcgctta cagagacgca ttgcccacct gtacgaggca      60
gacagccaat ttgcggctgc gcgtcctagc gaggcggtga ataccgccgt ggcggaacca     120
```

-continued

```
gagctgcgtc tgccggctgt cgtcaaaggt gtctttgcgg gctatgcgga tcgtccggcg      180
ctgggtcaac gcgccgtgga gtatgttacc gacgcggacg tcgtacctc  tgcccaattg      240
ctgccgcgtt ttgacacgat cacgtaccgt caactgggtg accgcgtcca agcagttacg      300
aacgcgtggc acaaccatcc ggtcaaacct ggcgaccgtg tagcgatcct gggctttact      360
agcgttgatt acaccaccgt tgatacggcc ctgatcgaat gggcgctgt  gagcgtcccg      420
ctgcagactt ctgcaccggt caccacgctg cgcccgatcg tcgcagagac ggagccgacc      480
gtgattgcgg cttctattga tttcctggat gatgcggtgg aactggtcaa aagcggtccg      540
gcaccgcgtc gtctggttgt gttcgactac cgcccacgtg tcgacgccca gcgcgaggca      600
tttgaagcag ccaaagcggc actggcgggt actgacgttg tagttgagcc gctggcggat      660
gtcctggacc gcggtcgtag cttggcggat gcgccgctgt acaccccggg tcagccggac      720
ccgctgacca tgctgattta cacgagcggt tccacgggca ccccgaaggg tgcgatgtat      780
ccggagagca aagtcgctaa catgtggcaa ctggcgacga aggcgacgtg ggatgagaac      840
caagcggcgc tgccggccat caccctgaac tttatgccga tgagccatgt gatgggccgt      900
ggcatcctga ttggtaccct gagcagcggt ggcaccgcat acttcgcggc tcgcagcgat      960
ctgagcacct tcctggaaga tctggcattg gttcgtccga cccagttgag ctttgttccg     1020
cgtatttggg atatgctgtt ccaggaatat cagagccgtc tggaccgttc tggtgcgcca     1080
gaggacgagg tgctggccga ggtccgccaa gacctgctgg gcggtcgttt cgtgagcgcg     1140
atgacgggtt ctgcgccgat tagcgcggaa atgaagaatt gggtggaacg tctgctggac     1200
atgcatctgc tggaaggcta tggttccacc gaagcaggct ccgtgtttgt ggacggtcat     1260
attcaacgtc gccggttat  tgactataaa ctggttgatg tcccggacct gggttatttc     1320
ttgacgacc  gtccgcatcc gcgtggcgag ctgctggtga agagcgagca aatgttccca     1380
ggttactaca agcgtccgga gattaccgct gaaatgttcg atgaggatgg ctactaccgc     1440
accggcgaca tcgtggcgga attgggtccg gatcaagttg agtatctgga ccgtcgtaat     1500
aacgttctga aattgtctca gggtgagttt gtgacggtta gcaaactgga agcggtgttc     1560
ggcgacagcc cgctggttcg tcagatcttc gtttatggta acagcgcacg ttcctacctg     1620
ctggcagttg tggttccgac cgacccgtcg ctgagcaagc aggcgatcgg cgattcgttg     1680
caggacgcgg cacgcgctgc aggtctgcaa tcctacgaga ttccgcgtga ctttatcgtc     1740
gaaacgaccc ctttttagcct ggagaacggc ctgctgacgg gcattcgcaa actggctcgc     1800
ccaaacctga aggcctacta cggcgatcgt ctggagcagc tgtacaccga gctggcagag     1860
ggccaagcga atgagttgag cgagctgcgt cgcaatggcg ctcaagcccc ggtcctggat     1920
accgtgagcc gtgcagcggg tgctctgttg gcggcagcgg ctagcgatct ggctccagag     1980
gcgcatttta ccgacttggg tggcgatagc ttgagcgcgc tgacctttgg taacctgctg     2040
caagagatct ttgatgtcga agtcccggtg agcgcaattg tttcgccggc atccgacttg     2100
cgtacgatcg cagagtatat cgaagctcaa cgttccggcg cagacgtccg cccgaccttc     2160
acgtccgtgc acggtcgcaa tgcgaccgag gtgcatgcga gcgatttgac gctggataag     2220
ttcattgatg ccgccacgct ggcggcagcc ccgagcctgc cggtccggt  gagcgagatt     2280
cgcactgtct tgctgaccgg tgcgacgggt ttcttgggcc gctatctggc gctggaatgg     2340
ctggaacgta tggatctggt tgatggtaaa gtgatctgct tggttcgtgc gaagagcgac     2400
gaagaggcgc gtgcccgcct ggacaaaact ttcgacagcg gcgatccgaa gctgtgggcc     2460
cactatcaga agctggcagc cgatcatctg gaagtgatcg cgggtgacaa gggtgaggca     2520
```

```
gacctgggcc tggatcaggt tacctggcag cgtctggcgg ataccgtgga tttcatcgtg   2580
gatccggcag cgctggttaa tcacgttctg ccttatagcg aactgttttgg tccgaatgct   2640
ctgggtactg ccgagctgat ccgtattgcg ctgaccaccc gtatcaaacc gttcgcgtac   2700
gtgagcacga tcggcgtggg tggtggtatc gagccgggta agttcgtcga ggcgggtgac   2760
attcgtgcga tctctcctgt ccgtcgcgtt gacgatggtt acgcaaatgg ctacggcaac   2820
agcaaatggg ccggtgaagt cctgctgcgc gaagcccacg atctggcggg tctgccagtg   2880
accgtttttc gctgtgatat gatcttggcc gacaccacct acgcaggtca gttgaatctg   2940
cctgacatgt tcacgcgtat gatgttttcc ctggttgcga ccggtgtggc gccgaagagc   3000
tttaatcaac tggatgcaga cggcaaccgc cagcgtagcc actatgacgg tctgccggtc   3060
gagtttattg cagaagctat cagcaccctg ggcgcacacg ttcaggacgg cttcgaaact   3120
tatcacgtta tgaatccgca cgacgacggt attggtatgg atgagttcgt tgattggctg   3180
atcgaagccg gttacccgat tcagcgcgtc gaggactatc aggagtggct ggcgcgcttc   3240
gaaaccaccc tgcgtgccct gccggataaa cagcgtcagg cgagcctgct gccgctgctg   3300
cacaactacc agcaaccggg tgtcccggtt aacggcgcca tggcaccgac cgacgttttc   3360
cgtacggccg tccaagacgc gaaaattggt ccggacaagg atattccgca cgtcagccgt   3420
gaagttattg tgaagtacat cagcgatttg aaactgctgg gtttgctgta a            3471

<210> SEQ ID NO 7
<211> LENGTH: 3522
<212> TYPE: DNA
<213> ORGANISM: Artificial Sequence
<220> FEATURE:
<223> OTHER INFORMATION: synthetic gene

<400> SEQUENCE: 7
atgagcactg caacgcatga tgagagactg gatagacgcg tacatgaact gatcgcaacc     60
gacccgcaat ttgcggcagc acagccggac ccggctatta cggcggcatt ggagcaaccg    120
ggtctgcgtc tgccgcagat cattcgtacc gtcctggacg gctatgcgga tcgtccggcg    180
ttgggtcaac gcgtcgttga gtttgttacc gacgcgaaaa ccggtcgcac gagcgcgcag    240
ctgctgccgc gttttgaaac cattacctac tccgaagtgg cacaacgcgt tagcgcgctg    300
ggtcgtgcgc tgtccgacga cgcagttcat ccgggtgatc gtgtgtgtgt cctgggtttt    360
aacagcgttg attacgcgac catcgatatg gcactgggtg cgattggcgc ggtgtcggtt    420
ccgctgcaaa cctctgcagc gattagctcc ctgcagccta ttgtcgcgga aaccgaaccg    480
acgctgatcg cgagcagcgt taatcagctg agcgatgccg tgcagctgat caccggtgca    540
gagcaggccc ctacccgttt ggtggtgttc gattatcacc gcaagtcga tgaccagcgc    600
gaggctgttc aggacgcggc tgcgcgcttg tccagcaccg gcgttgccgt gcaaaccctg    660
gccgagctgc tggagcgcgg taaagacctg ccggctgtgg cggagccgcc agcggatgag    720
gacagcctgg cgttgctgat ttacaccagc ggcagcacgg gtgctccgaa aggtgcgatg    780
tacccacaga gcaatgttgg taagatgtgg cgtcgtggct ctaaaaactg gttcggcgaa    840
agcgctgcta gcattaccct gaacttcatg ccgatgagcc atgtgatggg ccgtagcatc    900
ttgtacggca ccctgggtaa cggcggtacg gcctatttcg ctgctcgtag cgatctgagc    960
accctgctgg aagatctgga gctggtgcgt ccgacggaac tgaattttgt tccacgcatt   1020
tgggaaacct tgtatggtga gttccaacgt caagtggaac gccgcctgag cgaggctggc   1080
```

-continued

```
gacgcgggtg agcgtcgtgc tgtggaagcg gaagtgctgg cggagcagcg ccaatatctg    1140
ctgggcggtc gtttcacctt tgcgatgacg ggcagcgccc ctatttcgcc tgagctgcgc    1200
aactgggtcg agtccctgct ggagatgcat ctgatggatg ttacggtag cacggaagcg    1260 ggcatggtcc tgtttgacgg tgagatccaa cgtccgccgg ttattgatta caagttggtg    1320
gacgttccgg atttgggtta ctttagcacc gatcgcccgc acccgcgtgg tgagctgctg    1380
ctgcgtacgg agaatatgtt cccgggttac tataagcgtg ccgaaactac cgcgggtgtt    1440
tttgatgagg acggttacta ccgcacgggc gatgtgtttg ccgaaatcgc accggatcgc    1500
ctggtgtatg ttgaccgtcg caacaacgta ttgaaactgg cacaaggcga gttcgtcacg    1560
ttggccaagc tggaagcggt gtttggtaat tccccgctga ttcgtcagat ctatgtctat    1620
ggtaacagcg cgcaaccgta tctgctggcc gttgtcgttc cgactgaaga agccctggcc    1680
agcggtgatc ctgagacgct gaagccgaaa atcgcagata gcctgcagca gtggcgaaaa    1740
gaagcaggtc tgcagagcta cgaagttccg cgcgacttta tcatcgagac gacgccgttt    1800
agcctggaaa acggcctgtt gacgggcatc cgcaaactgg cttggccgaa actgaagcaa    1860
cactacggcg agcgtctgga gcaaatgtac gccgacctgg cagcgggcca agcaaatgaa    1920
ctggcagagc tgcgtcgtaa tggcgcccaa gccccggtgc tgcagacggt tagccgtgca    1980
gcgggtgcaa tgtttgggctc tgccgcgagc gatttgagcc cagatgcgca cttcaccgac    2040
ctgggtggtg acagcctgtc tgctctgacc ttcggtaacc tgctgcgtga tcttcgac    2100 gtcgatgtcc cggtcggcgt gatcgtcagc ccggcaaatg atctggcggc gattgcgagc    2160
tatattgaag cagaacgtca gggtagcaaa cgtccgacct tgcgagcgt ccatggtcgc    2220 gacgcgaccg ttgttcgtgc tgccgacttg accctggaca gttttttgga cgctgaaacg    2280
ttggctgcgg caccgaacct gccgaagccg gcgaccgagg ttcgcaccgt tctgctgacc    2340
ggtgctactg gtttcctggg tcgttacctg gctctggagt ggctggagcg tatggatatg    2400
gttgacggta aggtcattgc attggtgcgt gcgcgttctg atgaagaggc ccgtgcccgt    2460
ctggataaga cctttgacag cggtgacccg aaactgctgg cgcactatca gcagctggcg    2520
gcagaccacc tggaagtgat cgccggtgac aagggtgagg ccaatctggg tctgggtcag    2580
gacgtgtggc aacgtctggc ggacaccgtt gatgtcattg tggacccggc agcgctggtg    2640
aaccacgtcc tgccgtactc cgaactgttc ggtccgaatg cgttgggcac tgcagagctg    2700
atccgtctgg cactgaccag caagcagaaa ccgtatactt acgttagcac catcggcgtc    2760
ggcgaccaaa tcgaaccggg taaattcgtt gaaaatgcag atattcgtca aatgtcggcg    2820
acccgtgcga ttaatgacag ctacgcgaac ggctatggca actccaagtg ggcgggtgag    2880
gttctgctgc gcgaggcgca tgatctgtgc ggtctgccgg tagcggtgtt ccgttgcgac    2940
atgatcctgg cagacacgac ctacgcaggt cagttgaatc tgccggatat gttcacgcgc    3000
ctgatgttga gcctggtagc gacgggtatt gcaccgggtt cttctatga gttggatgcc    3060 gatggcaatc gccagcgcgc acactatgac ggcctgccgg tcgagtttat cgcagcggcg    3120
attagcacgc tgggttccca gatcaccgat agcgataccg gcttccagac gtaccacgtc    3180
atgaatcctt acgacgacgg cgtcggcctg acgagtacg tcgactggct ggttgatgcg    3240
ggttattcga ttgagcgtat tgccgactac tctgaatggt tgcgtcgctt cgaaaccagc    3300
ctgcgtgcgc tgccggatcg tcaacgccag tatagcctgc tgccactgtt gcacaactac    3360 cgtacccccgg agaaaccgat taacggcagc atcccccga cggatgtttt ccgtgcggca    3420
gtccaggaag cgaagatcgg tccagacaag gacatcccgc acgtgtcccc gccagtgatc    3480
```
gtgaaataca ttaccgacct gcagctgttg ggcctgctgt aa         3522

<210> SEQ ID NO 8
<211> LENGTH: 3435
<212> TYPE: DNA
<213> ORGANISM: Artificial Sequence
<220> FEATURE:
<223> OTHER INFORMATION: synthetic gene

<400> SEQUENCE: 8

| | |
|---|---|
| atgaatgaaa gcagcgcaga ccagagcagc ggtaatgtat cagagggttg gccggacgcg | 60 |
| agcgtcaccg cgcgtgcgct gcaagcgcac ctgcgttacg aacagatcat cgacgctatc | 120 |
| ctgagcggct atgcggaacg tccggcactg gcggagcgca gctacctggt ccgtccagat | 180 |
| ccgagcacgg gccaaaccgt tcgcgtccac gagcaggcgt tcgttctat cagctaccgt | 240 |
| acgctgcaag aacgcgtcca cgccctgacc atggcgtggc gtctgcaccc ggactcccg | 300 |
| gtacaagcgg gtgcattcgt cgtgctggtt ggctttgcca gcatcgatta tgcggttctg | 360 |
| gacctggccc tggcctatac caagggtgtc ccggttccgc tgagcccgaa ccactctagc | 420 |
| gaggacgatg acgcaatctt gggcaccgtg caaccggtga ccctggccgt ttctatctct | 480 |
| gagttctccg gctgcgtgga tctgattgct cgtagcacca gcatccgtac ggttattgtg | 540 |
| tttgatttgg atccggcggt ggattgtgag cgtgcagccc tggagtccgg tattcgtgcg | 600 |
| ctgaacgaga agggtagcga tgtcgttgtg caaaccctgc aagacctgat cgatgtcggc | 660 |
| cgtgatgcgg agtttagctt tctgcctatt caggcgcaag accaggatga tttggctctg | 720 |
| ctgattcata ccagcggtag caccggcacg ccgaagggcg cttgcatcag cagccgtgcc | 780 |
| ctgatcaaca cctggcgtca cgtcagcggt ccgtatccta agtgaccgt cgttctggcg | 840 |
| ccgtttcacc acatgatggg tcgtgacagc atgattaccg ccctgggtgc aggcggcacc | 900 |
| gcgtacttca cgttgcgtcc ggatctgagc actgttattg aggacatccg cctggcacgc | 960 |
| ccgaccggcc tggtgctgtt cccgcgtctg tgcgaggtga tcgagcacca tctgacgacc | 1020 |
| gctccggagt actctggtaa cgagatcctg ggtggccgtc tgcagtccat tgtcgtagcg | 1080 |
| agcgctccga ttactccgcg tctgaaagcg agcttggagt gtttgctggg cgttccggtg | 1140 |
| agcgagggtt attccagcac ggagacggca agcggtggtt tggcaatgaa cggcctgttg | 1200 |
| aatcgcaaca atattctggc gtaccgcttg cgtgacgttc cggaagcggg ttactctgtt | 1260 |
| aacgaccgcc cgtttccgcg tggcgaactg tgtgttaaga cgcgctttgg tattagcggc | 1320 |
| tattttcgca atccggaagc gaccgcggaa ctgttcgacg atgacggttt ctactgcacg | 1380 |
| ggtgacattg ttgaagaacg tgcaccagat cagatcgcga tcattgaccg ccgcaaaaac | 1440 |
| gtcattaaac tggctcaggg cgagtacgtg gctgtgggtc gtctggagca attgtttcaa | 1500 |
| gaaggctgcg gttgcgtgca acagattcat ctgcatggtg acagcacccg tgcatacctg | 1560 |
| ctggcggtcg ttgttccgga ccgcaatacc ttggcgccac tggttcgcg tcaggcgtct | 1620 |
| gaggcagagt tgaaagcgcg cgtccgcgaa gagattctga ccctggcaaa tcagcgcgag | 1680 |
| ctgcgtggct ttgaaatccc gcgtgacctg attctggcgg aagaaccgtt cagccaacag | 1740 |
| aatggcctgc tgagcagctt gggtaaaccg atccgtccgg ctatccgtgc acgctaccgt | 1800 |
| agccgtctgg aaagcctgta tgcgagccat gaagccaccc gtggtaccga gctggaagca | 1860 |
| atccgtgcgt ccgcaggtgc cgttgatgtg gaaaccacgc tgttggccct gctgtctagc | 1920 |
| actctgggcg tggtctgtgg tgccgcggat cgccagacct cttttcgcga gctgggtggc | 1980 |

| | |
|---|---:|
| gacagcctgg ccgcagtgca gctggccatg agatcaaaa agcagttcgg tgtgggcctg | 2040 |
| gaaggtagcc aaatcctggg tccgggtggt acggtcgagg cgtgggcccg tcgcatccac | 2100 |
| accgcgagca ttcagcaggc accgcaccaa cgcgtgggca gcccgctggc tgcaattccg | 2160 |
| gccgaaggct ggctgaaacc ggatcactat cgtctggaga acttgatcgg cattccgatt | 2220 |
| ggtaccccgt ccgcagaggt tgctcgcccg actggcggtc cgccgaccgt gctgctgacg | 2280 |
| ggtgcgactg gtttcttggg tggccgcctg tgcctggaat ggctgcaacg tctggcgggt | 2340 |
| caggggtggtc gcctgatctg tctggtgcgt cctagcaaca gccacagcgc ctgggaacgt | 2400 |
| ctgcgcaacc gcttcagcca cctggagccg agcaggttg cgcgttttcg tgaactggca | 2460 |
| ggccgccatc tggaagttat tccggcagat atcggcgagc cggttgg cctggagcct | 2520 |
| ggttgtcaag agcgtctggc caccgaggtc gacgcgatct gtcattgtgc agccgaggtt | 2580 |
| aaccatcgtc tgccgtaccg tcacctgtat cgtccgaatg tgattggtac cgcagagatc | 2640 |
| attcatctgg ctattactac ccgtctgaag agcgtggact tcatttcgag catcggtgtg | 2700 |
| gcgagcctgc cgcgtcgtcc gggtggctcg attccggtcg agggcggtta cgcacgcggc | 2760 |
| tatttcgctt ccaagtgggc gtgcgaacaa ctgctgcgta gcacccatga ttgcaccggt | 2820 |
| gttccggtgc gtgtcattcg tccgagcctg attctgccag accgtgtcct ggccggtgaa | 2880 |
| atgaatcctg acgacctgct gtctcgcttg ctgtactcga ttctggttac gggtatcgcg | 2940 |
| ccaggctgct tcggtgaaga gagccagaac agcggtcgca gcggtttcag cgttcaaggt | 3000 |
| ctgccggtgg atcagctggc gcagacgatc ctggcactgg gcgaggcacg cacggaaggc | 3060 |
| ttccacgttt tgaatctgaa tgcggactcc ggtagcggtg tcccgttgga tgcgattttg | 3120 |
| caagacatcg cggcgaaagg tattcgtctg cgtcgtgtcg agggttacga tctgtggctg | 3180 |
| gacgcaatta ccacgcgcct gcgtcgtttt ccagcggaac agcgtgcgcg cagcctgttg | 3240 |
| gatgtggcag aggcgtacgc cggcagcgct ggccagacga cgcaatccag cggtgagatg | 3300 |
| caagcgggta gctcgtcctg cccagaagaa atcaccagcc tgcagccgga cttcagccgt | 3360 |
| gcctatcgtc gtaagatcgt tgacgatctg gcgcgctggg gtctgatcga accaccgggt | 3420 |
| ccggttgatc agtaa | 3435 |

<210> SEQ ID NO 9
<211> LENGTH: 3492
<212> TYPE: DNA
<213> ORGANISM: Artificial Sequence
<220> FEATURE:
<223> OTHER INFORMATION: synthetic gene

<400> SEQUENCE: 9

| | |
|---|---:|
| atgacggcag cgcagcagc aagagtggct aaattatttg aatccgaccc tcaatttcgt | 60 |
| gcggcgatgc cggacccggc agtgatggat agcctgctgg caccgggttt cgcctgtcc | 120 |
| caggtgctgc acgccctgct gtcgggttac gcggagcgtc cggtgatggg tttccgtagc | 180 |
| cgtgaaagcg ttgtagatac ggccaccggc cgtactgtcg accgtctgct gccggcattt | 240 |
| gaaacgatta cgtatggcca gttgctggaa gatatcagcg ctatcctggc cgagtggcag | 300 |
| cacggtgata tcccgatggg tgctggtgac ttcatcgcga cgattggctt tagcagcccg | 360 |
| gactatgtca ctctggacct ggcgaccctg atgaacggca gcgtcagcat cccgctgcaa | 420 |
| cataacacca gcgtcgcgca gctgcgtatg atgctggaag agacgagccc gcgtctggtt | 480 |
| gccgcgagcg cggactgttt ggatttggct gttgaagcgg ctgttggctt gacggacctg | 540 |
| cgccgtgtgg ttgtgttcga ctaccgtgcg gagacggacg accatcgtga gaaactggcg | 600 |

```
accgcgcgtg aacgtctgca cgcagcgggt atggacgtgg tcgtagagcc gctggcggaa    660
gtcatcggcc gtggtcgcga tctgccggag ccggttctgt acaccgccgg tgatgaccaa    720
cgcacggcgt tgattatgta cacgagcggt tccacgggtg ccccgaaagg cgcgatgttt    780
acggagtgga ccgttacccg tttttggagc tccggtgcgg caccgaaccg cgatacgccg    840
attatcaatg tcaatttcct gccgctgaac catctggcgg tcgcgtcgg tctgctgacc    900
gcgttcattc cgggtggcac ctgctacttc gtcccggaga gcgatttgtc caccctgttt    960
gaggattggc agctggctcg cccgacgcac atgggcgtcg tgcctcgcgt cgtggacatg    1020
ctgttccagc actatcagac ccgtgtggac gcgctgatgg ccgtggtac cgatgttgac    1080
accgccgacc gtctggctaa gaccgaattg cgcgaggatg ttttgggtgg ccgtgtagtt    1140
gcgggtatgt tggcgaccgc tccgctgagc cctgagatga aagcgttcct ggagtcctcg    1200
ttggactttc acctgctgga cctgtatggt ttgaccgagg ttggcggcgt tttccgtgat    1260
ggcaagatca gccgtccgcc ggtgctggat tacaaactgg tcgacgttcc ggaactgggt    1320
tactatacga cggataaacc gcatccacgt ggcgaactgc tggtgaagtc tgcgaccgcg    1380
accccaggct attacaaacg tccagacgtt acggccgagg tctttgacgc cgatggttac    1440
tatcgtactg gcgacgtgat ggcagaggtc gcgccagacc agctggtgta cgttgatcgt    1500
cgcaataatg tgattaagtt ggctcagggc gagttcgttg cggttgcgaa tctgagact    1560
gtttacgtgg gtgcgccgct ggtgcgtcag attttttgttt acggtaacag cgaacgtgcc    1620
tatctgctgg ccgttgtggt gccgaccgaa gaggcgctgc cgcacaccc ggatccggtt    1680
gagctgaaga acagcattcg tgaatccctg cagcgtaccg cgcgtagcaa ccacctgcac    1740
tcttatgagc tgccggcaga cttcattatt gaaaccaccc cgttcacgat cgaaagcggc    1800
atgctggctg cggtgggcaa accgatccgc ccgaagatga ttgaacatta tggtgatcgc    1860
ctggagcagc tgtacgtgga tctggcagag gcccgtgttc aggagttgcg tcagctgcgt    1920
gacaccgcac aacaacgccc ggttttggat accgttactg aggcagcgca ggcactgctg    1980
ggcatgagcg ccgacgctgt gcgtccggat catcatttca tcgatctggg tggtgacagc    2040
ctgagcgcgc tgaccttcag caatctgctg cgcgacctgt tcgacgtcga ggtgccggtg    2100
ggcgtgatta ccggtccggc agcggatttg cgtaaactgg cggcgtatat tcaacatgaa    2160
cgcgaacact ctaccgctac cgcagcgagc gttcacggtt tggacactac cgttatcagc    2220
gcaaccgagc tgacgttgga taagttcatc gatgctgaaa ccttgcacaa cgcgagccaa    2280
ctggacgtcc ctgccggtgc ggtcgcaacg gtcctgctga ccggtgcgaa tggttatctg    2340
ggtcgctttc tgtgcctgga atggctgcag cgcctgagcc aaactggtgg tcaactgatc    2400
tgtctggttc gtggtgacaa cgcggatcag gccctgcgc gtctggtcgc ggcatatggc    2460
gacaccgacc gtaccctgct ggaagaattt cacaccctgg cacgtcgcca tctgcgtgtt    2520
attgcggcag acattgcgca accgcgtttc ggcgttgacg atgctacgtg ggagcaactg    2580
gcacgcgatg tggataagat cgttcacccg gctgccctgg tgaatcacgt gctgccgtac    2640
aatcaattgt ttggcccaaa cgtatttggt accgccgagg tgatccgtct ggcgttgacc    2700
acgcgcatta agccggttac gtacctgagc accatggccg tggcgatgac cgtcccggac    2760
ttcgatgagg acggtgacat ccgcacggtg tctccgacgc gtcatatcga cccgggctat    2820
gccaatggct acgcaaattc gaaatgggca ggtgaagtcc tgctgcgtga ggcacatgac    2880
atttgcggcc tgccggttag cgttttttcgt agcgatatga ttctgaccca ccgtcgttat    2940
```

| | |
|---|---|
| agcggtcagc tgaacgtcac cgatgcgttt acgcgtatgc tgctgtctct ggttctgacc | 3000 |
| ggtatcgccc ctcgcagctt ttatcaaggt gatggttccg gtgcgcgtcc acgcgcccac | 3060 |
| tacgaaggtc tgccggtgga ctttgtcacc gaggccatta ccagcctggg tctgagcagc | 3120 |
| tccgagggct tccgtagcta cgatgtcatg aatccgcacg atgatggtat tagcgtcgat | 3180 |
| accttcgtcg attggctgat ggaagatggt cacagcattg acatcattga caactacgac | 3240 |
| gagtggctgt ctcgcttcga aactgcactg cgcggcttgc cggatgagca acgtcgcgcg | 3300 |
| agcgtcctgc cgttgctgga cgcgtaccgc attccgggca cccctcgccg tgctgcagcg | 3360 |
| accccgaacc acgtgttccg caaggcagtg caggagaaca atatcggcgg tgacggtgca | 3420 |
| gacatcccgc aaattgatcg cgcgctgatc gcaaaataca tcgcggatct gcgtgcgcat | 3480 |
| cgtctgctgt aa | 3492 |

<210> SEQ ID NO 10
<211> LENGTH: 3453
<212> TYPE: DNA
<213> ORGANISM: Artificial Sequence
<220> FEATURE:
<223> OTHER INFORMATION: synthetic gene

<400> SEQUENCE: 10

| | |
|---|---|
| atgtttgcag aggatgaaca agtgaaggcg gcggtaccag atcaggaagt tgtggaagcg | 60 |
| atccgcgcac cgggtctgcg cctggctcaa atcatggcga cggtgatgga gcgctacgcc | 120 |
| gaccgtccgg ccgttggtca acgtgcttct gagccggtta ccgagagcgg ccgtacgacg | 180 |
| tttcgtctgc tgccggagtt tgagacgttg acctaccgtg aactgtgggc gcgtgtccgt | 240 |
| gcagtcgccg cagcttggca cggtgacgct gagcgtccac tgcgcgcagg tgacttcgtc | 300 |
| gcgctgctgg gctttgccgg tatcgactac ggcaccctgg acttggcgaa catccacctg | 360 |
| ggcttggtta ccgtcccgct gcagtctggc gcgaccgctc cgcaactggc ggcgatcctg | 420 |
| gccgaaacga ccccgcgtgt cttggcgcg acgccggatc atctggatat tgcggttgag | 480 |
| ttgctgactg gtggcgcgag cccggaacgc ttggttgtgt tcgactaccg tccggcagat | 540 |
| gatgaccacc gtgcagcatt ggagagcgca cgtcgccgtt tgagcgatgc aggcagcgcg | 600 |
| gtcgttgttg aaaccttgga cgcggtgcgt gctcgtggtt ccgaactgcc ggcagcaccg | 660 |
| ctgttcgtcc cggctgcgga tgaagatccg ttggcgctgc tgatttacac gagcggtagc | 720 |
| accggcaccc cgaaaggcgc aatgtatacc gagcgcctga tcgtacgac ctggctgagc | 780 |
| ggtgcgaagg cgtgggcct gacgttgggt tatatgccga tgagccatat cgcgggtcgt | 840 |
| gcgagcttcg cgggtgtgct ggcgcgtggt ggtaccgtct actttaccgc ccgtagcgat | 900 |
| atgagcactc tgtttgagga tttggcgctg gtccgtccga cggagatgtt cttcgttccg | 960 |
| cgcgtgtgcg acatgatctt tcagcgttat caagcggagt tgtcgcgtcg tgcgccagcc | 1020 |
| gcagcggcaa gccctgaact ggaacaggaa ctgaaaaccg agctgcgtct gtccgcggtt | 1080 |
| ggcgaccgcc tgctgggtgc gattgcgggt tctgcaccgc tgagcgcgga gatgcgtgag | 1140 |
| tttatggagt ccttgctgga tctggagttg catgacggct acggttccac cgaggccggc | 1200 |
| atcggtgtcc tgcaagacaa tatcgttcaa cgtccgccgg ttattgatta caagctggtg | 1260 |
| gacgttccgg agttgggcta tttccgtacc gaccagccgc accctcgcgg tgaactgctg | 1320 |
| ctgaaaacgg aagtatgat tccgggttat ttccgtcgcc cggaagttac cgcggagatt | 1380 |
| ttcgatgagg acggcttcta tcgtacgggt gatatcgttg cggaactgga ccagaccgc | 1440 |
| ctgatctatc tggaccgtcg caataacgta ctgaagctgg cgcaaggcga gtttgtcacg | 1500 |

```
gtggcccatc tggaagcagt gttcgcgacg tctccgctga tccgtcagat ctacatctat    1560
ggtaacagcg agcgtagctt tttgctggca gtcattgtgc cgaccgcgga cgcgctggcg    1620
gacggtgtga ccgatgccct gaacaccgct ctgactgagt cgctgcgcca gttggcgaaa    1680
gaagccggtc tgcagagcta tgaactgccg cgtgagttcc tggtcgagac ggagccgttc    1740
accgttgaga atggtctgct gagcggtatt gcgaaactgc tgcgtccgaa gctgaaagaa    1800
cactacggtg aacgcctgga gcagttgtat cgcgacattg aagccaatcg caacgatgaa    1860
ctgatcgagc tgcgccgtac cgcagcggag ttgccggttc tggaaactgt gacgcgtgcg    1920
gcacgcagca tgctgggtct ggccgcgagc gaactgcgtc cagacgcgca ttttaccgac    1980
ctgggtggtg actctctgtc ggcgctgtcc tttagcaccc tgctgcaaga tatgttggaa    2040
gttgaggtgc cggtgggcgt tattgtgtct ccggcaaaca gcctggctga cctgccaag     2100 tatattgagg cggaacgtca ctccggtgtc cgccgtccga gcctgatcag cgtgcacggc    2160
ccaggtaccg agattcgcgc tgcagatctg acgctggaca aattcattga cgagcgcacc    2220
ctggcagcgg cgaaggcagt tccggctgca cctgcccaag cacagaccgt gctgctgacc    2280
ggtgcaaatg gttacctggg tcgtttcttg tgcctggaat ggctgcagcg tctggatcaa    2340
accggcggta cgctggtctg tattgtgcgc ggcaccgatg cggcagcagc gcgtaagcgc    2400
ctggatgcgg ttttcgacag cggtgatcct gagctgctgg atcactaccg taagctggca    2460
gccgagcacc tggaagttct ggcgggtgac atcggtgacc cgaacctggg tctggatgag    2520
gccacgtggc agcgcctggc cgcgaccgtg atctgattg gcatccggc tgctttggtt     2580 aatcacgtgc tgccgtacag ccagctgttc ggtccgaacg tcgtcggcac cgcagagatt    2640
attcgcctgg cgattaccga gcgtcgtaaa ccggtgacct acctgagcac tgtcgcggtt    2700
gccgcccaag tggaccctgc gggcttcgat gaagaacgtg acatccgcga gatgagcgcg    2760
gtccgtagca ttgacgcggg ctacgcgaac ggctatggta atagcaaatg ggctggtgag    2820
gttctgctgc gcgaggcaca cgatctgtgt ggtctgccgg tggccgtatt ccgcagcgat    2880
atgattctgg cacactccaa atacgttggc cagctgaacg tgccggacgt ttttacgcgt    2940
ctgattctga gcctggccct gacgggcatc gctccgtata gcttttacgg tactgacagc    3000
gccggtcaac gtcgtcgtgc acactatgac ggcctgccgg cagatttcgt cgccgaagct    3060
attaccacgc tgggcgctcg cgcagaaagc ggctttcaca cctacgacgt ttggaacccg    3120
tacgacgacg gtatttccct ggacgaattt gtggactggc tgggcgattt tggcgttccg    3180
attcaacgta tcgatgatta tgacgagtgg ttccgccgtt cgaaaccgc gatccgtgcg     3240 ctgccggaga aacagcgcga cgcgagcctg ctgccgctgc tggatgccca tcgtcgtcca    3300
ttgcgtgcag tgcgtggtag cctgttgccg gcgaagaatt ttcaggctgc ggtccagtcg    3360
gcacgcatcg gtccggacca ggatatcccg catctgagcc cgcaactgat cgataagtac    3420
gtcaccgatt tgcgtcattt gggcctgctg taa                                 3453

<210> SEQ ID NO 11
<211> LENGTH: 3567
<212> TYPE: DNA
<213> ORGANISM: Artificial Sequence
<220> FEATURE:
<223> OTHER INFORMATION: synthetic gene

<400> SEQUENCE: 11
atgacggata cggttacgga cagcggtcgc gagcagagac tgacggaaag agttgaacag      60
```

```
ctgtatgcga atgacccgca gtttcgtgca gccgctccga gccctgaggt taccgaggca    120
gcgcaccgtg ccggtctgcg tctggcagag gttgtggaca tttacctgtc cggttatgcg    180
gaccgtccgg cgctgggcca acgtgcgtgc gaagtggcac gcgatccggc gacgggtcgt    240
gctgccacca gcctgttgag cggttttgag actatcacct accgcgaact gggtgatcgt    300
gtcgccgcct tggcggctgc gtggcgttcc ggcctgccgg gtggtttgcg tccgggtgat    360
ttcgtcggtg ttctgggctt tacgtccatc gattatgtcg tgcactacct ggcttgcatc    420
cgtctgggtg cggtgtttgt gccgctgcaa acgagcagca ccgccgcaca actggcgccg    480
attgtggcgg agacggcgcc tcgcatcctg gcggtatctg tggagtccct ggcgaccgca    540
gttgacgtcg ttctggaagc gccgagcgtt cagcgtctgg tggtctttga ttacacctct    600
gatgacgatg agcagcgcgg tcgttacgat gatgcacgcg ctcgtctgcg cgacgcaggt    660
cacggtgcgg agatggtggc gttggctgct gagttggcaa gcggccgtga acgtcctgcg    720
ccggaagcgc acgtcccagg tcagggtgaa aacccgctgg caactctgat ctataccagc    780
ggtagcaccg gcacccccaaa gggtgcaatg tacaccgcgg acatgatgac gcgtatctgg    840
caacgtcctc actccccgag cgtcgacatc ggtcgtgtca ttccggcgat ccacctgcag    900
tatatgccgc tgtcccacgt ctacggtctg gagtggctga tcgcgaccct gagctccggt    960
ggcattggtt atttcgcagc caaaagcgac atgagcaccc tgttcgacga cattggtctg   1020
gtccgtccga cggcgctgaa cctggttccg cgcgtgtgtg atatgttttt ccgtcgctac   1080
cgtaaagagc tggaccaacg tgcaggtgac ggtctgaccg cagagcagcg cgatgaagcc   1140
gttaaagccg aactgcgcca ggatttcatt ggtggccgtg tcattagcgc gatgtgcggt   1200
agcgcaccgt tgagcaagca gatgcatgcg ttcatggaga gcctgctgga tgtgaccgtt   1260
gcggatggct atggcgccac cgaaacgggt ggcggcatta tgcgttcggg tcgcatccgt   1320
cgtccgccgg tcactgatta caagctggtg acgtgccgg aactgggtta cctgacgacc   1380
gacaagccgt accccgcgtgg cgagttcac ctgaaggcga gcaacgttat cccgggttac   1440
tttaagcatc cggaactgag cgcgcagatt tttgatgatg aaggtttcta caaaacgggt   1500
gacattatgg cggaactggg ccctgaccat ctgatgtacc tggaccgtag caacaacgtg   1560
atcaagctga ccagggcga gtttgtggcg gtgagccagc tggaagccac gttttcgacc   1620
agcccgtaca ttcgtcagat tttcctgtat ggcagctctg aacaaccgtt tctgctggcg   1680
gttatcgtcc gaatgttga tgcagtcggt ggtggcgatg cgcgtgcgtt gatcgccgag   1740
agcctgcagc agattgcggc ggacagctac ctgcacccgt atgaggtgcc acgcgacttc   1800
ctgctggagc cgcaacgttt taccccgcgat aacggcttgc tgtctggtgt tggtaaactg   1860
ctgcgtccgg cactgaaagc gcgttacggc gaacgtttgg acgcaatgta tgatgagatt   1920
gaggcatctc acggtaatca actggacgaa ttgcgtagcg cgagccgcga gttgccgacg   1980
attgacaccg ttcgccgtgc cgctgccgcg accttgggcc tgccggctga tgccgccctg   2040
cgtggcgacg cgaagtttat tgagctgggt ggcgattccc tgagcgcatt cagctttgcg   2100
accctgctgt cggaaatctt tcacatcgac gtgccggtgc aaactatcgt tagcccgacc   2160
gccaccttgg cgaccatcgc gaattatgtt gacggtgaac gcactagcga atcgacgcgt   2220
ccgaccttcg ctagcgtgca tggtcgtggt gcaaccgtgg cacgtgccgc tgacttgacg   2280
ctggcgaagt tcatcgatga cgatacgctg gcagcagcgc cgcacctgcc ggctccaacg   2340
ggtgcggtca acactgtgct gctgaccggc gcaaatggct acctgggccg cttcctgtgc   2400
ttggactggc tggaacgcct ggccccgacc ggtggcaccg taatttgtct ggcgcgtggc   2460
```

-continued

```
gccgatccga cggcaggtcg ccaacgtatt gaggccgcta tcgacagcgg cgatgcggaa    2520
ttgagccgtc gtttctgtca gctggcggac aaacacctgc aagttctggt gggtgatgtg    2580
ggtgctgcga acctgggcct ggacaccccg acgtatcaac gcctggcgcg cagcgttgat    2640
ttggtcgtcc acagcgcagc cctggttaat catgtgctgc cgtatagcca attgttcggt    2700
ccgaacgtgg ttggtaccgc agagatcgtc aagctggcga tttccgaacg cctgaaaccg    2760
attaactaca tttccacggt tgcggtcacc accctgccgg acggcagctt catcggcgag    2820
gacgcggacg tccgttctgc atctccgagc cgtagcctgg acgagagcta cgctagcggt    2880
tatgcgacca gcaaatgggc aggcgaggtt ctgctgcgcg aggcgcacga cctgtgcggt    2940
gtgccggttg cagttttcg tagcgacatg attctggccc atagcgactt cgcgggtcag    3000
ttgaacgtgc cggatatgtt cacccgcctg atcttgagcc tggttgcgac gggtatcgca    3060
ccacgtagct tctatcagct ggacgcgagc ggtaatcgtc agcgtgcgca ttacgacggc    3120
ctgccagcgg atttcactgc tgaggcaatc acgacgctgg gtgcacgtac ccgccaaggc    3180
taccatacct ataatgtgct gaatacccac gatgatggcg tctccctgga cacctttgtt    3240
gattggctga ttgccgatgg ccacaaaatc gagcgcgtgg acgactacga cgagtggctg    3300 gcgcgttta ccgctgcgat gaaatctctg ccggataatc agcgcaaaag cagcctgctg    3360
ccactgatga gcgcgtacgc gaaaccgggc caacctaccc atggcaccgg tatgccggct    3420
gagaagttcc gcgcagcggt ccaaagcgct ggtattggtg ccactcgtga tgtcccgcat    3480
gttacccagg ccctgattga caagtatgtt gcggatctgc aacgtttggg cctgctgcgt    3540
acccgcgctg gtgcccatgc aggctaa                                       3567
```

<210> SEQ ID NO 12
<211> LENGTH: 3468
<212> TYPE: DNA
<213> ORGANISM: Artificial Sequence
<220> FEATURE:
<223> OTHER INFORMATION: synthetic gene

<400> SEQUENCE: 12

```
atggagagca ctagagcaac ccgcctgaga cagagaatcg cagccctgta cgcagatgac     60
gcgcaggtcc gtgacgcacg tccagacgaa gctatctcta ccgcgctgcg cgaaccgggc    120
ttgcgtttgc gcgagctggt cgcgaccgtc gttgatggtt atcgtgaccg tccggctttg    180
gcggcacgta gcgtccaacc ggctgtcgac gcggcgaccg tgcgtgcgt ggcgcgtctg    240 ttgccggagt acaccacgat gagctacggt gagctgggcc tgcgcctgcg tgccgttgcg    300
gcagcgtggc agcacgacga tgagacgcgc ttgcgtccag gcgaatttgt tgcgacgttg    360
ggttttacgt cccggatta cgcagtggtg gacctggcgt gcgtgtgggc gggtgcggtt    420
gcagtaccgt tgcaagcgag cgccagcgtg acccagctga cggcaattct ggcagaaacc    480
gcaccagcga tcctggccac cggtctggat accctgccgc atgccgtgga ttgtgtcctg    540
gcgggtgcaa cgccgcgtgc gctgcacgtg ttcgacttcg atccggcaat tgatgcgcag    600
cgcaccgttt acgaagcagc atgcgcacg ttggcgggca ccggcgtccg cgttcgcacg    660
ttggcggaag ttgaggaccg tggtcgtgcc ctgccaccgg cggttattga tgatggtccg    720
ggtgacgacc gcctggcgtt gctgatctat acgagcggta gcaccggtac gccgaagggc    780
gcaatgtata ctgagcgctt ggttgctctg atgtggctgg ccagccgca agttgcagcg    840 ctgacggtca attatctgcc gctgagccac gtcgcaggcc gtctggcgct gttcggcctg    900
```

```
ctggcgcgtg gcggcaccgc gtatttcacc gcccgtgcag acatgtccac cctgtttgag     960
gatctggctc tggcgcgtcc gaccgagctg tttgtcgtac cgcgtgtgtg cgaaatggtt    1020
ctgcaacgtt tccaaactga gcgtctgcgt cgccaagcgg acgatgatcg cgtgaaggca    1080
gatctgcgcc tggagctgtt cggtgaccgc ctgttgagcg ttgtttgtgg tagcgcacca    1140
ctggctcctg aactgaaagc gttcatggag agcgtgctgg acctgacctt gcacgacggt    1200
tatggctcca ccgaagcagg tggtagcgtc gtcatcgaca ccaccgtgcg tcgtccgccg    1260
gttctggact atcgtctggc ggacgtgccg gagctgggtt actttcgtac ggataaaccg    1320
catccgcgtg gcgagctgct gctgaaaacg accaccatga tcccgggcta ctaccgtcgc    1380
ccggagctga atgctcaaat cttttgatgag gacggttttt accgcaccgg cgacgtggtt    1440
gcggagctgg caccggatcg cctggtgtac gttgaccgtc gcaataacgt tctgaagctg    1500
gcgcagggtg aattcgtgac gattgcacgt ttggaagcga ttttcgcgaa cagcccgttg    1560
gtccgccaaa tctttgttta cggtaacagc gaacgtgcct atctgctggc cgtgattgtt    1620
ccgtctcgtc aagcaatggc tggcgacccg gcgaccctga aaacccgtat cgcggagagc    1680
ctgcagctga ttggtcgcga gcggagctg gaagcgtacg agatccctcg cgatttcctg    1740
atcgagacgg agccgttcac cacgaatcc ggcctgctgt ccggtattgg taaaatcctg    1800
cgtccggcgg tcgaagcacg ctatcgcgat cgtctggagc agctgtacgc ggacctggca    1860
gcagcgcagc aagacgagtt ggcagccctg cgtcgcgagg caggtcagcg tccggtcctg    1920
gagactgtga cccgtgccgc agcggcgatt ctgggcggta ccgctagcga cctgtcccct    1980
gcggcccact ttaccgattt gggtggtgat agcctggcgg cgttggcgct gtcgaatctg    2040
ctgcgcgaga ttttcgccgt agaggttccg gtcggtgtga ttaccggtcc ggcgaccgat    2100
ctgcgtggcc tggccgcaca tatcgcggca gaacgtgaaa accgtacgga aacgccgctg    2160
ttcgatcgtg tccatccgga tcagattttg atccgtgcga ccgacctggc gctggaaaag    2220
tttttcgatg cggaagagct ggcggcagcc gcgaccgcag caccgccggt agccgagccg    2280
cgtgtggttt tgctgacggg tgcgaacggt tacctgggtc gcttcctgtg cctggagtgg    2340
ctggagcgtc tggaccgtgt cgacggccgt ctgatttgtc tggttcgtgg cgcggacgaa    2400
gcagcggcac tggctcgtct ggaagcggcg ttcgacagcg gcgatcctga gttggtgcgt    2460
cgctttaaag aactggccca acgtcgtctg accgtggtgg cgggtgatat cggcgagcct    2520
ggcctgggtc tggcaaccgc cacctggcgc cgtctggccg ctgaggttga acatatcgtt    2580
cacccttgctg ccctggtgaa ccatgtcctg ccgtatcgcc agctgtttgg cccgaacgtt    2640
gcgggcacgg cggagatcct gcgtctggcc ctgacggagc gccgcaaacc gatcgatttc    2700
ttgagcacgg ttgccgtcgc tgcgcagatc cggcagacc gcttcgccga agatggtgac    2760
attcgtgtga tcagccctac tcgcactgtc gatcgtggct atgcaaatgg ttacggcaat    2820
agcaagtggg cggcagaagt tctgctgcgt gcggcgcatg accgcttcga tctgccggtg    2880
gcggtgttcc gtagcgatat gattctggcc catggcagct tgccggtca attgaatatt    2940
ccggatgtct ttaccgtctc gttgctgtct ctgttggtga ccggcattgc cccagcatct    3000
tttcacgccg ctacggtcac tggtgaacgt ccgcgtgctc actatgatgg tctgccggct    3060
gatttcacgg ctgccgcgat caccgccctg ggtgcccgta cggctggctt tcacacgtac    3120
gacgttctga accgcacga tgacggtatc agcctggaca ccttcgtgga ctggctgatt    3180
gaagcgggtc acccgatcga acgtattccg gagcacagcg aatgggtcac ccgctttgag    3240
acggccctgc acgcgctgcc ggagcgtcag cgtaagcatt cgctgctgcc gctgctgcac    3300
```

-continued

| | |
|---|---|
| gcgtatcgtc gtccggttcc ggccctgcgt ggtagcgcgt tgccagctgc agagtttcgt | 3360 |
| gcagcggtgc gtgctgctgg tattaccgcg gacggtgaca ttccgcacct gacccgcgct | 3420 |
| ctgattgaaa agtacgtcgc cgacctgcgc ttgcatggtc tgctgtaa | 3468 |

<210> SEQ ID NO 13
<211> LENGTH: 3525
<212> TYPE: DNA
<213> ORGANISM: Artificial Sequence
<220> FEATURE:
<223> OTHER INFORMATION: synthetic gene

<400> SEQUENCE: 13

| | |
|---|---|
| atgtccccaa ttacccgtga agaacgcctg gagcgccgta ttcaagacct gtacgcgaat | 60 |
| gacccgcagt tcgctgcggc gaagccggtg actgcgatta cggcagcaat tgagcgccca | 120 |
| ggtctgccgc tgccgcagat tatcgaaacc gtgatgaccg gctacgcaga tcgcccagcg | 180 |
| ttggcgcagc gctccgtcga gttcgttacc gacgcgggta ccggtcacac gactctgcgt | 240 |
| ctgctgccgc actttgagac gattagctat ggcgagctgt gggatcgtat tagcgctttg | 300 |
| gcagacgtgc tgagcacgga gcaaaccgtt aaaccgtcgg atcgtgtctg cctgctgggt | 360 |
| tcaacagcg tcgattacgc cacgatcgac atgaccttgg cgcgcttggg tgcggtcgcc | 420 |
| gtgccgctgc aaacgtccgc agcgatcacg caactgcagc cgatcgtggc tgagacgcag | 480 |
| cctaccatga ttgccgcgag cgtggacgca ttggcagatg caaccgagct ggcactgagc | 540 |
| ggtcaaaccg cgacgcgtgt cctggttttt gaccaccacc gtcaggtgga cgcgcatcgt | 600 |
| gccgcggtcg agtcggcccg tgaacgcctg gcgggcagcg cagtggttga gactctggcg | 660 |
| gaagcaattg cacgtggcga cgttccgcgt ggcgcgagcg cgggttctgc acctggcacg | 720 |
| gatgttagcg atgacagcct ggcactgctg atctacacga gcggttctac cggtgctccg | 780 |
| aaaggtgcga tgtatccgcg tcgcaacgtt gccactttct ggcgtaaacg tacgtggttt | 840 |
| gaaggcggtt atgagccgag cattaccctg aatttcatgc cgatgagcca cgttatgggc | 900 |
| cgtcagatcc tgtatggtac cctgtgtaat ggcggtacgg cgtatttcgt tgttaagagc | 960 |
| gacctgagca cgctgtttga agatctggcc ctggttcgcc cgaccgagct gaccttttgtt | 1020 |
| ccgcgcgtct gggatatggt gttcgacgag tttcagagcg aggtggatcg tcgtttggtg | 1080 |
| gatggtgctg accgtgtggc actggaagcg caggttaagg cagagatccg caatgatgtc | 1140 |
| ctgggtggcc gttacaccag cgcgctgacc ggtagcgcgc ctatttccga cgagatgaaa | 1200 |
| gcgtggggttg aagaactgct ggatatgcac ctggtggaag gctacggtag caccgaagcg | 1260 |
| ggcatgattt tgatcgatgg tgcgattcgt cgcccagccg ttctggacta caaactggtt | 1320 |
| gacgtcccag acttgggtta cttcctgacg gatcgtccgc accgcgtgg tgagctgctg | 1380 |
| gttaagacgg acagcctgtt cccgggctac taccaacgcg ctgaagtcac cgcagacgtc | 1440 |
| tttgacgcgg atggtttcta ccgcaccggt gacatcatgg ccgaggttgg cccggagcaa | 1500 |
| ttcgtgtatt tggaccgccg taataacgtc ctgaaactga gccagggcga attcgtgacc | 1560 |
| gtttccaagc tggaagcggt cttttggcgac agcccgctgg ttcgccaaat ctatatctac | 1620 |
| ggtaactccg cgcgtgcgta tctgctggcg gtgattgtgc cgacccaaga ggccctggac | 1680 |
| gccgtcccgg tggaagagct gaaagcacgt ctgggcgaca gcttgcagga agtggccaag | 1740 |
| gctgcgggcc tgcaatccta cgagatcccg cgtgacttca tcattgagac gacccgtggg | 1800 |
| actctgcaga atggtctgct gacgggtatt cgcaagctgg cgcgtccgca gctgaagaag | 1860 |

```
cactatggtg aattgctgga gcagatctac acggacctgg cgcacggcca agcggacgag    1920
ctgcgtagcc tgcgtcagag cggtgcagac gcgcctgttc tggtcaccgt ctgccgcgct    1980
gctgcagcgt tgctgggtgg cagcgcaagc gacgtgcagc cggatgcgca ttttaccgac    2040
ctgggcggtg atagcctgtc tgcgctgagc tttaccaatt tgttgcacga gattttgat    2100 atcgatgttc cggtgggcgt catcgtgtcc ccggcaaacg acttgcaggc gctggcagac    2160
tacgtagagg ccgcacgcaa accgggtagc agcgtccga ccttcgcttc tgtgcatggt    2220
gccagcaatg agcaggtcac cgaagtccat gcgggtgatc tgagcctgga caaattcatc    2280
gatgccgcta ccctgcaga agctccgcgt ttgccggcag caaacaccca agtgcgcacg    2340
gtgctgttga ccggtgcaac cggttttctg ggtcgttatt tggcgctgga gtggctggag    2400
cgtatggacc tggtggatgg caaattgatc tgcctggtgc gcgccaagtc cgacactgaa    2460
gcgcgtgcgc gtctggagaa aaccttcgac agcggtgcgc cggaactgtt ggcgcattat    2520
cgcgccctgg ctggcgatca cctggaagtt ctggcgggtg acaagggcga ggcggacctg    2580
ggcctggatc gtcaaacgtg gcagcgtctg ccgacaccg ttgatctgat tgttgatccg    2640
gcagcgctgg tcaaccatgt cctgccgtac agccagctgt ttggtccgaa tgcgctgggc    2700
accgcggagc tgttgcgtct ggccctgacc agcaagatca aaccgtacag ctatacgagc    2760
accattggtg ttgctgacca gatcccgcct agcgcgttca ccgaagatgc agacatccgt    2820
gttatcagcg ccacccgtgc cgtcgacgat agctatgcca acggctacag caactctaag    2880
tgggcaggtg aagtactgct gcgtgaagct catgtgctgt gtggtctgcc ggttgccgtt    2940
tttcgctgtg acatgatctt ggctgatacc acctgggcgg gtcaactgaa cgtgccggat    3000
atgttcacgc gcatgattct gagcttggcg gcgacgggca ttgcaccggg ttcgttctat    3060
gagctggctc ggacggtgc ccgtcaacgt gcgcattacg atggcctgcc ggtcgagttt    3120
attgcagaag ccatctctac cctgggtgcg cagagccagg atggtttcca cacgtatcac    3180
gtgatgaacc cgtacgatga tggtatcggt ctggatgagt cgtggattg gctgaacgag    3240 tctggctgcc ctattcaacg cattgcggat tatggtgatt ggttgcagcg cttttgagact   3300 gcgctgcgtg ccctgccgga tcgtcaacgt catagctcgc tgctgccgct gctgcacaat    3360
taccgccaac cggaacgtcc ggtgcgtggt tccattgctc cgaccgaccg ttttcgtgcg    3420
gcggttcaag aagccaagat cggcccagac aaagatatcc cgcacgttgg tgcgccgatt    3480
atcgtcaaat acgtcagcga cctgcgcctg ctgggcttgc tgtaa                    3525
```

<210> SEQ ID NO 14
<211> LENGTH: 3483
<212> TYPE: DNA
<213> ORGANISM: Artificial Sequence
<220> FEATURE:
<223> OTHER INFORMATION: synthetic gene

<400> SEQUENCE: 14

```
atgactgtaa tgcctgcaaa accaccagcc gatgtatccc cacttagccg cgcagcacgt      60
ctggtcgccg agttgagcgc gcacgatccg cagtatcgtg ccgcaatgcc gctgccggca    120
gttcgtgaag cggttcgcga ggccgcacgc gaccaagttc tgagccgcac cgttgcaacc    180
gtcatggcag gttatgcgga ccgtccggcg ctggcacgcc gtgccaccga gccggtgacc    240
gatccggtta cggccgtac tagcttgcgt cgtctgccgg agtttacgac ggtcacgtac    300
ggtgaactgt gggcgcgtgc aggtgcggtg agcgcggagt gggcagccga cacccgcctg    360
ccgctgagcc caggcgactt tgttgccatc tacggttca cgagcggcga ctatgttact    420
```

```
gtcgatttgg cctgtctgcg ccatggtgcg gttagcgtcc cgctgcagtc gggtgcgccg      480
gttgccggcc tggccccgat tctggcgaaa acgggtccga aagtcctggc ggtgtccttg      540
gaattgctgg accgtggtgt tgaactggcg ttgagcgccg aggttgctcc gcgtctggtg      600
gtctttgact ccacgccggt gacgacgct cagcgcgagg cctttgaagc ggcaagcgca       660
cgcctgaccg cggcaggcca tgcggctccg ctgccgctgg aagcggtgat tgaacgcggt      720
cgtgcactgc cgccagcgcc actgttcgtt ccgggtccgg acgaagatcc ggttcgtctg      780
ctgatttaca ccagcggtag caccggtacc ccgaaaggcg ccattcaaac ggagcgcatg      840
ctgcatcgcg catgggcagg cgcggtgccg attccggacg acgtcgcgtc catcgtcgtg      900
aattacctgc cgctgtccca cgtcgctggt cgtagctctc tggttgagac gctgcgtcgt      960
ggcggcatta gctatttcac ggcacatagc gacctgtctg atctgttcga ggacatcgcc     1020
ctggcgcgtc ctaccgcgct gttgtttgtt ccgcgtgtgt gcgatttgct gttccaagaa     1080
tatcaggctg aattggcacg tcgcgcaggt gagtttgcgg acgcgggtgc gctggacgcg     1140
gctgttaagg cagatctgcg tgaacgtttc gttggtggcc gcctgattca agcgctgtac     1200
ggcagcgcac cgctgtccgc cgaactgcgt gagtttatgc acacctgtct ggacctgcct     1260
gtgctggacg gttatggtag caccgaaacg ggttccgtgt tgttgaacac ccgcgtgcaa     1320
cgtccgccgt tcaccgatat caagctggtg gatgtcccgg aactgggtta cttcgccacc     1380
gattccccgt acccacgcgg cgaattggtg ctgaaaagcg cgaccctgac gcctggctat     1440
taccgtcgcc cagaggtcac cgcagctgct ttcgacgcgg atggctttta ccgtacgggc     1500
gacattatgg cggaagttgg cccggaccag tacgtgtacg ttgatcgtcg taataacgtt     1560
gtgaagctgg cccagggtga gttcgttgcg ctgtctcgtc tggaaggtgt gtatgtgact     1620
cacccgctga ttcgccagat ttacgtgtac ggcaatagcg agcgtgcaca cttgctggct     1680
gtgatcgtgc cgacgcgcga gaattgtacg cacgaggatc tggcagccgc gctgcagcag     1740
gcagcccgtg agagcgagtt gaactcttac gagatcccgc gtgcgttcct ggttgaaacc     1800
gagccgttct ccctggccaa cggttttgctg agcgacaccc gtaagaatct gccgccacgt     1860
ctgaaggcgc gctatggcga gcgtctggaa gcgctgtatg aagagctggc acgtgaacaa     1920
gaggatgcgg ttcgtgtgct gcgcgatgaa ggtacgggtc gccctgtttc ggaaacggtc     1980
gagcgtgcag cgcgtgcgct gctgggtagc agcgcagcgg acgcgcgttt taccgacttg     2040
ggcggtgatt ctctgtcggc gttgtccttc agcaccctgc tggcagagat cttcggtgtc     2100
gaggtgccgg tgggtactgt cctgagcccg gcaaacgacc tgcgtgcatt ggcagcgcac     2160
atcgaagctc gtcgtgcgtc tggtgcgagc cgtccgacct cgctagcgt tcatggcgtg      2220 ggccgtacgg tcgtgcgtgc gggcgacctg gcactggaga gtttctgga tgccggtgcg      2280 ctggcggaag cggcgcagct gccggcaccg ggtcgtgaaa cgccgcgtac ggtcctgctg     2340
accggtgcga acggttatct gggtcgtttc atgtgcctgg actggctgga acgtctggct     2400
tcgggcggtg gccgtctggt gtgcgtggtt cgcggtaaag acgacgccga tgcccgtgca     2460
cgtctggatg cggcgttcga cagcggtgat ccggagctgc tgcgtcgcta ccgcgaactg     2520
gcagcgggtc gcctggatgt cttggctggc gatatcggtg cggagcgtct gggtctggcg     2580
ggtgagacgt ggcgtcgcct ggccgaggat gtggatctga tcgcccaccc ggctgccctg     2640
gtcaaccacg tcttgccgta cgagcaactg tttggtccga acgttgtagg caccgctgaa     2700
ctgattcgcc tggcactgac cgcgcgtgtt aaaccgttcg tgtatgttag caccaccgcg     2760
```

| attagcacca cgctggacga gacgagcgat attcgtgaga gcatcccgga acgcgccctg | 2820 |
| accgatgcat atgcagcggg ctacggtacc agcaaatggg cgggtgaggt gctgctgcgc | 2880 |
| gaggcgcacg ctcgcctggc gctgccggtt gcggtctttc gcagcgactt gattctggcg | 2940 |
| cacccgcatc acaccggcca actgaatccg gccgacgtac tgacccgtct gctgtttagc | 3000 |
| atcctgagca ctggcttggc gccgactagc ttttactctg aagagggtcg cgcgcacttc | 3060 |
| gacggtctgc cggtggattt taccgctgag gctatcaaca ccctgggcgc acagccgatt | 3120 |
| agcgcgcacc gtacctataa tgcggtaaat ccgcatgacg acggcgtgag cctggatacc | 3180 |
| ttcatcactt ggctggaaga ggctggtcac ccgctgcgcc gtttgccgca tacgacctgg | 3240 |
| agcccgcgtc tggaaaccgc cttgcgcagc ctgccggaac atcaccgtcc gcacacgttg | 3300 |
| ctgcctctgc tgcatgcgtt tgcaaccccct cagccgccga ccccgaccag cccggttccg | 3360 |
| gccacccatt ttcatgaggc agtgcgtgag gctggcatcg gcccagataa tgatatcccg | 3420 |
| cacatcacgc aaaacttgat taccaagtac gcgacggatc tgcgccaact gggtctgcgc | 3480 |
| taa | 3483 |

<210> SEQ ID NO 15
<211> LENGTH: 3582
<212> TYPE: DNA
<213> ORGANISM: Artificial Sequence
<220> FEATURE:
<223> OTHER INFORMATION: synthetic gene

<400> SEQUENCE: 15

| atgactgacg acgcaaagag agcaaaagta tccagcaccg gtccgatttc tgcagcacgt | 60 |
| cagcaagttg cggaccgcat tcgcgatctg gacgcgcgtg acgaagaatt cgcacgacc | 120 |
| aaaccggact ctgcgctgca gctggcggca cgtgaaccgg tctgcgtct gccgcaaatc | 180 |
| ctggaaatct ttgccgaagg ttacgcggat cgtccggcgc tgggctggcg tgcgcgcagc | 240 |
| ctgaccaccg atgcggcgac tggccgtacc agcgctcagt tgctgccgcg cttcgacacg | 300 |
| atgacgtacc gtgaactgtg ggcgaatgtc cgcgcaatcg ccggtgcttg gcgccacgat | 360 |
| gctaccaacc cggtggcacc gggtgatgtt gtggcaactg ttggtttcgc gagcgcagaa | 420 |
| tacctgacca tcgatctggt ctgtgcgtat ctgggcctgg ttgccgtgcc gctgcaacat | 480 |
| aacgcgaccg catcccgtct gcgtccgatc gtcgaagagg ttgagccgtc gacgttggcg | 540 |
| gctggcgtgg gctacctgga cttggccgtc gaggcggcct tgggcagctc cagcctgcgc | 600 |
| cgtgtggttt gtttgatta tcgtccggaa gttgacgaac agcgcgaggc ggttgaccgt | 660 |
| gcgcgtagca aactggcggg tgcaggtatc gcggtcaccg ttgagacgct gggtgacgtc | 720 |
| attgagcgtg gccgtaccct gccgcctgag ccgatgttta ccggcgatac ggacgagcgt | 780 |
| ctggcaatga ttatgtatac cagcggttcc accggtttgc cgaaaggcgc catgtatacc | 840 |
| gagcgtatgc tgtgccgtct gtggaccact gaactgatgc cggatttcgc cgacaccccg | 900 |
| gttatcaatg tcaacttcat gccgctgaat cacctgggtg tcgtatccc gctgagcacc | 960 |
| gcgttccagg ccggtggtac ctcttatttc gttccggaga gcgatctgag caccctgttc | 1020 |
| gatgattgga atctggtccg tccgaccgag atgggcctgg tgccgcgtgt ggcagaaatg | 1080 |
| ttgtaccagc gttaccagag cgcggtcgat cgctttgaag ttgctggcac ggacacggcg | 1140 |
| acggcacaag cgcgtgctca ggccgaactc gtgagcagg tgctgggcgg tcgcattgtt | 1200 |
| actgccttct gtggcaccgc accgctggct gccgagatgc gcagcttcat tgagacgtgc | 1260 |
| ctgagcgtgc atgtgctgga cggttacggt ctgacggaag ttggtatggt caccaaggat | 1320 |

```
ggtttgatta cgcaaccgcc ggttttggac tataagctga tcgatgttcc ggagctgggt    1380
tacttcctga ccgacaaacc gtatccgcgt ggcgagctgc tggttaaatc cctgaccgca    1440
accccgggtt acttcaagcg tccagatgtc accgccaatg cattcgaccc agaaggctat    1500
taccgtacgg cgacgtgat ggcggagctg gaacctagcc gtctggccta cgtggatcgt    1560
cgcaataacg tcctgaagct ggcacaaggt gagttcgttg ccgtcgctcg tctggaagcc    1620 gttttttagca cgcgccgcact ggtgcgtcaa atctttgtgt acggcaacag cgagcgcccg    1680
tacttgctgg cggtcgtggt accgacggat gacgcagccc aaaagtatgc gggtgacccg    1740
ggtggtctga aaagcgcgtt gggtgagagc ctgcgccaag cggctaagct ggcagaactg    1800
caaagctacg aagttccggt tgatttttgtt gtggaaaccg agccgtttag cgaggataat    1860
ggcttgctga cgcgtgtcgg caaactgctg cgtccaaaac tgaaagagca ctacggcgca    1920
cgcctggaac agctgtatgc agacctggct gaaagccgcg ttacggagct gcgtgccctg    1980
cgtgagggtg ctgctgatca ccctgtgatc ttcacgttga cccgtgcggc ggaagcgctg    2040
ctgggtttgg ccggtggtcc gcctgcgccg gatgcgttgt tcattgaact gggtggtgat    2100
agcttgagcg cgctgacgtt tagcaatctg ttgcgtgaca tcttcgacgt tgaggtgccg    2160
gtcggtatga ttaccggtcc ggcgaccgac ctgggtcagc tggcagagta tgtggaatcc    2220
gaacgtgcgt ccggcagccg tcgtccgacc tttgcgaccg tccacggtcg cggtgccacg    2280
caggtgcgcg ctgcagactt gacgttggat aagttcatcg acgcaaccac cctggcagaa    2340
gcaccggcat tgccgcgtgc gaccggtacc ccgcacactg tgctgctgac cggtgcgaac    2400
ggctacctgg ccgtttctt gattctggag tggttggaac gtctggcgga cgggtggc    2460 aagctgatta gcattattcg tgcagcggac gctgcggcag cagcgaaacg cctggagagc    2520
gtgttcgaca gcggcgatcc gcaactgctg gagcgtttcc gcacgctggc agcggatcat    2580
ctggaagtta tcgtcggtga tattggtgag ccaaacctgg gtctgcaaca gggcacctgg    2640
gagcgcctgg cgcagtcggt cgatttgatt gtccatccag cagcactggt caaccatgtg    2700
ctgccgtacg accagctgtt cggtccgaat gtcgtcggca ctgcgagct gattcgtttg    2760 gccatcacca ctcgcattaa acctgtcacg tacatgtcca ccgtggctgt cgcgctgagc    2820
gttgacccgg ctgccttcgc cgaggacggc gacatccgca cggtttcggc tctgcgtccg    2880
gttgatggtg gctatgcgaa tggttacgca aactcgaagt gggcgggtga agtactgctg    2940
cgcgaggcac acgatctgtg cggcctgccg gttgcggttt ttcgcagcga catgatcctg    3000
gcacatagcc gttacgcagg ccaactgaac gtgccggacg cgtttacgcg tctgatcttt    3060
agcctgctga cgaccggcat cgcaccgggt agcttttatc aaaccgaccc tcgcggcaac    3120
cgtgctattg cgcactacga cggtctgcca gcggattttg tcgctgaagc ggttaccacg    3180
ctgggcgagc agatcgcgac tgccgcgcag gattctggtg catatcgcag ctttgatgtt    3240
atgaacccgc acgacgatgg catctctctg gacgtgttcg tggattggct gattgcgggt    3300
ggtcacgata ttcgccgtat cgatgactat gacgagtggc tgagccgctt taccaccgcc    3360
ctgcgcgcac tgccggacaa acaacgtcag cactccgtcc tgccgctgct ggacgcttat    3420
cgtaagccgg aaaccccgct gcgtggtgcg cctgcgccta ccgatgtgtt tcgtagcgcg    3480
gttcgtgagg cgaagattgg tgcggccgag gatatcccac atctgagcgc ggcactgatt    3540
gacaaatacg tggccgactt gcgtttgctg ggtctggtgt aa                       3582
```

<210> SEQ ID NO 16

<211> LENGTH: 9269
<212> TYPE: DNA
<213> ORGANISM: Artificial Sequence
<220> FEATURE:
<223> OTHER INFORMATION: vector

<400> SEQUENCE: 16

```
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg   120
caccgtcacc ctggatgctg taggcatagg cttggttatg ccggtactgc cgggcctctt   180
gcgggatatc gtccattccg acagcatcgc cagtcactat ggcgtgctgc tagcgctata   240
tgcgttgatg caatttctat gcgcacccgt tctcggagca ctgtccgacc gctttggccg   300
ccgcccagtc ctgctcgctt cgctacttgg agccactatc gactacgcga tcatggcgac   360
cacacccgtc ctgtggatcc tctacgccgg acgcatcgtg gccggcatca ccggcgccac   420
aggtgcggtt gctggcgcct atatcgccga catcaccgat ggggaagatc gggctcgcca   480
cttcgggctc atgagcgctt gtttcggcgt gggtatggtg caggccccg tggccggggg   540
actgttgggc gccatctcct tgcatgcacc attccttgcg gcggcggtgc tcaacggcct   600
caacctacta ctgggctgct tcctaatgca ggagtcgcat aagggagagc gtcgaccgat   660
gcccttgaga gccttcaacc cagtcagctc cttccggtgg gcgcggggca tgactatcgt   720
cgccgcactt atgactgtct tctttatcat gcaactcgta ggacaggtgc cggcagcgct   780
ctgggtcatt ttcggcgagg accgctttcg ctggagcgcg acgatgatcg gcctgtcgct   840
tgcggtattc ggaatcttgc acgccctcgc tcaagccttc gtcactggtc cgccaccaa   900
acgtttcggc gagaagcagg ccattatcgc cggcatggcg gccgacgcgc tgggctacgt   960
cttgctggcg ttcgcgacgc gaggctggat ggccttcccc attatgattc ttctcgcttc  1020
cggcggcatc gggatgcccg cgttgcaggc catgctgtcc aggcaggtag atgacgacca  1080
tcagggacag cttcaaggat cgctcgcggc tcttaccagc ctaacttcga tcattggacc  1140
gctgatcgtc acggcgattt atgccgcctc ggcgagcaca tggaacgggt tggcatggat  1200
tgtaggcgcc gccctatacc ttgtctgcct ccccgcgttg cgtcgcggtg catggagccg  1260
ggccacctcg acctgaatgg aagccggcgg cacctcgcta acggattcac cactccaaga  1320
attggagcca atcaattctt gcggagaact gtgaatgcgc aaaccaaccc ttggcagaac  1380
atatccatcg cgtccgccat ctccagcagc cgcacgcggc gcatctcggg cagcgttggg  1440
tcctggccac gggtgcgcat gatcgtgctc ctgtcgttga ggacccggct aggctggcgg  1500
ggttgcctta ctggttagca gaatgaatca ccgatacgcg agcgaacgtg aagcgactgc  1560
tgctgcaaaa cgtctgcgac ctgagcaaca acatgaatgg tcttcggttt ccgtgtttcg  1620
taaagtctgg aaacgcggaa gtcccctacg tgctgctgaa gttgcccgca acagagagtg  1680
gaaccaaccg gtgataccac gatactatga ctgagagtca acgccatgag cggcctcatt  1740
tcttattctg agttacaaca gtccgcaccg ctgccggtag ctattgacta ccggctgca  1800
ctagccctgc gtcagatggc tctgatccaa ggcaaactgc caaatatct gctggcaccg  1860
gaagtcagcg ccctgcacca ttatgttccg gatctgcatc gcaggatgct gctggctacc  1920
ctgtggaaca cctacatctg tattaacgaa gcgctggcat tgaccctgag tgatttttct  1980
ctggtgccgc cctatccctt gtgcagcttg ccacgctca aggggtttg aggtccaacc  2040
gtacgaaaac gtacggtaag aggaaaatta tcgtctgaaa aatcgattag tagacaagaa  2100
agtccgttaa gtgccaattt tcgattaaaa agacaccgtt tgatggcgt tttccaatgt  2160
```

```
acattatgtt tcgatatatc agacagttac ttcactaacg tacgttttcg ttctattggc    2220
cttcagaccc catatcctta atgtccttta tttgctgggg ttatcagatc cccccgacac    2280
gtttaattaa tgcttttctcc gccggagatc gacgcacagc gttctgtgct ctatgatgtt    2340
atttcttaat aatcatccag gtattctctt tatcaccata cgtagtgcga gtgtccacct    2400
taacgcaggg ctttccgtca cagcgcgata tgtcagccag cggggctttc ttttgccaga    2460
ccgcttccat cctctgcatt tcagcaatct ggctatacccc gtcattcata aaccacgtaa    2520
atgccgtcac gcaggaagcc aggacgaaga atatcgtcag tacaagataa atcgcggatt    2580
tccacgtata gcgtgacatc tcacgacgca tttcatggat catcgctttc gccgtatcgg    2640
cagcctgatt cagcgcttct gtcgccggtt tctgctgtgc taatccggct tgtttcagtt    2700 cttctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagccttta tccggcttct gtcgtatctg ttcggcgagt cgctgtcgtt    3000 cttttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgttc cctctgggca acaaggtatt    3540
ctttgcgttc ggtcggtgtt tccccgaaac gtgcctttt tgcgccaccg cgctccggct    3600
ctttggtgtt agcccgttta aaatactgct cagggtcacg gtgaataccg tcattaatgc    3660
gttcagagaa catgatatgg gcgtggggct gctcgccacc ggctatcgct gctttcggat    3720 tatgatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact ccttgtgctc aaggtcggag tcttttttcac    3960 gggcatactt tccctcacgc gcaatataat cggcatgagg agaggcactg cctttttccgc    4020 cggttttttac gctgagatga taggatgcca tcgtgttttta tcccgctgaa ggcgcgcacc    4080
gtttctgaac gaagtgaaga aacgtctaag tgcgccctga taaataaaag agttatcagg    4140
gattgtagtg ggatttgacc tcctctgcca tcactgagca taatcattcc gttagcattc    4200
aggaggtaaa cagcatgaat aaaagcgaaa aacaggaaca atgggcagca gaaagagtgc    4260
agtatattcg cggcttaaag tcgccgaatg agcaacagaa acttatgctg atactgacgg    4320
ataaagcaga taaaacagca caggatatca aaacgctgtc cctgctgatg aaggctgaac    4380
aggcagcaga gaaagcgcag gaagccgagc gaaagtcat gaacctgata caggcagaaa    4440
agcgagccga agccagagcc gcccgtaaag cccgtgacca tgctctgtac cagtctgccg    4500
```

```
gattgcttat cctggcgggt ctggttgaca gtaagacggg taagcctgtt gatgataccg   4560
ctgccttact gggtgcatta gccagtctga atgacctgtc acgggataat ccgaagtggt   4620
cagactggaa aatcagaggg caggaactgc tgaacagcaa aaagtcagat agcaccacat   4680
agcagacccg ccataaaacg ccctgagaag cccgtgacgg gcttttcttg tattatgggt   4740
agtttccttg catgaatcca taaaaggcgc ctgtagtgcc atttaccccc attcactgcc   4800
agagccgtga gcgcagcgaa ctgaatgtca cgaaaaagac agcgactcag gtgcctgatg   4860
gtcggagaca aaaggaatat tcagcgattt gcccgagctt gcgagggtgc tacttaagcc   4920
tttagggttt taaggtctgt tttgtagagg agcaaacagc gtttgcgaca tccttttgta   4980
atactgcgga actgactaaa gtagtgagtt atacacaggg ctgggatcta ttcttttat   5040 cttttttat tctttcttta ttctataaat tataaccact tgaatataaa caaaaaaac    5100 acacaaaggt ctagcggaat ttacagaggg tctagcagaa tttacaagtt ttccagcaaa   5160
ggtctagcag aatttacaga tacccacaac tcaaaggaaa aggactagta attatcattg   5220
actagcccat ctcaattggt atagtgatta aaatcaccta gaccaattga gatgtatgtc   5280
tgaattagtt gttttcaaag caaatgaact agcgattagt cgctatgact taacggagca   5340
tgaaaccaag ctaattttat gctgtgtggc actactcaac cccacgattg aaaacccta    5400 aaggaaagaa cggacggtat cgttcactta taaccaatac gctcagatga tgaacatcag   5460
tagggaaaat gcttatggtg tattagctaa agcaaccaga gagctgatga cgagaactgt   5520
ggaaatcagg aatcctttgg ttaaaggctt tgagattttc cagtggacaa actatgccaa   5580
gttctcaagc gaaaaattag aattagtttt tagtgaagag atattgcctt atcttttcca   5640
gttaaaaaaa ttcataaaat ataatctgga acatgttaag tcttttgaaa acaaatactc   5700
tatgaggatt tatgagtggt tattaaaaga actaacacaa aagaaaactc acaaggcaaa   5760
tatagagatt agccttgatg aatttaagtt catgttaatg cttgaaaata actaccatga   5820
gtttaaaagg cttaaccaat gggttttgaa accaataagt aaagatttaa acacttacag   5880
caatatgaaa ttggtggttg ataagcgagg ccgcccgact gatacgttga ttttccaagt   5940
tgaactagat agacaaatgg atctcgtaac cgaacttgag aacaaccaga taaaaatgaa   6000
tggtgacaaa ataccaacaa ccattacatc agattcctac ctacataacg gactaagaaa   6060
aacactacac gatgctttaa ctgcaaaaat tcagctcacc agttttgagg caaaattttt   6120
gagtgacatg caaagtaagt atgatctcaa tggttcgttc tcatggctca cgcaaaaaca   6180
acgaaccaca ctagagaaca tactggctaa atacggaagg atctgaggtt cttatggctc   6240
ttgtatctat cagtgaagca tcaagactaa caaacaaaag tagaacaact gttcaccgtt   6300
acatatcaaa gggaaaactg tccatatgca cagatgaaaa cggtgtaaaa agatagata   6360 catcagagct tttacgagtt tttggtgcat tcaaagctgt tcaccatgaa cagatcgaca   6420
atgtaacaga tgaacagcat gtaacaccta atagaacagg tgaaaccagt aaaacaaagc   6480
aactagaaca tgaaattgaa cacctgagac aacttgttac agctcaacag tcacacatag   6540
acagcctgaa acaggcgatg ctgcttatcg aatcaaagct gccgacaaca cgggagccag   6600
tgacgcctcc cgtggggaaa aaatcatggc aattctggaa gaaatagcgc tttcagccgg   6660
caaaccggct gaagccggat ctgcgattct gataacaaac tagcaacacc agaacagccc   6720
gtttgcgggc agcaaaaccc gtactttggt acgttccggc ggtttttgt ggcgagtggt    6780 gttcgggcg tgcgcgcaag atccattatg ttaaacgggc gagtttacat ctcaaaccg     6840 cccgcttaac accatcagaa atcctcagcg cgattttaag caccaacccc ccccgtaac    6900
```

```
acccaaatcc atactgaaag tggctttgtt gaataaatcg aacttttgct gagttgaagg    6960
atcagatcac gcatcctccc gacaacacag accattccgt ggcaaagcaa aagttcagaa    7020
tcaccaactg gtccacctac aacaaagctc tcatcaaccg tggctccctc actttctggc    7080
tggatgatga ggcgattcag gcctggtatg agtcggcaac accttcatca cgaggaaggc    7140
cccagcgcta ttctgatctc gccatcacca ccgttctggt gattaaacgc gtattccggc    7200
tgaccctgcg ggctgcgcag ggttttattg attccatttt tgccctgatg aacgttccgt    7260
tgcgctgccc ggattacacc agtgtcagta agcgggcaaa gtcggttaat gtcagtttca    7320
aaacgtccac ccgggggtgaa atcgcacacc tggtgattga ttccaccggg ctgaaggtct    7380
ttggtgaagg cgaatggaaa gtcagaaagc acggcaaaga gcgccgtcgt atctggcgaa    7440
agttgcatct tgctgttgac agcaacacac atgaagttgt ctgtgcagac ctgtcgctga    7500
ataacgtcac ggactcagaa gccttcccgg gccttatccg gcagactcac agaaaaatca    7560
gggcagccgc ggcagacggg gcttacgata cccggctctg tcacgatgaa ctgcgccgca    7620
aaaaaatcag cgcgcttatt cctccccgaa aaggtgcggg ttactggccc ggtgaatatg    7680
cagaccgtaa ccgtgcagtg gctaatcagc gaatgaccgg gagtaatgcg cggtggaaat    7740
ggacaacaga ttacaaccgt cgctcgatag cggaaacggc gatgtaccgg gtaaaacagc    7800
tgttcggggg ttcactgacg ctgcgtgact acgatggtca ggttgcggag gctatggccc    7860
tggtacgagc gctgaacaaa atgacgaaag caggtatgcc tgaaagcgtg cgtattgcct    7920
gaaaacacaa cccgctacgg gggagactta cccgaaatct gatttattca acaaagccgg    7980
gtgtggtgaa ctacaaagca gacccgttga ggttatcagt tcgatgcaca atcagcagcg    8040
cataaaatat gcacaagaac aggagcaccc ttcgcattaa gctgtggtgg taacaagtag    8100
tgccgggcta ccatcagcga gcatgatgcg ctcccacagc attcgccttg gcagtatgga    8160
agttcctcgc tccagttcgg gccggtatcc acctcgagtg accccagccg cccctcatgc    8220
caaccgagcc cattaagcgc agagtcggcc gcaactatct cggggacgca taaacacgca    8280
gcgatttacc aaggagttcg gctaggtcaa tccgcaattc cctttgcctg gccggagatg    8340
ccgcgagcaa acaatgtgtc cggtcgctac cagatggact ttgtgggcgg aggattgcac    8400
cagacgcttc agcgcagcgt cgtacgatga atcggaaggc ccggtaagca attgaagaac    8460
cgctgaccac ctcccatccg acaatgcaag ggtgccccgc tcccagcgcg acacggttgc    8520
ctgatccaca cccattaatt cagctaggtg actttgcttc atatgacgaa gcaaccgcgc    8580
cctccgcacc tgccgccccc tgtcattcgt caacattctt cagcacctca atgtcgttcg    8640
tagtgagcct catttttcca agaccgccga tgatgagagc caggcctcgc tcgaatgccg    8700
cgtccggacc gccttcgtag acgattttca tcgcgctctg taggcgcgcc ggcatcgtag    8760
acgctgaggt ggtcaactga tcttcgcccc gctcctcggc gtctgcctcg ctagcttgct    8820
gctcaagaac agcgccgacg gtgaagtagc tgattgccat caacgcatag gtcgcgtcac    8880
ctgccgaaaa gccagcatcg caaaggaagc gaagctgcgc gtcggctttt tccatctgcg    8940
gcgcggctgg ccgcgtcccg gcatgaatac gcgcgccatc gcgataagcg agcaacgccc    9000
gtcgaaaact gcatgcattg cccttcagga acgaacgcca gtcgtcgtca tcccttggcg    9060
tcgaatgcgt gtgatttatc gtcagcatgg cttcggcaag tgcgtcgagc aacgcacgct    9120
tgttcttgaa atgccagtag agcgctggct gttgcacccc gaggcgctca gccagtcggc    9180
gcgtcgttag accttccatg cccacgtcgt taagcagttc gagcgcggtt cggatcacgg    9240
```

```
cctcgcgttg gagcttgttc attcgcgaa                                       9269
```

<210> SEQ ID NO 17
<211> LENGTH: 13712
<212> TYPE: DNA
<213> ORGANISM: Artificial Sequence
<220> FEATURE:
<223> OTHER INFORMATION: vector

<400> SEQUENCE: 17

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg caggccccg tggccggggg     540
actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc cgccaccaa     900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggacccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcccctacg tgctgctgaa gttgcccgca acagagagtg   1680
gaaccaaccg gtgataccac gatactatga ctgagagtca acgccatgag cggcctcatt   1740
tcttattctg agttacaaca gtccgcaccg ctgccggtag ctacttgact atccggctgc   1800
actagccctg cgtcagatgg ctctgatcca aggcaaactg ccaaaatatc tgctggcacc   1860
ggaagtcagc gccctgcacc attatgttcc ggatctgcat cgcaggatgc tgctggctac   1920
cctgtggaac acctacatct gtattaacga agcgctggca ttgaccctga gtgatttttc   1980
tctggtgccg cccgtatccct ttgtgcagct tgccacgctc aaaggggttt gaggtccaac   2040
```

```
cgtacgaaaa cgtacggtaa gaggaaaatt atcgtctgaa aaatcgatta gtagacaaga   2100
aagtccgtta agtgccaatt ttcgattaaa aagacaccgt tttgatggcg ttttccaatg   2160
tacattatgt ttcgatatat cagacagtta cttcactaac gtacgttttc gttctattgg   2220
ccttcagacc ccatatcctt aatgtccttt atttgctggg gttatcagat cccccccgaca  2280 cgtttaatta atgctttctc cgccggagat cgacgcacag gcttctgtgt ctatgatgtt   2340
atttcttaat aatcatccag gtattctctt tatcaccata cgtagtgcga gtgtccacct   2400
taacgcaggg ctttccgtca cagcgcgata tgtcagccag cggggctttc ttttgccaga   2460
ccgcttccat cctctgcatt tcagcaatct ggctataccc gtcattcata aaccacgtaa   2520
atgccgtcac gcaggaagcc aggacgaaga atatcgtcag tacaagataa atcgcggatt   2580
tccacgtata gcgtgacatc tcacgacgca tttcatggat catcgctttc gccgtatcgg   2640
cagcctgatt cagcgcttct gtcgccggtt tctgctgtgc taatccggct tgtttcagtt   2700
ctttctcaac ctgagtgagc gcggaactca ccgatttcct gacggtgtca gtcatattac   2760
cggacgcgct gtccagctca cgaatgaccc tgctcagcgt ttcactttgc tgctgtaatt   2820
gtgatgaggc ggcctgaaac tgttctgtca gagaagtaac acgcttttcc agcgcctgat   2880
gatgcccgat aagggcggca atttgtttaa tttcgtcgct catacaaaat cctgcctatc   2940
gtgagaatga ccagccttta tccggcttct gtcgtatctg ttcggcgagt cgctgtcgtt   3000
ctttctcctg ctgacgctgt ttttccgcca gacgttcgcg ctctctctgc ctttccatct   3060
cctgatgtat cccctggaac tccgccatcg catcgttaac aagggactga agatcgattt   3120
cttcctgtat atccttcatg gcatcactga ccagtgcgtt cagcttgtca ggctctttt    3180 caaaatcaaa cgttctgccg gaatgggatt cctgctcagg ctctgacttc agctcctgtt   3240
ttagcgtcag agtatccctc tcgctgaggg cttcccgtaa cgaggtagtc acgtcaatta   3300
cgctgtcacg ttcatcacgg gactgctgca cctgcctttc agcctccctg cgctcaagaa   3360
tggcctgtag ctgctcagta tcgaatcgct gaacctgacc cgcgcccaga tgccgctcag   3420
gctcacggtc aatgccctgc gccttcaggg aacgggaatc aacccggtca gcgtgctgat   3480
accgttcaag gtgcttattc tggaggtcag cccagcgtct ccctctgggc aacaaggtat   3540
tctttgcgtt cggtcggtgt ttccccgaaa cgtgcctttt ttgcgccacc gcgtccggct   3600
ctttggtgtt agcccgttta aaatactgct cagggtcacg gtgaataccg tcattaatgc   3660
gttcagagaa catgatatgg gcgtggggct gctgccacc ggctatcgct gctttcggat    3720 tatgatagc gaactgatag gcatggcggt cgccaatttc ctgttggaca aaatcgcgga    3780
caagctcaag acgttgttcg ggttttaact cacgcggcag ggcaatctcg atttcacggt   3840
aggtacagcc gttggcacgt tcagacgtgt cagcggcttt ccagaactcg gacggtttat   3900
gcgctgccca cgccggcata ttgccggact ccttgtgctc aaggtcggag tcttttttcac 3960 gggcatactt tccctcacgc gcaatataat cggcatgagg agaggcactg cctttttccgc 4020 cggttttttac gctgagatga taggatgcca tcgtgtttta tcccgctgaa gggcgcacgt  4080
ttctgaacga agtgaagaaa gtctaagtgc gccctgataa ataaaagagt tatcagggat   4140
tgtagtggga tttgacctcc tctgccatca tgagcgtaat cattccgtta gcattcagga   4200
ggtaaacagc atgaataaaa gcgaaaaaac aggaacaatg ggcagcagaa agagtgcagt   4260
atattcgcgg cttaaagtcg ccgaatgagc aacagaaact tatgctgata ctgacgata    4320 aagcagataa aacagcacag gatatcaaaa cgctgtccct gctgatgaag gctgaacagg   4380
```

```
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt taccccccatt cactgccaga    4800 gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg ggatctattc ttttttatctt    5040 tttttattct ttctttattc tataaattat aaccacttga atataaacaa aaaaaacaca    5100
caaaggtcta gcgaatttta cagagggtct agcagaattt acaagttttc cagcaaaggt    5160
ctagcagaat ttacagatac ccacaactca aaggaaaagg actagtaatt atcattgact    5220
agcccatctc aattggtata gtgattaaaa tcacctagac caattgagat gtatgtctga    5280
attagttgtt ttcaaagcaa atgaactagc gattagtcgc tatgacttaa cggagcatga    5340
aaccaagcta attttatgct gtgtggcact actcaacccc acgattgaaa ccctacaag    5400 gaaagaacgg acggtatcgt tcacttataa ccaatacgct cagatgatga acatcagtag    5460
ggaaaatgct tatggtgtat tagctaaagc aaccagagag ctgatgacga aactgtggaa    5520
aatcaggaat cctttggtta aaggctttga gattttccag tggacaaaact atgccaagtt    5580 ctcaagcgaa aaattagaat tagttttttag tgaagagata ttgccttatc ttttccagtt    5640
aaaaaaattc ataaaatata atctggaaca tgttaagtct tttgaaaaca aatactctat    5700
gaggatttat gagtggttat taaaagaact aacacaaaag aaaactcaca aggcaaatat    5760
agagattagc cttgatgaat ttaagttcat gttaatgctt gaaaataact accatgagtt    5820
taaaaggctt aaccaatggg ttttgaaacc aataagtaaa gatttaaaca cttacagcaa    5880
tatgaaattg gtggttgata agcgaggccg cccgactgat acgttgattt ccaagttga    5940 actagataga caaatggatc tcgtaaccga acttgagaac aaccagataa aaatgaatgg    6000
tgacaaaata ccaacaacca ttacatcaga ttcctaccta cgtaacggac taagaaaaac    6060 actcacgat gctttaactg caaaaattca gctcaccagt tttgaggcaa aatttttgag    6120
tgacatgcaa agtaagcatg atctcaatgg ttcgttctca tggctcacgc aaaaacaacg    6180
aaccacacta gagaacatac tggctaaata cggaaggatc tgaggttctt atggctcttg    6240
tatctatcag tgaagcatca agactaacaa acaaaagtag aacaactgtt caccgttaga    6300
tatcaaaggg aaaactgtcc atatgcacag atgaaaacgg tgtaaaaaag atagatacat    6360
cagagctttt acgagttttt ggtgcattta agctgttca ccatgaacag atcgacaatg    6420
taacagatga acagcatgta acacctaata gaacaggtga accagtaaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg gagccagtga    6600
cgcctcccgt ggggaaaaaa tcatggcaat tctggaagaa atagcgcttt cagccggcaa    6660
acctgaagcc ggatctgcga ttctgataac aaactagcaa caccgaaaca gcccgtttgc    6720
gggcagcaaa accgtactt ttggacgttc cggcggtttt ttgtggcgag tggtgttcgg    6780
```

```
gcggtgcgcg caagatccat tatgttaaac gggcgagttt acatctcaaa accgcccgct    6840
taacaccatc agaaatcctc agcgcgattt taagcaccaa ccccccccg taacacccaa     6900 atccatactg aaagtggctt tgttgaataa atcgaacttt tgctgagttg aaggatcaga    6960
tcacgcatcc tcccgacaac acagaccatt ccgtggcaaa gcaaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca tttttgccct gatgaacgtt ccgttgcgct    7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga agcacggca agagcgccg tcgtatctgg cgaaagttgc     7440
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccggagtaa tgcgcggtgg aaatggacaa     7740
cagattacaa ccgtcgctcg atagcggaaa cggcgatgta ccgggtaaaa cagctgttcg    7800
ggggttcact gacgctgcgt gactacgatg gtcaggttgc ggaggctatg gccctggtac    7860
gagcgctgaa caaaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccaccctcg agtggcagtg agcgcaacgc aattaatgta    8220
agttagctca ctcattaggc accccaggct tgacacttta tgcttccggc tcgtataatg    8280
tgtggaattg tgagcggata caataacaa tttcacacag gatctaggaa ccaaggagag    8340
tggcatatga caattgaaac gcgcgaagat agatttaaca gacgtattga tcaccttttt    8400
gaaacagacc cgcagttcgc agcggcacgt ccggacgaag ctattagcgc tgcagcagcc    8460
gatccggagc tgcgcctgcc agccgcagtc aagcagattc tggccggtta tgcggaccgt    8520
ccggccctgg gtaagcgtgc tgtggagttc gttacggacg aagaaggccg taccaccgca    8580
aagttgctgc cgcgtttcga tacgatcacc taccgtcaat tggcaggtcg tattcaggcg    8640
gtgactaacg cgtggcacaa tcacccggtg aatgcgggtg accgtgtcgc aattttgggc    8700
ttcacgagcg ttgactatac gaccatcgat atcgcactgc tggaactggg tgctgttagc    8760
gttccgttgc aaacgtctgc tccggttgcg cagctgcaac cgattgtggc cgaaaccgag    8820
ccgaaggtca ttgcgagcag cgtcgatttc ctggcagatg cggtcgcact ggttgagagc    8880
ggtccagccc cgagccgtct ggtcgttttt gattatagcc acgaggtcga cgatcagcgt    8940
gaggccttcg aagcggccaa gggtaaactg gcgggtaccg tgttgtggt ggaaacgatt     9000 acggatgtct tggatcgcgg tcgcagcctg gctgatgcgc cgctgtatgt cccagacgaa    9060
acggacccgc tgaccctgct gatctatacc agcggtagca ccggtacgcc gaagggtgct    9120
```

```
atgtatccgg aatccaagac cgcgacgatg tggcaagctg gtagcaaggc gcgttgggat    9180
gaaaccctgg gcgttatgcc gagcatcacc ctgaacttca tgccaatgtc ccacgtgatg    9240
ggtcgcggca tcctgtgtag caccctggcg agcggcggta ctgcgtattt tgccgcacgt    9300
agcgacttgt ctacctttct ggaggacctg gcgttggtcc gcccgaccca actgaatttc    9360
gtccctcgca tctgggatat gctgttccaa gagtatcaga gccgtctgga caatcgtcgt    9420
gccgagggta gcgaggatcg cgcggaagcg gccgtactgg aagaggttcg tacccaattg    9480 ctggcggtc gtttcgtttc cgctctgacc ggtagcgctc caatcagcgc ggaaatgaaa    9540
agctgggtcg aggacctgct ggacatgcat ttgctggaag gttacggttc caccgaggcg    9600
ggtgccgtgt tcattgacgg tcaaatccaa cgtccacctg ttatcgatta caaactggtt    9660
gatgttccgg acttgggtta ctttgcgacc gatcgtccat accctcgcgg cgagctgctg    9720
gtgaagagcg agcagatgtt cccgggctac tataagcgtc cggagattac ggcggagatg    9780
tttgacgagg acggttatta ccgtaccggc gacatcgtgg ccgaactggg tccggatcat    9840
ctggagtatc tggaccgccg taacaacgtc ctgaagctga gccagggtga gtttgttacc    9900
gtttccaaac tggaagcggt ctttggcgat agcccactgg tgcgccagat ttatgtctac    9960
ggtaactctg cacgcagcta tctgctggcg gttgtcgttc cgaccgaaga ggcactgagc    10020
cgctgggacg gcgatgaact gaagagccgc atcagcgaca gcttgcaaga tgcggcacgt    10080
gccgcaggtt tgcaaagcta tgagatcccg cgtgactttc tggttgaaac cacgccgttc    10140
acgttggaga acggtctgct gaccggcatt cgcaaactgg cgcgtccgaa gctgaaagcg    10200
cattatggcg aacgtctgga acaactgtac acggatctgg ctgaaggcca agccaatgag    10260
ctgcgtgaac tgcgccgtaa tggtgcggat cgtccggttg ttgaaacggt ttcgcgtgcc    10320
gcggtcgcct tgctgggtgc gtctgtgacg gacctgcgtt ctgacgccca ctttacggac    10380
ctgggcggtg attccctgag cgccctgagc ttcagcaacc tgctgcacga gattttgac    10440 gtcgatgtcc cggtgggcgt gattgtcagc ccggcaaccg acctggccgg tgttgccgcc    10500
tatattgagg gtgagctgcg tggtagcaaa cgtccgacct acgcaagcgt ccacggtcgt    10560
gacgcaaccg aggtgcgtgc tcgcgatctg gcgctgggca aattcatcga cgcaaaaacg    10620
ctgagcgcag caccgggtct gccgcgctcc ggtacggaga tccgtacggt gctgctgacg    10680
ggtgcgaccg gttttctggg tcgctacttg gccttggagt ggctggaacg tatgaccctg    10740
gttgacggca aggtgatctg tttggttcgt gcgcgtagcg acgacgaagc acgtgcgcgt    10800
ctggacgcaa ccttcgatac cggcgatgct accttgctgg agcactaccg tgccctggcg    10860
gctgaccatc tggaagttat tgcgggtgat aagggtgaag ccgacttggg cctggatcac    10920
gatacctggc agcgtctggc agatacggtc gacctgatcg ttgacccggc tgcgctggtt    10980
aaccacgttt tgccgtacag ccagatgttc ggcccaaacg ctctgggcac tgcagagctg    11040
attcgcattg cactgaccac caccattaaa ccgtacgtct acgtgagcac cattggtgtt    11100
ggtcagggca tcagcccaga agcctttgtt gaagatgcgg acatccgcga aatcagcgcc    11160
acgcgtcgcg ttgacgacag ctacgcgaat ggttatggta acagcaaatg ggcaggtgag    11220
gttctgctgc gcgaagcgca cgactggtgc ggcctgccgg tgagcgtgtt tcgttgtgac    11280
atgatcttgg ccgacaccac ctactccggc cagctgaatc tgccggatat gttcacccgt    11340
ctgatgttga gcctggtggc aactggcatc gcaccgggca gcttttatga gctgacgcg    11400 gacggtaatc gtcaacgtgc acattatgat ggtctgccgg tggagtttat cgcggaagca    11460
atcagcacga tcggctctca agtgactgac ggtttcgaaa cgttccatgt catgaatcct    11520
```

```
tatgatgatg gtatcggcct ggacgagtac gtcgactggc tgattgaggc tggctacccg    11580
gttcaccgtg ttgatgatta tgcgacgtgg ttgagccgtt ttgaaaccgc cttgcgtgcg    11640
ctgccggagc gtcaacgtca ggcatccctg ctgccgctgt tgcacaacta ccagcagcct    11700
tctccgccgg tttgcggtgc tatggctcct accgaccgtt tccgtgcagc tgtccaggac    11760
gccaaaattg gcccagataa agacatccca catgtaacgg cggacgtgat cgtgaaatac    11820
attagcaact tgcagatgct gggtctgctg taagtctaag agaaggagtt ctatcgtcta    11880
tgattgaaac catcttacca gccggcgtcg aatcagcaga gttacttgag taccctgaag    11940
atctgaaggc gcatccggct gaagagcatc tgatcgcaaa gagcgtagag aagcgtcgtc    12000
gcgacttcat tggcgcacgt cattgcgccc gtctggcact ggcggagctg ggtgaaccgc    12060
cggttgcgat tggcaagggt gaacgtggtg cgccgatttg gccgcgtggt gtcgtgggct    12120
ctctgaccca ttgcgatggc tatcgcgcag cggcggttgc tcacaaaatg cgttttcgca    12180
gcatcggcat cgacgccgaa ccgcacgcga ccctgccgga aggtgtcctg gattcggtta    12240
gcctgccgcc tgagcgtgag tggctgaaaa ccaccgacag cgcactgcac ctggaccgtt    12300
tgctgttttg tgcgaaagaa gcaacttaca aagcgtggtg gccgctgacg gcacgttggc    12360
tgggtttcga agaagcgcac attaccttcg aaatcgagga tggtagcgcc gactctggta    12420
atggcacgtt tcacagcgaa ctgctggtgc cgggtcagac caatgacggt ggtaccccgc    12480
tgctgtcttt cgacggtcgc tggctgatcg ctgatggctt catcctgacg gcgattgcat    12540
acgcatgata atgataacct aggctgctgc caccgctgag caataactag cataacccct    12600
tggggcctct aaacgggtct tgaggggttt tttgcctcga gtgaccccag ccgcccctca    12660
tgccaaccga gcccattaag cgcagagtcg gccgcaacta tctcggggac gcataaacac    12720
gcagcgattt accaaggagt tcggctaggt caatccgcaa ttcccttgc ctggccggag    12780 atgccgcgag caaacaatgt gtccggtcgc taccagatgg actttgtggg cggaggattg    12840
caccagacgc ttcagcgcag cgtcgtacga tgaatcggaa ggcccggtaa gcaattgaag    12900
aaccgctgac cacctcccat ccgacaatgc aagggtgccc cgctcccagc gcgacacggt    12960
tgcctgatcc acacccatta attcagctag gtgactttgc ttcatatgac gaagcaaccg    13020
cgccctccgc acctgccgcc ccctgtcatt cgtcaacatt cttcagcacc tcaatgtcgt    13080
tcgtagtgag cctcattttt tcaagaccgc cgatgatgag agccaggcct cgctcgaatg    13140
ccgcgtccgg accgccttcg tagacgattt tcatcgcgct ctgtaggcgc gccggcatcg    13200
tagacgctga ggtggtcaac tgatcttcgc cccgctcctc ggcgtctgcc tcgctagctt    13260
gctgctcaag aacagcgccg acggtgaagt agctgattgc catcaacgca taggtcgcgt    13320
cacctgccga aaagccagca tcgcaaagga agcgaagctg cgcgtcggct ttttccatct    13380
gcggcgcggc tggccgcgtc ccggcatgaa tacgcgcgcc atcgcgataa gcgagcaacg    13440
cccgtcgaaa actgcatgca ttgcccttca ggaacgaacg ccagtcgtcg tcatcccttg    13500
gcgtcgaatg cgtgtgattt atcgtcagca tggcttcggc aagtgcgtcg agcaacgcac    13560
gcttgttctt gaaatgccag tagagcgctg gctgttgcac cccgaggcgc tcagccagtc    13620
ggcgcgtcgt tagaccttcc atgcccacgt cgttaagcag ttcgagcgcg gttcggatca    13680
cggcctcgcg ttggagcttg ttcattcgcg aa                                  13712
```

<210> SEQ ID NO 18
<211> LENGTH: 13719
<212> TYPE: DNA

<213> ORGANISM: Artificial Sequence
<220> FEATURE:
<223> OTHER INFORMATION: vector

<400> SEQUENCE: 18

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360
cacacccgtc ctgtggatcc tctacgccga acgcatcgtg gccggcatca ccggcgccac     420
aggtgcggtt gctggcgcct atatcgccga catcaccgat ggggaagatc gggctcgcca     480
cttcgggctc atgagcgctt gtttcggcgt gggtatggtg caggccccg tggccggggg      540
actgttgggc gccatctcct tgcatgcacc attccttgcg gcggcggtgc tcaacggcct     600
caacctacta ctgggctgct tcctaatgca ggagtcgcat aagggagagc gtcgaccgat     660
gcccttgaga gccttcaacc cagtcagctc cttccggtgg gcgcggggca tgactatcgt     720
cgccgcactt atgactgtct tctttatcat gcaactcgta ggacaggtgc cggcagcgct     780
ctgggtcatt ttcggcgagg accgctttcg ctggagcgcg acgatgatcg gcctgtcgct     840
tgcggtattc ggaatcttgc acgccctcgc tcaagccttc gtcactggtc cgccaccaa     900
acgtttcggc gagaagcagg ccattatcgc cggcatggcg gccgacgcgc tgggctacgt     960
cttgctggcg ttcgcgacgc gaggctggat ggccttcccc attatgattc ttctcgcttc    1020
cggcggcatc gggatgcccg cgttgcaggc catgctgtcc aggcaggtag atgacgacca    1080
tcagggacag cttcaaggat cgctcgcggc tcttaccagc ctaacttcga tcactggacc    1140
gctgatcgtc acggcgattt atgccgcctc ggcgagcaca tggaacgggt tggcatggat    1200
tgtaggcgcc gccctatacc ttgtctgcct ccccgcgttg cgtcgcggtg catggagccg    1260
ggccacctcg acctgaatgg aagccggcgg cacctcgcta acggattcac cactccaaga    1320
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
ggttgcctta ctggttagca gaatgaatca ccgatacgcg agcgaacgtg aagcgactgc    1560
tgctgcaaaa cgtctgcgac ctgagcaaca acatgaatgg tcttcggttt ccgtgtttcg    1620
taaagtctgg aaacgcggaa gtcccctacg tgctgctgaa gttgcccgca acagagagtg    1680
gaaccaaccg gtgataccac gatactatga ctgagagtca acgccatgag cggcctcatt    1740
tcttattctg agttacaaca gtccgcaccg ctgccggtag ctacttgact atccggctgc    1800
actagccctg cgtcagatgg ctctgatcca aggcaaactg ccaaaatatc tgctggcacc    1860
ggaagtcagc gccctgcacc attatgttcc ggatctgcat cgcaggatgc tgctggctac    1920
cctgtggaac acctacatct gtattaacga agcgctggca ttgaccctga gtgatttttc    1980
tctggtgccg ccctatccct tgtgcagct tgccacgctc aaagggggttt gaggtccaac    2040
cgtacgaaaa cgtacggtaa gaggaaaatt atcgtctgaa aaatcgatta gtagacaaga    2100
aagtccgtta agtgccaatt ttcgattaaa aagacaccgt tttgatggcg ttttccaatg    2160
tacattatgt ttcgatatat cagacagtta cttcactaac gtacgttttc gttctattgg    2220
```

```
ccttcagacc ccatatcctt aatgtcctttt atttgctggg gttatcagat cccccccgaca    2280
cgtttaatta atgctttctc cgccggagat cgacgcacag gcttctgtgt ctatgatgtt    2340
atttcttaat aatcatccag gtattctctt tatcaccata cgtagtgcga gtgtccacct    2400
taacgcaggg cttccgtca cagcgcgata tgtcagccag cggggctttc ttttgccaga    2460
ccgcttccat cctctgcatt tcagcaatct ggctataccc gtcattcata aaccacgtaa    2520
atgccgtcac gcaggaagcc aggacgaaga atatcgtcag tacaagataa atcgcggatt    2580
tccacgtata gcgtgacatc tcacgacgca tttcatggat catcgctttc gccgtatcgg    2640
cagcctgatt cagcgcttct gtcgccggtt tctgctgtgc taatccggct tgtttcagtt    2700
ctttctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagccttta tccggcttct gtcgtatctg ttcggcgagt cgctgtcgtt    3000
cttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctctttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc gcgtccggct    3600
ctttggtgtt agcccgtttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact cccttgtgctc aaggtcggag tcttttttcac    3960
gggcatactt tccctcacgc gcaatataat cggcatgagg agaggcactg cctttttccgc    4020
cggttttttac gctgagatga taggatgcca tcgtgtttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
```

```
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt taccccccatt cactgccaga   4800
gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg ggatctattc tttttatctt    5040
tttttattct ttctttattc tataaattat aaccacttga atataaacaa aaaaaacaca    5100
caaaggtcta gcggaattta cagagggtct agcagaattt acaagttttc cagcaaaggt    5160
ctagcagaat ttacagatac ccacaactca aggaaaagg actagtaatt atcattgact      5220
agcccatctc aattggtata gtgattaaaa tcacctagac caattgagat gtatgtctga    5280
attagttgtt ttcaaagcaa atgaactagc gattagtcgc tatgacttaa cggagcatga    5340
aaccaagcta attttatgct gtgtggcact actcaacccc acgattgaaa accctacaag    5400
gaaagaacgg acggtatcgt tcacttataa ccaatacgct cagatgatga acatcagtag    5460
ggaaaatgct tatggtgtat tagctaaagc aaccagagag ctgatgacga gaactgtgga    5520
aatcaggaat cctttggtta aaggctttga gattttccag tggacaaact atgccaagtt    5580
ctcaagcgaa aaattagaat tagttttttag tgaagagata ttgccttatc ttttccagtt   5640
aaaaaaattc ataaaatata atctggaaca tgttaagtct tttgaaaaca aatactctat    5700
gaggatttat gagtggttat taaaagaact aacacaaaag aaaactcaca aggcaaatat    5760
agagattagc cttgatgaat ttaagttcat gttaatgctt gaaaataact accatgagtt    5820
taaaaggctt aaccaatggg ttttgaaacc aataagtaaa gatttaaaca cttacagcaa    5880
tatgaaattg gtggttgata agcgaggccg cccgactgat acgttgattt tccaagttga    5940
actagataga caaatggatc tcgtaaccga acttgagaac aaccagataa aaatgaatgg    6000
tgacaaaata ccaacaacca ttacatcaga ttcctaccta cgtaacggac taagaaaaac    6060
actacacgat gctttaactg caaaaattca gctcaccagt tttgaggcaa aattttttgag   6120
tgacatgcaa agtaagcatg atctcaatgg ttcgttctca tggctcacgc aaaaacaacg    6180
aaccacacta gagaacatac tggctaaata cggaaggatc tgaggttctt atggctcttg    6240
tatctatcag tgaagcatca agactaacaa acaaaagtag aacaactgtt caccgttaga    6300
tatcaaaggg aaaactgtcc atatgcacag atgaaaacgg tgtaaaaaag atagatacat    6360
cagagctttt acgagttttt ggtgcattta agctgttca ccatgaacag atcgacaatg     6420
taacagatga acagcatgta acacctaata gaacaggtga aaccagtaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg gagccagtga    6600
cgcctcccgt ggggaaaaaa tcatggcaat tctggaagaa atagcgcttt cagccggcaa    6660
acctgaagcc ggatctgcga ttctgataac aaactagcaa caccagaaca gcccgtttgc    6720
gggcagcaaa accgtacttt tggacgttc cggcggtttt ttgtggcgag tggtgttcgg     6780
gcggtgcgcg caagatccat tatgttaaac gggcgagttt acatctcaaa accgcccgct    6840
taacaccatc agaaatcctc agcgcgattt taagcaccaa ccccccccccg taacacccaa   6900
atccatactg aaagtggctt tgttgaataa atcgaacttt tgctgagttg aaggatcaga    6960
```

```
tcacgcatcc tcccgacaac acagaccatt ccgtggcaaa gcaaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca tttttgccct gatgaacgtt ccgttgcgct    7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga aagcacggca aagagcgccg tcgtatctgg cgaaagttgc    7440
atcttgctgt tgacagcaac acacatgaag ttgtctgtgc agacctgtcg ctgaataacg    7500
tcacggactc agaagccttc ccgggccctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccgggagtaa tgcgcggtgg aaatggacaa    7740
cagattacaa ccgtcgctcg atagcggaaa cggcgatgta ccgggtaaaa cagctgttcg    7800
ggggttcact gacgctgcgt gactacgatg gtcaggttgc ggaggctatg gccctggtac    7860
gagcgctgaa caaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccacctcg agtggcagtg agcgcaacgc aattaatgta    8220
agttagctca ctcattaggc accccaggct tgacacttta tgcttccggc tcgtataatg    8280
tgtggaattg tgagcggata caataacaa tttcacacag gatctaggaa ccaaggagag    8340
tggcatatga ctagcgatgt acatgacgcg actgacggtg tgacagagac agcattagat    8400
gacgagcaaa gcacccgtcg cattgcgaaa ctgtatgcaa cggatccgga gtttgcagct    8460
gccgcaccgc tgccggctgt tgtcgacgct gcacataaac cgggtctgcg tctggcggag    8520
attctgcaga ccctgtttac cggttacggc gatcgtccgg ccctgggcta ccgtgctcgt    8580
gaactggcga cggatgaggg tggccgtacc gtgacccgtt tgttgccgcg ttttgacacg    8640
ctgacgtacg cgcaagtctg gagccgtgtc caggctgtgg cagcagcgct gcgccataac    8700
ttcgcgcagc ctatctatcc aggtgacgcg gttgcgacca tcggctttgc aagcccagac    8760
tatctgacgc tggatctggt ctgcgcgtat ttgggcctgg tcagcgtgcc actgcagcac    8820
aacgctcctg tgagccgttt ggcgccgatt ctggccgagg ttgagccgcg tatcctgacg    8880
gtcagcgccg aataccgga cctggcggtc gagagcgtgc gtgatgtgaa ttctgtctcg    8940
caattggtcg ttttcgacca ccacccggaa gtcgatgacc accgcgatgc gctggcacgc    9000
gcacgtgaac agctggccgg taaaggtatt gccgttacga ctctggacgc gattgcggac    9060
gaaggcgctg gtctgccagc ggagccgatc tataccgccg atcacgatca acgcctggcg    9120
atgatcctgt acaccagcgg ttctaccggc gctccgaagg gtgcgatgta tactgaggcc    9180
atgctggcgc gtctgtggac catgtccttt atcaccggcg acccgactcc tgtgattaat    9240
gtgaacttta tgccgctgaa tcacctgggt ggtcgtattc cgattagcac cgcggtccag    9300
```

```
aacggcggta cgagctactt cgttccggag agcgacatgt ctaccctgtt tgaggacctg      9360
gccttggttc gcccgacgga actgggtctg gttccgcgtg tggcggacat gttgtaccag      9420
catcacctgg caactgttga ccgtctggtt acccagggcg cagacgagct gaccgcagag      9480
aagcaggcag gcgcagaact gcgtgaacag gtgctgggcg gtcgtgtgat taccggcttc      9540
gtgagcacgg cgccactggc ggctgagatg cgtgccttcc tggatatcac gctgggtgcc      9600
cacatcgttg atggttacgg tttgaccgaa accggtgcgg tgacgcgtga tggcgttatc      9660
gtccgtccgc cggtcattga ttacaagctg attgatgttc cagagctggg ctacttcagc      9720
accgataaac cgtacccacg tggcgaactg ttggttcgta gccaaacgtt gaccccgggt      9780
tactataaac gtccggaagt taccgcatcg gtgtttgatc gcgacggcta ttaccatacc      9840
ggtgacgtta tggcagaaac cgctccagat cacctggtat atgtggaccg ccgcaataac      9900
gttctgaaac tggcgcaggg tgaatttgtc gcagtcgcaa acctggaagc cgttttcagc      9960
ggtgccgcgc tggttcgcca aatcttcgtg tacggcaaca gcgagcgcag cttcctgttg     10020
gcggtggtgg tgccgacgcc agaagccctg gaacaatacg atccggcagc cctgaaggcg     10080
gccttggcag atagcctgca gcgcacggct cgtgatgcgg agctgcaatc gtatgaagtt     10140
ccggccgatt tcattgtgga aaccgagccg ttcagcgccg caaatggtct gttgagcggt     10200
gtcggcaagt tgctgcgtcc gaacctgaaa gatcgttatg gtcaacgtct ggagcaaatg     10260
tatgccgata ttgccgcgac ccaggcgaat cagctgcgcg agctgcgtcg tgccgcagcc     10320
acccagccgg tgattgatac cctgacgcag gctgctgcga cgattttggg taccggtagc     10380
gaagtggcgt ctgatgccca ctttacggat ctggtggcg acagcctgtc cgctctgacc      10440
ttgtccaatt tgctgagcga tttctttggt tttgaggttc cggttggtac cattgttaac     10500
ccggcgacta atctggcgca gctggcacag cacatcgaag cacagcgcac cgccggtgac     10560
cgccgtccga gctttaccac ggtgcatggt gcggacgcga cggaaattcg tgcgagcgaa     10620
ctgaccctgg ataagtttat tgacgcagaa accctgcagg cagcaccagg cctgccgaag     10680
gtgaccaccg agccgcgcac cgtcctgctg agcggtgcca atggttggtt gggtcgcttc     10740
ctgaccctgc aatggctgga acgtctggcg cctgttggtg gtacgctgat caccattgtc     10800
cgcggtcgtg acgacgctgc ggctcgtgct cgcctgaccc aagcttacga caccgaccca     10860
gagttgtctc gccgcttcgc agaactggcg gaccgccatc tgcgtgttgt agcaggcgat     10920
atcggtgatc gaatctgggg cctgacccca gaaatctggc accgtctggc tgctgaggtg     10980
gatttggttg tgcatccagc ggcgttggtg aaccacgtct gccgtatcg tcagctgttc      11040
ggcccgaacg tcgtgggcac cgccgaagtg attaagctgg cgctgacgga gcgcatcaag     11100
ccagttacct acctgagcac cgtcagcgtt gcaatgggta tcccggactt tgaagaggat     11160
ggtgatatcc gtaccgtttc ccctgttcgt ccgctggacg gcggctatgc taatggctac     11220
ggcaactcta gtgggctgg tgaggtcctg ctgcgtgagg cccacgacct gtgtggcctg      11280
ccggtggcca cgttccgtag cgacatgatt ttggcacacc cgcgctaccg tggtcaggtt     11340
aatgtgccgg atatgttcac tcgtctgttg ttgtcgctgc tgatcactgg cgtggctccg     11400
cgctcttct acattggtga tggtgaacgt cctcgtgcgc attatccggg tctgactgtc     11460
gactttgtgg ccgaggccgt gacgaccctg ggtgcacagc agcgtgaagg ctacgttagc     11520
tacgatgtca tgaacccgca tgacgatggc atcagcctgg atgttttcgt ggactggctg     11580
atccgcgcag gccatccgat tgaccgtgtg gacgattacg acgattgggt gcgtcgcttc     11640
gagactgcac tgacggcgct gccggaaaaa cgtcgcgcac aaaccgttct gccgttgctg     11700
```

```
cacgcgttcc gtgccccgca agcgccgctg cgtggtgccc cggagccaac cgaggttttc   11760
catgcggcgg ttcgtaccgc aaaagtcggt ccaggcgaca ttccgcactt ggatgaagcg   11820
ctgattgata agtacatccg tgatctgcgt gagtttggcc tgatctaata agagaaggag   11880
ttctatcatg attgaaacca tcttaccagc cggcgtcgaa tcagcagagt tacttgagta   11940
ccctgaagat ctgaaggcgc atccggctga agagcatctg atcgcaaaga gcgtagagaa   12000
gcgtcgtcgc gacttcattg gcgcacgtca ttgcgcccgt ctggcactgg cggagctggg   12060
tgaaccgccg gttgcgattg caagggtga acgtggtgcg ccgatttggc cgcgtggtgt   12120
cgtgggctct ctgacccatt gcgatggcta tcgcgcagcg gcggttgctc acaaaatgcg   12180
ttttcgcagc atcggcatcg acgccgaacc gcacgcgacc ctgccggaag gtgtcctgga   12240
ttcggttagc ctgccgcctg agcgtgagtg gctgaaaacc accgacagcg cactgcacct   12300
ggaccgtttg ctgttttgtg cgaaagaagc aacttacaaa gcgtggtggc cgctgacggc   12360
acgttggctg ggtttcgaag aagcgcacat taccttcgaa atcgaggatg gtagcgccga   12420
ctctggtaat ggcacgtttc acagcgaact gctggtgccg ggtcagacca atgacggtgg   12480
taccccgctg ctgtctttcg acggtcgctg gctgatcgct gatggcttca tcctgacggc   12540
gattgcatac gcatgataaa ttaacctagg ctgctgccac cgctgagcaa taactagcat   12600
aaccccttgg ggcctctaaa cgggtcttga ggggttttt gcctgagtg accccagccg   12660 cccctcatgc caaccgagcc cattaagcgc agagtcggcc gcaactatct cggggacgca   12720
taaacacgca gcgatttacc aaggagttcg gctaggtcaa tccgcaattc cctttgcctg   12780
gccggagatg ccgcgagcaa acaatgtgtc cggtcgctac cagatggact ttgtgggcgg   12840
aggattgcac cagacgcttc agcgcagcgt cgtacgatga atcggaaggc ccggtaagca   12900
attgaagaac cgctgaccac ctcccatccg acaatgcaag ggtgccccgc tcccagcgcg   12960
acacggttgc ctgatccaca cccattaatt cagctaggtg actttgcttc atatgacgaa   13020
gcaaccgcgc cctccgcacc tgccgccccc tgtcattcgt caacattctt cagcacctca   13080
atgtcgttcg tagtgagcct cattttttca agaccgccga tgatgagagc caggcctcgc   13140
tcgaatgccg cgtccggacc gccttcgtag acgattttca tcgcgctctg taggcgcgcc   13200
ggcatcgtag acgctgaggt ggtcaactga tcttcgcccc gctcctcggc gtctgcctcg   13260
ctagcttgct gctcaagaac agcgccgacg gtgaagtagc tgattgccat caacgcatag   13320
gtcgcgtcac ctgccgaaaa gccagcatcg caaaggaagc gaagctgcgc gtcggcttt   13380 tccatctgcg gcgcggctgg ccgcgtcccg gcatgaatac gcgcgccatc gcgataagcc   13440
agcaacgccc gtcgaaaact gcatgcattg cccttcagga acgaacgcca gtcgtcgtca   13500
tcccttggcg tcgaatgcgt gtgatttatc gtcagcatgg cttcggcaag tgcgtcgagc   13560
aacgcacgct tgttcttgaa atgccagtag agcgctggct gttgcacccc gaggcgctca   13620
gccagtcggc gcgtcgttag accttccatg cccacgtcgt taagcagttc gagcgcggtt   13680
cggatcacgg cctcgcgttg gagcttgttc attcgcgaa                          13719
```

<210> SEQ ID NO 19
<211> LENGTH: 13785
<212> TYPE: DNA
<213> ORGANISM: Artificial Sequence
<220> FEATURE:
<223> OTHER INFORMATION: vector

<400> SEQUENCE: 19

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360
cacacccgtc ctgtggatcc tctacgccgg acgcatcgtg gccggcatca ccggcgccac     420
aggtgcggtt gctggcgcct atatcgccga catcaccgat ggggaagatc gggctcgcca     480
cttcgggctc atgagcgctt gtttcggcgt gggtatggtg gcaggccccg tggccggggg     540
actgttgggc gccatctcct tgcatgcacc attccttgcg gcggcggtgc tcaacgcct      600
caacctacta ctgggctgct tcctaatgca ggagtcgcat aagggagagc gtcgaccgat     660
gcccttgaga gccttcaacc cagtcagctc cttccggtgg gcgcggggca tgactatcgt     720
cgccgcactt atgactgtct tctttatcat gcaactcgta ggacaggtgc cggcagcgct     780
ctgggtcatt ttcggcgagg accgctttcg ctggagcgcg acgatgatcg gcctgtcgct     840
tgcggtattc ggaatcttgc acgccctcgc tcaagccttc gtcactggtc ccgccaccaa     900
acgtttcggc gagaagcagg ccattatcgc cggcatggcg gccgacgcgc tgggctacgt     960
cttgctggcg ttcgcgacgc gaggctggat ggccttcccc attatgattc ttctcgcttc    1020
cggcggcatc gggatgcccg cgttgcaggc catgctgtcc aggcaggtag atgacgacca    1080
tcagggacag cttcaaggat cgctcgcggc tcttaccagc ctaacttcga tcactggacc    1140
gctgatcgtc acggcgattt atgccgcctc ggcgagcaca tggaacgggt tggcatggat    1200
tgtaggcgcc gccctatacc ttgtctgcct ccccgcgttg cgtcgcggtg catggagccg    1260
ggccacctcg acctgaatgg aagccggcgg cacctcgcta acggattcac cactccaaga    1320
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
ggttgcctta ctggttagca gaatgaatca ccgatacgcg agcgaacgtg aagcgactgc    1560
tgctgcaaaa cgtctgcgac ctgagcaaca acatgaatgg tcttcggttt ccgtgtttcg    1620
taaagtctgg aaacgcggaa gtcccctacg tgctgctgaa gttgcccgca acagagagtg    1680
gaaccaaccg gtgataccac gatactatga ctgagagtca acgccatgag cggcctcatt    1740
tcttattctg agttacaaca gtccgcaccg ctgccggtag ctacttgact atccggctgc    1800
actagccctg cgtcagatgg ctctgatcca aggcaaactg ccaaaatatc tgctggcacc    1860
ggaagtcagc gccctgcacc attatgttcc ggatctgcat cgcaggatgc tgctggctac    1920
cctgtggaac acctacatct gtattaacga agcgctggca ttgaccctga gtgattttc     1980
tctggtgccg cccatccct ttgtgcagct tgccacgctc aaagggggttt gaggtccaac    2040
cgtacgaaaa cgtacggtaa gaggaaaatt atcgtctgaa aaatcgatta gtagacaaga    2100
aagtccgtta agtgccaatt ttcgattaaa aagacaccgt tttgatggcg ttttccaatg    2160
tacattatgt ttcgatatat cagacagtta cttcactaac gtacgttttc gttctattgg    2220
ccttcagacc ccatatcctt aatgtccttt atttgctggg ttatcagat cccccgaca     2280
cgtttaatta atgctttctc cgccggagat cgacgcacag gcttctgtgt ctatgatgtt    2340
atttcttaat aatcatccag gtattctctt tatcaccata cgtagtgcga gtgtccacct    2400
```

```
taacgcaggg ctttccgtca cagcgcgata tgtcagccag cggggctttc ttttgccaga    2460
ccgcttccat cctctgcatt tcagcaatct ggctataccc gtcattcata aaccacgtaa    2520
atgccgtcac gcaggaagcc aggacgaaga atatcgtcag tacaagataa atcgcggatt    2580
tccacgtata gcgtgacatc tcacgacgca tttcatggat catcgctttc gccgtatcgg    2640
cagcctgatt cagcgcttct gtcgccggtt tctgctgtgc taatccggct tgtttcagtt    2700 cttctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagccttta tccggcttct gtcgtatctg ttcggcgagt cgctgtcgtt    3000
ctttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgccttt ttgcgccacc cgtgtccggct    3600 ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg acggtttat    3900 gcgctgccca cgccggcata ttgccggact ccttgtgctc aaggtcggag tctttttcac    3960
gggcatactt tccctcacgc gcaatataat cggcatgagg agaggcactg ccttttccgc    4020 cggttttac gctgagatga taggatgcca tcgtgtttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg gcagcagaa agagtgcagt    4260 atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680 agaccccgcca taaaacgccc tgagaagccc gtgacgggct tttcttgtat tatgggtagt    4740
```

| | |
|---|---|
| ttccttgcat gaatccataa aaggcgcctg tagtgccatt taccccccatt cactgccaga | 4800 |
| gccgtgagcg cagcgaactg aatgtcacga aaaagacagc gactcaggtg cctgatggtc | 4860 |
| ggagacaaaa ggaatattca gcgatttgcc cgagcttgcg agggtgctac ttaagccttt | 4920 |
| agggttttaa ggtctgtttt gtagaggagc aaacagcgtt tgcgacatcc ttttgtaata | 4980 |
| ctgcggaact gactaaagta gtgagttata cacagggctg ggatctattc tttttatctt | 5040 |
| tttttattct ttctttattc tataaattat aaccacttga atataaacaa aaaaacaca | 5100 |
| caaaggtcta gcggaattta cagagggtct agcagaattt acaagttttc cagcaaaggt | 5160 |
| ctagcagaat ttacagatac ccacaactca aaggaaaagg actagtaatt atcattgact | 5220 |
| agcccatctc aattggtata gtgattaaaa tcacctagac caattgagat gtatgtctga | 5280 |
| attagttgtt ttcaaagcaa atgaactagc gattagtcgc tatgacttaa cggagcatga | 5340 |
| aaccaagcta attttatgct gtgtggcact actcaacccc acgattgaaa accctacaag | 5400 |
| gaaagaacgg acggtatcgt tcacttataa ccaatacgct cagatgatga acatcagtag | 5460 |
| ggaaaatgct tatggtgtat tagctaaagc aaccagagag ctgatgacga aactgtggaa | 5520 |
| aatcaggaat cctttggtta aaggctttga gattttccag tggacaaact atgccaagtt | 5580 |
| ctcaagcgaa aaattagaat tagttttttag tgaagagata ttgccttatc ttttccagtt | 5640 |
| aaaaaaattc ataaaatata atctggaaca tgttaagtct tttgaaaaca aatactctat | 5700 |
| gaggatttat gagtggttat taaaagaact aacacaaaag aaaactcaca aggcaaatat | 5760 |
| agagattagc cttgatgaat ttaagttcat gttaatgctt gaaaataact accatgagtt | 5820 |
| taaaaggctt aaccaatggg ttttgaaacc aataagtaaa gatttaaaca cttacagcaa | 5880 |
| tatgaaattg gtggttgata agcgaggccg cccgactgat acgttgattt ccaagttga | 5940 |
| actagataga caaatggatc tcgtaaccga acttgagaac aaccagataa aaatgaatgg | 6000 |
| tgacaaaata ccaacaacca ttacatcaga ttcctaccta cgtaacggac taagaaaaac | 6060 |
| actacacgat gctttaactg caaaaattca gctcaccagt tttgaggcaa aattttttgag | 6120 |
| tgacatgcaa agtaagcatg atctcaatgg ttcgttctca tggctcacgc aaaaacaacg | 6180 |
| aaccacacta gagaacatac tggctaaata cggaaggatc tgaggttctt atggctcttg | 6240 |
| tatctatcag tgaagcatca agactaacaa acaaaagtag aacaactgtt caccgttaga | 6300 |
| tatcaaaggg aaaactgtcc atatgcacag atgaaaacgg tgtaaaaaag atagatacat | 6360 |
| cagagctttt acgagttttt ggtgcattta agctgttca ccatgaacag atcgacaatg | 6420 |
| taacagatga acagcatgta acacctaata gaacaggtga aaccagtaaa acaaagcaac | 6480 |
| tagaacatga aattgaacac ctgagacaac ttgttacagc tcaacagtca cacatagaca | 6540 |
| gcctgaaaca ggcgatgctg cttatcgaat caaagctgcc gacaacacgg gagccagtga | 6600 |
| cgcctcccgt ggggaaaaaa tcatggcaat tctggaagaa atagcgcttt cagccggcaa | 6660 |
| acctgaagcc ggatctgcga ttctgataac aaactagcaa caccagaaca gcccgtttgc | 6720 |
| gggcagcaaa accgtactt ttggacgttc cggcggtttt ttgtggcgag tggtgttcgg | 6780 |
| gcggtgcgcg caagatccat tatgttaaac gggcgagttt acatctcaaa accgcccgct | 6840 |
| taacaccatc agaaatcctc agcgcgattt aagcaccaa ccccccccg taacacccaa | 6900 |
| atccatactg aaagtggctt tgttgaataa atcgaacttt gctgagttg aaggatcaga | 6960 |
| tcacgcatcc tcccgacaac acagaccatt ccgtggcaaa gcaaaagttc agaatcacca | 7020 |
| actggtccac ctacaacaaa gctctcatca accgtggctc cctcactttc tggctggatg | 7080 |
| atgaggcgat tcaggcctgg tatgagtcgg caacaccttc atcacgagga aggccccagc | 7140 |

```
gctattctga tctcgccatc accaccgttc tggtgattaa acgcgtattc cggctgaccc    7200
tgcgggctgc gcagggtttt attgattcca tttttgccct gatgaacgtt ccgttgcgct    7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga aagcacggca agagcgccg tcgtatctgg cgaaagttgc     7440
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccggagtaa tgcgcggtgg aaatggacaa     7740
cagattacaa ccgtcgctcg atagcggaaa cggcgatgta ccgggtaaaa cagctgttcg    7800
ggggttcact gacgctgcgt gactacgatg gtcaggttgc ggaggctatg gccctggtac    7860
gagcgctgaa caaaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccacctcg cacctggtgt ttaaacggat ttaaattgca    8220
ggggcagtga gcgcaacgca attaatgtaa gttagctcac tcattaggca ccccaggctt    8280
gacactttat gcttccggct cgtataatgt gtggaattgt gagcggataa caataacaat    8340
ttaaatcagg atctaggaac caaggagagt ggcatatgag cactgcaatt cacgatgaac    8400
acttggatcg ccgcattgaa gaactgattg caaacgatcc gcaattcgct gcggcacgcc    8460
cggacccggc gattaccgca gcgaccgagg ccccaggtct gcgtctgccg cagatcatcc    8520
gtacggtcct ggacggttat gccgatcgtc cggcgctggc gcaacgcgtg gttgaattcg    8580
ttaccgacgc caaaaccggt cgtaccaccg cagagttgct gccacgtttt gaaaccatca    8640
cgtacggtga gctgggtgag cgtgtgagcg cactgggtcg cgcatgggcc ggtgacgccg    8700
tgcgccctgg cgaccgcgtt tgcgtcctgg gtttcaactc cgtggattac gcgacgattg    8760
acatcgcgct gggtaccatc ggtgcggtga gcgtgccgct gcaaaccagc gcagcgatta    8820
gcagcctgca gccgattgtg gcggaaaccg agccgagcct gattgcgagc agcgtgaatc    8880
agctgccgga cgccgtcgag ctgattctgg caggtgacca tgttccgggt aagctggtcg    8940
tatttgatta tcaaccgcaa gttgatgacc agcgtgaggc ggttgaggca gcggctgcgc    9000
gcctggcaga cagcggcgtc gcagtggaag cgctggcgga tgttctgcgt cgtggtaaag    9060
acctgccggc agttgaaccg ccagcgtccg atgaggatag cctggctctg ttgatttaca    9120
cctctggcag caccggtgcg ccgaagggcg cgatgtaccc gcagagcaac gtgggtaaaa    9180
tgtggcgtcg cggtagcaag aactggtttg gtgagagcgc cgcaagcatc accctgaatt    9240
tcatgccgat gagccatgtt atgggtcgcg gtattttgta tggcacgttg ggtaacggcg    9300
gcaccgcgta tttcgcggct cgtagcgatt tgtctacgct gctggaagat ctggagttgg    9360
tgcgccctac ggagatgaat tttgtcccgc gtatttggga aacgctgtat ggtgagttcc    9420
agcgtcaggt ggagcgccgt ctggcggacg gtgacgctgg cccggaagcc cgtgaaaccg    9480
```

```
tcgaggcggc agtgctggaa gagcagcgtc aatatctgct gggtggccgt tttatcttcg   9540
ccatgaccgg ctctgcgccg acgagcccgg agctgaaagc atgggcggag agcttgctgc   9600
aaatgcacct gatggacggt tacggcagca ccgaggcggg catggtgctg ttcgacggtg   9660
agatccagcg tccgccggtc atcgattaca aactggtgga tgtcccggat ctgggttact   9720
tttcgacgga ccgtccgcat ccgcgtggtg agctgttgct gcgtaccgag aacatgttcc   9780
cgggttacta taaacgcgcg gaaaccaccg caaatgtttt cgacgaggat ggttactacc   9840
gcaccggcga tgtgttcgcg gagatcgcac cggaccgttt ggtttacgtc gatcgtcgca   9900
ataacgtctt gaaactggcc cagggtgagt ttgtaaccct ggccaaactg gaagcggttt   9960
tcggtaactc gccgctgatc cgccagatct acgtgtacgg caacagcagc cagccgtacc  10020
tgctggcggt ggtggtcccg accgaagagg cgctggccga taatgacttg gaaagcttga  10080
agccgaaaat cgcagactcc ctgcaaaaag ttgcaaaaga aactggcctg cagtcctatg  10140
aggttccgcg tgatttcatc atcgagacta cgccgttcac cctggagaac ggtttgctga  10200
ccggcattcg taagctggcg tggcctaagc tgaaggccca ctatgcgat cgtctggagc  10260 aaatgtacgc tgagctggct gcgggtcagg cgaatgagct ggcggagctg cgccgtagcg  10320
gtgcggcagc gccggtggcc cagaccgtgt cccgcgcagc agcggcgctg ctgggcgctg  10380
ctgctggtga tctgagcgcg gatgcccact ttactgacct gggtggtgat tccctgtccg  10440
cactgacctt tggtaacctg ctgcgtgaga ttttgacgt cgatgttccg gttggcgtta  10500
ttgtctcccc tgctaacgac ttggcgggca ttgccgcata cattgaagca gagcgtcaag  10560
gtagcaaacg tccgacgttc gcagcagtgc atggtcgcgg tgccacgatg gtgcatgcga  10620
gcgacttgac tctggataag tttctggacg aagccaccct ggcagcagcc ccaagcctgc  10680
cgaaaccggc gacggaagtt cgtacggttc tgctgaccgg tgcgacgggt tttctgggcc  10740
gttatctggc actggactgg ctggagcgca tggatatggt tgacggcaaa gttattgcgc  10800
tggtccgtgc gcgcaccgat gaagaagcgc gtgcgcgttt ggacaagacg tttgacagcg  10860
gcgacccgaa actgctggct cactaccaac gtctggcagc ggaccacttg aagttatcg  10920 cgggtgacaa aggtgaggct aatctgggct tggacccgca aacctggcag cgtctggccg  10980
aagaagtgga cgtgatcgtt gacccggcag cgctggtgaa ccatgtcctg ccgtactctg  11040
aattgtttgg cccgaacgca ctgggcacgg ccgaactgat ccgcatcgcg ctgacctcta  11100
agcaaaaacc gtatacgtat gttagcacca ttggtgttgg cgatcagatt caaccgggtg  11160
agttcgttga aaatgctgat atccgtcaga tcagcgcgac gcgtgagatc aacgatggct  11220
acgctaatgg ttatggcaat agcaagtggg cgggtgaggt tctgctgcgc gaggcgcacg  11280
acctgtgtgg cctgccggtc accgtgttcc gttgcgatat gatcctggct gacaccacgt  11340
acgctggcca gctgaatctg ccggacatgt ttacccgttt gatgctgagc ctggtcgcga  11400
ccggtatcgc accgggcagc ttttacgaac tggacacgga tggcaatcgc cagcgtgtcc  11460
actatgatgg tctgccagtc gagttcattg ctgcggccat cagcacccctg gcacccaaa  11520 tcacggatag cgacaccggt ttccagactt atcatgtaat gaatccatac gatgacggta  11580
ttggtctgga tgagtacatt gactggctga ttgaggctgg ttacagcatc gaacgtattg  11640
cggactatag cgaatggctg cgtcgcttcg aaacgtcgct gcgtgccctg cctgaccgtc  11700
aacgccagta ttcgctgctg ccgctgttgc acaattatca aaagccggag aagccgatta  11760
acggtagcat ggcgccaact gatgtctttc gtgcagccgt tcaagaagcg aagatcggtc  11820
cggataagga cattccgcac gtctctgcgc cggtgattgt caagtacatc accgacctgg  11880
```

```
agctgctggg tttgctgtaa taagtttaaa cagagaagga gttctatcat gattgaaacc   11940
atcttaccag ccggcgtcga atcagcagag ttacttgagt accctgaaga tctgaaggcg   12000
catccggctg aagagcatct gatcgcaaag agcgtagaga agcgtcgtcg cgacttcatt   12060
ggcgcacgtc attgcgcccg tctggcactg gcggagctgg gtgaaccgcc ggttgcgatt   12120
ggcaagggtg aacgtggtgc gccgatttgg ccgcgtggtg tcgtgggctc tctgacccat   12180
tgcgatggct atcgcgcagc ggcggttgct cacaaaatgc gttttcgcag catcggcatc   12240
gacgccgaac cgcacgcgac cctgccggaa ggtgtcctgg attcggttag cctgccgcct   12300
gagcgtgagt ggctgaaaac caccgacagc gcactgcacc tggaccgttt gctgttttgt   12360
gcgaaagaag caacttacaa agcgtggtgg ccgctgacgg cacgttggct gggtttcgaa   12420
gaagcgcaca ttccttcga aatcgaggat ggtagcgccg actctggtaa tggcacgttt   12480
cacagcgaac tgctggtgcc gggtcagacc aatgacggtg gtaccccgct gctgtctttc   12540
gacggtcgct ggctgatcgc tgatggcttc atcctgacgg cgattgcata cgcatgataa   12600
attaacctag gctgctgcca ccgctgagca ataactagca taaccccttg gggcctctaa   12660
acgggtcttg aggggttttt tgctgaaacc tcaggcattt gagaagccct cgagtgaccc   12720
cagccgcccc tcatgccaac cgagcccatt aagcgcagag tcggccgcaa ctatctcggg   12780
gacgcataaa cacgcagcga tttaccaagg agttcggcta ggtcaatccg caattccctt   12840
tgcctggccg gagatgccgc gagcaaacaa tgtgtccggt cgctaccaga tggactttgt   12900
gggcggagga ttgcaccaga cgcttcagcg cagcgtcgta cgatgaatcg gaaggcccgg   12960
taagcaattg aagaaccgct gaccacctcc catccgacaa tgcaagggtg ccccgctccc   13020
agcgcgacac ggttgcctga tccacaccca ttaattcagc taggtgactt tgcttcatat   13080
gacgaagcaa ccgcgccctc cgcacctgcc gcccctgtc attcgtcaac attcttcagc    13140
acctcaatgt cgttcgtagt gagcctcatt ttttcaagac cgccgatgat gagagccagg   13200
cctcgctcga atgccgcgtc cggaccgcct tcgtagacga ttttcatcgc gctctgtagg   13260
cgcgccggca tcgtagacgc tgaggtggtc aactgatctt cgccccgctc ctcggcgtct   13320
gcctcgctag cttgctgctc aagaacagcg ccgacggtga agtagctgat tgccatcaac   13380
gcataggtcg cgtcacctgc cgaaaagcca gcatcgcaaa ggaagcgaag ctgcgcgtcg   13440 gcttttcca tctgcggcgc ggctggccgc gtcccggcat gaatacgcgc gccatcgcga    13500
taagcgagca acgcccgtcg aaaactgcat gcattgccct tcaggaacga acgccagtcg   13560
tcgtcatccc ttggcgtcga atgcgtgtga tttatcgtca gcatggcttc ggcaagtgcg   13620
tcgagcaacg cacgcttgtt cttgaaatgc cagtagagcg ctggctgttg caccccgagg   13680
cgctcagcca gtcggcgcgt cgttagacct tccatgccca cgtcgttaag cagttcgagc   13740
gcggttcgga tcacggcctc gcgttggagc ttgttcattc gcgaa                   13785
```

<210> SEQ ID NO 20
<211> LENGTH: 13731
<212> TYPE: DNA
<213> ORGANISM: Artificial Sequence
<220> FEATURE:
<223> OTHER INFORMATION: vector

<400> SEQUENCE: 20

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
```

```
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacaccgtc ctgtggatcc tctacgccgg acgcatcgtg gccggcatca ccggcgccac     420
aggtgcggtt gctggcgcct atatcgccga catcaccgat ggggaagatc gggctcgcca    480
cttcgggctc atgagcgctt gtttcggcgt gggtatggtg gcaggccccg tggccggggg    540
actgttgggc gccatctcct tgcatgcacc attccttgcg gcggcggtgc tcaacgcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc    1020
cggcggcatc gggatgcccg cgttgcaggc catgctgtcc aggcaggtag atgacgacca    1080
tcagggacag cttcaaggat cgctcgcggc tcttaccagc ctaacttcga tcactggacc    1140
gctgatcgtc acggcgattt atgccgcctc ggcgagcaca tggaacgggt tggcatggat    1200
tgtaggcgcc gccctatacc ttgtctgcct ccccgcgttg cgtcgcggtg catggagccg    1260
ggccacctcg acctgaatgg aagccggcgg cacctcgcta acggattcac cactccaaga    1320
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
ggttgcctta ctggttagca gaatgaatca ccgatacgcg agcgaacgtg aagcgactgc    1560
tgctgcaaaa cgtctgcgac ctgagcaaca acatgaatgg tcttcggttt ccgtgtttcg    1620
taaagtctgg aaacgcggaa gtcccctacg tgctgctgaa gttgcccgca acagagagtg    1680
gaaccaaccg gtgataccac gatactatga ctgagagtca acgccatgag cggcctcatt    1740
tcttattctg agttacaaca gtccgcaccg ctgccggtag ctacttgact atccggctgc    1800
actagccctg cgtcagatgg ctctgatcca aggcaaactg ccaaaatatc tgctggcacc    1860
ggaagtcagc gccctgcacc attatgttcc ggatctgcat cgcaggatgc tgctggctac    1920
cctgtggaac acctacatct gtattaacga agcgctggca ttgaccctga gtgattttc    1980
tctggtgccg ccctatccct tgtgcagct tgccacgctc aaaggggttt gaggtccaac    2040
cgtacgaaaa cgtacggtaa gaggaaaatt atcgtctgaa aaatcgatta gtagacaaga    2100
aagtccgtta agtgccaatt ttcgattaaa aagacaccgt tttgatggcg ttttccaatg    2160
tacattatgt ttcgatatat cagacagtta cttcactaac gtacgttttc gttctattgg    2220
ccttcagacc ccatatcctt aatgtccttt atttgctggg gttatcagat ccccccgaca    2280
cgtttaatta atgctttctc cgccggagat cgacgcacag gcttctgtgt ctatgatgtt    2340
atttcttaat aatcatccag gtattctctt tatcaccata cgtagtgcga gtgtccacct    2400
taacgcaggg ctttccgtca cagcgcgata tgtcagccag cggggctttc ttttgccaga    2460
ccgcttccat cctctgcatt tcagcaatct ggctataccc gtcattcata aaccacgtaa    2520
```

```
atgccgtcac gcaggaagcc aggacgaaga atatcgtcag tacaagataa atcgcggatt    2580
tccacgtata gcgtgacatc tcacgacgca tttcatggat catcgctttc gccgtatcgg    2640
cagcctgatt cagcgcttct gtcgccggtt tctgctgtgc taatccggct tgtttcagtt    2700 cttttctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagcctta tccggcttct gtcgtatctg ttcggcgagt cgctgtcgtt    3000
ctttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc gcgtccggct    3600
ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact ccttgtgctc aaggtcggag tcttttttcac    3960 gggcatactt tccctcacgc gcaatataat cggcatgagg agaggcactg cctttccgc    4020 cggttttttac gctgagatga taggatgcca tcgtgtttta tcccgctgaa gggcgcacgt    4080
ttctgaacga agtgaagaaa gtctaagtgc gccctgataa ataaaagagt tatcaggat    4140 tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt tacccccatt cactgccaga    4800
gccgtgagcg cagcgaactg aatgtcacga aaaagacagc gactcaggtg cctgatggtc    4860
```

```
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg ggatctattc ttttttatctt  5040
tttttattct ttctttattc tataaattat aaccacttga atataaacaa aaaaaacaca   5100
caaaggtcta gcggaattta cagagggtct agcagaattt acaagttttc cagcaaaggt   5160
ctagcagaat ttacagatac ccacaactca aaggaaaagg actagtaatt atcattgact   5220
agcccatctc aattggtata gtgattaaaa tcacctagac caattgagat gtatgtctga   5280
attagttgtt ttcaaagcaa atgaactagc gattagtcgc tatgacttaa cggagcatga   5340
aaccaagcta attttatgct gtgtggcact actcaacccc acgattgaaa accctacaag   5400
gaaagaacgg acggtatcgt tcacttataa ccaatacgct cagatgatga acatcagtag   5460
ggaaaatgct tatggtgtat tagctaaagc aaccagagag ctgatgacga aactgtgga    5520
aatcaggaat cctttggtta aaggctttga gattttccag tggacaaact atgccaagtt   5580
ctcaagcgaa aaattagaat tagttttttag tgaagagata ttgccttatc ttttccagtt  5640
aaaaaaattc ataaaatata atctggaaca tgttaagtct tttgaaaaca aatactctat   5700
gaggatttat gagtggttat taaaagaact aacacaaaag aaaactcaca aggcaaatat   5760
agagattagc cttgatgaat ttaagttcat gttaatgctt gaaataact accatgagtt    5820
taaaaggctt aaccaatggg ttttgaaacc aataagtaaa gatttaaaca cttacagcaa   5880
tatgaaattg gtggttgata agcgaggccg cccgactgat acgttgattt ccaagttga    5940
actagataga caaatggatc tcgtaaccga acttgagaac aaccagataa aaatgaatgg   6000
tgacaaaata ccaacaacca ttacatcaga ttcctaccta cgtaacggac taagaaaaac   6060
actacacgat gctttaactg caaaaattca gctcaccagt tttgaggcaa aattttttgag 6120
tgacatgcaa agtaagcatg atctcaatgg ttcgttctca tggctcacgc aaaaacaacg   6180
aaccacacta gagaacatac tggctaaata cggaaggatc tgaggttctt atggctcttg   6240
tatctatcag tgaagcatca agactaacaa acaaaagtag aacaactgtt caccgttaga   6300
tatcaaaggg aaaactgtcc atatgcacag atgaaaacgg tgtaaaaaag atagatacat   6360
cagagctttt acgagttttt ggtgcattta aagctgttca ccatgaacag atcgacaatg   6420
taacagatga acagcatgta acacctaata gaacaggtga aaccagtaaa acaaagcaac   6480
tagaacatga aattgaacac ctgagacaac ttgttacagc tcaacagtca cacatagaca   6540
gcctgaaaca ggcgatgctg cttatcgaat caaagctgcc gacaacacgg gagccagtga   6600
cgcctcccgt gggggaaaaa tcatggcaat tctggaagaa atagcgcttt cagccggcaa   6660
acctgaagcc ggatctgcga ttctgataac aaactagcaa caccagaaca gcccgtttgc   6720
gggcagcaaa accgtacttt tggacgttc cggcggtttt ttgtggcgag tggtgttcgg    6780
gcggtgcgcg caagatccat tatgttaaac gggcagtttt acatctcaaa accgcccgct   6840
taacaccatc agaaatcctc agcgcgattt aagcaccaa ccccccccg taacacccaa     6900
atccatactg aaagtggctt tgttgaataa atcgaacttt tgctgagttg aaggatcaga   6960
tcacgcatcc tcccgacaac acagaccatt ccgtggcaaa gcaaaagttc agaatcacca   7020
actggtccac ctacaacaaa gctctcatca accgtggctc cctcactttc tggctggatg   7080
atgaggcgat tcaggcctgg tatgagtcgg caacaccttc atcacgagga aggccccagc   7140
gctattctga tctcgccatc accaccgttc tggtgattaa acgcgtattc cggctgaccc   7200
tgcgggctgc gcagggtttt attgattcca tttttgccct gatgaacgtt ccgttgcgct   7260
```

```
gcccggatta caccagtgtc agtaagcggg caaagtcggt taatgtcagt ttcaaaacgt   7320
ccacccgggg tgaaatcgca cacctggtga ttgattccac cgggctgaag gtctttggtg   7380
aaggcgaatg gaaagtcaga aagcacggca aagagcgccg tcgtatctgg cgaaagttgc   7440
atcttgctgt tgacagcaac acacatgaag ttgtctgtgc agacctgtcg ctgaataacg   7500
tcacggactc agaagccttc ccgggcctta tccggcagac tcacagaaaa atcagggcag   7560
ccgcggcaga cggggcttac gatacccggc tctgtcacga tgaactgcgc cgcaaaaaaa   7620
tcagcgcgct tattcctccc cgaaaaggtg cgggttactg gcccggtgaa tatgcagacc   7680
gtaaccgtgc agtggctaat cagcgaatga ccggagtaa tgcgcggtgg aaatggacaa   7740
cagattacaa ccgtcgctcg atagcggaaa cggcgatgta ccgggtaaaa cagctgttcg   7800
ggggttcact gacgctgcgt gactacgatg gtcaggttgc ggaggctatg gcccggtac   7860 gagcgctgaa caaaatgacg aaagcaggta tgcctgaaag cgtgcgtatt gcctgaaaac   7920
acaacccgct acgggggaga cttacccgaa atctgattta ttcaacaaag ccgggtgtgg   7980
tgaactacaa agcagacccg ttgaggttat cagttcgatg cacaatcagc agcgcataaa   8040
atatgcacaa gaacaggagc acccttcgca ttaagctgtg gtggtaacaa gtagtgccgg   8100
gctaccatca gcgagcatga tgcgctccca cagcattcgc cttggcagta tggaagttcc   8160
tcgctccagt tcgggccggt atccacctcg cacctggtgt ttaaacggat ttaaattgca   8220
ggggcagtga gcgcaacgca attaatgtaa gttagctcac tcattaggca ccccaggctt   8280
gacactttat gcttccggct cgtataatgt gtggaattgt gagcggataa caataacaat   8340
ttaaatcagg atctaggaac caaggagagt ggcatatgac gaccgaaacc agagaagatc   8400
gcttacagag acgcattgcc cacctgtacg aggcagacag ccaatttgcg gctgcgcgtc   8460
ctagcgaggc ggtgaatacc gccgtggcgg aaccagagct gcgtctgccg gctgtcgtca   8520
aaggtgtctt tgcgggctat gcggatcgtc cggcgctggg tcaacgcgcc gtggagtatg   8580
ttaccgacgc ggacggtcgt acctctgccc aattgctgcc gcgttttgac acgatcacgt   8640
accgtcaact gggtgaccgc gtccaagcag ttacgaacgc gtggcacaac catccggtca   8700
aacctggcga ccgtgtagcg atcctgggct ttactagcgt tgattacacc accgttgata   8760
cggccctgat cgaattgggc gctgtgagcg tcccgctgca gacttctgca ccggtcacca   8820
cgctgcgccc gatcgtcgca gagacggagc cgaccgtgat tgcggcttct attgatttcc   8880
tggatgatgc ggtggaactg gtcaaaagcg gtccggcacc cgtcgtctg gttgtgttcg   8940 actaccgccc acgtgtcgac gcccagcgcg aggcatttga agcagccaaa gcggcactgg   9000
cgggtactga cgttgtagtt gagccgctgg cggatgtcct ggaccgcggt cgtagcttgg   9060
cggatgcgcc gctgtacacc ccgggtcagc cggacccgct gaccatgctg atttacacga   9120
gcggttccac gggcacccg aagggtgcga tgtatccgga gagcaaagtc gctaacatgt   9180
ggcaactggc gacgaaggcg acgtgggatg agaaccaagc ggcgctgccg gccatcaccc   9240
tgaactttat gccgatgagc catgtgatgg gccgtggcat cctgattggt accctgagca   9300
gcggtggcac cgcatacttc gcggctcgca gcgatctgag caccttcctg gaagatctgg   9360
cattggttcg tccgacccag ttgagctttg ttccgcgtat ttgggatatg ctgttccagg   9420
aatatcagag ccgtctggac cgttctggtg cgccagagga cgaggtgctg gccgaggtcc   9480
gccaagacct gctgggcggt cgtttcgtga gcgcgatgac gggttctgcg ccgattagcg   9540
cggaaatgaa gaattgggtg gaacgtctgc tggacatgca tctgctggaa ggctatggtt   9600
```

```
ccaccgaagc aggctccgtg tttgtggacg gtcatattca acgtccgccg gttattgact    9660
ataaactggt tgatgtcccg gacctgggtt atttcttgac ggaccgtccg catccgcgtg    9720
gcgagctgct ggtgaagagc gagcaaatgt tcccaggtta ctacaagcgt ccggagatta    9780
ccgctgaaat gttcgatgag gatggctact accgcaccgg cgacatcgtg gcggaattgg    9840
gtccggatca agttgagtat ctggaccgtc gtaataacgt tctgaaattg tctcagggtg    9900
agtttgtgac ggttagcaaa ctggaagcgg tgttcggcga cagcccgctg gttcgtcaga    9960
tcttcgttta tggtaacagc gcacgttcct acctgctggc agttgtggtt ccgaccgacc   10020
cgtcgctgag caagcaggcg atcggcgatt cgttgcagga cgcggcacgc gctgcaggtc   10080
tgcaatccta cgagattccg cgtgacttta tcgtcgaaac gacccctttt agcctggaga   10140
acggcctgct gacgggcatt cgcaaactgg ctcgcccaaa cctgaaggcc tactacggcg   10200
atcgtctgga gcagctgtac accgagctgg cagagggcca agcgaatgag ttgagcgagc   10260
tgcgtcgcaa tggcgctcaa gccccggtcc tggataccgt gagccgtgca gcgggtgctc   10320
tgttgggcgc agcggctagc gatctggctc cagaggcgca ttttaccgac ttgggtggcg   10380
atagcttgag cgcgctgacc tttggtaacc tgctgcaaga gatctttgat gtcgaagtcc   10440
cggtgagcgc aattgtttcg ccggcatccg acttgcgtac gatcgcagag tatatcgaag   10500
ctcaacgttc cggcgcagac gtccgcccga ccttcacgtc cgtgcacggt cgcaatgcga   10560
ccgaggtgca tgcgagcgat ttgacgctgg ataagttcat tgatgccgcc acgctggcgg   10620
cagccccgag cctgccgggt ccggtgagcg agattcgcac tgtcttgctg accggtgcga   10680
cgggtttctt gggccgctat ctggcgctgg aatggctgga acgtatggat ctggttgatg   10740
gtaaagtgat ctgcttggtt cgtgcgaaga gcgacgaaga ggcgcgtgcc cgcctggaca   10800
aaactttcga cagcggcgat ccgaagctgt gggcccacta tcagaagctg gcagccgatc   10860
atctggaagt gatcgcgggt gacaaggggtg aggcagacct gggcctggat caggttacct   10920
ggcagcgtct ggcggatacc gtggatttca tcgtggatcc ggcagcgctg gttaatcacg   10980
ttctgcctta tagcgaactg tttggtccga atgctctggg tactgccgag ctgatccgta   11040
ttgcgctgac caccgtatc aaaccgttcg cgtacgtgag cacgatcggc gtgggtggtg   11100
gtatcgagcc gggtaagttc gtcgaggcgg gtgacattcg tgcgatctct cctgtccgtc   11160
gcgttgacga tggttacgca aatggctacg gcaacagcaa atgggccggt gaagtcctgc   11220
tgcgcgaagc ccacgatctg gcgggtctgc cagtgaccgt ttttcgctgt gatatgatct   11280
tggccgacac cacctacgca ggtcagttga atctgcctga catgttcacg cgtatgatgt   11340
tttccctggt tgcgaccggt gtggcgccga agagctttaa tcaactggat gcagacggca   11400
accgccagcg tagccactat gacggtctgc cggtcgagtt tattgcagaa gctatcagca   11460
ccctgggcgc acacgttcag gacggcttcg aaacttatca cgttatgaat ccgcacgacg   11520
acggtattgg tatggatgag ttcgttgatt ggctgatcga agccggttac ccgattcagc   11580
gcgtcgagga ctatcaggag tggctggcgc gcttcgaaac cacctgcgt gccctgccgg   11640
ataaacagcg tcaggcgagc ctgctgccgc tgctgcacaa ctaccagcaa ccgggtgtcc   11700
cggttaacgg cgccatggca ccgaccgacg ttttccgtac ggccgtccaa gacgcgaaaa   11760
ttggtccgga caaggatatt ccgcacgtca gccgtgaagt tattgtgaag tacatcagcg   11820
atttgaaact gctgggttg ctgtaataag tttaaacaga gaaggagttc tatcatgatt   11880
gaaaccatct taccagccgg cgtcgaatca gcagagttac ttgagtaccc tgaagatctg   11940
aaggcgcatc cggctgaaga gcatctgatc gcaaagagcg tagagaagcg tcgtcgcgac   12000
```

```
ttcattggcg cacgtcattg cgcccgtctg gcactggcgg agctgggtga accgccggtt    12060
gcgattggca agggtgaacg tggtgcgccg atttggccgc gtggtgtcgt gggctctctg    12120
acccattgcg atggctatcg cgcagcggcg gttgctcaca aaatgcgttt tcgcagcatc    12180
ggcatcgacg ccgaaccgca cgcgaccctg ccggaaggtg tcctggattc ggttagcctg    12240
ccgcctgagc gtgagtggct gaaaaccacc gacagcgcac tgcacctgga ccgtttgctg    12300
ttttgtgcga agaagcaac ttacaaagcg tggtggccgc tgacggcacg ttggctgggt    12360
ttcgaagaag cgcacattac cttcgaaatc gaggatggta gcgccgactc tggtaatggc    12420
acgtttcaca gcgaactgct ggtgccgggt cagaccaatg acggtggtac cccgctgctg    12480
tctttcgacg gtcgctggct gatcgctgat ggcttcatcc tgacggcgat tgcatacgca    12540
tgataaatta acctaggctg ctgccaccgc tgagcaataa ctagcataac cccttggggc    12600
ctctaaacgg gtcttgaggg gttttttgct gaaacctcag gcatttgaga agccctcgag    12660
tgaccccagc cgcccctcat gccaaccgag cccattaagc gcagagtcgg ccgcaactat    12720
ctcggggacg cataaacacg cagcgattta ccaaggagtt cggctaggtc aatccgcaat    12780
tcccttttgcc tggccggaga tgccgcgagc aaacaatgtg tccggtcgct accagatgga    12840
ctttgtgggc ggaggattgc accagacgct tcagcgcagc gtcgtacgat gaatcggaag    12900
gcccggtaag caattgaaga accgctgacc acctcccatc cgacaatgca agggtgcccc    12960
gctcccagcg cgacacggtt gcctgatcca cacccattaa ttcagctagg tgactttgct    13020
tcatatgacg aagcaaccgc gccctccgca cctgccgccc cctgtcattc gtcaacattc    13080
ttcagcacct caatgtcgtt cgtagtgagc ctcattttt caagaccgcc gatgatgaga    13140
gccaggcctc gctcgaatgc cgcgtccgga ccgccttcgt agacgatttt catcgcgctc    13200
tgtaggcgcg ccggcatcgt agacgctgag gtggtcaact gatcttcgcc ccgctcctcg    13260
gcgtctgcct cgctagcttg ctgctcaaga acagcgccga cggtgaagta gctgattgcc    13320
atcaacgcat aggtcgcgtc acctgccgaa aagccagcat cgcaaaggaa gcgaagctgc    13380
gcgtcggctt tttccatctg cggcgcggct ggccgcgtcc cggcatgaat acgcgcgcca    13440
tcgcgataag cgagcaacgc ccgtcgaaaa ctgcatgcat tgcccttcag gaacgaacgc    13500
cagtcgtcgt catcccttgg cgtcgaatgc gtgtgattta tcgtcagcat ggcttcggca    13560
agtgcgtcga gcaacgcacg cttgttcttg aaatgccagt agagcgctgg ctgttgcacc    13620
ccgaggcgct cagccagtcg gcgcgtcgtt agaccttcca tgcccacgtc gttaagcagt    13680
tcgagcgcgt tcggatcac ggcctcgcgt tggagcttgt tcattcgcga a             13731
```

<210> SEQ ID NO 21
<211> LENGTH: 13782
<212> TYPE: DNA
<213> ORGANISM: Artificial Sequence
<220> FEATURE:
<223> OTHER INFORMATION: vector

<400> SEQUENCE: 21

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
```

```
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg gcaggccccg tggccggggg    540
actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatgggc gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggacccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcccctacg tgctgctgaa gttgcccgca acagagagtg   1680
gaaccaaccg gtgataccac gatactatga ctgagagtca acgccatgag cggcctcatt   1740
tcttattctg agttacaaca gtccgcaccg ctgccggtag ctacttgact atccggctgc   1800
actagccctg cgtcagatgg ctctgatcca aggcaaactg ccaaaatatc tgctggcacc   1860
ggaagtcagc gccctgcacc attatgttcc ggatctgcat cgcaggatgc tgctggctac   1920
cctgtggaac acctacatct gtattaacga agcgctggca ttgaccctga gtgattttc    1980
tctggtgccg ccctatccct tgtgcagct tgccacgctc aaagggggttt gaggtccaac   2040
cgtacgaaaa cgtacggtaa gaggaaaatt atcgtctgaa aaatcgatta gtagacaaga   2100
aagtccgtta agtgccaatt ttcgattaaa aagacaccgt tttgatggcg ttttccaatg   2160
tacattatgt ttcgatatat cagacagtta cttcactaac gtacgttttc gttctattgg   2220
ccttcagacc ccatatcctt aatgtccttt atttgctggg gttatcagat cccccccgaca   2280
cgtttaatta atgctttctc cgccggagat cgacgcacag gcttctgtgt ctatgatgtt   2340
atttcttaat aatcatccag gtattctctt tatcaccata cgtagtgcga gtgtccacct   2400
taacgcaggg ctttccgtca cagcgcgata tgtcagccag cggggctttc ttttgccaga   2460
ccgcttccat cctctgcatt tcagcaatct ggctataccc gtcattcata aaccacgtaa   2520
atgccgtcac gcaggaagcc aggacgaaga atatcgtcag tacaagataa atcgcggatt   2580
tccacgtata gcgtgacatc tcacgacgca tttcatggat catcgctttc gccgtatcgg   2640
cagcctgatt cagcgcttct gtcgccggtt tctgctgtgc taatccggct tgtttcagtt   2700
```

```
ctttctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagcccttta tccggcttct gtcgtatctg ttcggcgagt cgctgtcgtt    3000
ctttctcctg ctgacgctgt ttttccgcca gacgttgcgc tctctctgc ctttccatct    3060 cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc gcgtccggct    3600
ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact ccttgtgctc aaggtcggag tcttttttcac    3960 gggcatactt tccctcacgc gcaatataat cggcatgagg agaggcactg ccttttccgc    4020 cggttttttac gctgagatga taggatgcca tcgtgttttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actgaaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt tacccccatt cactgccaga    4800
gccgtgagcg cagcgaactg aatgtcacga aaagacagc gactcaggtg cctgatggtc    4860
ggagacaaaa ggaatattca gcgatttgcc cgagcttgcg aggtgctac ttaagccttt    4920 agggttttaa ggtctgtttt gtagaggagc aaacagcgtt tgcgacatcc ttttgtaata    4980
ctgcggaact gactaaagta gtgagttata cacagggctg ggatctattc tttttatctt    5040
```

```
tttttattct ttctttattc tataaattat aaccacttga atataaacaa aaaaaacaca      5100
caaaggtcta gcggaattta cagagggtct agcagaattt acaagttttc cagcaaaggt      5160
ctagcagaat ttacagatac ccacaactca aaggaaaagg actagtaatt atcattgact      5220
agcccatctc aattggtata gtgattaaaa tcacctagac caattgagat gtatgtctga      5280
attagttgtt ttcaaagcaa atgaactagc gattagtcgc tatgacttaa cggagcatga      5340
aaccaagcta attttatgct gtgtggcact actcaacccc acgattgaaa accctacaag      5400
gaaagaacgg acggtatcgt tcacttataa ccaatacgct cagatgatga acatcagtag      5460
ggaaaatgct tatggtgtat tagctaaagc aaccagagag ctgatgacga aactgtgga       5520 aatcaggaat cctttggtta aaggctttga gattttccag tggacaaact atgccaagtt      5580
ctcaagcgaa aaattagaat tagttttag tgaagagata ttgccttatc ttttccagtt       5640
aaaaaaattc ataaaatata atctggaaca tgttaagtct tttgaaaaca aatactctat      5700
gaggatttat gagtggttat taaagaact aacacaaaag aaaactcaca aggcaaatat       5760
agagattagc cttgatgaat ttaagttcat gttaatgctt gaaaataact accatgagtt      5820
taaaaggctt aaccaatggg ttttgaaacc aataagtaaa gatttaaaca cttacagcaa      5880
tatgaaattg gtggttgata agcgaggccg cccgactgat acgttgattt tccaagttga      5940
actagataga caaatggatc tcgtaaccga acttgagaac aaccagataa aaatgaatgg      6000
tgacaaaata ccaacaacca ttacatcaga ttcctaccta cgtaacggac taagaaaaac      6060
actacacgat gctttaactg caaaaattca gctcaccagt tttgaggcaa aatttttgag      6120
tgacatgcaa agtaagcatg atctcaatgg ttcgttctca tggctcacgc aaaaacaacg      6180
aaccacacta gagaacatac tggctaaata cggaaggatc tgaggttctt atggctcttg      6240
tatctatcag tgaagcatca agactaacaa acaaaagtag aacaactgtt caccgttaga      6300
tatcaaaggg aaaactgtcc atatgcacag atgaaaacgg tgtaaaaaag atagatacat      6360
cagagctttt acgagttttt ggtgcattta agctgttca ccatgaacag atcgacaatg       6420
taacagatga acagcatgta acacctaata gaacaggtga aaccagtaaa acaaagcaac      6480
tagaacatga aattgaacac ctgagacaac ttgttacagc tcaacagtca cacatagaca      6540
gcctgaaaca ggcgatgctg cttatcgaat caaagctgcc gacaacacgg gagccagtga      6600
cgcctcccgt ggggaaaaaa tcatggcaat tctggaagaa atagcgcttt cagccggcaa      6660
acctgaagcc ggatctgcga ttctgataac aaactagcaa caccagaaca gcccgtttgc      6720
gggcagcaaa acccgtactt ttggacgttc cggcggtttt ttgtggcgag tggtgttcgg      6780
gcggtgcgcg caagatccat tatgttaaac gggcgagttt acatctcaaa accgcccgct      6840
taacaccatc agaaatcctc agcgcgattt taagcaccaa ccccccccg taacacccaa       6900 atccatactg aaagtggctt tgttaataa atcgaacttt tgctgagttg aaggatcaga      6960
tcacgcatcc tcccgacaac acagaccatt ccgtggcaaa gcaaaagttc agaatcacca      7020
actggtccac ctacaacaaa gctctcatca accgtggctc cctcactttc tggctggatg      7080
atgaggcgat tcaggcctgg tatgagtcgg caacaccttc atcacgagga aggccccagc      7140
gctattctga tctcgccatc accaccgttc tggtgattaa acgcgtattc cggctgaccc      7200
tgcgggctgc gcagggtttt attgattcca ttttgccct gatgaacgtt ccgttgcgct      7260
gcccggatta caccagtgtc agtaagcggg caaagtcggt taatgtcagt ttcaaaacgt      7320
ccaccccggg tgaaatcgca cacctggtga ttgattccac cgggctgaag gtctttggtg      7380
aaggcgaatg gaaagtcaga aagcacggca aagagcgccg tcgtatctgg cgaaagttgc      7440
```

```
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccgggagtaa tgcgcggtgg aaatggacaa    7740
cagattacaa ccgtcgctcg atagcggaaa cggcgatgta ccgggtaaaa cagctgttcg    7800
ggggttcact gacgctgcgt gactacgatg gtcaggttgc ggaggctatg gccctggtac    7860
gagcgctgaa caaaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccacctcg cacctggtgt ttaaacggat ttaaattgca    8220
ggggcagtga gcgcaacgca attaatgtaa gttagctcac tcattaggca ccccaggctt    8280
gacactttat gcttccggct cgtataatgt gtggaattgt gagcggataa caataacaat    8340
ttaaatcagg atctaggaac caaggagagt ggcatatgag cactgcaacg catgatgaga    8400
gactggatag acgcgtacat gaactgatcg caaccgaccc gcaatttgcg gcagcacagc    8460 cggaccggc tattacggcg gcattggagc aaccgggtct gcgtctgccg cagatcattc    8520
gtaccgtcct ggacggctat gcggatcgtc cggcgttggg tcaacgcgtc gttgagtttg    8580
ttaccgacgc gaaaaccggt cgcacgagcg cgcagctgct gccgcgtttt gaaaccatta    8640
cctactccga agtggcacaa cgcgttagcg cgctgggtcg tgcgctgtcc gacgacgcag    8700
ttcatccggg tgatcgtgtg tgtgtcctgg gttttaacag cgttgattac gcgaccatcg    8760
atatggcact gggtgcgatt ggcgcggtgt cggttccgct gcaaacctct gcagcgatta    8820
gctccctgca gcctattgtc gcggaaaccg aaccgacgct gatcgcgagc agcgttaatc    8880
agctgagcga tgccgtgcag ctgatcaccg gtgcagagca ggcccctacc cgtttggtgg    8940
tgttcgatta tcacccgcaa gtcgatgacc agcgcgaggc tgttcaggac gcggctgcgc    9000
gcttgtccag caccggcgtt gccgtgcaaa ccctggccga gctgctggag cgcggtaaag    9060
acctgccggc tgtggcggag ccgccagcgg atgaggacag cctggcgttg ctgatttaca    9120
ccagcggcag cacgggtgct ccgaaaggtg cgatgtaccc acagagcaat gttggtaaga    9180
tgtggcgtcg tggctctaaa aactggttcg gcgaaagcgc tgctagcatt accctgaact    9240
tcatgccgat gagccatgtg atgggccgta gcatcttgta cggcaccctg ggtaacggcg    9300
gtacggccta tttcgctgct cgtagcgatc tgagcacccc tgctggaagat ctggagctgg    9360 tgcgtccgac ggaactgaat tttgttccac gcatttggga aaccttgtat ggtgagttcc    9420
aacgtcaagt ggaacgccgc ctgagcgagg ctggcgacgc gggtgagcgt cgtgctgtgg    9480
aagcggaagt gctggcggag cagcgccaat atctgctggg cggtcgtttc acctttgcga    9540
tgacgggcag cgcccctatt tcgcctgagc tgcgcaactg ggtcgagtcc ctgctggaga    9600
tgcatctgat ggatggttac ggtagcacgg aagcgggcat ggtcctgttt gacggtgaga    9660
tccaacgtcc gccggttatt gattacaagt tggtggacgt tccggatttg ggttacttta    9720
gcaccgatcg cccgcacccg cgtggtgagc tgctgctgcg tacggagaat atgttcccgg    9780
```

```
gttactataa gcgtgccgaa actaccgcgg gtgttttga tgaggacggt tactaccgca    9840
cgggcgatgt gtttgccgaa atcgcaccgg atcgcctggt gtatgttgac cgtcgcaaca    9900
acgtattgaa actggcacaa ggcgagttcg tcacgttggc caagctggaa gcggtgtttg    9960
gtaattcccc gctgattcgt cagatctatg tctatggtaa cagcgcgcaa ccgtatctgc   10020
tggccgttgt cgttccgact gaagaagccc tggccagcgg tgatcctgag acgctgaagc   10080
cgaaaatcgc agatagcctg cagcaagtgg cgaaagaagc aggtctgcag agctacgaag   10140
ttccgcgcga ctttatcatc gagacgacgc cgtttagcct ggaaaacggc ctgttgacgg   10200
gcatccgcaa actggcttgg ccgaaactga agcaacacta cggcgagcgt ctggagcaaa   10260
tgtacgccga cctggcagcg ggccaagcaa atgaactggc agagctgcgt cgtaatggcg   10320
cccaagcccc ggtgctgcag acggttagcc gtgcagcggg tgcaatgttg ggctctgccg   10380
cgagcgattt gagcccagat gcgcacttca ccgacctggg tggtgacagc ctgtctgctc   10440
tgaccttcgg taacctgctg cgtgagatct tcgacgtcga tgtcccggtc ggcgtgatcg   10500
tcagcccggc aaatgatctg gcggcgattg cgagctatat tgaagcagaa cgtcagggta   10560
gcaaacgtcc gaccttttgcg agcgtccatg gtcgcgacgc gaccgttgtt cgtgctgccg   10620
acttgacccct ggacaagttt ttggacgctg aaacgttggc tgcggcaccg aacctgccga   10680
agccggcgac cgaggttcgc accgttctgc tgaccggtgc tactggtttc ctgggtcgtt   10740
acctggctct ggagtggctg gagcgtatgg atatggttga cggtaaggtc attgcattgg   10800
tgcgtgcgcg ttctgatgaa gaggcccgtg cccgtctgga taagaccttt gacagcggtg   10860
acccgaaact gctggcgcac tatcagcagc tggcggcaga ccacctggaa gtgatcgccg   10920
gtgacaaggg tgaggccaat ctgggtctgg tcaggacgt gtggcaacgt ctggcggaca   10980
ccgttgatgt cattgtggac ccggcagcgc tggtgaacca cgtcctgccg tactccgaac   11040
tgttcggtcc gaatgcgttg ggcactgcag agctgatccg tctggcactg accagcaagc   11100
agaaaccgta tacttacgtt agcaccatcg gcgtcggcgc ccaaatcgaa ccgggtaaat   11160
tcgttgaaaa tgcagatatt cgtcaaatgt cggcgacccg tgcgattaat gacagctacg   11220
cgaacggcta tggcaactcc aagtgggcgg gtgaggttct gctgcgcgag gcgcatgatc   11280
tgtgcggtct gccggtagcg gtgttccgtt gcgacatgat cctggcagac acgacctacg   11340
caggtcagtt gaatctgccg gatatgttca cgcgcctgat gttgagcctg gtagcgacgg   11400
gtattgcacc gggttctttc tatgagttgg atgccgatgg caatcgccag cgcgcacact   11460
atgacggcct gccggtcgag tttatcgcag cggcgattag cacgctgggt tcccagatca   11520
ccgatagcga taccggcttc cagacgtacc acgtcatgaa tccttacgac gacggcgtcg   11580
gcctggacga gtacgtcgac tggctggttg atgcgggtta ttcgattgag cgtattgccg   11640
actactctga atggttgcgt cgcttcgaaa ccagcctgcg tgcgctgccg gatcgtcaac   11700
gccagtatag cctgctgcca ctgttgcaca actaccgtac cccggagaaa ccgattaacg   11760
gcagcatcgc cccgacggat gttttccgtg cggcagtcca ggaagcgaag atcggtccag   11820
acaaggacat cccgcacgtg tccccgccag tgatcgtgaa atacattacc gacctgcagc   11880
tgttgggcct gctgtaataa gtttaaacag agaaggagtt ctatcatgat tgaaaccatc   11940
ttaccagccg gcgtcgaatc agcagagtta cttgagtacc ctgaagatct gaaggcgcat   12000
ccggctgaag agcatctgat cgcaaagagc gtagagaagc gtcgtcgcga cttcattggc   12060
gcacgtcatt gcgcccgtct ggcactggcg gagctgggtg aaccgccggt tgcgattggc   12120
aagggtgaac gtggtgcgcc gatttggccg cgtggtgtcg tgggctctct gacccattgc   12180
```

```
gatggctatc gcgcagcggc ggttgctcac aaaatgcgtt ttcgcagcat cggcatcgac    12240
gccgaaccgc acgcgaccct gccggaaggt gtcctggatt cggttagcct gccgcctgag    12300
cgtgagtggc tgaaaaccac cgacagcgca ctgcacctgg accgtttgct gttttgtgcg    12360
aaagaagcaa cttacaaagc gtggtggccg ctgacggcac gttggctggg tttcgaagaa    12420
gcgcacatta ccttcgaaat cgaggatggt agcgccgact ctggtaatgg cacgtttcac    12480
agcgaactgc tggtgccggg tcagaccaat gacggtggta ccccgctgct gtctttcgac    12540
ggtcgctggc tgatcgctga tggcttcatc ctgacggcga ttgcatacgc atgataaatt    12600
aacctaggct gctgccaccg ctgagcaata actagcataa cccttggggg cctctaaacg    12660
ggtcttgagg ggttttttgc tgaaacctca ggcatttgag aagccctcga gtgaccccag    12720
ccgcccctca tgccaaccga gcccattaag cgcagagtcg gccgcaacta tctcggggac    12780
gcataaacac gcagcgattt accaaggagt tcggctaggt caatccgcaa ttcccttttgc   12840 ctggccggag atgccgcgag caaacaatgt gtccggtcgc taccagatgg actttgtggg    12900
cggaggattg caccagacgc ttcagcgcag cgtcgtacga tgaatcggaa ggcccggtaa    12960
gcaattgaaa accgctgac cacctcccat ccgacaatgc aagggtgccc cgctcccagc    13020
gcgacacggt tgcctgatcc acacccatta attcagctag gtgactttgc ttcatatgac    13080
gaagcaaccg cgccctccgc acctgccgcc cctgtcatt cgtcaacatt cttcagcacc     13140
tcaatgtcgt tcgtagtgag cctcattttt tcaagaccgc cgatgatgag agccaggcct    13200
cgctcgaatg ccgcgtccgg accgccttcg tagacgattt tcatcgcgct ctgtaggcgc    13260
gccggcatcg tagacgctga ggtggtcaac tgatcttcgc cccgctcctc ggcgtctgcc    13320
tcgctagctt gctgctcaag aacagcgccg acggtgaagt agctgattgc catcaacgca    13380
taggtcgcgt cacctgccga aaagccagca tcgcaaagga agcgaagctg cgcgtcggct    13440
ttttccatct gcggcgcggc tggccgcgtc ccggcatgaa tacgcgcgcc atcgcgataa    13500
gcgagcaacg cccgtcgaaa actgcatgca ttgcccttca ggaacgaacg ccagtcgtcg    13560
tcatcccttg gcgtcgaatg cgtgtgattt atcgtcagca tggcttcggc aagtgcgtcg    13620
agcaacgcac gcttgttctt gaaatgccag tagagcgctg gctgttgcac cccgaggcgc    13680
tcagccagtc ggcgcgtcgt tagaccttcc atgcccacgt cgttaagcag ttcgagcgcg    13740
gttcggatca cggcctcgcg ttggagcttg ttcattcgcg aa                       13782
```

<210> SEQ ID NO 22
<211> LENGTH: 13695
<212> TYPE: DNA
<213> ORGANISM: Artificial Sequence
<220> FEATURE:
<223> OTHER INFORMATION: vector

<400> SEQUENCE: 22

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
```

-continued

```
aggtgcggtt gctggcgcct atatcgccga catcaccgat ggggaagatc gggctcgcca    480
cttcgggctc atgagcgctt gtttcggcgt gggtatggtg gcaggcccg tggccggggg     540
actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggc gccgacgcgc tgggctacgt     960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggacccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcccctacg tgctgctgaa gttgcccgca acagagagtg   1680
gaaccaaccg gtgataccac gatactatga ctgagagtca acgccatgag cggcctcatt   1740
tcttattctg agttacaaca gtccgcaccg ctgccggtag ctacttgact atccggctgc   1800
actagccctg cgtcagatgg ctctgatcca aggcaaactg ccaaaatatc tgctggcacc   1860
ggaagtcagc gccctgcacc attatgttcc ggatctgcat cgcaggatgc tgctggctac   1920
cctgtggaac acctacatct gtattaacga agcgctggca ttgaccctga gtgattttc    1980
tctggtgccg ccctatccct tgtgcagct tgccacgctc aaaggggttt gaggtccaac     2040
cgtacgaaaa cgtacggtaa gaggaaaatt atcgtctgaa aaatcgatta gtagacaaga   2100
aagtccgtta agtgccaatt ttcgattaaa aagacaccgt tttgatggcg ttttccaatg   2160
tacattatgt ttcgatatat cagacagtta cttcactaac gtacgttttc gttctattgg   2220
ccttcagacc ccatatcctt aatgtccttt atttgctggg gttatcagat cccccccgaca   2280
cgtttaatta atgctttctc cgccggagat cgacgcacag gcttctgtgt ctatgatgtt   2340
atttcttaat aatcatccag gtattctctt tatcaccata cgtagtgcga gtgtccacct   2400
taacgcaggg ctttccgtca cagcgcgata tgtcagccag cggggctttc ttttgccaga   2460
ccgcttccat cctctgcatt tcagcaatct ggctataccc gtcattcata aaccacgtaa   2520
atgccgtcac gcaggaagcc aggacgaaga atatcgtcag tacaagataa atcgcggatt   2580
tccacgtata gcgtgacatc tcacgacgca tttcatggat catcgctttc gccgtatcgg   2640
cagcctgatt cagcgcttct gtcgccggtt tctgctgtgc taatccggct tgtttcagtt   2700
ctttctcaac ctgagtgagc gcggaactca ccgatttcct gacggtgtca gtcatattac   2760
cggacgcgct gtccagctca cgaatgaccc tgctcagcgt ttcactttgc tgctgtaatt   2820
```

```
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagcctttta tccggcttct gtcgtatctg ttcggcgagt cgctgtcgtt   3000
cttcctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc gcgtccggct    3600
ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact ccttgtgctc aaggtcggag tcttttttcac   3960 gggcatactt tccctcacgc gcaatataat cggcatgagg agaggcactg ccttttccgc    4020 cggttttttac gctgagatga taggatgcca tcgtgtttta tcccgctgaa gggcgcacgt   4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt taccccccatt cactgccaga   4800 gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg gatctattc ttttttatctt    5040 tttttattct ttctttattc tataaattat aaccacttga atataaacaa aaaaaacaca    5100
caaaggtcta gcggaattta cagagggtct agcagaattt acaagttttc cagcaaaggt    5160
```

| | |
|---|---|
| ctagcagaat ttacagatac ccacaactca aaggaaaagg actagtaatt atcattgact | 5220 |
| agcccatctc aattggtata gtgattaaaa tcacctagac caattgagat gtatgtctga | 5280 |
| attagttgtt ttcaaagcaa atgaactagc gattagtcgc tatgacttaa cggagcatga | 5340 |
| aaccaagcta attttatgct gtgtggcact actcaacccc acgattgaaa accctacaag | 5400 |
| gaaagaacgg acggtatcgt tcacttataa ccaatacgct cagatgatga acatcagtag | 5460 |
| ggaaaatgct tatggtgtat tagctaaagc aaccagagag ctgatgacga aactgtgga | 5520 |
| aatcaggaat cctttggtta aaggctttga gattttccag tggacaaact atgccaagtt | 5580 |
| ctcaagcgaa aaattagaat tagttttag tgaagagata ttgccttatc ttttccagtt | 5640 |
| aaaaaaattc ataaaatata atctggaaca tgttaagtct tttgaaaaca aatactctat | 5700 |
| gaggatttat gagtggttat taaaagaact aacacaaaag aaaactcaca aggcaaatat | 5760 |
| agagattagc cttgatgaat ttaagttcat gttaatgctt gaaaataact accatgagtt | 5820 |
| taaaaggctt aaccaatggg ttttgaaacc aataagtaaa gatttaaaca cttacagcaa | 5880 |
| tatgaaattg gtggttgata agcgaggccg cccgactgat acgttgattt ccaagttga | 5940 |
| actagataga caaatggatc tcgtaaccga acttgagaac aaccagataa aaatgaatgg | 6000 |
| tgacaaaata ccaacaacca ttacatcaga ttcctaccta cgtaacggac taagaaaaac | 6060 |
| actacacgat gctttaactg caaaaattca gctcaccagt tttgaggcaa aattttgag | 6120 |
| tgacatgcaa agtaagcatg atctcaatgg ttcgttctca tggctcacgc aaaaacaacg | 6180 |
| aaccacacta gagaacatac tggctaaata cggaaggatc tgaggttctt atggctcttg | 6240 |
| tatctatcag tgaagcatca agactaacaa acaaaagtag aacaactgtt caccgttaga | 6300 |
| tatcaaaggg aaaactgtcc atatgcacag atgaaaacgg tgtaaaaag atagatacat | 6360 |
| cagagctttt acgagttttt ggtgcattta aagctgttca ccatgaacag atcgacaatg | 6420 |
| taacagatga acagcatgta acacctaata gaacaggtga accagtaaa acaaagcaac | 6480 |
| tagaacatga aattgaacac ctgagacaac ttgttacagc tcaacagtca cacatagaca | 6540 |
| gcctgaaaca ggcgatgctg cttatcgaat caaagctgcc gacaacacgg gagccagtga | 6600 |
| cgcctcccgt ggggaaaaaa tcatggcaat tctggaagaa atagcgcttt cagccggcaa | 6660 |
| acctgaagcc ggatctgcga ttctgataac aaactagcaa caccagaaca gcccgtttgc | 6720 |
| gggcagcaaa acccgtactt ttggacgttc cggcggtttt ttgtggcgag tggtgttcgg | 6780 |
| gcggtgcgcg caagatccat tatgttaaac gggcgagttt acatctcaaa accgcccgct | 6840 |
| taacaccatc agaaatcctc agcgcgattt taagcaccaa cccccccccg taacacccaa | 6900 |
| atccatactg aaagtggctt tgttgaataa atcgaacttt tgctgagttg aaggatcaga | 6960 |
| tcacgcatcc tcccgacaac acagaccatt ccgtggcaaa gcaaaagttc agaatcacca | 7020 |
| actggtccac ctacaacaaa gctctcatca accgtggctc cctcactttc tggctggatg | 7080 |
| atgaggcgat tcaggcctgg tatgagtcgg caacaccttc atcacgagga aggccccagc | 7140 |
| gctattctga tctcgccatc accaccgttc tggtgattaa acgcgtattc cggctgaccc | 7200 |
| tgcgggctgc gcagggtttt attgattcca ttttttgccct gatgaacgtt ccgttgcgct | 7260 |
| gcccggatta caccagtgtc agtaagcggg caaagtcggt taatgtcagt ttcaaaacgt | 7320 |
| ccacccgggg tgaaatcgca cacctggtga ttgattccac cgggctgaag gtctttggtg | 7380 |
| aaggcgaatg gaaagtcaga aagcacggca aagagcgccg tcgtatctgg cgaaagttgc | 7440 |
| atcttgctgt tgacagcaac acacatgaag ttgtctgtgc agacctgtcg ctgaataacg | 7500 |
| tcacggactc agaagccttc ccgggcctta tccggcagac tcacagaaaa atcagggcag | 7560 |

```
ccgcggcaga cggggcttac gatacccggc tctgtcacga tgaactgcgc cgcaaaaaaa      7620
tcagcgcgct tattcctccc cgaaaaggtg cgggttactg gcccggtgaa tatgcagacc      7680
gtaaccgtgc agtggctaat cagcgaatga ccgggagtaa tgcgcggtgg aaatggacaa      7740
cagattacaa ccgtcgctcg atagcggaaa cggcgatgta ccgggtaaaa cagctgttcg      7800
ggggttcact gacgctgcgt gactacgatg gtcaggttgc ggaggctatg gccctggtac      7860
gagcgctgaa caaaatgacg aaagcaggta tgcctgaaag cgtgcgtatt gcctgaaaac      7920
acaacccgct acgggggaga cttacccgaa atctgattta ttcaacaaag ccgggtgtgg      7980
tgaactacaa agcagacccg ttgaggttat cagttcgatg cacaatcagc agcgcataaa      8040
atatgcacaa gaacaggagc acccttcgca ttaagctgtg gtggtaacaa gtagtgccgg      8100
gctaccatca gcgagcatga tgcgctccca cagcattcgc cttggcagta tggaagttcc      8160
tcgctccagt tcgggccggt atccacctcg cacctggtgt ttaaacggat ttaaattgca      8220
ggggcagtga gcgcaacgca attaatgtaa gttagctcac tcattaggca ccccaggctt      8280
gacactttat gcttccggct cgtataatgt gtggaattgt gagcggataa caataacaat      8340
ttaaatcagg atctaggaac caaggagagt ggcatatgaa tgaaagcagc gcagaccaga      8400
gcagcggtaa tgtatcagag ggttggccgg acgcgagcgt caccgcgcgt gcgctgcaag      8460
cgcacctgcg ttacgaacag atcatcgacg ctatcctgag cggctatgcg gaacgtccgg      8520
cactggcgga gcgcagctac ctggtccgtc cagatccgag cacgggccaa accgttcgcg      8580
tccacgagca ggcgtttcgt tctatcagct accgtacgct gcaagaacgc gtccacgccc      8640
tgaccatggc gtggcgtctg caccccggact ccccggtaca agcgggtgca ttcgtcgtgc      8700
tggttggctt tgccagcatc gattatgcgg ttctggacct ggccctggcc tataccaagg      8760
gtgtcccggt tccgctgagc ccgaaccact ctagcgagga cgatgacgca atcttgggca      8820
ccgtgcaacc ggtgaccctg gccgtttcta tctctgagtt ctccggctgc gtggatctga      8880
ttgctcgtag caccagcatc cgtacggtta ttgtgtttga tttggatccg gcggtggatt      8940
gtgagcgtgc agccctggag tccggtattc gtgcgctgaa cgagaagggt agcgatgtcg      9000
ttgtgcaaac cctgcaagac ctgatcgatg tcggccgtga tgcggagttt agctttctgc      9060
ctattcaggc gcaagaccag gatgatttgg ctctgctgat tcataccagc ggtagcaccg      9120
gcacgccgaa gggcgcttgc atcagcagcc gtgcccgtgat caacacctgg cgtcacgtca      9180
gcggtccgta tcctaaagtg accgtcgttc tggcgccgtt tcaccacatg atgggtcgtg      9240
acagcatgat taccgccctg ggtgcaggcg gcaccgcgta cttcacgttg cgtccggatc      9300
tgagcactgt tattgaggac atccgcctgg cacgcccgac cggcctggtg ctgttcccgc      9360
gtctgtgcga ggtgatcgag caccatctga cgaccgctcc ggagtactct ggtaacgaga      9420
tcctgggtgg ccgtctgcag tccattgtcg tagcgagcgc tccgattact ccgcgtctga      9480
aagcgagctt ggagtgtttg ctgggcgttc cggtgagcga gggttattcc agcacggaga      9540
cggcaagcgg tggtttggca atgaacggcc tgttgaatcg caacaatatt ctggcgtacc      9600
gcttgcgtga cgttccggaa gcgggttact ctgttaacga ccgcccgttt ccgcgtggcg      9660
aactgtgtgt taagacgcgc tttggtatta gcggctattt tcgcaatccg gaagcgaccg      9720
cggaactgtt cgacgatgac ggtttctact gcacgggtga cattgttgaa gaacgtgcac      9780
cagatcagat cgcgatcatt gaccgccgca aaaacgtcat taaactggct cagggcgagt      9840
acgtggctgt gggtcgtctg gagcaattgt ttcaagaagg ctgcggttgc gtgcaacaga      9900
```

```
ttcatctgca tggtgacagc acccgtgcat acctgctggc ggtcgttgtt ccggaccgca    9960
ataccttggc gccacctggt tcgcgtcagg cgtctgaggc agagttgaaa gcgcgcgtcc   10020
gcgaagagat tctgaccctg gcaaatcagc gcgagctgcg tggctttgaa atcccgcgtg   10080
acctgattct ggcggaagaa ccgttcagcc aacagaatgg cctgctgagc agcttgggta   10140
aaccgatccg tccggctatc cgtgcacgct accgtagccg tctggaaagc ctgtatgcga   10200
gccatgaagc cacccgtggt accgagctgg aagcaatccg tgcgtccgca ggtgccgttg   10260
atgtggaaac cacgctgttg gccctgctgt ctagcactct gggcgtggtc tgtggtgccg   10320
cggatcgcca gacctctttt cgcgagctgg gtggcgacag cctggccgca gtgcagctgg   10380
ccatggagat caaaaagcag ttcggtgtgg gcctggaagg tagccaaatc ctgggtccgg   10440
gtggtacggt cgaggcgtgg gcccgtcgca tccacaccgc gagcattcag caggcaccgc   10500
accaacgcgt gggcagcccg ctggctgcaa ttccggccga aggctggctg aaaccggatc   10560
actatcgtct ggagaacttg atcggcattc cgattggtac cccgtccgca gaggttgctc   10620
gcccgactgg cggtccgccg accgtgctgc tgacgggtgc gactggtttc ttgggtggcc   10680
gcctgtgcct ggaatggctg caacgtctgg cgggtcaggg tggtcgcctg atctgtctgg   10740
tgcgtcctag caacagccac agcgcctggg aacgtctgcg caaccgcttc agccacctgg   10800
agccggagca ggttgcgcgt tttcgtgaac tggcaggccg ccatctggaa gttattccgg   10860
cagatatcgg cgagccgggt ttgggcctgg agcctggttg tcaagagcgt ctggccaccg   10920
aggtcgacgc gatctgtcat tgtgcagccg aggttaacca tcgtctgccg taccgtcacc   10980
tgtatcgtcc gaatgtgatt ggtaccgcag agatcattca tctggctatt actacccgtc   11040
tgaagagcgt ggacttcatt tcgagcatcg gtgtggcgag cctgccgcgt cgtccgggtg   11100
gctcgattcc ggtcgagggc ggttacgcac gcggctattt cgcttccaag tgggcgtgcg   11160
aacaactgct gcgtagcacc catgattgca ccggtgttcc ggtgcgtgtc attcgtccga   11220
gcctgattct gccagaccgt gtcctggccg gtgaaatgaa tcctgacgac ctgctgtctc   11280
gcttgctgta ctcgattctg gttacgggta tcgcgccagg ctgcttcggt gaagagagcc   11340
agaacagcgg tcgcagcggt ttcagcgttc aaggtctgcc ggtggatcag ctggcgcaga   11400
cgatcctggc actgggcgag gcacgcacgg aaggcttcca cgttttgaat ctgaatgcgg   11460
actccggtag cggtgtcccg ttggatgcga ttttgcaaga catcgcggcg aaaggtattc   11520
gtctgcgtcg tgtcgagggt tacgatctgt ggctggacgc aattaccacg cgcctgcgtc   11580
gtttgccagc ggaacagcgt gcgcgcagcc tgttggatgt ggcagaggcg tacgccggca   11640
gcgctggcca gacgacgcaa tccagcggtg agatgcaagc gggtagctcg tcctgcccag   11700
aagaaatcac cagcctgcag ccggacttca gccgtgccta tcgtcgtaag atcgttgacg   11760
atctggcgcg ctggggtctg atcgaaccac cgggtccggt tgatcagtaa taagtttaaa   11820
cagagaagga gttctatcat gattgaaacc atcttaccag ccggcgtcga atcagcagag   11880
ttacttgagt accctgaaga tctgaaggcg catccggctg aagagcatct gatcgcaaag   11940
agcgtagaga agcgtcgtcg cgacttcatt ggcgcacgtc attgcgcccg tctggcactg   12000
gcggagctgg gtgaaccgcc ggttgcgatt ggcaagggtg aacgtggtgc gccgatttgg   12060
ccgcgtggtg tcgtgggctc tctgacccat tgcgatggct atcgcgcagc ggcggttgct   12120
cacaaaatgc gttttcgcag catcggcatc gacgccgaac cgcacgcgac cctgccggaa   12180
ggtgtcctga ttcggttag cctgccgcct gagcgtgagt ggctgaaaac caccgacagc   12240
gcactgcacc tggaccgttt gctgtttgt gcgaaagaag caacttacaa agcgtggtgg   12300
```

```
ccgctgacgg cacgttggct gggtttcgaa gaagcgcaca ttaccttcga aatcgaggat  12360
ggtagcgccg actctggtaa tggcacgttt cacagcgaac tgctggtgcc gggtcagacc  12420
aatgacggtg gtaccccgct gctgtctttc gacggtcgct ggctgatcgc tgatggcttc  12480
atcctgacgg cgattgcata cgcatgataa attaacctag gctgctgcca ccgctgagca  12540
ataactagca taaccccttg gggcctctaa acgggtcttg aggggttttt tgctgaaacc  12600
tcaggcattt gagaagccct cgagtgaccc cagccgcccc tcatgccaac cgagcccatt  12660
aagcgcagag tcggccgcaa ctatctcggg gacgcataaa cacgcagcga tttaccaagg  12720
agttcggcta ggtcaatccg caattccctt tgcctggccg gagatgccgc gagcaaacaa  12780
tgtgtccggt cgctaccaga tggactttgt gggcggagga ttgcaccaga cgcttcagcg  12840
cagcgtcgta cgatgaatcg gaaggcccgg taagcaattg aagaaccgct gaccacctcc  12900
catccgacaa tgcaagggtg ccccgctccc agcgcgacac ggttgcctga tccacaccca  12960
ttaattcagc taggtgactt tgcttcatat gacgaagcaa ccgcgccctc cgcacctgcc  13020
gccccctgtc attcgtcaac attcttcagc acctcaatgt cgttcgtagt gagcctcatt  13080
ttttcaagac cgccgatgat gagagccagg cctcgctcga atgccgcgtc cggaccgcct  13140
tcgtagacga ttttcatcgc gctctgtagg cgcgccggca tcgtagacgc tgaggtggtc  13200
aactgatctt cgccccgctc ctcggcgtct gcctcgctag cttgctgctc aagaacagcg  13260
ccgacggtga agtagctgat tgccatcaac gcataggtcg cgtcacctgc cgaaaagcca  13320
gcatcgcaaa ggaagcgaag ctgcgcgtcg gctttttcca tctgcggcgc ggctggccgc  13380
gtcccggcat gaatacgcgc gccatcgcga taagcgagca acgcccgtcg aaaactgcat  13440
gcattgccct tcaggaacga acgccagtcg tcgtcatccc ttggcgtcga atgcgtgtga  13500
tttatcgtca gcatggcttc ggcaagtgcg tcgagcaacg cacgcttgtt cttgaaatgc  13560
cagtagagcg ctggctgttg caccccgagg cgctcagcca gtcggcgcgt cgttagacct  13620
tccatgccca cgtcgttaag cagttcgagc gcggttcgga tcacggcctc gcgttggagc  13680
ttgttcattc gcgaa                                                   13695
```

```
<210> SEQ ID NO 23
<211> LENGTH: 13728
<212> TYPE: DNA
<213> ORGANISM: Artificial Sequence
<220> FEATURE:
<223> OTHER INFORMATION: vector

<400> SEQUENCE: 23
```

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg gcaggccccg tggccggggg    540
actgttgggc gccatctcct tgcatgcacc attccttgcg gcggcggtgc tcaacggcct    600
```


```
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagcggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggacccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcccctacg tgctgctgaa gttgcccgca acagagagtg   1680
gaaccaaccg tgataccacg atactatga ctgagagtca acgccatgag cggcctcatt   1740
tcttattctg agttacaaca gtccgcaccg ctgccggtag ctacttgact atccggctgc   1800
actagccctg cgtcagatgg ctctgatcca aggcaaactg ccaaaatatc tgctggcacc   1860
ggaagtcagc gccctgcacc attatgttcc ggatctgcat cgcaggatgc tgctggctac   1920
cctgtggaac acctacatct gtattaacga agcgctggca ttgaccctga gtgattttc    1980
tctggtgccg ccctatccct tgtgcagct tgccacgctc aaaggggttt gaggtccaac    2040
cgtacgaaaa cgtacggtaa gaggaaaatt atcgtctgaa aaatcgatta gtagacaaga    2100
aagtccgtta agtgccaatt ttcgattaaa aagacaccgt tttgatggcg ttttccaatg    2160
tacattatgt ttcgatatat cagacagtta cttcactaac gtacgttttc gttctattgg    2220
ccttcagacc ccatatcctt aatgtccttt atttgctggg gttatcagat cccccgaca    2280
cgtttaatta atgctttctc cgccggagat cgacgcacag gcttctgtgt ctatgatgtt   2340
atttcttaat aatcatccag gtattctctt tatcaccata cgtagtgcga gtgtccacct   2400
taacgcaggg cttccgtca cagcgcgata tgtcagccag cggggctttc ttttgccaga    2460
ccgcttccat cctctgcatt tcagcaatct ggctatatccc gtcattcata aaccacgtaa   2520
atgccgtcac gcaggaagcc aggacgaaga atatcgtcag tacaagataa atcgcggatt   2580
tccacgtata gcgtgacatc tcacgacgca tttcatggat catcgctttc gccgtatcgg   2640
cagcctgatt cagcgcttct gtcgccggtt tctgctgtgc taatccggct tgtttcagtt   2700
cttctcaac ctgagtgagc gcggaactca ccgatttcct gacggtgtca gtcatattac    2760
cggacgcgct gtccagctca cgaatgaccc tgctcagcgt tcactttgc tgctgtaatt    2820
gtgatgaggc ggcctgaaac tgttctgtca gagaagtaac acgcttttcc agcgcctgat   2880
gatgcccgat aagggcggca atttgtttaa tttcgtcgct catacaaaat cctgcctatc   2940
gtgagaatga ccagcccttta tccggcttct gtcgtatctg ttcggcgagt cgctgtcgtt   3000
```

```
ctttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg ctttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc gcgtccggct    3600
ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact ccttgtgctc aaggtcggag tcttttttcac    3960 gggcatactt tccctcacgc gcaatataat cggcatgagg agaggcactg ccttttccgc    4020 cggttttttac gctgagatga taggatgcca tcgtgtttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta gacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680 agaccccgcca taaacgcccc tgagaagccc gtgacgggct tttcttgtat tatgggtagt    4740
ttccttgcat gaatccataa aaggcgcctg tagtgccatt tacccccatt cactgccaga    4800
gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg gatctattc tttttatctt    5040 tttttattct ttctttattc tataaattat aaccacttga atataaacaa aaaaaacaca    5100
caaaggtcta gcggaattta cagagggtct agcagaattt acaagttttc cagcaaaggt    5160
ctagcagaat ttacagatac ccacaactca aggaaaagg actagtaatt atcattgact    5220
agcccatctc aattggtata gtgattaaaa tcacctagac caattgagat gtatgtctga    5280
attagttgtt ttcaaagcaa atgaactagc gattagtcgc tatgacttaa cggagcatga    5340
```

-continued

```
aaccaagcta attttatgct gtgtggcact actcaacccc acgattgaaa accctacaag    5400
gaaagaacgg acggtatcgt tcacttataa ccaatacgct cagatgatga acatcagtag    5460
ggaaaatgct tatggtgtat tagctaaagc aaccagagag ctgatgacga gaactgtgga    5520
aatcaggaat cctttggtta aaggctttga gattttccag tggacaaact atgccaagtt    5580
ctcaagcgaa aaattagaat tagtttttag tgaagagata ttgccttatc ttttccagtt    5640
aaaaaaattc ataaaatata atctggaaca tgttaagtct tttgaaaaca aatactctat    5700
gaggatttat gagtggttat taaaagaact aacacaaaag aaaactcaca aggcaaatat    5760
agagattagc cttgatgaat ttaagttcat gttaatgctt gaaaataact accatgagtt    5820
taaaaggctt aaccaatggg ttttgaaacc aataagtaaa gatttaaaca cttacagcaa    5880
tatgaaattg gtggttgata agcgaggccg cccgactgat acgttgattt ccaagttga    5940
actagataga caaatggatc tcgtaaccga acttgagaac aaccagataa aaatgaatgg    6000
tgacaaaata ccaacaacca ttacatcaga ttcctaccta cgtaacggac taagaaaaac    6060
actacacgat gctttaactg caaaaattca gctcaccagt tttgaggcaa aatttttgag    6120
tgacatgcaa agtaagcatg atctcaatgg ttcgttctca tggctcacgc aaaaacaacg    6180
aaccacacta gagaacatac tggctaaata cggaaggatc tgaggttctt atggctcttg    6240
tatctatcag tgaagcatca agactaacaa acaaaagtag aacaactgtt caccgttaga    6300
tatcaaaggg aaaactgtcc atatgcacag atgaaaacgg tgtaaaaaag atagatacat    6360
cagagctttt acgagttttt ggtgcattta aagctgttca ccatgaacag atcgacaatg    6420
taacagatga acagcatgta acacctaata gaacaggtga aaccagtaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg gagccagtga    6600
cgcctcccgt ggggaaaaaa tcatggcaat tctggaagaa atagcgcttt cagccggcaa    6660
acctgaagcc ggatctgcga ttctgataac aaactagcaa caccagaaca gcccgtttgc    6720
gggcagcaaa accgtacttt tggacgttc cggcggtttt ttgtggcgag tggtgttcgg    6780
gcggtgcgcg caagatccat tatgttaaac gggcgagttt acatctcaaa accgcccgct    6840
taacaccatc agaaatcctc agcgcgattt taagcaccaa cccccccccg taacacccaa    6900
atccatactg aaagtggctt tgttgaataa atcgaacttt tgctgagttg aaggatcaga    6960
tcacgcatcc tcccgacaac acagaccatt ccgtggcaaa gcaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca ttttttgccct gatgaacgtt ccgttgcgct    7260
gcccggatta caccagtgtc agtaagcggg caaagtcggt taatgtcagt ttcaaaacgt    7320
ccaccccgggg tgaaatcgca cacctggtga ttgattccac cgggctgaag gtctttggtg    7380
aaggcgaatg gaaagtcaga aagcacggca agagcgccg tcgtatctgg cgaaagttgc    7440
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccggagtaa tgcgcggtgg aaatggacaa    7740
```

```
cagattacaa ccgtcgctcg atagcggaaa cggcgatgta ccgggtaaaa cagctgttcg    7800
ggggttcact gacgctgcgt gactacgatg gtcaggttgc ggaggctatg gccctggtac    7860
gagcgctgaa caaaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccaccgca cctggtgttt aaacggattt aaattgcagg    8220
ggcagtgagc gcaacgcaat taatgtaagt tagctcactc attaggcacc ccaggcttga    8280
cactttatgc ttccggctcg tataatgtgt ggaattgtga gcggataaca ataacaattt    8340
aaatcaggat ctaggaacca aggagagtgg catatgacgg caggcgcagc agcaagagtg    8400
gctaaattat ttgaatccga ccctcaattt cgtgcggcga tgccgacccc ggcagtgatg    8460
gatagcctgc tggcaccggg tttgcgcctg tcccaggtgc tgcacgccct gctgtcgggt    8520
tacgcggagc gtccggtgat gggtttccgt agccgtgaaa gcgttgtaga tacgccacc    8580 ggccgtactg tcgaccgtct gctgccggca tttgaaacga ttacgtatgg ccagttgctg    8640
gaagatatca gcgctatcct ggccgagtgg cagcacggtg atatcccgat gggtgctggt    8700
gacttcatcg cgacgattgg cttttagcagc ccggactatg tcactctgga cctggcgacc    8760
ctgatgaacg gcagcgtcag catcccgctg caacataaca ccagcgtcgc gcagctgcgt    8820
atgatgctgg aagagacgag cccgcgtctg gttgccgcga gcgcggactg tttggatttg    8880
gctgttgaag cggctgttgg cttgacggac ctgcgccgtg tggttgtgtt cgactaccgt    8940
gcggagacgg acgaccatcg tgagaaactg gcgaccgcgc gtgaacgtct gcacgcagcg    9000 ggtatgacg tggtcgtaga gccgctggcg gaagtcatcg gccgtggtcg cgatctgccg    9060
gagccggttc tgtacaccgc cggtgatgac caacgcacgg cgttgattat gtacacgagc    9120
ggttccacgg gtgccccgaa aggcgcgatg tttacggagt ggaccgttac ccgttttgg    9180 agctccggtg cggcaccgaa ccgcgatacg ccgattatca atgtcaattt cctgccgctg    9240
aaccatctgg cgggtcgcgt cggtctgctg accgcgttca ttccgggtgg cacctgctac    9300
ttcgtcccgg agagcgattt gtccaccctg tttgaggatt ggcagctggc tcgcccgacg    9360
cacatgggcg tcgtgcctcg cgtcgtggac atgctgttcc agcactatca gacccgtgtg    9420
gacgcgctga tggccggtgg taccgatgtt gacaccgccg accgtctggc taagaccgaa    9480
ttgcgcgagg atgtttttggg tggccgtgta gttgcgggta tgttggcgac cgctccgctg    9540
agccctgaga tgaaagcgtt cctggagtcc tcgttggact ttcacctgct ggacctgtat    9600
ggtttgaccg aggttggcgg cgttttccgt gatggcaaga tcagccgtcc gccggtgctg    9660
gattacaaac tggtcgacgt tccggaactg ggttactata cgacggataa accgcatcca    9720
cgtggcgaac tgctggtgaa gtctgcgacc gcgacccag gctattacaa acgtccagac    9780
gttacgcccg aggtctttga cgccgatggt tactatcgta ctggcgacgt gatggcagag    9840
gtcgcgccag accagctggt gtacgttgat cgtcgcaata atgtgattaa gttggctcag    9900
ggcgagttcg ttgcggttgc gaatctggag actgtttacg tgggtgcgcc gctggtgcgt    9960
cagatttttg tttacggtaa cagcgaacgt gcctatctgc tggccgttgt ggtgccgacc    10020
gaagaggcgc tgcgcgcaca cccggatccg gttgagctga agaacagcat tcgtgaatcc    10080
```

```
ctgcagcgta ccgcgcgtag caaccacctg cactcttatg agctgccggc agacttcatt   10140
attgaaacca ccccgttcac gatcgaaagc ggcatgctgg ctgcggtggg caaaccgatc   10200
cgcccgaaga tgattgaaca ttatggtgat cgcctggagc agctgtacgt ggatctggca   10260
gaggcccgtg ttcaggagtt gcgtcagctg cgtgacaccg cacaacaacg cccggttttg   10320
gataccgtta ctgaggcagc gcaggcactg ctgggcatga gcgccgacgc tgtgcgtccg   10380
gatcatcatt tcatcgatct gggtggtgac agcctgagcg cgctgacctt cagcaatctg   10440
ctgcgcgacc tgttcgacgt cgaggtgccg gtgggcgtga ttaccggtcc ggcagcggat   10500
ttgcgtaaac tggcggcgta tattcaacat gaacgcgaac actctaccgc taccgcagcg   10560
agcgttcacg gtttggacac taccgttatc agcgcaaccg agctgacgtt ggataagttc   10620
atcgatgctg aaaccttgca caacgcgagc caactgacgt ccctgccggg tgcggtcgca   10680
acggtcctgc tgaccggtgc gaatggttat ctgggtcgct ttctgtgcct ggaatggctg   10740
cagcgcctga gccaaactgg tggtcaactg atctgtctgg ttcgtggtga caacgcggat   10800
caggccctgg cgcgtctggt cgcggcatat ggcgacaccg accgtaccct gctggaagaa   10860
tttcacaccc tggcacgtcg ccatctgcgt gttattgcgg cagacattgc gcaaccgcgt   10920
ttcggcgttg acgatgctac gtgggagcaa ctggcacgcg atgtggataa gatcgttcac   10980
ccggctgccc tggtgaatca cgtgctgccg tacaatcaat tgtttggccc aaacgtattt   11040
ggtaccgccg aggtgatccg tctggcgttg accacgcgca ttaagccggt tacgtacctg   11100
agcaccatgg ccgtggcgat gaccgtcccg gacttcgatg aggacggtga catccgcacg   11160
gtgtctccga cgcgtcatat cgacccgggc tatgccaatg gctacgcaaa ttcgaaatgg   11220
gcaggtgaag tcctgctgcg tgaggcacat gacatttgcg gcctgccggt tagcgttttt   11280
cgtagcgata tgattctgac ccaccgtcgt tatagcggtc agctgaacgt caccgatgcg   11340
tttacgcgta tgctgctgtc tctggttctg accggtatcg cccctcgcag cttttatcaa   11400
ggtgatggtt ccggtgcgcg tccacgcgcc cactacgaag gtctgccggt ggactttgtc   11460
accgaggcca ttaccagcct gggtctgagc agctccgagg gcttccgtag ctacgatgtc   11520
atgaatccgc acgatgatgg tattagcgtc gataccttcg tcgattggct gatggaagat   11580
ggtcacagca ttgacatcat tgacaactac gacgagtggc tgtctcgctt cgaaactgca   11640
ctgcgcggct tgccggatga gcaacgtcgc gcgagcgtcc tgccgttgct ggacgcgtac   11700
cgcattccgg gcaaccctcg ccgtgctgca gcgaccccga ccacgtgttt ccgcaaggca   11760
gtgcaggaga caatatcgg cggtgacggt gcagacatcc cgcaaattga tcgcgcgctg   11820
atcgcaaaat acatcgcgga tctgcgtgcg catcgtctgc tgtaataagt ttaaacgaga   11880
aggagttcta tcatgattga aaccatctta ccagccggcg tcgaatcagc agagttactt   11940
gagtaccctg aagatctgaa ggcgcatccg gctgaagagc atctgatcgc aaagagcgta   12000
gagaagcgtc gtcgcgactt cattggcgca cgtcattgcg cccgtctggc actggcggag   12060
ctgggtgaac cgccggttgc gattggcaag ggtgaacgtg gtgcgccgat ttggccgcgt   12120
ggtgtcgtgg gctctctgac ccattgcgat ggctatcgcg cagcggcggt tgctcacaaa   12180
atgcgttttc gcagcatcgg catcgacgcc gaaccgcacg cgaccctgcc ggaaggtgtc   12240
ctggattcgg ttagcctgcc gcctgagcgt gagtggctga aaaccaccga cagcgcactg   12300
cacctggacc gtttgctgtt ttgtgcgaaa gaagcaactt acaaagcgtg gtggccgctg   12360
acggcacgtt ggctgggttt cgaagaagcg cacattacct tcgaaatcga ggatggtagc   12420
gccgactctg gtaatggcac gtttcacagc gaactgctgg tgccgggtca gaccaatgac   12480
```

```
ggtggtaccc cgctgctgtc tttcgacggt cgctggctga tcgctgatgg cttcatcctg   12540
acggcgattg catacgcatg ataaattaac ctaggctgct gccaccgctg agcaataact   12600
agcataaccc cttggggcct ctaaacgggt cttgaggggt ttttgctga gctcgagtga    12660 ccccagccgc ccctcatgcc aaccgagccc attaagcgca gagtcggccg caactatctc   12720
ggggacgcat aaacacgcag cgatttacca aggagttcgg ctaggtcaat ccgcaattcc   12780 cttttgcctgg ccgagatgc cgcgagcaaa caatgtgtcc ggtcgctacc agatggactt   12840
tgtgggcgga ggattgcacc agacgcttca gcgcagcgtc gtacgatgaa tcggaaggcc   12900
cggtaagcaa ttgaagaacc gctgaccacc tcccatccga caatgcaagg gtgccccgct   12960
cccagcgcga cacggttgcc tgatccacac ccattaattc agctaggtga ctttgcttca   13020
tatgacgaag caaccgcgcc ctccgcacct gccgccccct gtcattcgtc aacattcttc   13080
agcacctcaa tgtcgttcgt agtgagcctc atttttcaa gaccgccgat gatgagagcc    13140
aggcctcgct cgaatgccgc gtccggaccg ccttcgtaga cgattttcat cgcgctctgt   13200
aggcgcgccg gcatcgtaga cgctgaggtg gtcaactgat cttcgccccg ctcctcggcg   13260
tctgcctcgc tagcttgctg ctcaagaaca gcgccgacgg tgaagtagct gattgccatc   13320
aacgcatagg tcgcgtcacc tgccgaaaag ccagcatcgc aaaggaagcg aagctgcgcg   13380
tcggcttttt ccatctgcgg cgcggctggc gcgtcccgg catgaatacg cgcgccatcg    13440
cgataagcga gcaacgcccg tcgaaaactg catgcattgc ccttcaggaa cgaacgccag   13500
tcgtcgtcat cccttggcgt cgaatgcgtg tgatttatcg tcagcatggc ttcggcaagt   13560
gcgtcgagca acgcacgctt gttcttgaaa tgccagtaga gcgctggctg ttgcaccccg   13620
aggcgctcag ccagtcggcg cgtcgttaga ccttccatgc ccacgtcgtt aagcagttcg   13680
agcgcggttc ggatcacggc ctcgcgttgg agcttgttca ttcgcgaa                13728

<210> SEQ ID NO 24
<211> LENGTH: 13689
<212> TYPE: DNA
<213> ORGANISM: Artificial Sequence
<220> FEATURE:
<223> OTHER INFORMATION: vector

<400> SEQUENCE: 24
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360 cacaccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg gcaggccccg tggccggggg   540
actgttgggc gccatctcct tgcatgcacc attccttgcg gcggcggtgc tcaacggcct   600
caacctacta ctgggctgct tcctaatgca ggagtcgcat aagggagagc gtcgaccgat   660
gcccttgaga gccttcaacc cagtcagctc cttccggtgg gcgcggggca tgactatcgt   720
cgccgcactt atgactgtct ctttatcat gcaactcgta ggacaggtgc cggcagcgct    780
```

```
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggaccccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcccctacg tgctgctgaa gttgcccgca acagagagtg   1680
gaaccaaccg gtgataccac gatactatga ctgagagtca acgccatgag cggcctcatt   1740
tcttattctg agttacaaca gtccgcaccg ctgccggtag ctacttgact atccggctgc   1800
actagccctg cgtcagatgg ctctgatcca aggcaaactg ccaaaatatc tgctggcacc   1860
ggaagtcagc gccctgcacc attatgttcc ggatctgcat cgcaggatgc tgctggctac   1920
cctgtggaac acctacatct gtattaacga agcgctggca ttgaccctga gtgattttc   1980
tctggtgccg ccctatccct ttgtgcagct tgccacgctc aaaggggttt gaggtccaac   2040
cgtacgaaaa cgtacggtaa gaggaaaatt atcgtctgaa aaatcgatta gtagacaaga   2100
aagtccgtta agtgccaatt ttcgattaaa aagacaccgt tttgatggcg tttccaatg    2160
tacattatgt ttcgatatat cagacagtta cttcactaac gtacgttttc gttctattgg   2220
ccttcagacc ccatatcctt aatgtccttt atttgctggg gttatcagat cccccgaca    2280
cgtttaatta atgctttctc cgccggagat cgacgcacag gcttctgtgt ctatgatgtt   2340
atttcttaat aatcatccag gtattctctt tatcaccata cgtagtgcga gtgtccacct   2400
taacgcaggg ctttccgtca cagcgcgata tgtcagccag cggggctttc ttttgccaga   2460
ccgcttccat cctctgcatt tcagcaatct ggctataccc gtcattcata aaccacgtaa   2520
atgccgtcac gcaggaagcc aggacgaaga atatcgtcag tacaagataa atcgcggatt   2580
tccacgtata gcgtgacatc tcacgacgca tttcatggat catcgctttc gccgtatcgg   2640
cagcctgatt cagcgcttct gtcgccggtt tctgctgtgc taatccggct tgtttcagtt   2700
cttttctcaac ctgagtgagc gcggaactca ccgatttcct gacggtgtca gtcatattac   2760
cggacgcgct gtccagctca cgaatgaccc tgctcagcgt ttcactttgc tgctgtaatt   2820
gtgatgaggc ggcctgaaac tgttctgtca gagaagtaac acgcttttcc agcgcctgat   2880
gatgcccgat aagggcggca atttgtttaa tttcgtcgct catacaaaat cctgcctatc   2940
gtgagaatga ccagcctttta tccggcttct gtcgtatctg ttcggcgagt cgctgtcgtt   3000
ctttctcctg ctgacgctgt ttttccgcca gacgttcgcg ctctctctgc ctttccatct   3060
cctgatgtat cccctggaac tccgccatcg catcgttaac aagggactga agatcgattt   3120
cttcctgtat atccttcatg gcatcactga ccagtgcgtt cagcttgtca ggctcttttt   3180
```

```
caaaatcaaa cgttctgccg gaatgggatt cctgctcagg ctctgacttc agctcctgtt   3240
ttagcgtcag agtatccctc tcgctgaggg cttcccgtaa cgaggtagtc acgtcaatta   3300
cgctgtcacg ttcatcacgg gactgctgca cctgcctttc agcctccctg cgctcaagaa   3360
tggcctgtag ctgctcagta tcgaatcgct gaacctgacc cgcgcccaga tgccgctcag   3420
gctcacggtc aatgccctgc gccttcaggg aacgggaatc aacccggtca gcgtgctgat   3480
accgttcaag gtgcttattc tggaggtcag cccagcgtct ccctctgggc aacaaggtat   3540
tctttgcgtt cggtcggtgt ttccccgaaa cgtgcctttt ttgcgccacc gcgtccggct   3600
ctttggtgtt agcccgttta aaatactgct cagggtcacg gtgaataccg tcattaatgc   3660
gttcagagaa catgatatgg gcgtggggct gctcgccacc ggctatcgct gctttcggat   3720 tatgatagc gaactgatag gcatggcggt cgccaatttc ctgttggaca aaatcgcgga   3780
caagctcaag acgttgttcg ggttttaact cacgcggcag ggcaatctcg atttcacggt   3840
aggtacagcc gttggcacgt tcagacgtgt cagcggcttt ccagaactcg gacggtttat   3900
gcgctgccca cgccggcata ttgccggact ccttgtgctc aaggtcggag tcttttttcac  3960 gggcatactt tccctcacgc gcaatataat cggcatgagg agaggcactg ccttttccgc   4020 cggttttac gctgagatga taggatgcca tcgtgtttta tcccgctgaa gggcgcacgt    4080
ttctgaacga agtgaagaaa gtctaagtgc gccctgataa ataaaagagt tatcagggat   4140
tgtagtggga tttgacctcc tctgccatca tgagcgtaat cattccgtta gcattcagga   4200
ggtaaacagc atgaataaaa gcgaaaaaac aggaacaatg ggcagcagaa agagtgcagt   4260
atattcgcgg cttaaagtcg ccgaatgagc aacagaaact tatgctgata ctgacggata   4320
aagcagataa aacagcacag gatatcaaaa cgctgtccct gctgatgaag gctgaacagg   4380
cagcagagaa agcgcaggaa gccagagcga aagtcatgaa cctgatacag gcagaaaagc   4440
gagccgaagc cagagccgcc cgtaaagccc gtgaccatgc tctgtaccag tctgccggat   4500
tgcttatcct ggcgggtctg gttgacagta agacgggtaa gcctgttgat gataccgctg   4560
ccttactggg tgcattagcc agtctgaatg acctgtcacg ggataatccg aagtggtcag   4620
actggaaaat cagagggcag gaactgctga acagcaaaaa gtcagatagc accacatagc   4680
agacccgcca taaaacgccc tgagaagccc gtgacgggct tttcttgtat tatgggtagt   4740
ttccttgcat gaatccataa aaggcgcctg tagtgccatt taccccatt cactgccaga    4800 gccgtgagcg cagcgaactg aatgtcacga aaagacagc gactcaggtg cctgatggtc    4860
ggagacaaaa ggaatattca gcgatttgcc cgagcttgcg agggtgctac ttaagccttt   4920
agggttttaa ggtctgtttt gtagaggagc aaacagcgtt tgcgacatcc ttttgtaata   4980
ctgcggaact gactaaagta gtgagttata cacagggctg ggatctattc tttttatctt   5040
tttttattct ttctttattc tataaattat aaccacttga atataaacaa aaaaaacaca   5100
caaaggtcta gcggaattta cagagggtct agcagaattt acaagttttc agcaaaggt    5160 ctagcagaat ttacagatac ccacaactca aggaaaagg actagtaatt atcattgact    5220
agcccatctc aattggtata gtgattaaaa tcacctagac caattgagat gtatgtctga   5280
attagttgtt ttcaaagcaa atgaactagc gattagtcgc tatgacttaa cggagcatga   5340
aaccaagcta attttatgct gtgtggcact actcaacccc acgattgaaa accctacaag   5400
gaaagaacgg acggtatcgt tcacttataa ccaatacgct cagatgatga acatcagtag   5460
ggaaaatgct tatggtgtat tagctaaagc aaccagagag ctgatgacga aactgtggga   5520
```

```
aatcaggaat cctttggtta aaggctttga gattttccag tggacaaact atgccaagtt   5580
ctcaagcgaa aaattagaat tagtttttag tgaagagata ttgccttatc ttttccagtt   5640
aaaaaaattc ataaaatata atctggaaca tgttaagtct tttgaaaaca aatactctat   5700
gaggatttat gagtggttat taaaagaact aacacaaaag aaaactcaca aggcaaatat   5760
agagattagc cttgatgaat ttaagttcat gttaatgctt gaaataaact accatgagtt   5820
taaaaggctt aaccaatggg ttttgaaacc aataagtaaa gatttaaaca cttacagcaa   5880
tatgaaattg gtggttgata agcgaggccg cccgactgat acgttgattt tccaagttga   5940
actagataga caaatggatc tcgtaaccga acttgagaac aaccagataa aaatgaatgg   6000
tgacaaaata ccaacaacca ttacatcaga ttcctaccta cgtaacggac taagaaaaac   6060
actacacgat gctttaactg caaaaattca gctcaccagt tttgaggcaa aattttgag    6120
tgacatgcaa agtaagcatg atctcaatgg ttcgttctca tggctcacgc aaaaacaacg   6180
aaccacacta gagaacatac tggctaaata cggaaggatc tgaggttctt atggctcttg   6240
tatctatcag tgaagcatca agactaacaa acaaaagtag aacaactgtt caccgttaga   6300
tatcaaaggg aaaactgtcc atatgcacag atgaaaacgg tgtaaaaaag atagatacat   6360
cagagctttt acgagttttt ggtgcattta aagctgttca ccatgaacag atcgacaatg   6420
taacagatga acagcatgta acacctaata gaacaggtga aaccagtaaa acaaagcaac   6480
tagaacatga aattgaacac ctgagacaac ttgttacagc tcaacagtca cacatagaca   6540
gcctgaaaca ggcgatgctg cttatcgaat caaagctgcc gacaacacgg gagccagtga   6600
cgcctcccgt ggggaaaaaa tcatggcaat tctggaagaa atagcgcttt cagccggcaa   6660
acctgaagcc ggatctgcga ttctgataac aaactagcaa caccagaaca gcccgtttgc   6720
gggcagcaaa acccgtactt ttggacgttc cggcggtttt tgtggcgag tggtgttcgg    6780
gcggtgcgcg caagatccat tatgttaaac gggcgagttt acatctcaaa accgcccgct   6840
taacaccatc agaaatcctc agcgcgattt taagcaccaa ccccccccg taacacccaa    6900
atccatactg aaagtggctt tgttgaataa atcgaacttt tgctgagttg aaggatcaga   6960
tcacgcatcc tcccgacaac acagaccatt ccgtggcaaa gcaaaagttc agaatcacca   7020
actggtccac ctacaacaaa gctctcatca accgtggctc cctcactttc tggctggatg   7080
atgaggcgat tcaggcctgg tatgagtcgg caacaccttc atcacgagga aggccccagc   7140
gctattctga tctcgccatc accaccgttc tggtgattaa acgcgtattc cggctgaccc   7200
tgcgggctgc gcagggtttt attgattcca ttttttgccct gatgaacgtt ccgttgcgct   7260
gcccggatta caccagtgtc agtaagcggg caaagtcggt taatgtcagt ttcaaaacgt   7320
ccacccgggg tgaaatcgca cacctggtga ttgattccac cgggctgaag gtctttggtg   7380
aaggcgaatg gaaagtcaga aagcacggca agagcgccg tcgtatctgg cgaaagttgc    7440
atcttgctgt tgacagcaac acacatgaag ttgtctgtgc agacctgtcg ctgaataacg   7500
tcacggactc agaagccttc ccgggcctta tccggcagac tcacagaaaa atcagggcag   7560
ccgcggcaga cggggcttac gatacccggc tctgtcacga tgaactgcgc cgcaaaaaaa   7620
tcagcgcgct tattcctccc cgaaaaggtg cgggttactg gcccggtgaa tatgcagacc   7680
gtaaccgtgc agtggctaat cagcgaatga ccggagtaa tgcgcggtgg aaatggacaa    7740
cagattacaa ccgtcgctcg atagcggaaa cggcgatgta ccgggtaaaa cagctgttcg   7800
ggggttcact gacgctgcgt gactacgatg gtcaggttgc ggaggctatg gcctggtac    7860
gagcgctgaa caaaatgacg aaagcaggta tgcctgaaag cgtgcgtatt gcctgaaaac   7920
```

| | |
|---|---|
| acaacccgct acggggggaga cttacccgaa atctgattta ttcaacaaag ccgggtgtgg | 7980 |
| tgaactacaa agcagacccg ttgaggttat cagttcgatg cacaatcagc agcgcataaa | 8040 |
| atatgcacaa gaacaggagc acccttcgca ttaagctgtg gtggtaacaa gtagtgccgg | 8100 |
| gctaccatca gcgagcatga tgcgctccca cagcattcgc cttggcagta tggaagttcc | 8160 |
| tcgctccagt tcgggccggt atccaccgca cctggtgttt aaacggattt aaattgcagg | 8220 |
| ggcagtgagc gcaacgcaat taatgtaagt tagctcactc attaggcacc ccaggcttga | 8280 |
| cactttatgc ttccggctcg tataatgtgt ggaattgtga gcggataaca ataacaattt | 8340 |
| aaatcaggat ctaggaacca aggagagtgg catatgtttg cagaggatga acaagtgaag | 8400 |
| gcggcggtac cagatcagga agttgtggaa gcgatccgcg caccgggtct gcgcctggct | 8460 |
| caaatcatgg cgacggtgat ggagcgctac gccgaccgtc cggccgttgg tcaacgtgct | 8520 |
| tctgagccgg ttaccgagag cggccgtacg acgtttcgtc tgctgccgga gtttgagacg | 8580 |
| ttgacctacc gtgaactgtg ggcgcgtgtc cgtgcagtcg ccgcagcttg cacggtgac | 8640 |
| gctgagcgtc cactgcgcgc aggtgacttc gtcgcgctgc tgggctttgc cggtatcgac | 8700 |
| tacggcaccc tggacttggc gaacatccac ctgggcttgg ttaccgtccc gctgcagtct | 8760 |
| ggcgcgaccg ctccgcaact ggcggcgatc ctggccgaaa cgaccccgcg tgtcttggcg | 8820 |
| gcgacgccgg atcatctgga tattgcggtt gagttgctga ctggtggcgc gagcccggaa | 8880 |
| cgcttggttg tgttcgacta ccgtccggca gatgatgacc accgtgcagc attggagagc | 8940 |
| gcacgtcgcc gtttgagcga tgcaggcagc gcggtcgttg ttgaaacctt ggacgcggtg | 9000 |
| cgtgctcgtg gttccgaact gccggcagca ccgctgttcg tcccggctgc ggatgaagat | 9060 |
| ccgttgcgc tgctgattta cacgagcggt agcaccggca ccccgaaagg cgcaatgtat | 9120 |
| accgagcgcc tgaatcgtac gacctggctg agcggtgcga agggcgtggg cctgacgttg | 9180 |
| ggttatatgc cgatgagcca tatcgcgggt cgtgcgagct tcgcgggtgt gctggcgcgt | 9240 |
| ggtggtaccg tctactttac cgcccgtagc gatatgagca ctctgtttga ggatttggcg | 9300 |
| ctggtccgtc cgacggagat gttcttcgtt ccgcgcgtgt gcgacatgat ctttcagcgt | 9360 |
| tatcaagcgg agttgtcgcg tcgtgcgcca gccgcagcgg caagccctga actgaacag | 9420 |
| gaactgaaaa ccgagctgcg tctgtccgcg gttggcgacc gcctgctggg tgcgattgcg | 9480 |
| ggttctgcac cgctgagcgc ggagatgcgt gagtttatgg agtccttgct ggatctggag | 9540 |
| ttgcatgacg gctacggttc caccgaggcc ggcatcggtg tcctgcaaga caatatcgtt | 9600 |
| caacgtccgc cggttattga ttacaagctg gtggacgttc cggagttggg ctatttccgt | 9660 |
| accgaccagc cgcaccctcg cggtgaactg ctgctgaaaa cggaaggtat gattccgggt | 9720 |
| tatttccgtc gcccggaagt taccgcgcgag attttcgatg aggacggctt ctatcgtacg | 9780 |
| ggtgatatcg ttgcggaact ggagccagac cgcctgatct atctggaccg tcgcaataac | 9840 |
| gtactgaagc tggcgcaagg cgagtttgtc acggtggccc atctgaagc agtgttcgcg | 9900 |
| acgtctccgc tgatccgtca gatctacatc tatggtaaca gcgagcgtag cttttttgctg | 9960 |
| gcagtcattg tgccgaccgc ggacgcgctg gcggacggtg tgaccgatgc cctgaacacc | 10020 |
| gctctgactg agtcgctgcg ccagttggcg aaagaagccg gtctgcagag ctatgaactg | 10080 |
| ccgcgtgagt tcctggtcga gacggagccg ttcaccgttg agaatggtct gctgagcggt | 10140 |
| attgcgaaac tgctgcgtcc gaagctgaaa gaacactacg gtgaacgcct ggagcagttg | 10200 |
| tatcgcgaca ttgaagccaa tcgcaacgat gaactgatcg agctgcgccg taccgcagcg | 10260 |

```
gagttgccgg ttctggaaac tgtgacgcgt gcggcacgca gcatgctggg tctggccgcg    10320
agcgaactgc gtccagacgc gcattttacc gacctgggtg gtgactctct gtcggcgctg    10380
tcctttagca ccctgctgca agatatgttg gaagttgagg tgccggtggg cgttattgtg    10440
tctccggcaa acagcctggc tgacctggcc aagtatattg aggcggaacg tcactccggt    10500
gtccgccgtc cgagcctgat cagcgtgcac ggcccaggta ccgagattcg cgctgcagat    10560
ctgacgctgg acaaattcat tgacgagcgc accctggcag cggcgaaggc agttccggct    10620
gcacctgccc aagcacagac cgtgctgctg accggtgcaa atggttacct gggtcgtttc    10680
ttgtgcctgg aatggctgca gcgtctggat caaaccggcg gtacgctggt ctgtattgtg    10740
cgcggcaccg atgcggcagc agcgcgtaag cgcctggatg cggttttcga cagcggtgat    10800
cctgagctgc tggatcacta ccgtaagctg gcagccgagc acctggaagt tctggcgggt    10860
gacatcggtg acccgaacct gggtctggat gaggccacgt ggcagcgcct ggccgcgacc    10920
gtggatctga ttgtgcatcc ggctgctttg gttaatcacg tgctgccgta cagccagctg    10980
ttcggtccga acgtcgtcgg caccgcagag attattcgcc tggcgattac cgagcgtcgt    11040
aaaccggtga cctacctgag cactgtcgcg gttgccgccc aagtggaccc tgcgggcttc    11100
gatgaagaac gtgacatccg cgagatgagc gcggtccgta gcattgacgc gggctacgcg    11160
aacggctatg gtaatagcaa atgggctggt gaggttctgc tgcgcgaggc acacgatctg    11220
tgtggtctgc cggtggccgt attccgcagc gatatgattc tggcacactc caaatacgtt    11280
ggccagctga acgtgccgga cgttttacg cgtctgattc tgagcctggc cctgacgggc    11340
atcgctccgt atagcttta cggtactgac agcgccggtc aacgtcgtcg tgcacactat    11400
gacggcctgc cggcagattt cgtcgccgaa gctattacca cgctgggcgc tcgcgcagaa    11460
agcggctttc acacctacga cgtttggaac ccgtacgacg acggtatttc cctggacgaa    11520
tttgtggact ggctgggcga ttttggcgtt ccgattcaac gtatcgatga ttatgacgag    11580
tggttccgcc gtttcgaaac cgcgatccgt gcgctgccgg agaaacagcg cgacgcgagc    11640
ctgctgccgc tgctggatgc ccatcgtcgt ccattgcgtg cagtgcgtgg tagcctgttg    11700
ccggcgaaga atttcaggc tgcggtccag tcggcacgca tcggtccgga ccaggatatc    11760
ccgcatctga gcccgcaact gatcgataag tacgtcaccg atttgcgtca tttgggcctg    11820
ctgtaataag tttaaacgag aaggagttct atcatgattg aaaccatctt accagccggc    11880
gtcgaatcag cagagttact tgagtaccct gaagatctga aggcgcatcc ggctgaagag    11940
catctgatcg caaagagcgt agagaagcgt cgtcgcgact tcattggcgc acgtcattgc    12000
gcccgtctgg cactggcgga gctgggtgaa ccgccggttg cgattggcaa gggtgaacgt    12060
ggtgcgccga tttggccgcg tggtgtcgtg ggctctctga cccattgcga tggctatcgc    12120
gcagcggcgg ttgctcacaa aatgcgtttt cgcagcatcg gcatcgacgc cgaaccgcac    12180
gcgaccctgc cggaaggtgt cctggattcg gttagcctgc cgcctgagcg tgagtggctg    12240
aaaaccaccg acagcgcact gcacctggac cgtttgctgt tttgtgcgaa agaagcaact    12300
tacaaagcgt ggtggccgct gacggcacgt tggctgggtt tcgaagaagc gcacattacc    12360
ttcgaaatcg aggatggtag cgccgactct ggtaatggca cgtttcacag cgaactgctg    12420
gtgccgggtc agaccaatga cggtggtacc ccgctgctgt cttcgacgg tcgctggctg    12480 atcgctgatg gcttcatcct gacggcgatt gcatacgcat gataaattaa cctaggctgc    12540
tgccaccgct gagcaataac tagcataacc ccttggggcc tctaaacggg tcttgagggg    12600 tttttttgctg agctcgagtg accccagccg cccctcatgc caaccgagcc cattaagcgc    12660
```

```
agagtcggcc gcaactatct cggggacgca taaacacgca gcgatttacc aaggagttcg    12720
gctaggtcaa tccgcaattc cctttgcctg gccggagatg ccgcgagcaa acaatgtgtc    12780
cggtcgctac cagatggact ttgtgggcgg aggattgcac cagacgcttc agcgcagcgt    12840
cgtacgatga atcggaaggc ccggtaagca attgaagaac cgctgaccac ctcccatccg    12900
acaatgcaag ggtgccccgc tcccagcgcg acacggttgc ctgatccaca cccattaatt    12960
cagctaggtg actttgcttc atatgacgaa gcaaccgcgc cctccgcacc tgccgccccc    13020
tgtcattcgt caacattctt cagcacctca atgtcgttcg tagtgagcct cattttttca    13080
agaccgccga tgatgagagc caggcctcgc tcgaatgccg cgtccggacc gccttcgtag    13140
acgattttca tcgcgctctg taggcgcgcc ggcatcgtag acgctgaggt ggtcaactga    13200
tcttcgcccc gctcctcggc gtctgcctcg ctagcttgct gctcaagaac agcgccgacg    13260
gtgaagtagc tgattgccat caacgcatag gtcgcgtcac ctgccgaaaa gccagcatcg    13320
caaaggaagc gaagctgcgc gtcggctttt tccatctgcg gcgcggctgg ccgcgtcccg    13380
gcatgaatac gcgcgccatc gcgataagcg agcaacgccc gtcgaaaact gcatgcattg    13440
cccttcagga acgaacgcca gtcgtcgtca tcccttggcg tcgaatgcgt gtgatttatc    13500
gtcagcatgg cttcggcaag tgcgtcgagc aacgcacgct tgttcttgaa atgccagtag    13560
agcgctggct gttgcacccc gaggcgctca gccagtcggc gcgtcgttag accttccatg    13620
cccacgtcgt taagcagttc gagcgcggtt cggatcacgg cctcgcgttg gagcttgttc    13680
attcgcgaa                                                             13689

<210> SEQ ID NO 25
<211> LENGTH: 13803
<212> TYPE: DNA
<213> ORGANISM: Artificial Sequence
<220> FEATURE:
<223> OTHER INFORMATION: vector

<400> SEQUENCE: 25
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360
cacacccgtc ctgtggatcc tctacgccgg acgcatcgtg gccggcatca ccggcgccac     420
aggtgcggtt gctggcgcct atatcgccga catcaccgat ggggaagatc gggctcgcca     480
cttcgggctc atgagcgctt gtttcggcgt gggtatggtg gcaggccccg tggccggggg     540
actgttgggc gccatctcct tgcatgcacc attccttgcg gcggcggtgc tcaacggcct     600
caacctacta ctgggctgct tcctaatgca ggagtcgcat aagggagagc gtcgaccgat     660
gcccttgaga gccttcaacc cagtcagctc cttccggtgg gcgcggggca tgactatcgt     720
cgccgcactt atgactgtct tctttatcat gcaactcgta ggacaggtgc cggcagcgct     780
ctgggtcatt ttcggcgagg accgctttcg ctggagcgcg acgatgatcg gcctgtcgct     840
tgcggtattc ggaatcttgc acgccctcgc tcaagccttc gtcactggtc ccgccaccaa     900
acgtttcggc gagaagcagg ccattatcgc cggcatggcg gccgacgcgc tgggctacgt     960
```

```
cttgctggcg ttcgcgacgc gaggctggat ggccttcccc attatgattc ttctcgcttc    1020
cggcggcatc gggatgcccg cgttgcaggc catgctgtcc aggcaggtag atgacgacca    1080
tcagggacag cttcaaggat cgctcgcggc tcttaccagc ctaacttcga tcactggacc    1140
gctgatcgtc acggcgattt atgccgcctc ggcgagcaca tggaacgggt tggcatggat    1200
tgtaggcgcc gccctatacc ttgtctgcct ccccgcgttg cgtcgcggtg catggagccg    1260
ggccacctcg acctgaatgg aagccggcgg cacctcgcta acggattcac cactccaaga    1320
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
ggttgcctta ctggttagca gaatgaatca ccgatacgcg agcgaacgtg aagcgactgc    1560
tgctgcaaaa cgtctgcgac ctgagcaaca acatgaatgg tcttcggttt ccgtgtttcg    1620
taaagtctgg aaacgcggaa gtcccctacg tgctgctgaa gttgcccgca acagagagtg    1680
gaaccaaccg gtgataccac gatactatga ctgagagtca acgccatgag cggcctcatt    1740
tcttattctg agttacaaca gtccgcaccg ctgccggtag ctacttgact atccggctgc    1800
actagccctg cgtcagatgg ctctgatcca aggcaaactg ccaaaatatc tgctggcacc    1860
ggaagtcagc gccctgcacc attatgttcc ggatctgcat cgcaggatgc tgctggctac    1920
cctgtggaac acctacatct gtattaacga agcgctggca ttgaccctga gtgattttc    1980 tctggtgccg ccctatccct ttgtgcagct tgccacgctc aaaggggttt gaggtccaac    2040
cgtacgaaaa cgtacggtaa gaggaaaatt atcgtctgaa aaatcgatta gtagacaaga    2100
aagtccgtta agtgccaatt ttcgattaaa aagacaccgt tttgatggcg ttttccaatg    2160
tacattatgt ttcgatatat cagacagtta cttcactaac gtacgttttc gttctattgg    2220
ccttcagacc ccatatcctt aatgtccttt atttgctggg gttatcagat cccccgaca    2280 cgtttaatta atgctttctc cgccggagat cgacgcacag gcttctgtgt ctatgatgtt    2340
atttcttaat aatcatccag gtattctctt tatcaccata cgtagtgcga gtgtccacct    2400
taacgcaggg ctttccgtca cagcgcgata tgtcagccag cggggctttc ttttgccaga    2460
ccgcttccat cctctgcatt tcagcaatct ggctataccc gtcattcata aaccacgtaa    2520
atgccgtcac gcaggaagcc aggacgaaga atatcgtcag tacaagataa atcgcggatt    2580
tccacgtata gcgtgacatc tcacgacgca tttcatggat catcgctttc gccgtatcgg    2640
cagcctgatt cagcgcttct gtcgccggtt tctgctgtgc taatccggct tgtttcagtt    2700 cttttctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagccttta tccggcttct gtcgtatctg ttcggcgagt cgctgtcgtt    3000
ctttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
```

```
tggcctgtag ctgctcagta tcgaatcgct gaacctgacc cgcgcccaga tgccgctcag   3420
gctcacggtc aatgccctgc gccttcaggg aacgggaatc aacccggtca gcgtgctgat   3480
accgttcaag gtgcttattc tggaggtcag cccagcgtct ccctctgggc aacaaggtat   3540
tctttgcgtt cggtcggtgt ttccccgaaa cgtgccttt tgcgccacc gcgtccggct     3600 ctttggtgtt agcccgttta aaatactgct cagggtcacg gtgaataccg tcattaatgc   3660
gttcagagaa catgatatgg gcgtggggct gctcgccacc ggctatcgct gctttcggat   3720
tatggatagc gaactgatag gcatggcggt cgccaatttc ctgttggaca aaatcgcgga   3780
caagctcaag acgttgttcg ggttttaact cacgcggcag ggcaatctcg atttcacggt   3840
aggtacagcc gttggcacgt tcagacgtgt cagcggcttt ccagaactcg acggtttat    3900 gcgctgccca cgccggcata ttgccggact ccttgtgctc aaggtcggag tcttttcac    3960 gggcatactt tccctcacgc gcaatataat cggcatgagg agaggcactg ccttttccgc   4020 cggttttac gctgagatga taggatgcca tcgtgtttta tcccgctgaa gggcgcacgt    4080
ttctgaacga agtgaagaaa gtctaagtgc gccctgataa ataaagagt tatcagggat    4140 tgtagtggga tttgacctcc tctgccatca tgagcgtaat cattccgtta gcattcagga   4200
ggtaaacagc atgaataaaa gcgaaaaaac aggaacaatg ggcagcagaa agagtgcagt   4260
atattcgcgg cttaaagtcg ccgaatgagc aacagaaact tatgctgata ctgacggata   4320
aagcagataa aacagcacag gatatcaaaa cgctgtccct gctgatgaag gctgaacagg   4380
cagcagagaa agcgcaggaa gccagagcga aagtcatgaa cctgatacag gcagaaaagc   4440
gagccgaagc cagagccgcc cgtaaagccc gtgaccatgc tctgtaccag tctgccggat   4500
tgcttatcct ggcgggtctg gttgacagta agacgggtaa gcctgttgat gataccgctg   4560
ccttactggg tgcattagcc agtctgaatg acctgtcacg ggataatccg aagtggtcag   4620
actggaaaat cagagggcag gaactgctga acagcaaaaa gtcagatagc accacatagc   4680
agacccgcca taaaacgccc tgagaagccc gtgacgggct tttcttgtat tatgggtagt   4740
ttccttgcat gaatccataa aaggcgcctg tagtgccatt tacccccatt cactgccaga   4800
gccgtgagcg cagcgaactg aatgtcacga aaaagacagc gactcaggtg cctgatggtc   4860
ggagacaaaa ggaatattca gcgatttgcc cgagcttgcg agggtgctac ttaagccttt   4920
agggttttaa ggtctgtttt gtagaggagc aaacagcgtt tgcgacatcc ttttgtaata   4980
ctgcggaact gactaaagta gtgagttata cacagggctg ggatctattc ttttatctt    5040 tttttattct ttctttattc tataaattat aaccacttga atataaacaa aaaaaacaca   5100
caaaggtcta gcggaattta cagagggtct agcagaattt acaagttttc cagcaaaggt   5160
ctagcagaat ttacagatac ccacaactca aggaaaagg actagtaatt atcattgact    5220
agcccatctc aattggtata gtgattaaaa tcacctagac caattgagat gtatgtctga   5280
attagttgtt ttcaaagcaa atgaactagc gattagtcgc tatgacttaa cggagcatga   5340
aaccaagcta attttatgct gtgtggcact actcaacccc acgattgaaa accctacaag   5400
gaaagaacgg acggtatcgt tcacttataa ccaatacgct cagatgatga acatcagtag   5460
ggaaaatgct tatggtgtat tagctaaagc aaccagagag ctgatgacga aactgtggaa   5520
aatcaggaat cctttggtta aaggctttga gattttccag tggacaaact atgccaagtt   5580
ctcaagcgaa aaattagaat tagttttag tgaagagata ttgccttatc ttttccagtt    5640
aaaaaaattc ataaaatata atctggaaca tgttaagtct tttgaaaaca aatactctat   5700
```

```
gaggatttat gagtggttat taaaagaact aacacaaaag aaaactcaca aggcaaatat    5760
agagattagc cttgatgaat ttaagttcat gttaatgctt gaaaataact accatgagtt    5820
taaaaggctt aaccaatggg ttttgaaacc aataagtaaa gatttaaaca cttacagcaa    5880
tatgaaattg gtggttgata agcgaggccg cccgactgat acgttgattt tccaagttga    5940
actagataga caaatggatc tcgtaaccga acttgagaac aaccagataa aaatgaatgg    6000
tgacaaaata ccaacaacca ttacatcaga ttcctaccta cgtaacggac taagaaaaac    6060
actacacgat gctttaactg caaaaattca gctcaccagt tttgaggcaa aattttttgag   6120 tgacatgcaa agtaagcatg atctcaatgg ttcgttctca tggctcacgc aaaaacaacg    6180
aaccacacta gagaacatac tggctaaata cggaaggatc tgaggttctt atggctcttg    6240
tatctatcag tgaagcatca agactaacaa acaaaagtag aacaactgtt caccgttaga    6300
tatcaaaggg aaaactgtcc atatgcacag atgaaaacgg tgtaaaaaag atagatacat    6360
cagagctttt acgagttttt ggtgcattta aagctgttca ccatgaacag atcgacaatg    6420
taacagatga acagcatgta acacctaata gaacaggtga aaccagtaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg gagccagtga    6600
cgcctcccgt ggggaaaaaa tcatggcaat tctggaagaa atagcgcttt cagccggcaa    6660
acctgaagcc ggatctgcga ttctgataac aaactagcaa caccagaaca gcccgtttgc    6720
gggcagcaaa accgtactt ttggacgttc cggcggtttt ttgtggcgag tggtgttcgg    6780
gcggtgcgcg caagatccat tatgttaaac gggcgagttt acatctcaaa accgcccgct    6840
taacaccatc agaaatcctc agcgcgattt taagcaccaa cccccccccg taacacccaa    6900
atccatactg aaagtggctt tgttaataa atcgaacttt tgctgagttg aaggatcaga    6960
tcacgcatcc tcccgacaac acagaccatt ccgtggcaaa gcaaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca ttttttgccct gatgaacgtt ccgttgcgct    7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga aagcacggca aagagcgccg tcgtatctgg cgaaagttgc    7440
atcttgctgt tgacagcaac acacatgaag ttgtctgtgc agacctgtcg ctgaataacg    7500
tcacggactc agaagccttc ccgggcctta tccggcagac tcacagaaaa tcagggcag    7560 ccgcggcaga cggggcttac gatacccggc tctgtcacga tgaactgcgc cgcaaaaaaa    7620
tcagcgcgct tattcctccc cgaaaaggtg cgggttactg gccggtgaa tatgcagacc    7680 gtaaccgtgc agtggctaat cagcgaatga ccggagtaa tgcgcggtgg aaatggacaa    7740
cagattacaa ccgtcgctcg atagcggaaa cggcgatgta ccgggtaaaa cagctgttcg    7800
ggggttcact gacgctgcgt gactacgatg gtcaggttgc ggaggctatg ccctggtac    7860 gagcgctgaa caaaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
```

```
gctaccatca gcgagcatga tgcgctccca cagcattcgc cttggcagta tggaagttcc    8160
tcgctccagt tcgggccggt atccaccgca cctggtgttt aaacggattt aaattgcagg    8220
ggcagtgagc gcaacgcaat taatgtaagt tagctcactc attaggcacc ccaggcttga    8280
cactttatgc ttccggctcg tataatgtgt ggaattgtga gcggataaca ataacaattt    8340
aaatcaggat ctaggaacca aggagagtgg catatgacgg atacggttac ggacagcggt    8400
cgcgagcaga gactgacgga aagagttgaa cagctgtatg cgaatgaccc gcagtttcgt    8460
gcagccgctc cgagccctga ggttaccgag gcagcgcacc gtgccggtct cgtctggca    8520
gaggttgtgg acatttacct gtccggttat gcggaccgtc cggcgctggg ccaacgtgcg    8580
tgcgaagtgg cacgcgatcc ggcgacgggt cgtgctgcca ccagcctgtt gagcggtttt    8640
gagactatca cctaccgcga actgggtgat cgtgtcgccg ccttggcggc tgcgtggcgt    8700
tccggcctgc cgggtggttt cgtccgggt gatttcgtcg gtgttctggg ctttacgtcc    8760
atcgattatg tcgtgcacta cctggcttgc atccgtctgg gtgcggtgtt tgtgccgctg    8820
caaacgagca gcaccgccgc acaactggcg ccgattgtgg cggagacggc gcctcgcatc    8880
ctggcggtat ctgtggagtc cctggcgacc gcagttgacg tcgttctgga agcgccgagc    8940
gttcagcgtc tggtggtctt tgattacacc tctgatgacg atgagcagcg cggtcgttac    9000
gatgatgcac gcgctcgtct gcgcgacgca ggtcacggtg cggagatggt ggcgttggct    9060
gctgagttgg caagcggccg tgaacgtcct gcgccggaag cgcacgtccc aggtcagggt    9120
gaaaacccgc tggcaactct gatctatacc agcggtagca ccggcacccc aaagggtgca    9180
atgtacaccg cggacatgat gacgcgtatc tggcaacgtc ctcactcccc gagcgtcgac    9240
atcggtcgtg tcattccggc gatccacctg cagtatatgc cgctgtccca cgtctacggt    9300
ctggagtggc tgatcgcgac cctgagctcc ggtggcattg gttatttcgc agccaaaagc    9360
gacatgagca ccctgttcga cgacattggt ctggtccgtc cgacggcgct gaacctggtt    9420
ccgcgcgtgt gtgatatgtt tttccgtcgc taccgtaaag agctggacca acgtgcaggt    9480
gacggtctga ccgcagagca gcgcgatgaa gccgttaaag ccgaactgcg ccaggatttc    9540
attggtggcc gtgtcattag cgcgatgtgc ggtagcgcac cgttgagcaa gcagatgcat    9600
gcgttcatgg agagcctgct ggatgtgacc gttgcggatg ctatggcgc caccgaaacg    9660
ggtggcggca ttatgcgttc gggtcgcatc cgtcgtccgc cggtcactga ttacaagctg    9720
gtggacgtgc cggaactggg ttacctgacg accgacaagc cgtacccgcg tggcgagttg    9780
cacctgaagg cgagcaacgt tatcccgggt tactttaagc atccggaact gagcgcgcag    9840
attttgatg atgaaggttt ctacaaaacg ggtgacatta tggcggaact gggccctgac    9900
catctgatgt acctggaccg tagcaacaac gtgatcaagc tgagccaggg cgagtttgtg    9960
gcggtgagcc agctggaagc cacgttttcg accagcccgt acattcgtca gattttcctg    10020
tatggcagct ctgaacaacc gtttctgctg gcggttatcg tcccgaatgt tgatgcagtc    10080
ggtggtggcg atgcgcgtgc gttgatcgcc gagagcctgc agcagattgc ggcggacagc    10140
tacctgcacc cgtatgaggt gccacgcgac ttcctgctgg agccgcaacg ttttacccgc    10200
gataacggct tgctgtctgg tgttggtaaa ctgctgcgtc cggcactgaa agcgcgttac    10260
ggcgaacgtt tggacgcaat gtatgatgag attgaggcat ctcacggtaa tcaactggac    10320
gaattgcgta gcgcgagccg cgagttgccg acgattgaca ccgttcgccg tgccgctgcc    10380
gcgaccttgg gcctgccggc tgatgccgcc ctgcgtggcg acgcgaagtt tattgagctg    10440
```

```
ggtggcgatt ccctgagcgc attcagctttt gcgaccctgc tgtcggaaat ctttcacatc    10500
gacgtgccgg tgcaaactat cgttagcccg accgccacct ggcgaccat cgcgaattat      10560
gttgacggtg aacgcactag cgaatcgacg cgtccgacct tcgctagcgt gcatggtcgt    10620
ggtgcaaccg tggcacgtgc cgctgacttg acgctggcga agttcatcga tgacgatacg    10680
ctggcagcag cgccgcacct gccggctcca acgggtgcgg tcaacactgt gctgctgacc    10740
ggcgcaaatg gctacctggg ccgcttcctg tgcttggact ggctggaacg cctggccccg    10800
accggtggca ccgtaatttg tctggcgcgt ggcgccgatc cgacggcagg tcgccaacgt    10860
attgaggccg ctatcgacag cggcgatgcg gaattgagcc gtcgtttctg tcagctggcg    10920
gacaaacacc tgcaagttct ggtgggtgat gtgggtgctg cgaacctggg cctggacacc    10980
ccgacgtatc aacgcctggc gcgcagcgtt gatttggtcg tccacagcgc agccctggtt    11040
aatcatgtgc tgccgtatag ccaattgttc ggtccgaacg tggttggtac cgcagagatc    11100
gtcaagctgg cgatttccga acgcctgaaa ccgattaact acatttccac ggttgcggtc    11160
accaccctgc cggacggcag cttcatcggc gaggacgcgg acgtccgttc tgcatctccg    11220
agccgtagcc tggacgagag ctacgctagc ggttatgcga ccagcaaatg ggcaggcgag    11280
gttctgctgc gcgaggcgca cgacctgtgc ggtgtgccgg ttgcagtttt tcgtagcgac    11340
atgattctgg cccatagcga cttcgcgggt cagttgaacg tgccggatat gttcacccgc    11400
ctgatcttga gcctggttgc gacgggtatc gcaccacgta gcttctatca gctggacgcg    11460
agcggtaatc gtcagcgtgc gcattacgac ggcctgccag cggatttcac tgctgaggca    11520
atcacgacgc tgggtgcacg taccccgccaa ggctaccata cctataatgt gctgaatacc    11580
cacgatgatg gcgtctccct ggacaccttt gttgattggc tgattgccga tggccacaaa    11640
atcgagcgcg tggacgacta cgacgagtgg ctggcgcgtt ttaccgctgc gatgaaatct    11700
ctgccggata atcagcgcaa aagcagcctg ctgccactga tgagcgcgta cgcgaaaccg    11760
ggccaaccta cccatggcac cggtatgccg gctgagaagt tccgcgcagc ggtccaaagc    11820
gctggtattg gtgccactcg tgatgtcccg catgttaccc aggccctgat tgacaagtat    11880
gttgcggatc tgcaacgttt gggcctgctg cgtacccgcg ctggtgccca tgcaggctaa    11940
taagtttaaa cgagaaggag ttctatcatg attgaaacca tcttaccagc cggcgtcgaa    12000
tcagcagagt tacttgagta ccctgaagat ctgaaggcgc atccggctga agagcatctg    12060
atcgcaaaga gcgtagagaa gcgtcgtcgc gacttcattg gcgcacgtca ttgcgcccgt    12120
ctggcactgg cggagctggg tgaaccgccg gttgcgattg gcaagggtga acgtggtgcg    12180
ccgatttggc cgcgtggtgt cgtgggctct ctgacccatt gcgatggcta tcgcgcagcg    12240
gcggttgctc acaaaatgcg ttttcgcagc atcggcatcg acgccgaacc gcacgcgacc    12300
ctgccggaag gtgtcctgga ttcggttagc ctgccgcctg agcgtgagtg gctgaaaacc    12360
accgacagcg cactgcacct ggaccgtttg ctgttttgtg cgaaagaagc aacttacaaa    12420
gcgtggtggc cgctgacggc acgttggctg ggtttcgaag aagcgcacat taccttcgaa    12480
atcgaggatg gtagcgccga ctctggtaat ggcacgtttc acagcgaact gctggtgccg    12540
ggtcagacca atgacggtgg taccccgctg ctgtctttcg acggtcgctg gctgatcgct    12600
gatggcttca tcctgacggc gattgcatac gcatgataaa ttaacctagg ctgctgccac    12660
cgctgagcaa taactagcat aaccccttgg ggcctctaaa cgggtcttga ggggttttt    12720
gctgagctca agtgaccccca gccgcccctc atgccaaccg agcccattaa gcgcagagtc    12780
ggccgcaact atctcgggga cgcataaaca cgcagcgatt taccaaggag ttcggctagg    12840
```

-continued

```
tcaatccgca attcccttg cctggccgga gatgccgcga gcaaacaatg tgtccggtcg    12900
ctaccagatg gactttgtgg gcggaggatt gcaccgacg cttcagcgca gcgtcgtacg    12960
atgaatcgga aggcccggta agcaattgaa gaaccgctga ccacctccca tccgacaatg   13020
caagggtgcc ccgctcccag cgcgacacgg ttgcctgatc cacacccatt aattcagcta   13080
ggtgactttg cttcatatga cgaagcaacc gcgccctccg cacctgccgc ccctgtcat    13140 tcgtcaacat tcttcagcac ctcaatgtcg ttcgtagtga gcctcatttt ttcaagaccg   13200
ccgatgatga gagccaggcc tcgctcgaat gccgcgtccg gaccgccttc gtagacgatt   13260
ttcatcgcgc tctgtaggcg cgccggcatc gtagacgctg aggtggtcaa ctgatcttcg   13320
ccccgctcct cggcgtctgc ctcgctagct tgctgctcaa gaacagcgcc gacggtgaag   13380
tagctgattg ccatcaacgc ataggtcgcg tcacctgccg aaaagccagc atcgcaaagg   13440
aagcgaagct gcgcgtcggc ttttccatc tgcggcgcgg ctggccgcgt cccggcatga    13500
atacgcgcgc catcgcgata agcgagcaac gcccgtcgaa aactgcatgc attgcccttc   13560
aggaacgaac gccagtcgtc gtcatcccct ggcgtcgaat gcgtgtgatt tatcgtcagc   13620
atggcttcgg caagtgcgtc gagcaacgca cgcttgttct tgaaatgcca gtagagcgct   13680
ggctgttgca ccccgaggcg ctcagccagt cggcgcgtcg ttagaccttc catgcccacg   13740
tcgttaagca gttcgagcgc ggttcggatc acggcctcgc gttggagctt gttcattcgc   13800
gaa                                                                 13803
```

<210> SEQ ID NO 26
<211> LENGTH: 13704
<212> TYPE: DNA
<213> ORGANISM: Artificial Sequence
<220> FEATURE:
<223> OTHER INFORMATION: vector

<400> SEQUENCE: 26

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg caggccccg tggcggggg    540 actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc cgccaccaa    900 acgtttcggc gagaagcagg ccattatcgc cggcatggcg gccgacgcgc tgggctacgt    960
cttgctggcg ttcgcgacgc gaggctggat ggccttcccc attatgattc ttctcgcttc    1020
```

```
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggaccccggct aggctggcgg   1500 ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcccctacg tgctgctgaa gttgcccgca acagagagtg   1680
gaaccaaccg gtgataccac gatactatga ctgagagtca acgccatgag cggcctcatt   1740
tcttattctg agttacaaca gtccgcaccg ctgccggtag ctacttgact atccggctgc   1800
actagccctg cgtcagatgg ctctgatcca aggcaaactg ccaaaatatc tgctggcacc   1860
ggaagtcagc gccctgcacc attatgttcc ggatctgcat cgcaggatgc tgctggctac   1920
cctgtggaac acctacatct gtattaacga agcgctggca ttgaccctga gtgattttc   1980 tctggtgccg ccctatccct ttgtgcagct tgccacgctc aaaggggttt gaggtccaac   2040
cgtacgaaaa cgtacggtaa gaggaaaatt atcgtctgaa aaatcgatta gtagacaaga   2100
aagtccgtta agtgccaatt ttcgattaaa aagacaccgt tttgatggcg ttttccaatg   2160
tacattatgt ttcgatatat cagacagtta cttcactaac gtacgttttc gttctattgg   2220
ccttcagacc ccatatcctt aatgtccttt atttgctggg gttatcagat ccccccgaca   2280
cgtttaatta atgctttctc cgccggagat cgacgcacag gcttctgtgt ctatgatgtt   2340
atttcttaat aatcatccag gtattctctt tatcaccata cgtagtgcga gtgtccacct   2400
taacgcaggg cttccgtca cagcgcgata tgtcagccag cggggctttc ttttgccaga   2460
ccgcttccat cctctgcatt tcagcaatct ggctataccc gtcattcata aaccacgtaa   2520
atgccgtcac gcaggaagcc aggacgaaga atatcgtcag tacaagataa atcgcggatt   2580
tccacgtata gcgtgacatc tcacgacgca tttcatggat catcgctttc gccgtatcgg   2640
cagcctgatt cagcgcttct gtcgccggtt tctgctgtgc taatccggct tgtttcagtt   2700 cttttctcaac ctgagtgagc gcggaactca ccgatttcct gacggtgtca gtcatattac   2760
cggacgcgct gtccagctca cgaatgaccc tgctcagcgt ttcactttgc tgctgtaatt   2820
gtgatgaggc ggcctgaaac tgttctgtca gagaagtaac acgcttttcc agcgcctgat   2880
gatgcccgat aagggcggca atttgtttaa tttcgtcgct catacaaaat cctgcctatc   2940
gtgagaatga ccagcccttta tccggcttct gtcgtatctg ttcggcgagt cgctgtcgtt   3000 cttttctcctg ctgacgctgt ttttccgcca gacgttcgcg ctctctctgc ctttccatct   3060
cctgatgtat cccctggaac tccgccatcg catcgttaac aagggactga agatcgattt   3120
cttcctgtat atccttcatg gcatcactga ccagtgcgtt cagcttgtca ggctctttt   3180 caaaatcaaa cgttctgccg gaatgggatt cctgctcagg ctctgacttc agctcctgtt   3240
ttagcgtcag agtatccctc tcgctgaggg cttcccgtaa cgaggtagtc acgtcaatta   3300
cgctgtcacg ttcatcacgg gactgctgca cctgcctttc agcctccctg cgctcaagaa   3360
tggcctgtag ctgctcagta tcgaatcgct gaacctgacc cgcgcccaga tgccgctcag   3420
```

```
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc gcgtccggct    3600
ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg acggtttat    3900
gcgctgccca cgccggcata ttgccggact ccttgtgctc aaggtcggag tcttttcac    3960
gggcatactt tccctcacgc gcaatataat cggcatgagg agaggcactg ccttttccgc    4020
cggttttac gctgagatga taggatgcca tcgtgtttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt taccccatt cactgccaga    4800
gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cagggctg ggatctattc ttttttatctt    5040
tttttattct ttctttattc tataaattat aaccacttga atataaacaa aaaaacaca    5100
caaaggtcta gcggaattta cagagggtct agcagaattt acaagttttc cagcaaaggt    5160
ctagcagaat ttacagatac ccacaactca aggaaaagg actagtaatt atcattgact    5220
agcccatctc aattggtata gtgattaaaa tcacctagac caattgagat gtatgtctga    5280
attagttgtt ttcaaagcaa atgaactagc gattagtcgc tatgacttaa cggagcatga    5340
aaccaagcta attttatgct gtgtggcact actcaacccc acgattgaaa accctacaag    5400
gaaagaacgg acggtatcgt tcacttataa ccaatacgct cagatgatga acatcagtag    5460
ggaaaatgct tatggtgtat tagctaaagc aaccagagag ctgatgacga gaactgtgga    5520
aatcaggaat cctttggtta aaggctttga gattttccag tggacaaact atgccaagtt    5580
ctcaagcgaa aaattagaat tagttttttag tgaagagata ttgccttatc ttttccagtt    5640
aaaaaaattc ataaaatata atctggaaca tgttaagtct tttgaaaaca aatactctat    5700
gaggatttat gagtggttat taaaagaact aacacaaaag aaaactcaca aggcaaatat    5760
```

```
agagattagc cttgatgaat ttaagttcat gttaatgctt gaaaataact accatgagtt    5820
taaaaggctt aaccaatggg ttttgaaacc aataagtaaa gatttaaaca cttacagcaa    5880
tatgaaattg gtggttgata agcgaggccg cccgactgat acgttgattt ccaagttga    5940
actagataga caaatggatc tcgtaaccga acttgagaac aaccagataa aaatgaatgg    6000
tgacaaaata ccaacaacca ttacatcaga ttcctaccta cgtaacggac taagaaaaac    6060
actacacgat gctttaactg caaaaattca gctcaccagt tttgaggcaa aattttgag    6120
tgacatgcaa agtaagcatg atctcaatgg ttcgttctca tggctcacgc aaaaacaacg    6180
aaccacacta gagaacatac tggctaaata cggaaggatc tgaggttctt atggctcttg    6240
tatctatcag tgaagcatca agactaacaa acaaaagtag aacaactgtt caccgttaga    6300
tatcaaaggg aaaactgtcc atatgcacag atgaaacgg tgtaaaaaag atagatacat    6360
cagagctttt acgagttttt ggtgcattta agctgttca ccatgaacag atcgacaatg    6420
taacagatga acagcatgta acacctaata gaacaggtga aaccagtaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg agccagtga    6600
cgcctcccgt ggggaaaaaa tcatggcaat tctggaagaa atagcgcttt cagccggcaa    6660
acctgaagcc ggatctgcga ttctgataac aaactagcaa caccagaaca gcccgtttgc    6720
gggcagcaaa acccgtactt ttggacgttc cggcggtttt ttgtggcgag tggtgttcgg    6780
gcggtgcgcg caagatccat tatgttaaac gggcgagttt acatctcaaa accgcccgct    6840
taacaccatc agaaatcctc agcgcgattt taagcaccaa ccccccccg taacacccaa    6900
atccatactg aaagtggctt tgttgaataa atcgaacttt tgctgagttg aaggatcaga    6960
tcacgcatcc tcccgacaac acagaccatt ccgtggcaaa gcaaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca ttttttgccct gatgaacgtt ccgttgcgct    7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga aagcacggca aagagcgccg tcgtatctgg cgaaagttgc    7440
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccgggagtaa tgcgcggtgg aaatggacaa    7740
cagattacaa ccgtcgctcg atagcggaaa cggcgatgta ccgggtaaaa cagctgttcg    7800
ggggttcact gacgctgcgt gactacgatg gtcaggttgc ggaggctatg ccctggtac    7860
gagcgctgaa caaaatgacg aaagcaggta tgcctgaaag cgtgcgtatt gcctgaaaac    7920
acaacccgct acggggagga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
```

```
tcgctccagt tcgggccggt atccaccgca cctggtgttt aaacggattt aaattgcagg   8220
ggcagtgagc gcaacgcaat taatgtaagt tagctcactc attaggcacc ccaggcttga   8280
cactttatgc ttccggctcg tataatgtgt ggaattgtga gcggataaca ataacaattt   8340
aaatcaggat ctaggaacca aggagagtgg catatgagca gcactagagc aacccgcctg   8400
agacagagaa tcgcagccct gtacgcagat gacgcgcagg tccgtgacgc acgtccagac   8460
gaagctatct ctaccgcgct gcgcgaaccg ggcttgcgtt tgcgcgagct ggtcgcgacc   8520
gtcgttgatg gttatcgtga ccgtccggct ttggcggcac gtagcgtcca accggctgtc   8580
gacgcggcga ccgtgcgtg cgtggcgcgt ctgttgccgg agtacaccac gatgagctac   8640
ggtgagctgg gcctgcgcct gcgtgccgtt gcggcagcgt ggcagcacga cgatgagacg   8700
cgcttgcgtc caggcgaatt tgttgcgacg ttgggttta cgtccccgga ttacgcagtg   8760
gtggacctgg cgtgcgtgtg ggcgggtgcg gttgcagtac cgttgcaagc gagcgccagc   8820
gtgacccagc tgacggcaat tctgcagaa accgcaccag cgatcctggc caccggtctg   8880
gataccctgc cgcatgccgt ggattgtgtc ctggcgggtg caacgccgcg tgcgctgcac   8940
gtgttcgact tcgatccggc aattgatgcg cagcgcaccg tttacgaagc agcatgcgca   9000
cgcttggcgg gcaccggcgt ccgcgttcgc acgttggcgg aagttgagga ccgtggtcgt   9060
gccctgccac cggcggttat tgatgatggt ccgggtgacg accgcctggc gttgctgatc   9120
tatacgagcg gtagcaccgg tacgccgaag ggcgcaatgt atactgagcg cttggttgct   9180
ctgatgtggc tgggccagcc gcaagttgca gcgctgacgg tcaattatct gccgctgagc   9240
cacgtcgcag gccgtctggc gctgttcggc ctgctggcgc gtggcggcac cgcgtatttc   9300
accgcccgtg cagacatgtc caccctgttt gaggatctgg ctctggcgcg tccgaccgag   9360
ctgtttgtcg taccgcgtgt gtgcgaaatg gttctgcaac gtttccaaac tgagcgtctg   9420
cgtcgccaag cggacgatga tcgcgtgaag gcagatctgc gcctggagct gttcggtgac   9480
cgcctgttga gcgttgtttg tggtagcgca ccactggctc ctgaactgaa agcgttcatg   9540
gagagcgtgc tggacctgac cttgcacgac ggttatggct ccaccgaagc aggtggtagc   9600
gtcgtcatcg acaccaccgt gcgtcgtccg ccggttctgg actatcgtct ggcggacgtg   9660
ccggagctgg gttactttcg tacggataaa ccgcatccgc gtggcgagct gctgctgaaa   9720
acgaccacca tgatcccggg ctactaccgt cgcccggagc tgaatgctca aatctttgat   9780
gaggacggtt tttaccgcac cggcgacgtg gttgcggagc tggcaccgga tcgcctggtg   9840
tacgttgacc gtcgcaataa cgttctgaag ctggcgcagg gtgaattcgt gacgattgca   9900
cgtttggaag cgattttcgc gaacagcccg ttggtccgcc aaatctttgt ttacggtaac   9960
agcgaacgtg cctatctgct ggccgtgatt gttccgtctc gtcaagcaat ggctggcgac  10020
ccggcgaccc tgaaaacccg tatcgcggag agcctgcagc tgattggtcg cgacgcggag  10080
ctggaagcgt acgagatccc tcgcgatttc ctgatcgaga cggagccgtt caccacgaa   10140
tccggcctgc tgtccggtat tggtaaaatc ctgcgtccgg cggtcgaagc acgctatcgc  10200
gatcgtctgg agcagctgta cgcggacctg gcagcagcgc agcaagacga gttggcagcc  10260
ctgcgtcgcg aggcaggtca gcgtccggtc ctggagactg tgacccgtgc cgcagcggcg  10320
attctgggcg gtaccgctag cgacctgtcc cctgcggccc actttaccga tttgggtggt  10380
gatagcctgg cggcgttggc gctgtcgaat ctgctgcgcg agattttcgc cgtagaggtt  10440
ccggtcggtg tgattaccgg tccggcgacc gatctgcgtg gcctggccgc acatatcgcg  10500
```

```
gcagaacgtg aaaaccgtac ggaaacgccg ctgttcgatc gtgtccatcc ggatcagatt    10560
ttgatccgtg cgaccgacct ggcgctggaa aagtttttcg atgcggaaga gctggcggca    10620
gccgcgaccg cagcaccgcc ggtagccgag ccgcgtgtgg ttttgctgac gggtgcgaac    10680
ggttacctgg gtcgcttcct gtgcctggag tggctggagc gtctggaccg tgtcgacggc    10740
cgtctgattt gtctggttcg tggcgcggac gaagcagcgg cactggctcg tctggaagcg    10800
gcgttcgaca gcgcgatcc tgagttggtg cgtcgcttta agaactggc ccaacgtcgt    10860 ctgaccgtgg tggcgggtga tatcggcgag cctggcctgg gtctggcaac cgccacctgg    10920
cgccgtctgg ccgctgaggt tgaacatatc gttcaccctg ctgccctggt gaaccatgtc    10980
ctgccgtatc gccagctgtt tggcccgaac gttgcgggca cggcggagat cctgcgtctg    11040
gccctgacgg agcgccgcaa accgatcgat ttcttgagca cggttgccgt cgctgcgcag    11100
atcccggcag accgcttcgc cgaagatggt gacattcgtg tgatcagccc tactcgcact    11160
gtcgatcgtg gctatgcaaa tggttacggc aatagcaagt gggcggcaga agttctgctg    11220
cgtgcggcgc atgaccgctt cgatctgccg gtggcggtgt ccgtagcga tatgattctg    11280 gcccatggca gctttgccgg tcaattgaat attccggatg tctttacccg tctgttgctg    11340
tctctgttgg tgaccggcat tgccccagca tcttttcacg ccgctacggt cactggtgaa    11400
cgtccgcgtg ctcactatga tggtctgccg gctgatttca cggctgccgc gatcaccgcc    11460
ctgggtgccc gtacgctgg cttttcacacg tacgacgttc tgaacccgca cgatgacggt    11520
atcagcctgg acaccttcgt ggactggctg attgaagcgg gtcacccgat cgaacgtatt    11580
ccggagcaca gcgaatgggt cacccgcttt gagacggccc tgcacgcgct gccggagcgt    11640
cagcgtaagc attcgctgct gccgctgctg cacgcgtatc gtcgtccggt tccggccctg    11700
cgtggtagcg cgttgccagc tgcagagttt cgtgcagcgg tgcgtgctgc tggtattacc    11760
gcggacggtg acattccgca cctgacccgc gctctgattg aaaagtacgt cgccgacctg    11820
cgcttgcatg gtctgctgta ataagtttaa acgagaagga gttctatcat gattgaaacc    11880
atcttaccag ccggcgtcga atcagcagag ttacttgagt accctgaaga tctgaaggcg    11940
catccggctg aagagcatct gatcgcaaag agcgtagaga agcgtcgtcg cgacttcatt    12000
ggcgcacgtc attgcgcccg tctggcactg gcggagctgg gtgaaccgcc ggttgcgatt    12060 ggcaaggggtg aacgtggtgc gccgatttgg ccgcgtggtg tcgtgggctc tctgacccat    12120
tgcgatggct atcgcgcagc ggcggttgct cacaaaatgc gttttcgcag catcggcatc    12180
gacgccgaac cgcacgcgac cctgccggaa ggtgtcctgg attcggttag cctgccgcct    12240
gagcgtgagt ggctgaaaac caccgacagc gcactgcacc tggaccgttt gctgttttgt    12300
gcgaaagaag caacttacaa agcgtggtgg ccgctgacgg cacgttggct gggtttcgaa    12360
gaagcgcaca ttaccttcga aatcgaggat ggtagcgccg actctggtaa tggcacgttt    12420
cacagcgaac tgctggtgcc gggtcagacc aatgacggtg gtaccccgct gctgtctttc    12480
gacggtcgct ggctgatcgc tgatggcttc atcctgacgg cgattgcata cgcatgataa    12540
attaacctag gctgctgcca ccgctgagca ataactagca taaccccttg ggcctctaa    12600 acgggtcttg aggggttttt tgctgagctc gagtgacccc agccgcccct catgccaacc    12660
gagcccatta agcgcagagt cggccgcaac tatctcgggg acgcataaac acgcagcgat    12720
ttaccaagga gttcggctag gtcaatccgc aattcccttt gcctggccgg agatgccgcg    12780
agcaaacaat gtgtccggtc gctaccagat ggactttgtg ggcggaggat tgcaccgac    12840 gcttcagcgc agcgtcgtac gatgaatcgg aaggcccggt aagcaattga agaaccgctg    12900
```

```
accacctccc atccgacaat gcaagggtgc cccgctccca gcgcgacacg gttgcctgat     12960
ccacacccat taattcagct aggtgactttt gcttcatatg acgaagcaac cgcgccctcc     13020
gcacctgccg cccctgtca ttcgtcaaca ttcttcagca cctcaatgtc gttcgtagtg     13080
agcctcattt tttcaagacc gccgatgatg agagccaggc ctcgctcgaa tgccgcgtcc     13140
ggaccgcctt cgtagacgat tttcatcgcg ctctgtaggc gcgccggcat cgtagacgct     13200
gaggtggtca actgatcttc gccccgctcc tcggcgtctg cctcgctagc ttgctgctca     13260
agaacagcgc cgacggtgaa gtagctgatt gccatcaacg cataggtcgc gtcacctgcc     13320
gaaaagccag catcgcaaag gaagcgaagc tgcgcgtcgg cttttccat ctgcggcgcg     13380 gctggccgcg tcccggcatg aatacgcgcg ccatcgcgat aagcgagcaa cgcccgtcga     13440
aaactgcatg cattgccctt caggaacgaa cgccagtcgt cgtcatccct tggcgtcgaa     13500
tgcgtgtgat ttatcgtcag catggcttcg gcaagtgcgt cgagcaacgc acgcttgttc     13560
ttgaaatgcc agtagagcgc tggctgttgc accccgaggc gctcagccag tcggcgcgtc     13620
gttagacctt ccatgcccac gtcgttaagc agttcgagcg cggttcggat cacggcctcg     13680
cgttggagct tgttcattcg cgaa                                             13704

<210> SEQ ID NO 27
<211> LENGTH: 13761
<212> TYPE: DNA
<213> ORGANISM: Artificial Sequence
<220> FEATURE:
<223> OTHER INFORMATION: vector

<400> SEQUENCE: 27
ttctcatgtt tgacagctta tcatcgataa gctttaatgc ggtagtttat cacagttaaa       60
ttgctaacgc agtcaggcac cgtgtatgaa atctaacaat gcgctcatcg tcatcctcgg      120
caccgtcacc ctggatgctg taggcatagg cttggttatg ccggtactgc cgggcctctt      180
gcgggatatc gtccattccg acagcatcgc cagtcactat ggcgtgctgc tagcgctata      240
tgcgttgatg caatttctat gcgcacccgt tctcggagca ctgtccgacc gctttggccg      300
ccgcccagtc ctgctcgctt cgctacttgg agccactatc gactacgcga tcatggcgac      360
cacacccgtc ctgtggatcc tctacgccgg acgcatcgtg gccggcatca ccggcgccac      420
aggtgcggtt gctggcgcct atatcgccga catcaccgat ggggaagatc gggctcgcca      480
cttcgggctc atgagcgctt gtttcggcgt gggtatggtg caggccccg tggccggggg      540 actgttgggc gccatctcct tgcatgcacc attccttgcg gcggcggtgc tcaacggcct      600
caacctacta ctgggctgct tcctaatgca ggagtcgcat aagggagagc gtcgaccgat      660
gcccttgaga gccttcaacc cagtcagctc cttccggtgg gcgcggggca tgactatcgt      720
cgccgcactt atgactgtct tctttatcat gcaactcgta ggacaggtgc cggcagcgct      780
ctgggtcatt ttcggcgagg accgctttcg ctggagcgcg acgatgatcg gcctgtcgct      840
tgcggtattc ggaatcttgc acgccctcgc tcaagccttc gtcactggtc cgccaccaa      900 acgtttcggc gagaagcagg ccattatcgc cggcatggcg gccgacgcgc tgggctacgt      960
cttgctggcg ttcgcgacgc gaggctggat ggccttcccc attatgattc ttctcgcttc     1020
cggcggcatc gggatgcccg cgttgcaggc catgctgtcc aggcaggtag atgacgacca     1080
tcagggacag cttcaaggat cgctcgcggc tcttaccagc ctaacttcga tcactggacc     1140
gctgatcgtc acggcgattt atgccgcctc ggcgagcaca tggaacgggt tggcatggat     1200
```

```
tgtaggcgcc gccctatacc ttgtctgcct ccccgcgttg cgtcgcggtg catggagccg     1260
ggccacctcg acctgaatgg aagccggcgg cacctcgcta acggattcac cactccaaga     1320
attggagcca atcaattctt gcggagaact gtgaatgcgc aaaccaaccc ttggcagaac     1380
atatccatcg cgtccgccat ctccagcagc cgcacgcggc gcatctcggg cagcgttggg     1440
tcctggccac gggtgcgcat gatcgtgctc ctgtcgttga ggacccggct aggctggcgg     1500
ggttgcctta ctggttagca gaatgaatca ccgatacgcg agcgaacgtg aagcgactgc     1560
tgctgcaaaa cgtctgcgac ctgagcaaca acatgaatgg tcttcggttt ccgtgtttcg     1620
taaagtctgg aaacgcggaa gtcccctacg tgctgctgaa gttgcccgca acagagagtg     1680
gaaccaaccg gtgataccac gatactatga ctgagagtca acgccatgag cggcctcatt     1740
tcttattctg agttacaaca gtccgcaccg ctgccggtag ctacttgact atccggctgc     1800
actagccctg cgtcagatgg ctctgatcca aggcaaactg ccaaaatatc tgctggcacc     1860
ggaagtcagc gccctgcacc attatgttcc ggatctgcat cgcaggatgc tgctggctac     1920
cctgtggaac acctacatct gtattaacga agcgctggca ttgaccctga gtgattttc      1980 tctggtgccg ccctatccct ttgtgcagct tgccacgctc aaaggggttt gaggtccaac     2040
cgtacgaaaa cgtacggtaa gaggaaaatt atcgtctgaa aaatcgatta gtagacaaga     2100
aagtccgtta agtgccaatt ttcgattaaa aagacaccgt tttgatggcg ttttccaatg     2160
tacattatgt ttcgatatat cagacagtta cttcactaac gtacgttttc gttctattgg     2220
ccttcagacc ccatatcctt aatgtccttt atttgctggg gttatcagat cccccgaca     2280 cgtttaatta atgctttctc cgccggagat cgacgcacag gcttctgtgt ctatgatgtt     2340
atttcttaat aatcatccag gtattctctt tatcaccata cgtagtgcga gtgtccacct     2400
taacgcaggg ctttccgtca cagcgcgata tgtcagccag cggggctttc ttttgccaga     2460
ccgcttccat cctctgcatt tcagcaatct ggctataccc gtcattcata aaccacgtaa     2520
atgccgtcac gcaggaagcc aggacgaaga atatcgtcag tacaagataa atcgcggatt     2580
tccacgtata gcgtgacatc tcacgacgca tttcatggat catcgctttc gccgtatcgg     2640
cagcctgatt cagcgcttct gtcgccggtt tctgctgtgc taatccggct tgtttcagtt     2700
ctttctcaac ctgagtgagc gcggaactca ccgatttcct gacggtgtca gtcatattac     2760
cggacgcgct gtccagctca cgaatgaccc tgctcagcgt ttcactttgc tgctgtaatt     2820
gtgatgaggc ggcctgaaac tgttctgtca gagaagtaac acgcttttcc agcgcctgat     2880
gatgcccgat aagggcggca atttgtttaa tttcgtcgct catacaaaat cctgcctatc     2940
gtgagaatga ccagccttta tccggcttct gtcgtatctg ttcggcgagt cgctgtcgtt     3000
ctttctcctg ctgacgctgt ttttccgcca gacgttcgcg ctctctctgc ctttccatct     3060
cctgatgtat ccctggaac tccgccatcg catcgttaac aagggactga agatcgattt     3120
cttcctgtat atccttcatg gcatcactga ccagtgcgtt cagcttgtca ggctctttt      3180 caaaatcaaa cgttctgccg gaatgggatt cctgctcagg ctctgacttc agctcctgtt     3240
ttagcgtcag agtatccctc tcgctgaggg cttcccgtaa cgaggtagtc acgtcaatta     3300
cgctgtcacg ttcatcacgg gactgctgca cctgcctttc agcctccctg cgctcaagaa     3360
tggcctgtag ctgctcagta tcgaatcgct gaacctgacc cgcgcccaga tgccgctcag     3420
gctcacggtc aatgccctgc gccttcaggg aacgggaatc aacccggtca gcgtgctgat     3480
accgttcaag gtgcttattc tggaggtcag cccagcgtct ccctctgggc aacaaggtat     3540
tctttgcgtt cggtcggtgt ttccccgaaa cgtgcctttt ttgcgccacc gcgtccggct     3600
```

```
ctttggtgtt agcccgttta aaatactgct cagggtcacg gtgaataccg tcattaatgc    3660
gttcagagaa catgatatgg gcgtggggct gctcgccacc ggctatcgct gctttcggat    3720
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg gacggtttat    3900
gcgctgccca cgccggcata ttgccggact ccttgtgctc aaggtcggag tcttttcac    3960 gggcatactt tccctcacgc gcaatataat cggcatgagg agaggcactg ccttttccgc    4020 cggttttac gctgagatga taggatgcca tcgtgtttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt tacccccatt cactgccaga    4800
gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg ggatctattc tttttatctt    5040
tttttattct ttctttattc tataaattat aaccacttga atataaacaa aaaaaacaca    5100
caaaggtcta gcggaattta cagagggtct agcagaattt acaagttttc cagcaaaggt    5160
ctagcagaat ttacagatac ccacaactca aggaaaagg actagtaatt atcattgact    5220
agcccatctc aattggtata gtgattaaaa tcacctagac caattgagat gtatgtctga    5280
attagttgtt ttcaaagcaa atgaactagc gattagtcgc tatgacttaa cggagcatga    5340
aaccaagcta attttatgct gtgtggcact actcaacccc acgattgaaa accctacaag    5400
gaaagaacgg acggtatcgt tcacttataa ccaatacgct cagatgatga acatcagtag    5460
ggaaaatgct tatggtgtat tagctaaagc aaccagagag ctgatgacga aactgtgga    5520 aatcaggaat cctttggtta aaggctttga gattttccag tggacaaact atgccaagtt    5580
ctcaagcgaa aaattagaat tagttttag tgaagagata ttgccttatc ttttccagtt    5640
aaaaaaattc ataaaatata atctggaaca tgttaagtct tttgaaaaca aatactctat    5700
gaggatttat gagtggttat taaaagaact aacacaaaag aaaactcaca aggcaaatat    5760
agagattagc cttgatgaat ttaagttcat gttaatgctt gaaaataact accatgagtt    5820
taaaaggctt aaccaatggg ttttgaaacc aataagtaaa gatttaaaca cttacagcaa    5880
tatgaaattg gtggttgata agcgaggccg cccgactgat acgttgattt tccaagttga    5940
```

```
actagataga caaatggatc tcgtaaccga acttgagaac aaccagataa aaatgaatgg    6000
tgacaaaata ccaacaacca ttacatcaga ttcctaccta cgtaacggac taagaaaaac    6060
actacacgat gctttaactg caaaaattca gctcaccagt tttgaggcaa aattttttgag   6120 tgacatgcaa agtaagcatg atctcaatgg ttcgttctca tggctcacgc aaaaacaacg    6180
aaccacacta gagaacatac tggctaaata cggaaggatc tgaggttctt atggctcttg    6240
tatctatcag tgaagcatca agactaacaa acaaaagtag aacaactgtt caccgttaga    6300
tatcaaaggg aaaactgtcc atatgcacag atgaaaacgg tgtaaaaaag atagatacat    6360
cagagctttt acgagttttt ggtgcattta agctgttca ccatgaacag atcgacaatg     6420
taacagatga acagcatgta acacctaata gaacaggtga aaccagtaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg gagccagtga    6600
cgcctcccgt ggggaaaaaa tcatggcaat tctggaagaa atagcgcttt cagccggcaa    6660
acctgaagcc ggatctgcga ttctgataac aaactagcaa caccagaaca gcccgtttgc    6720
gggcagcaaa accgtactt ttggacgttc cggcggtttt ttgtggcgag tggtgttcgg     6780
gcggtgcgcg caagatccat tatgttaaac gggcgagttc acatctcaaa accgcccgct    6840
taacaccatc agaaatcctc agcgcgattt taagcaccaa ccccccccg taacacccaa     6900 atccatactg aaagtggctt tgttgaataa atcgaacttt tgctgagttg aaggatcaga    6960
tcacgcatcc tcccgacaac acagaccatt ccgtggcaaa gcaaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca tttttgccct gatgaacgtt ccgttgcgct    7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga aagcacggca aagagcgccg tcgtatctgg cgaaagttgc    7440
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccgggagtaa tgcgcggtgg aaatggacaa    7740
cagattacaa ccgtcgctcg atagcggaaa cggcgatgta ccgggtaaaa cagctgttcg    7800
ggggttcact gacgctgcgt gactacgatg gtcaggttgc ggaggctatg gccctggtac    7860
gagcgctgaa caaaatgacg aaagcaggta tgcctgaaag cgtgcgtatt gcctgaaaac    7920
acaacccgct acggggagga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccaccgca cctggtgttt aaacggattt aaattgcagg    8220
ggcagtgagc gcaacgcaat taatgtaagt tagctcactc attaggcacc ccaggcttga    8280
cactttatgc ttccggctcg tataatgtgt ggaattgtga gcggataaca ataacaattt    8340
```

```
aaatcaggat ctaggaacca aggagagtgg catatgtccc caattacccg tgaagaacgc    8400
ctggagcgcc gtattcaaga cctgtacgcg aatgacccgc agttcgctgc ggcgaagccg    8460
gtgactgcga ttacggcagc aattgagcgc ccaggtctgc cgctgccgca gattatcgaa    8520
accgtgatga ccggctacgc agatcgccca gcgttggcgc agcgctccgt cgagttcgtt    8580
accgacgcgg gtaccggtca cacgactctg cgtctgctgc cgcactttga gacgattagc    8640
tatggcgagc tgtgggatcg tattagcgct ttggcagacg tgctgagcac ggagcaaacc    8700
gttaaaccgt cggatcgtgt ctgcctgctg ggtttcaaca gcgtcgatta cgccacgatc    8760
gacatgacct tggcgcgctt gggtgcggtc gccgtgccgc tgcaaacgtc cgcagcgatc    8820
acgcaactgc agccgatcgt ggctgagacg cagcctacca tgattgccgc gagcgtggac    8880
gcattggcag atgcaaccga gctggcactg agcggtcaaa ccgcgacgcg tgtcctggtt    8940
tttgaccacc accgtcaggt ggacgcgcat cgtgccgcgg tcgagtcggc ccgtgaacgc    9000
ctggcgggca gcgcagtggt tgagactctg gcggaagcaa ttgcacgtgg cgacgttccg    9060
cgtggcgcga gcgcgggttc tgcacctggc acggatgtta gcgatgacag cctggcactg    9120
ctgatctaca cgagcggttc taccggtgct ccgaaaggtg cgatgtatcc gcgtcgcaac    9180
gttgccactt tctggcgtaa acgtacgtgg tttgaaggcg gttatgagcc gagcattacc    9240
ctgaatttca tgccgatgag ccacgttatg ggccgtcaga tcctgtatgg taccctgtgt    9300
aatggcggta cggcgtattt cgttgttaag agcgacctga gcacgctgtt tgaagatctg    9360
gccctggttc gcccgaccga gctgaccttt gttccgcgcg tctgggatat ggtgttcgac    9420
gagtttcaga gcgaggtgga tcgtcgtttg gtggatggtg ctgaccgtgt ggcactggaa    9480
gcgcaggtta aggcagagat ccgcaatgat gtcctgggtg gccgttacac cagcgcgctg    9540
accggtagcg cgcctatttc cgacgagatg aaagcgtggg ttgaagaact gctggatatg    9600
cacctggtgg aaggctacgg tagcaccgaa gcgggcatga ttttgatcga tggtgcgatt    9660
cgtcgcccag ccgttctgga ctacaaactg gttgacgtcc cagacttggg ttacttcctg    9720
acggatcgtc cgcacccgcg tggtgagctg ctggttaaga cggacagcct gttcccgggc    9780
tactaccaac gcgctgaagt caccgcagac gtctttgacg cggatggttt ctaccgcacc    9840
ggtgacatca tggccgaggt tggcccggag caattcgtgt atttggaccg ccgtaataac    9900
gtcctgaaac tgagccaggg cgaattcgtg accgtttcca gctggaagc ggtctttggc    9960 gacagcccgc tggttcgcca aatctatatc tacggtaact ccgcgcgtgc gtatctgctg    10020
gcggtgattg tgccgaccca agaggccctg acgccgtcc cggtggaaga gctgaaagca    10080
cgtctgggcg acagcttgca ggaagtggcc aaggctgcgg gcctgcaatc ctacgagatc    10140
ccgcgtgact tcatcattga gacgaccccg tggactctgc agaatggtct gctgacgggt    10200
attcgcaagc tggcgcgtcc gcagctgaag aagcactatg tgaattgct ggagcagatc    10260 tacacgacc tggcgcacgg ccaagcggac gagctgcgta gcctgcgtca gagcggtgca    10320
gacgcgcctg ttctggtcac cgtctgccgc gctgctgcag cgttgctggg tggcagcgca    10380
agcgacgtgc agccggatgc gcatttacc gacctgggcg gtgatagcct gtctgcgctg    10440
agctttacca atttgttgca cgagattttt gatatcgatg ttccggtggg cgtcatcgtg    10500
tccccggcaa acgacttgca ggcgctggca gactacgtag aggccgcacg caaaccgggt    10560
agcagccgtc cgaccttcgc ttctgtgcat ggtgccagca atgagcaggt caccgaagtc    10620
catgcgggtg atctgagcct ggacaaattc atcgatgccg ctaccctggc agaagctccg    10680
```

```
cgtttgccgg cagcaaacac ccaagtgcgc acggtgctgt tgaccggtgc aaccggtttt   10740
ctgggtcgtt atttggcgct ggagtggctg gagcgtatgg acctggtgga tggcaaattg   10800
atctgcctgg tgcgcgccaa gtccgacact gaagcgcgtg cgcgtctgga gaaaaccttc   10860
gacagcggtg cgccggaact gttggcgcat tatcgcgccc tggctggcga tcacctggaa   10920
gttctggcgg gtgacaaggg cgaggcggac ctgggcctgg atcgtcaaac gtggcagcgt   10980
ctggccgaca ccgttgatct gattgttgat ccggcagcgc tggtcaacca tgtcctgccg   11040
tacagccagc tgtttggtcc gaatgcgctg ggcaccgcgg agctgttgcg tctggccctg   11100
accagcaaga tcaaaccgta cagctatacg agcaccattg tgttgctga ccagatcccg   11160
cctagcgcgt tcaccgaaga tgcagacatc cgtgttatca gcgccacccg tgccgtcgac   11220
gatagctatg ccaacggcta cagcaactct aagtgggcag gtgaagtact gctgcgtgaa   11280
gctcatgtgc tgtgtggtct gccggttgcc gttttcgct gtgacatgat cttggctgat   11340
accacctggg cgggtcaact gaacgtgccg gatatgttca cgcgcatgat tctgagcttg   11400
gcggcgacgg gcattgcacc gggttcgttc tatgagctgg ctgcggacgg tgcccgtcaa   11460
cgtgcgcatt acgatggcct gccggtcgag tttattgcag aagccatctc taccctgggt   11520
gcgcagagcc aggatggttt ccacacgtat cacgtgatga cccgtacga tgatggtatc   11580
ggtctggatg agttcgtgga ttggctgaac gagtctggct gcccattca acgcattgcg   11640
gattatggtg attggttgca gcgctttgag actgcgctgc gtgccctgcc ggatcgtcaa   11700
cgtcatagct cgctgctgcc gctgctgcac aattaccgcc aaccggaacg tccggtgcgt   11760
ggttccattg ctccgaccga ccgttttcgt gcggcggttc aagaagccaa gatcggccca   11820
gacaaagata tcccgcacgt tggtgcgccg attatcgtca aatacgtcag cgacctgcgc   11880
ctgctgggct tgctgtaata agtttaaacg agaaggagtt ctatcatgat tgaaaccatc   11940
ttaccagccg gcgtcgaatc agcagagtta cttgagtacc ctgaagatct gaaggcgcat   12000
ccggctgaag agcatctgat cgcaaagagc gtagagaagc gtcgtcgcga cttcattggc   12060
gcacgtcatt gcgcccgtct ggcactggcg gagctgggtg aaccgccggt tgcgattggc   12120
aagggtgaac gtggtgcgcc gatttggccg cgtggtgtcg tgggctctct gacccattgc   12180
gatggctatc gcgcagcggc ggttgctcac aaaatgcgtt ttcgcagcat cggcatcgac   12240
gccgaaccgc acgcgaccct gccggaaggt gtcctggatt cggttagcct gccgcctgag   12300
cgtgagtggc tgaaaaccac cgacagcgca ctgcacctgg accgtttgct gttttgtgcg   12360
aaagaagcaa cttacaaagc gtggtggccg ctgacggcac gttggctggg tttcgaagaa   12420
gcgcacatta ccttcgaaat cgaggatggt agcgccgact ctggtaatgg cacgtttcac   12480
agcgaactgc tggtgccggg tcagaccaat gacggtggta ccccgctgct gtctttcgac   12540
ggtcgctggc tgatcgctga tggcttcatc ctgacggcga ttgcatacgc atgataaatt   12600
aacctaggct gctgccaccg ctgagcaata actagcataa cccccttgggg cctctaaacg   12660
ggtcttgagg ggttttttgc tgagctcgag tgacccagc cgcccctcat gccaaccgag   12720
cccattaagc gcagagtcgg ccgcaactat ctcgggacg cataaacacg cagcgattta   12780
ccaaggagtt cggctaggtc aatccgcaat tccctttgcc tggccggaga tgccgcgagc   12840
aaacaatgtg tccggtcgct accagatgga ctttgtgggc ggaggattgc accagacgct   12900
tcagcgcagc gtcgtacgat gaatcggaag gcccggtaag caattgaaga accgctgacc   12960
acctcccatc cgacaatgca agggtgcccc gctcccagcg cgacacggtt gcctgatcca   13020
cacccattaa ttcagctagg tgactttgct tcatatgacg aagcaaccgc gccctccgca   13080
```

```
cctgccgccc cctgtcattc gtcaacattc ttcagcacct caatgtcgtt cgtagtgagc    13140 ctcattttt caagaccgcc gatgatgaga gccaggcctc gctcgaatgc cgcgtccgga    13200
ccgccttcgt agacgatttt catcgcgctc tgtaggcgcg ccggcatcgt agacgctgag    13260
gtggtcaact gatcttcgcc ccgctcctcg gcgtctgcct cgctagcttg ctgctcaaga    13320
acagcgccga cggtgaagta gctgattgcc atcaacgcat aggtcgcgtc acctgccgaa    13380
aagccagcat cgcaaaggaa gcgaagctgc gcgtcggctt tttccatctg cggcgcggct    13440
ggccgcgtcc cggcatgaat acgcgcgcca tcgcgataag cgagcaacgc ccgtcgaaaa    13500
ctgcatgcat tgcccttcag gaacgaacgc cagtcgtcgt catcccttgg cgtcgaatgc    13560
gtgtgattta tcgtcagcat ggcttcggca agtgcgtcga gcaacgcacg cttgttcttg    13620
aaatgccagt agagcgctgg ctgttgcacc ccgaggcgct cagccagtcg gcgcgtcgtt    13680
agaccttcca tgcccacgtc gttaagcagt tcgagcgcgg ttcggatcac ggcctcgcgt    13740
tggagcttgt tcattcgcga a    13761

<210> SEQ ID NO 28
<211> LENGTH: 13719
<212> TYPE: DNA
<213> ORGANISM: Artificial Sequence
<220> FEATURE:
<223> OTHER INFORMATION: vector

<400> SEQUENCE: 28
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg caggccccg tggccggggg    540 actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc cgccaccaa    900 acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
```

-continued

```
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
ggttgcctta ctggttagca gaatgaatca ccgatacgcg agcgaacgtg aagcgactgc    1560
tgctgcaaaa cgtctgcgac ctgagcaaca acatgaatgg tcttcggttt ccgtgtttcg    1620
taaagtctgg aaacgcggaa gtcccctacg tgctgctgaa gttgcccgca acagagagtg    1680
gaaccaaccg gtgataccac gatactatga ctgagagtca acgccatgag cggcctcatt    1740
tcttattctg agttacaaca gtccgcaccg ctgccggtag ctacttgact atccggctgc    1800
actagccctg cgtcagatgg ctctgatcca aggcaaactg ccaaaatatc tgctggcacc    1860
ggaagtcagc gccctgcacc attatgttcc ggatctgcat cgcaggatgc tgctggctac    1920
cctgtggaac acctacatct gtattaacga agcgctggca ttgaccctga gtgattttc    1980 tctggtgccg ccctatccct ttgtgcagct tgccacgctc aaaggggttt gaggtccaac    2040
cgtacgaaaa cgtacggtaa gaggaaaatt atcgtctgaa aaatcgatta gtagacaaga    2100
aagtccgtta agtgccaatt ttcgattaaa aagacaccgt tttgatggcg ttttccaatg    2160
tacattatgt ttcgatatat cagacagtta cttcactaac gtacgtttc gttctattgg    2220 ccttcagacc ccatatcctt aatgtccttt atttgctggg gttatcagat cccccccgaca   2280 cgtttaatta atgctttctc cgccggagat cgacgcacag gcttctgtgt ctatgatgtt    2340
atttcttaat aatcatccag gtattctctt tatcaccata cgtagtgcga gtgtccacct    2400
taacgcaggg ctttccgtca cagcgcgata tgtcagccag cggggctttc ttttgccaga    2460
ccgcttccat cctctgcatt tcagcaatct ggctataccc gtcattcata aaccacgtaa    2520
atgccgtcac gcaggaagcc aggacgaaga atatcgtcag tacaagataa atcgcggatt    2580
tccacgtata gcgtgacatc tcacgacgca tttcatggat catcgctttc gccgtatcgg    2640
cagcctgatt cagcgcttct gtcgccggtt tctgctgtgc taatccggct tgtttcagtt    2700 cttctctcaac ctgagtgagc gcggaactca ccgatttcct gacggtgtca gtcatattac    2760
cggacgcgct gtccagctca cgaatgaccc tgctcagcgt ttcactttgc tgctgtaatt    2820
gtgatgaggc ggcctgaaac tgttctgtca gagaagtaac acgcttttcc agcgcctgat    2880
gatgcccgat aagggcggca atttgtttaa tttcgtcgct catacaaaat cctgcctatc    2940
gtgagaatga ccagcctta tccggcttct gtcgtatctg ttcggcgagt cgctgtcgtt    3000 cttttctcctg ctgacgctgt ttttccgcca gacgttcgcg ctctctctgc ctttccatct    3060
cctgatgtat cccctggaac tccgccatcg catcgttaac aagggactga agatcgattt    3120
cttcctgtat atccttcatg gcatcactga ccagtgcgtt cagcttgtca ggctcttttt    3180
caaaatcaaa cgttctgccg gaatgggatt cctgctcagg ctctgacttc agctcctgtt    3240
ttagcgtcag agtatccctc tcgctgaggg cttcccgtaa cgaggtagtc acgtcaatta    3300
cgctgtcacg ttcatcacgg gactgctgca cctgcctttc agcctccctg cgctcaagaa    3360
tggcctgtag ctgctcagta tcgaatcgct gaacctgacc cgcgcccaga tgccgctcag    3420
gctcacggtc aatgccctgc gccttcaggg aacgggaatc aacccggtca gcgtgctgat    3480
accgttcaag gtgcttattc tggaggtcag cccagcgtct ccctctgggc aacaaggtat    3540
tctttgcgtt cggtcggtgt ttccccgaaa cgtgcctttt ttgcgccacc cgtccggct    3600 ctttggtgtt agcccgttta aaatactgct cagggtcacg gtgaataccg tcattaatgc    3660
gttcagagaa catgatatgg gcgtggggct gctcgccacc ggctatcgct gctttcggat    3720
```

```
tatggatagc gaactgatag gcatggcggt cgccaatttc ctgttggaca aaatcgcgga    3780
caagctcaag acgttgttcg ggttttaact cacgcggcag ggcaatctcg atttcacggt    3840
aggtacagcc gttggcacgt tcagacgtgt cagcggcttt ccagaactcg acggtttat    3900 gcgctgccca cgccggcata ttgccggact ccttgtgctc aaggtcggag tcttttcac    3960 gggcatactt tccctcacgc gcaatataat cggcatgagg agaggcactg ccttttccgc    4020 cggttttac gctgagatga taggatgcca tcgtgtttta tcccgctgaa gggcgcacgt    4080
ttctgaacga agtgaagaaa gtctaagtgc gccctgataa ataaaagagt tatcagggat    4140
tgtagtggga tttgacctcc tctgccatca tgagcgtaat cattccgtta gcattcagga    4200
ggtaaacagc atgaataaaa gcgaaaaaac aggaacaatg ggcagcagaa agagtgcagt    4260
atattcgcgg cttaaagtcg ccgaatgagc aacagaaact tatgctgata ctgacggata    4320
aagcagataa aacagcacag gatatcaaaa cgctgtccct gctgatgaag gctgaacagg    4380
cagcagagaa agcgcaggaa gccagagcga aagtcatgaa cctgatacag gcagaaaagc    4440
gagccgaagc cagagccgcc cgtaaagccc gtgaccatgc tctgtaccag tctgccggat    4500
tgcttatcct ggcgggtctg gttgacagta agacgggtaa gcctgttgat gataccgctg    4560
ccttactggg tgcattagcc agtctgaatg acctgtcacg ggataatccg aagtggtcag    4620
actggaaaat cagagggcag gaactgctga acagcaaaaa gtcagatagc accacatagc    4680
agacccgcca taaaacgccc tgagaagccc gtgacgggct tttcttgtat tatgggtagt    4740
ttccttgcat gaatccataa aaggcgcctg tagtgccatt tacccccatt cactgccaga    4800
gccgtgagcg cagcgaactg aatgtcacga aaaagacagc gactcaggtg cctgatggtc    4860
ggagacaaaa ggaatattca gcgatttgcc cgagcttgcg agggtgctac ttaagccttt    4920
agggttttaa ggtctgtttt gtagaggagc aaacagcgtt tgcgacatcc ttttgtaata    4980
ctgcggaact gactaaagta gtgagttata cacagggctg ggatctattc tttttatctt    5040
tttttattct ttcttattc tataaattat aaccacttga atataaacaa aaaaaacaca    5100
caaaggtcta gcggaattta cagagggtct agcagaattt acaagttttc agcaaaggt    5160 ctagcagaat ttacagatac ccacaactca aggaaaagg actagtaatt atcattgact    5220
agcccatctc aattggtata gtgattaaaa tcacctagac caattgagat gtatgtctga    5280
attagttgtt ttcaaagcaa atgaactagc gattagtcgc tatgacttaa cggagcatga    5340
aaccaagcta atttatgct gtgtggcact actcaacccc acgattgaaa accctacaag    5400
gaaagaacgg acggtatcgt tcacttataa ccaatacgct cagatgatga acatcagtag    5460
ggaaaatgct tatggtgtat tagctaaagc aaccagagag ctgatgacga gaactgtgga    5520
aatcaggaat cctttggtta aaggctttga gattttccag tggacaaact atgccaagtt    5580
ctcaagcgaa aaattagaat tagtttttag tgaagagata ttgccttatc ttttccagtt    5640
aaaaaaattc ataaaatata atctggaaca tgttaagtct tttgaaaaca atactctat    5700 gaggatttat gagtggttat taaaagaact aacacaaaag aaaactcaca aggcaaatat    5760
agagattagc cttgatgaat ttaagttcat gttaatgctt gaaataact accatgagtt    5820 taaaaggctt aaccaatggg ttttgaaacc aataagtaaa gatttaaaca cttacagcaa    5880
tatgaaattg gtggttgata agcgaggccg cccgactgat acgttgattt ccaagttga    5940 actagataga caaatggatc tcgtaaccga acttgagaac aaccagataa aaatgaatgg    6000
tgacaaaata ccaacaacca ttacatcaga ttcctaccta cgtaacggac taagaaaaac    6060
```

```
actacacgat gctttaactg caaaaattca gctcaccagt tttgaggcaa aattttgag    6120
tgacatgcaa agtaagcatg atctcaatgg ttcgttctca tggctcacgc aaaaacaacg   6180
aaccacacta gagaacatac tggctaaata cggaaggatc tgaggttctt atggctcttg   6240
tatctatcag tgaagcatca agactaacaa acaaaagtag aacaactgtt caccgttaga   6300
tatcaaaggg aaaactgtcc atatgcacag atgaaaacgg tgtaaaaaag atagatacat   6360
cagagctttt acgagttttt ggtgcattta agctgttca ccatgaacag atcgacaatg    6420
taacagatga acagcatgta acacctaata gaacaggtga aaccagtaaa acaaagcaac   6480
tagaacatga aattgaacac ctgagacaac ttgttacagc tcaacagtca cacatagaca   6540
gcctgaaaca ggcgatgctg cttatcgaat caaagctgcc gacaacacgg gagccagtga   6600
cgcctcccgt ggggaaaaaa tcatggcaat tctggaagaa atagcgcttt cagccggcaa   6660
acctgaagcc ggatctgcga ttctgataac aaactagcaa caccagaaca gcccgtttgc   6720
gggcagcaaa acccgtactt ttggacgttc cggcggtttt ttgtggcgag tggtgttcgg   6780
gcggtgcgcg caagatccat tatgttaaac gggcgagttc acatctcaaa accgcccgct   6840
taacaccatc agaaatcctc agcgcgattt taagcaccaa cccccccccg taacacccaa   6900
atccatactg aaagtggctt tgttgaataa atcgaacttt tgctgagttg aaggatcaga   6960
tcacgcatcc tcccgacaac acagaccatt ccgtggcaaa gcaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca ttttgccct gatgaacgtt ccgttgcgct     7260
gcccggatta caccagtgtc agtaagcggg caaagtcggt taatgtcagt ttcaaaacgt     7320
ccacccgggg tgaaatcgca cacctggtga ttgattccac cgggctgaag gtctttggtg     7380
aaggcgaatg gaaagtcaga aagcacggca agagcgccg tcgtatctgg cgaaagttgc     7440
atcttgctgt tgacagcaac acacatgaag ttgtctgtgc agacctgtcg ctgaataacg     7500
tcacggactc agaagccttc ccgggcctta tccggcagac tcacagaaaa atcagggcag     7560
ccgcggcaga cggggcttac gatacccggc tctgtcacga tgaactgcgc cgcaaaaaaa     7620
tcagcgcgct tattcctccc cgaaaaggtg cgggttactg gcccggtgaa tatgcagacc     7680
gtaaccgtgc agtggctaat cagcgaatga ccgggagtaa tgcgcggtgg aaatggacaa     7740
cagattacaa ccgtcgctcg atagcggaaa cggcgatgta ccgggtaaaa cagctgttcg     7800
ggggttcact gacgctgcgt gactacgatg gtcaggttgc ggaggctatg gccctggtac     7860
gagcgctgaa caaaatgacg aaagcaggta tgcctgaaag cgtgcgtatt gcctgaaaac     7920
acaacccgct acggggagaa cttacccgaa atctgattta ttcaacaaag ccgggtgtgg    7980
tgaactacaa agcagacccg ttgaggttat cagttcgatg cacaatcagc agcgcataaa     8040
atatgcacaa gaacaggagc acccttcgca ttaagctgtg gtggtaacaa gtagtgccgg     8100
gctaccatca gcgagcatga tgcgctccca cagcattcgc cttggcagta tggaagttcc    8160
tcgctccagt tcgggccggt atccaccgca cctggtgttt aaacggattt aaattgcagg    8220
ggcagtgagc gcaacgcaat taatgtaagt tagctcactc attaggcacc ccaggcttga    8280
cactttatgc ttccggctcg tataatgtgt ggaattgtga gcggataaca ataacaattt    8340
aaatcaggat ctaggaacca aggagagtgg catatgactg taatgcctgc aaaaccacca    8400
gccgatgtat ccccacttag ccgcgcagca cgtctggtcg ccgagttgag cgcgcacgat    8460
```

```
ccgcagtatc gtgccgcaat gccgctgccg gcagttcgtg aagcggttcg cgaggccgca    8520
cgcgaccaag ttctgagccg caccgttgca accgtcatgg caggttatgc ggaccgtccg    8580
gcgctggcac gccgtgccac cgagccggtg accgatccgg ttagcggccg tactagcttg    8640
cgtcgtctgc cggagtttac gacggtcacg tacggtgaac tgtgggcgcg tgcaggtgcg    8700
gtgagcgcgg agtgggcagc cgacacccgc ctgccgctga gcccaggcga ctttgttgcc    8760
atctacggtt tcacgagcgg cgactatgtt actgtcgatt tggcctgtct gcgccatggt    8820
gcggttagcg tcccgctgca gtcgggtgcg ccggttgccg gcctggcccc gattctggcg    8880
aaaacgggtc cgaaagtcct ggcggtgtcc ttggaattgc tggaccgtgg tgttgaactg    8940
gcgttgagcg ccgaggttgc tccgcgtctg gtggtctttg acttccacgc cggtgacgac    9000
gctcagcgcg aggcctttga agcggcaagc gcacgcctga ccgcggcagg ccatgcggct    9060
ccgctgccgc tggaagcggt gattgaacgc ggtcgtgcac tgccgccagc gccactgttc    9120
gttccgggtc cggacgaaga tccggttcgt ctgctgattt acaccagcgg tagcaccggt    9180
accccgaaag gcgccattca aacggagcgc atgctgcatc gcgcatgggc aggcgcggtg    9240
ccgattccgg acgacgtcgc gtccatcgtc gtgaattacc tgccgctgtc ccacgtcgct    9300
ggtcgtagct ctctggttga gacgctgcgt cgtggcggca ttagctattt cacggcacat    9360
agcgacctgt ctgatctgtt cgaggacatc gccctggcgc gtcctaccgc gctgttgttt    9420
gttccgcgtg tgtgcgattt gctgttccaa gaatatcagg ctgaattggc acgtcgcgca    9480
ggtgagtttg cggacgcggg tgcgctggac gcggctgtta aggcagatct gcgtgaacgt    9540
ttcgttggtg gccgcctgat tcaagcgctg tacggcagcg caccgctgtc cgccgaactg    9600
cgtgagttta tgcacacctg tctggacctg cctgtgctgg acggttatgg tagcaccgaa    9660
acgggttccg tgttgttgaa cacccgcgtg caacgtccgc cggtcaccga tatcaagctg    9720
gtggatgtcc cggaactggg ttacttcgcc accgattccc cgtacccacg cggcgaattg    9780
gtgctgaaaa gcgcgaccct gacgcctggc tattaccgtc gcccagaggt caccgcagct    9840
gctttcgacg cggatggctt ttaccgtacg ggcgacatta tggcggaagt tggcccggac    9900
cagtacgtgt acgttgatcg tcgtaataac gttgtgaagc tggcccaggg tgagttcgtt    9960
gcgctgtctc gtctggaagg tgtgtatgtg actcacccgc tgattcgcca gatttacgtg   10020
tacggcaata gcgagcgtgc acacttgctg gctgtgatcg tgccgacgcg cgagaattgt   10080
acgcacgagg atctggcagc cgcgctgcag caggcagccc gtgagagcga gttgaactct   10140
tacgagatcc cgcgtgcgtt cctggttgaa accgagccgt tctccctggc caacggtttg   10200
ctgagcgaca cccgtaagaa tctgccgcca cgtctgaagg cgcgctatgg cgagcgtctg   10260
gaagcgctgt atgaagagct ggcacgtgaa caagaggatg cggttcgtgt gctgcgcgat   10320
gaaggtacgg gtcgccctgt ttcggaaacg gtcgagcgtg cagcgcgtgc gctgctgggt   10380
agcagcgcag cggacgcgcg ttttaccgac ttgggcggta ttctctgtc ggcgttgtcc   10440
ttcagcaccc tgctggcaga gatcttcggt gtcgaggtgc cggtgggtac tgtcctgagc   10500
ccggcaaacg acctgcgtgc attggcagcg cacatcgaag ctcgtcgtgc gtctggtgcg   10560
agccgtccga ccttcgctag cgttcatggc gtggccgta cggtcgtgcg tgcgggcgac   10620
ctggcactgg agaagtttct ggatgccggt gcgctggcgg aagcggcgca gctgccggca   10680
ccgggtcgtg aaacgccgcg tacggtcctg ctgaccggtg cgaacggtta tctgggtcgt   10740
ttcatgtgcc tggactggct ggaacgtctg gcttcgggcg gtggccgtct ggtgtgcgtg   10800
```

```
gttcgcggta aagacgacgc cgatgcccgt gcacgtctgg atgcggcgtt cgacagcggt   10860
gatccggagc tgctgcgtcg ctaccgcgaa ctggcagcgg gtcgcctgga tgtcttggct   10920
ggcgatatcg gtgcggagcg tctgggtctg gcgggtgaga cgtggcgtcg cctggccgag   10980
gatgtggatc tgatcgccca cccggctgcc ctggtcaacc acgtcttgcc gtacgagcaa   11040
ctgtttggtc cgaacgttgt aggcaccgct gaactgattc gcctggcact gaccgcgcgt   11100
gttaaaccgt tcgtgtatgt tagcaccacc gcgattagca ccacgctgga cgagacgagc   11160
gatattcgtg agagcatccc ggaacgcgcc ctgaccgatg catatgcagc gggctacggt   11220
accagcaaat gggcgggtga ggtgctgctg cgcgaggcgc acgctcgcct ggcgctgccg   11280
gttgcggtct ttcgcagcga cttgattctg gcgcacccgc atcacaccgg ccaactgaat   11340
ccggccgacg tactgacccg tctgctgttt agcatcctga gcactggctt ggcgccgact   11400
agcttttact ctgaagaggg tcgcgcgcac ttcgacggtc tgccggtgga ttttaccgct   11460
gaggctatca acaccctggg cgcacagccg attagcgcgc accgtaccta taatgcggta   11520
aatccgcatg acgacggcgt gagcctggat accttcatca cttggctgga agaggctggt   11580
cacccgctgc gccgttttgcc gcatacgacc tggagcccgc gtctggaaac cgccttgcgc   11640
agcctgccgg aacatcaccg tccgcacacg ttgctgcctc tgctgcatgc gtttgcaacc   11700
cctcagccgc cgaccccgac cagcccggtt ccggccaccc attttcatga ggcagtgcgt   11760
gaggctggca tcggcccaga taatgatatc ccgcacatca cgcaaaactt gattaccaag   11820
tacgcgacgg atctgcgcca actgggtctg cgctaataag tttaaacgag aaggagttct   11880
atcatgattg aaaccatctt accagccggc gtcgaatcag cagagttact tgagtaccct   11940
gaagatctga aggcgcatcc ggctgaagag catctgatcg caaagagcgt agagaagcgt   12000
cgtcgcgact tcattggcgc acgtcattgc gcccgtctgg cactggcgga gctgggtgaa   12060
ccgccggttg cgattggcaa gggtgaacgt ggtgcgccga tttggccgcg tggtgtcgtg   12120
ggctctctga cccattgcga tggctatcgc gcagcggcgg ttgctcacaa aatgcgtttt   12180
cgcagcatcg gcatcgacgc cgaaccgcac gcgaccctgc cggaaggtgt cctggattcg   12240
gttagcctgc cgcctgagcg tgagtggctg aaaaccaccg acagcgcact gcacctggac   12300
cgtttgctgt tttgtgcgaa agaagcaact tacaaagcgt ggtggccgct gacggcacgt   12360
tggctgggtt tcgaagaagc gcacattacc ttcgaaatcg aggatggtag cgccgactct   12420
ggtaatggca cgtttcacag cgaactgctg gtgccgggtc agaccaatga cggtggtacc   12480
ccgctgctgt ctttcgacgg tcgctggctg atcgctgatg gcttcatcct gacggcgatt   12540
gcatacgcat gataaattaa cctaggctgc tgccaccgct gagcaataac tagcataacc   12600
ccttggggcc tctaaacggg tcttgagggg ttttttgctg agctcgagtg accccagccg   12660
cccctcatgc caaccgagcc cattaagcgc agagtcggcc gcaactatct cggggacgca   12720
taaacacgca gcgatttacc aaggagttcg gctaggtcaa tccgcaattc cctttgcctg   12780
gccggagatg ccgcgagcaa acaatgtgtc cggtcgctac cagatggact tgtgggcgg   12840 aggattgcac cagacgcttc agcgcagcgt cgtacgatga tcggaaggc ccggtaagca   12900 attgaagaac cgctgaccac ctcccatccg acaatgcaag ggtgccccgc tcccagcgcg   12960
acacggttgc ctgatccaca cccattaatt cagctaggtg actttgcttc atatgacgaa   13020
gcaaccgcgc cctccgcacc tgccgccccc tgtcattcgt caacattctt cagcacctca   13080
atgtcgttcg tagtgagcct cattttttca agaccgccga tgatgagagc caggcctcgc   13140
tcgaatgccg cgtccggacc gccttcgtag acgattttca tcgcgctctg taggcgcgcc   13200
```

```
ggcatcgtag acgctgaggt ggtcaactga tcttcgcccc gctcctcggc gtctgcctcg    13260
ctagcttgct gctcaagaac agcgccgacg gtgaagtagc tgattgccat caacgcatag    13320
gtcgcgtcac ctgccgaaaa gccagcatcg caaaggaagc gaagctgcgc gtcggctttt    13380
tccatctgcg gcgcggctgg ccgcgtcccg gcatgaatac gcgcgccatc gcgataagcg    13440
agcaacgccc gtcgaaaact gcatgcattg cccttcagga acgaacgcca gtcgtcgtca    13500
tcccttggcg tcgaatgcgt gtgatttatc gtcagcatgg cttcggcaag tgcgtcgagc    13560
aacgcacgct tgttcttgaa atgccagtag agcgctggct gttgcacccc gaggcgctca    13620
gccagtcggc gcgtcgttag accttccatg cccacgtcgt taagcagttc gagcgcggtt    13680
cggatcacgg cctcgcgttg gagcttgttc attcgcgaa                           13719

<210> SEQ ID NO 29
<211> LENGTH: 13842
<212> TYPE: DNA
<213> ORGANISM: Artificial Sequence
<220> FEATURE:
<223> OTHER INFORMATION: vector

<400> SEQUENCE: 29
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360
cacacccgtc ctgtggatcc tctacgccgg acgcatcgtg gccggcatca ccggcgccac     420
aggtgcggtt gctggcgcct atatcgccga catcaccgat ggggaagatc gggctcgcca     480
cttcgggctc atgagcgctt gtttcggcgt gggtatggtg gcaggccccg tggccggggg     540
actgttgggc gccatctcct tgcatgcacc attccttgcg gcggcggtgc tcaacggcct     600
caacctacta ctgggctgct tcctaatgca ggagtcgcat aagggagagc gtcgaccgat     660
gcccttgaga gccttcaacc cagtcagctc cttccggtgg gcgcggggca tgactatcgt     720
cgccgcactt atgactgtct tctttatcat gcaactcgta ggacaggtgc cggcagcgct     780
ctgggtcatt ttcggcgagg accgctttcg ctggagcgcg acgatgatcg gcctgtcgct     840
tgcggtattc ggaatcttgc acgccctcgc tcaagccttc gtcactggtc cgccaccaa    900 acgtttcggc gagaagcagg ccattatcgc cggcatggcg gccgacgcgc tgggctacgt     960
cttgctggcg ttcgcgacgc gaggctggat ggccttcccc attatgattc ttctcgcttc    1020
cggcggcatc gggatgcccg cgttgcaggc catgctgtcc aggcaggtag atgacgacca    1080
tcagggacag cttcaaggat cgctcgcggc tcttaccagc ctaacttcga tcactggacc    1140
gctgatcgtc acggcgattt atgccgcctc ggcgagcaca tggaacgggt tggcatggat    1200
tgtaggcgcc gccctatacc ttgtctgcct ccccgcgttg cgtcgcggtg catggagccg    1260
ggccacctcg acctgaatgg aagccggcgg cacctcgcta acggattcac cactccaaga    1320
attggagcca atcaattctt gcggagaact gtgaatgcgc aaaccaaccc ttggcagaac    1380
atatccatcg cgtccgccat ctccagcagc cgcacgcggc gcatctcggg cagcgttggg    1440
tcctggccac gggtgcgcat gatcgtgctc ctgtcgttga ggacccggct aggctggcgg    1500
```

```
ggttgcctta ctggttagca gaatgaatca ccgatacgcg agcgaacgtg aagcgactgc  1560
tgctgcaaaa cgtctgcgac ctgagcaaca acatgaatgg tcttcggttt ccgtgtttcg  1620
taaagtctgg aaacgcggaa gtcccctacg tgctgctgaa gttgcccgca acagagagtg  1680
gaaccaaccg gtgataccac gatactatga ctgagagtca acgccatgag cggcctcatt  1740
tcttattctg agttacaaca gtccgcaccg ctgccggtag ctacttgact atccggctgc  1800
actagccctg cgtcagatgg ctctgatcca aggcaaactg ccaaaatatc tgctggcacc  1860
ggaagtcagc gccctgcacc attatgttcc ggatctgcat cgcaggatgc tgctggctac  1920
cctgtggaac acctacatct gtattaacga agcgctggca ttgaccctga gtgattttc  1980
tctggtgccg ccctatccct tgtgcagct tgccacgctc aaaggggttt gaggtccaac  2040
cgtacgaaaa cgtacggtaa gaggaaaatt atcgtctgaa aaatcgatta gtagacaaga  2100
aagtccgtta agtgccaatt ttcgattaaa aagacaccgt tttgatggcg ttttccaatg  2160
tacattatgt ttcgatatat cagacagtta cttcactaac gtacgttttc gttctattgg  2220
ccttcagacc ccatatcctt aatgtccttt atttgctggg gttatcagat ccccccgaca  2280
cgtttaatta atgctttctc cgccggagat cgacgcacag gcttctgtgt ctatgatgtt  2340
atttcttaat aatcatccag gtattctctt tatcaccata cgtagtgcga gtgtccacct  2400
taacgcaggg ctttccgtca cagcgcgata tgtcagccag cggggctttc ttttgccaga  2460
ccgcttccat cctctgcatt tcagcaatct ggctataccc gtcattcata aaccacgtaa  2520
atgccgtcac gcaggaagcc aggacgaaga atatcgtcag tacaagataa atcgcggatt  2580
tccacgtata gcgtgacatc tcacgacgca tttcatggat catcgctttc gccgtatcgg  2640
cagcctgatt cagcgcttct gtcgccggtt tctgctgtgc taatccggct tgtttcagtt  2700
cttttctcaac ctgagtgagc gcggaactca ccgatttcct gacggtgtca gtcatattac  2760
cggacgcgct gtccagctca cgaatgaccc tgctcagcgt ttcactttgc tgctgtaatt  2820
gtgatgaggc ggcctgaaac tgttctgtca gagaagtaac acgcttttcc agcgcctgat  2880
gatgcccgat aagggcggca atttgtttaa tttcgtcgct catacaaaat cctgcctatc  2940
gtgagaatga ccagccttta tccggcttct gtcgtatctg ttcggcgagt cgctgtcgtt  3000
ctttctcctg ctgacgctgt ttttccgcca gacgttcgcg ctctctctgc ctttccatct  3060
cctgatgtat cccctggaac tccgccatcg catcgttaac aagggactga agatcgattt  3120
cttcctgtat atccttcatg gcatcactga ccagtgcgtt cagcttgtca ggctcttttt  3180
caaaatcaaa cgttctgccg gaatgggatt cctgctcagg ctctgacttc agctcctgtt  3240
ttagcgtcag agtatccctc tcgctgaggg cttcccgtaa cgaggtagtc acgtcaatta  3300
cgctgtcacg ttcatcacgg gactgctgca cctgcctttc agcctccctg cgctcaagaa  3360
tggcctgtag ctgctcagta tcgaatcgct gaacctgacc cgcgcccaga tgccgctcag  3420
gctcacggtc aatgccctgc gccttcaggg aacgggaatc aacccggtca gcgtgctgat  3480
accgttcaag gtgcttattc tggaggtcag cccagcgtct ccctctgggc aacaaggtat  3540
tctttgcgtt cggtcggtgt ttccccgaaa cgtgcctttt ttgcgccacc gcgtccggct  3600
ctttggtgtt agcccgttta aaatactgct cagggtcacg gtgaataccg tcattaatgc  3660
gttcagagaa catgatatgg gcgtgggggct gctcgccacc ggctatcgct gctttcggat  3720
tatggatagc gaactgatag gcatggcggc gccaatttc ctgttggaca aaatcgcgga  3780
caagctcaag acgttgttcg ggttttaact cacgcggcag ggcaatctcg atttcacggt  3840
aggtacagcc gttggcacgt tcagacgtgt cagcggcttt ccagaactcg gacggtttat  3900
```

```
gcgctgccca cgccggcata ttgccggact ccttgtgctc aaggtcggag tcttttccac   3960
gggcatactt tccctcacgc gcaatataat cggcatgagg agaggcactg ccttttccgc   4020
cggtttttac gctgagatga taggatgcca tcgtgtttta tcccgctgaa gggcgcacgt   4080
ttctgaacga agtgaagaaa gtctaagtgc gccctgataa ataaaagagt tatcagggat   4140
tgtagtggga tttgacctcc tctgccatca tgagcgtaat cattccgtta gcattcagga   4200
ggtaaacagc atgaataaaa gcgaaaaaac aggaacaatg ggcagcagaa agagtgcagt   4260
atattcgcgg cttaaagtcg ccgaatgagc aacagaaact tatgctgata ctgacggata   4320
aagcagataa aacagcacag gatatcaaaa cgctgtccct gctgatgaag gctgaacagg   4380
cagcagagaa agcgcaggaa gccagagcga aagtcatgaa cctgatacag gcagaaaagc   4440
gagccgaagc cagagccgcc cgtaaagccc gtgaccatgc tctgtaccag tctgccggat   4500
tgcttatcct ggcgggtctg gttgacagta agacgggtaa gcctgttgat gataccgctg   4560
ccttactggg tgcattagcc agtctgaatg acctgtcacg ggataatccg aagtggtcag   4620
actggaaaat cagagggcag gaactgctga acagcaaaaa gtcagatagc accacatagc   4680
agacccgcca taaaacgccc tgagaagccc gtgacgggct tttcttgtat tatgggtagt   4740
ttccttgcat gaatccataa aaggcgcctg tagtgccatt tacccccatt cactgccaga   4800
gccgtgagcg cagcgaactg aatgtcacga aaaagacagc gactcaggtg cctgatggtc   4860
ggagacaaaa ggaatattca gcgatttgcc cgagcttgcg agggtgctac ttaagccttt   4920
agggttttaa ggtctgtttt gtagaggagc aaacagcgtt tgcgacatcc ttttgtaata   4980
ctgcggaact gactaaagta gtgagttata cacagggctg ggatctattc tttttatctt   5040
tttttattct ttctttattc tataaattat aaccacttga atataaacaa aaaaaacaca   5100
caaaggtcta gcggaattta cagagggtct agcagaattt acaagttttc cagcaaaggt   5160
ctagcagaat ttacagatac ccacaactca aggaaaagg actagtaatt atcattgact   5220
agcccatctc aattggtata gtgattaaaa tcacctagac caattgagat gtatgtctga   5280
attagttgtt ttcaaagcaa atgaactagc gattagtcgc tatgacttaa cggagcatga   5340
aaccaagcta attttatgct gtgtggcact actcaacccc acgattgaaa accctacaag   5400
gaaagaacgg acggtatcgt tcacttataa ccaatacgct cagatgatga acatcagtag   5460
ggaaaatgct tatggtgtat tagctaaagc aaccagagag ctgatgacga gaactgtgga   5520
aatcaggaat cctttggtta aaggctttga gattttccag tggacaaact atgccaagtt   5580
ctcaagcgaa aaattagaat tagttttttag tgaagagata ttgccttatc ttttccagtt   5640
aaaaaaattc ataaaatata atctggaaca tgttaagtct tttgaaaaca aatactctat   5700
gaggatttat gagtggttat taaaagaact aacacaaaag aaaactcaca aggcaaatat   5760
agagattagc cttgatgaat ttaagttcat gttaatgctt gaaaataact accatgagtt   5820
taaaaggctt aaccaatggg ttttgaaacc aataagtaaa gatttaaaca cttacagcaa   5880
tatgaaattg gtggttgata agcgaggccg cccgactgat acgttgattt tccaagttga   5940
actagataga caaatggatc tcgtaaccga acttgagaac aaccagataa aaatgaatgg   6000
tgacaaaata ccaacaacca ttacatcaga ttcctaccta cgtaacggac taagaaaaac   6060
actacacgat gctttaactg caaaaattca gctcaccagt tttgaggcaa aattttttgag   6120 tgacatgcaa agtaagcatg atctcaatgg ttcgttctca tggctcacgc aaaaacaacg   6180
aaccacacta gagaacatac tggctaaata cggaaggatc tgaggttctt atggctcttg   6240
```

```
tatctatcag tgaagcatca agactaacaa acaaaagtag aacaactgtt caccgttaga    6300
tatcaaaggg aaaactgtcc atatgcacag atgaaaacgg tgtaaaaaag atagatacat    6360
cagagctttt acgagttttt ggtgcattta agctgttca ccatgaacag atcgacaatg     6420
taacagatga acagcatgta acacctaata gaacaggtga aaccagtaaa acaaagcaac    6480
tagaacatga aattgaacac ctgagacaac ttgttacagc tcaacagtca cacatagaca    6540
gcctgaaaca ggcgatgctg cttatcgaat caaagctgcc gacaacacgg gagccagtga    6600
cgcctcccgt ggggaaaaaa tcatggcaat tctggaagaa atagcgcttt cagccggcaa    6660
acctgaagcc ggatctgcga ttctgataac aaactagcaa caccagaaca gcccgtttgc    6720
gggcagcaaa acccgtactt ttggacgttc cggcggtttt ttgtggcgag tggtgttcgg    6780
gcggtgcgcg caagatccat tatgttaaac gggcgagttt acatctcaaa accgcccgct    6840
taacaccatc agaaatcctc agcgcgattt taagcaccaa ccccccccg taacacccaa     6900 atccatactg aaagtggctt tgttaataa atcgaacttt tgctgagttg aaggatcaga     6960
tcacgcatcc tcccgacaac acagaccatt ccgtggcaaa gcaaaagttc agaatcacca    7020
actggtccac ctacaacaaa gctctcatca accgtggctc cctcactttc tggctggatg    7080
atgaggcgat tcaggcctgg tatgagtcgg caacaccttc atcacgagga aggccccagc    7140
gctattctga tctcgccatc accaccgttc tggtgattaa acgcgtattc cggctgaccc    7200
tgcgggctgc gcagggtttt attgattcca ttttgccct gatgaacgtt ccgttgcgct     7260
gcccggatta caccagtgtc agtaagcggg caaagtcggt taatgtcagt ttcaaaacgt    7320
ccacccgggg tgaaatcgca cacctggtga ttgattccac cgggctgaag gtctttggtg    7380
aaggcgaatg gaaagtcaga agcacggca agagcgccg tcgtatctgg cgaaagttgc      7440
atcttgctgt tgacagcaac acacatgaag ttgtctgtgc agacctgtcg ctgaataacg    7500
tcacggactc agaagccttc ccgggcctta tccggcagac tcacagaaaa atcagggcag    7560
ccgcggcaga cggggcttac gatacccggc tctgtcacga tgaactgcgc cgcaaaaaaa    7620
tcagcgcgct tattcctccc cgaaaaggtg cgggttactg gcccggtgaa tatgcagacc    7680
gtaaccgtgc agtggctaat cagcgaatga ccggagtaa tgcgcggtgg aaatggacaa     7740
cagattacaa ccgtcgctcg atagcggaaa cggcgatgta ccgggtaaaa cagctgttcg    7800
ggggttcact gacgctgcgt gactacgatg gtcaggttgc ggaggctatg gcctggtac     7860 gagcgctgaa caaaatgacg aaagcaggta tgcctgaaag cgtgcgtatt gcctgaaaac    7920
acaacccgct acgggggaga cttacccgaa atctgattta ttcaacaaag ccgggtgtgg    7980
tgaactacaa agcagacccg ttgaggttat cagttcgatg cacaatcagc agcgcataaa    8040
atatgcacaa gaacaggagc acccttcgca ttaagctgtg gtggtaacaa gtagtgccgg    8100
gctaccatca gcgagcatga tgcgctccca cagcattcgc cttggcagta tggaagttcc    8160
tcgctccagt tcgggccggt atccacctcg cacctggtgt ttaaacggat ttaaattgca    8220
ggggcagtga gcgcaacgca attaatgtaa gttagctcac tcattaggca ccccaggctt    8280
gacactttat gcttccggct cgtataatgt gtggaattgt gagcggataa caataacaat    8340
ttaaatcagg atctaggaac caaggagagt ggcatatgac tgacgacgca aagagagcaa    8400
aagtatccag caccggtccg atttctgcag cacgtcagca agttgcggac cgcattcgcg    8460
atctggacgc gcgtgacgaa gaatttcgca cgaccaaacc ggactctgcg ctgcagctgg    8520
cggcacgtga accgggtctg cgtctgccgc aaatcctgga aatctttgcc gaaggttacg    8580
cggatcgtcc ggcgctgggc tggcgtgcgc gcagcctgac caccgatgcg cgactggcc    8640
```

```
gtaccagcgc tcagttgctg ccgcgcttcg acacgatgac gtaccgtgaa ctgtgggcga    8700
atgtccgcgc aatcgccggt gcttggcgcc acgatgctac caacccggtg gcaccgggtg    8760
atgttgtggc aactgttggt ttcgcgagcg cagaatacct gaccatcgat ctggtctgtg    8820
cgtatctggg cctggttgcc gtgccgctgc aacataacgc gaccgcatcc cgtctgcgtc    8880
cgatcgtcga agaggttgag ccgtcgacgt tggcggctgg cgtgggctac ctggacttgg    8940
ccgtcgaggc ggccttgggc agctccagcc tgcgccgtgt ggttgtgttt gattatcgtc    9000
cggaagttga cgaacagcgc gaggcggttg accgtgcgcg tagcaaactg gcgggtgcag    9060
gtatcgcggt caccgttgag acgctgggtg acgtcattga gcgtggccgt accctgccgc    9120
ctgagccgat gtttaccggc gatacggacg agcgtctggc aatgattatg tataccagcg    9180
gttccaccgg tttgccgaaa ggcgccatgt ataccgagcg tatgctgtgc cgtctgtgga    9240
ccactgaact gatgccggat ttcgccgaca ccccggttat caatgtcaac ttcatgccgc    9300
tgaatcacct gggtggtcgt atcccgctga gcaccgcgtt ccaggccggt ggtacctctt    9360
atttcgttcc ggagagcgat ctgagcaccc tgttcgatga ttggaatctg gtccgtccga    9420
ccgagatggg cctggtgccg cgtgtggcag aaatgttgta ccagcgttac cagagcgcgg    9480
tcgatcgctt tgaagttgct ggcacggaca cggcgacggc acaagcgcgt gctcaggccg    9540
aactgcgtga gcaggtgctg gcggtcgca ttgttactgc cttctgtggc accgcaccgc    9600
tggctgccga gatgcgcagc ttcattgaga cgtgcctgag cgtgcatgtg ctggacggtt    9660
acgtctgac ggaagttggt atggtcacca aggatggttt gattacgcaa ccgccggttt    9720
tggactataa gctgatcgat gttccggagc tgggttactt cctgaccgac aaaccgtatc    9780
cgcgtggcga gctgctggtt aaatccctga ccgcaacccc gggttacttc aagcgtccag    9840
atgtcaccgc caatgcattc gacccagaag gctattaccg tacgggcgac gtgatggcgg    9900
agctggaacc tagccgtctg gcctacgtgg atcgtcgcaa taacgtcctg aagctggcac    9960
aaggtgagtt cgttgccgtc gctcgtctgg aagccgtttt tagcagcgcc gcactggtgc   10020
gtcaaatctt tgtgtacggc aacagcgagc gcccgtactt gctggcggtc gtggtaccga   10080
cggatgacgc agcccaaaag tatgcgggtg acccgggtgg tctgaaaagc gcgttgggtg   10140
agagcctgcg ccaagcggct aagctggcag aactgcaaag ctacgaagtt ccggttgatt   10200
ttgttgtgga aaccgagccg tttagcgagg ataatggctt gctgagcggt gtcggcaaac   10260
tgctgcgtcc aaaactgaaa gagcactacg gcgcacgcct ggaacagctg tatgcagacc   10320
tggctgaaag ccgcgttacg gagctgcgtg ccctgcgtga gggtgctgct gatcaccctg   10380
tgatcttcac gttgacccgt gcggcggaag cgctgctggg tttggccggt ggtccgcctg   10440
cgccggatgc gttgttcatt gaactgggtg gtgatagctt gagcgcgctg acgtttagca   10500
atctgttgcg tgacatcttc gacgttgagg tgccggtcgg tatgattacc ggtccggcga   10560
ccgacctggg tcagctggca gagtatgtgg aatccgaacg tgcgtccggc agccgtcgtc   10620
cgaccttgc gaccgtccac ggtcgcggtg ccacgcaggt gcgcgctgca gacttgacgt   10680
tggataagtt catcgacgca accacccctg cagaagcacc ggcattgccg cgtgcgaccg   10740
gtaccccgca cactgtgctg ctgaccggtg cgaacggcta cctgggccgt ttcttgattc   10800
tggagtggtt ggaacgtctg gcggagacgg gtggcaagct gattagcatt attcgtgcag   10860
cggacgctgc ggcagcagcg aaacgcctgg agagcgtgtt cgacagcggc gatccgcaac   10920
tgctggagcg tttccgcacg ctggcagcgg atcatctgga agttatcgtc ggtgatattg   10980
```

-continued

```
gtgagccaaa cctgggtctg caacagggca cctgggagcg cctggcgcag tcggtcgatt   11040
tgattgtcca tccagcagca ctggtcaacc atgtgctgcc gtacgaccag ctgttcggtc   11100
cgaatgtcgt cggcactgcg gagctgattc gtttggccat caccactcgc attaaacctg   11160
tcacgtacat gtccaccgtg gctgtcgcgc tgagcgttga cccggctgcc ttcgccgagg   11220
acggcgacat ccgcacggtt tcggctctgc gtccggttga tggtggctat gcgaatggtt   11280
acgcaaactc gaagtgggcg ggtgaagtac tgctgcgcga ggcacacgat ctgtgcggcc   11340
tgccggttgc ggttttttcgc agcgacatga tcctggcaca tagccgttac gcaggccaac   11400
tgaacgtgcc ggacgcgttt acgcgtctga tctttagcct gctgacgacc ggcatcgcac   11460
cgggtagctt ttatcaaacc gaccctcgcg gcaaccgtgc tattgcgcac tacgacggtc   11520
tgccagcgga ttttgtcgct gaagcggtta ccacgctggg cgagcagatc gcgactgccg   11580
cgcaggattc tggtgcatat cgcagctttg atgttatgaa cccgcacgac gatggcatct   11640
ctctggacgt gttcgtggat tggctgattg cgggtggtca cgatattcgc cgtatcgatg   11700
actatgacga gtggctgagc cgcttttacca ccgccctgcg cgcactgccg acaaacaac   11760
gtcagcactc cgtcctgccg ctgctggacg cttatcgtaa gccggaaacc ccgctgcgtg   11820
gtgcgcctgc gcctaccgat gtgtttcgta gcgcggttcg tgaggcgaag attggtgcgg   11880
ccgaggatat cccacatctg agcgcggcac tgattgacaa atacgtgccc gacttgcgtt   11940
tgctgggtct ggtgtaataa gtttaaacag agaaggagtt ctatcatgat tgaaaccatc   12000
ttaccagccg gcgtcgaatc agcagagtta cttgagtacc ctgaagatct gaaggcgcat   12060
ccggctgaag agcatctgat cgcaaagagc gtagagaagc gtcgtcgcga cttcattggc   12120
gcacgtcatt gcgcccgtct ggcactggcg gagctgggtg aaccgccggt tgcgattggc   12180
aagggtgaac gtggtcgcgc catttggccg cgtggtgtcg tgggctctct gacccattgc   12240
gatggctatc gcgcagcggc ggttgctcac aaaatgcgtt ttcgcagcat cggcatcgac   12300
gccgaaccgc acgcgaccct gccggaaggt gtcctggatt cggttagcct gccgcctgag   12360
cgtgagtggc tgaaaaccac cgacagcgca ctgcacctgg accgtttgct gttttgtgcg   12420
aaagaagcaa cttacaaagc gtggtggccg ctgacggcac gttggctggg tttcgaagaa   12480
gcgcacatta ccttcgaaat cgaggatggt agcgccgact ctggtaatgg cacgtttcac   12540
agcgaactgc tggtgccggg tcagaccaat gacggtggta ccccgctgct gtctttcgac   12600
ggtcgctggc tgatcgctga tggcttcatc ctgacggcga ttgcatacgc atgataaatt   12660
aacctaggct gctgccaccg ctgagcaata actagcataa cccccttgggg cctctaaacg   12720
ggtcttgagg ggtttttttgc tgaaacctca ggcatttgag aagccctcga gtgacccag   12780
ccgcccctca tgccaaccga gcccattaag cgcagagtcg gccgcaacta tctcggggac   12840
gcataaacac gcagcgattt accaaggagt tcggctaggt caatccgcaa ttcccttttgc   12900
ctggccggag atgccgcgag caaacaatgt gtccggtcgc taccagatgg actttgtggg   12960
cggaggattg caccagacgc ttcagcgcag cgtcgtacga tgaatcggaa ggcccggtaa   13020
gcaattgaag aaccgctgac cacctcccat ccgacaatgc aagggtgccc cgctcccagc   13080
gcgacacggt tgcctgatcc acacccatta attcagctag gtgactttgc ttcatatgac   13140
gaagcaaccg cgccctccgc acctgccgcc ccctgtcatt cgtcaacatt cttcagcacc   13200
tcaatgtcgt tcgtagtgag cctcattttt tcaagaccgc cgatgatgag agccaggcct   13260
cgctcgaatg ccgcgtccgg accgccttcg tagcgattt tcatcgcgct ctgtaggcgc   13320
gccggcatcg tagacgctga ggtggtcaac tgatcttcgc cccgctcctc ggcgtctgcc   13380
```

```
tcgctagctt gctgctcaag aacagcgccg acggtgaagt agctgattgc catcaacgca    13440
taggtcgcgt cacctgccga aaagccagca tcgcaaagga agcgaagctg cgcgtcggct    13500
ttttccatct gcggcgcggc tggccgcgtc ccggcatgaa tacgcgcgcc atcgcgataa    13560
gcgagcaacg cccgtcgaaa actgcatgca ttgcccttca ggaacgaacg ccagtcgtcg    13620
tcatcccttg gcgtcgaatg cgtgtgattt atcgtcagca tggcttcggc aagtgcgtcg    13680
agcaacgcac gcttgttctt gaaatgccag tagagcgctg gctgttgcac cccgaggcgc    13740
tcagccagtc ggcgcgtcgt tagaccttcc atgcccacgt cgttaagcag ttcgagcgcg    13800
gttcggatca cggcctcgcg ttggagcttg ttcattcgcg aa                      13842
```

<210> SEQ ID NO 30
<211> LENGTH: 256
<212> TYPE: PRT
<213> ORGANISM: Escherichia coli strain K-12 substrain W3110

<400> SEQUENCE: 30

```
Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
        35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255
```

<210> SEQ ID NO 31
<211> LENGTH: 448
<212> TYPE: PRT
<213> ORGANISM: Escherichia coli strain K-12 substrain W3110

```
<400> SEQUENCE: 31

Met Val Met Ser Gln Lys Thr Leu Phe Thr Lys Ser Ala Leu Ala Val
1               5                   10                  15

Ala Val Ala Leu Ile Ser Thr Gln Ala Trp Ser Ala Gly Phe Gln Leu
            20                  25                  30

Asn Glu Phe Ser Ser Ser Gly Leu Gly Arg Ala Tyr Ser Gly Glu Gly
            35                  40                  45

Ala Ile Ala Asp Asp Ala Gly Asn Val Ser Arg Asn Pro Ala Leu Ile
        50                  55                  60

Thr Met Phe Asp Arg Pro Thr Phe Ser Ala Gly Ala Val Tyr Ile Asp
65                  70                  75                  80

Pro Asp Val Asn Ile Ser Gly Thr Ser Pro Gly Arg Ser Leu Lys
                85                  90                  95

Ala Asp Asn Ile Ala Pro Thr Ala Trp Val Pro Asn Met His Phe Val
            100                 105                 110

Ala Pro Ile Asn Asp Gln Phe Gly Trp Gly Ala Ser Ile Thr Ser Asn
        115                 120                 125

Tyr Gly Leu Ala Thr Glu Phe Asn Asp Thr Tyr Ala Gly Gly Ser Val
    130                 135                 140

Gly Gly Thr Thr Asp Leu Glu Thr Met Asn Leu Asn Leu Ser Gly Ala
145                 150                 155                 160

Tyr Arg Leu Asn Asn Ala Trp Ser Phe Gly Leu Gly Phe Asn Ala Val
                165                 170                 175

Tyr Ala Arg Ala Lys Ile Glu Arg Phe Ala Gly Asp Leu Gly Gln Leu
            180                 185                 190

Val Ala Gly Gln Ile Met Gln Ser Pro Ala Gly Gln Thr Gln Gln Gly
        195                 200                 205

Gln Ala Leu Ala Ala Thr Ala Asn Gly Ile Asp Ser Asn Thr Lys Ile
    210                 215                 220

Ala His Leu Asn Gly Asn Gln Trp Gly Phe Gly Trp Asn Ala Gly Ile
225                 230                 235                 240

Leu Tyr Glu Leu Asp Lys Asn Asn Arg Tyr Ala Leu Thr Tyr Arg Ser
                245                 250                 255

Glu Val Lys Ile Asp Phe Lys Gly Asn Tyr Ser Ser Asp Leu Asn Arg
            260                 265                 270

Ala Phe Asn Asn Tyr Gly Leu Pro Ile Pro Thr Ala Thr Gly Gly Ala
        275                 280                 285

Thr Gln Ser Gly Tyr Leu Thr Leu Asn Leu Pro Glu Met Trp Glu Val
    290                 295                 300

Ser Gly Tyr Asn Arg Val Asp Pro Gln Trp Ala Ile His Tyr Ser Leu
305                 310                 315                 320

Ala Tyr Thr Ser Trp Ser Gln Phe Gln Gln Leu Lys Ala Thr Ser Thr
                325                 330                 335

Ser Gly Asp Thr Leu Phe Gln Lys His Glu Gly Phe Lys Asp Ala Tyr
            340                 345                 350

Arg Ile Ala Leu Gly Thr Thr Tyr Tyr Tyr Asp Asp Asn Trp Thr Phe
        355                 360                 365

Arg Thr Gly Ile Ala Phe Asp Asp Ser Pro Val Pro Ala Gln Asn Arg
    370                 375                 380

Ser Ile Ser Ile Pro Asp Gln Asp Arg Phe Trp Leu Ser Ala Gly Thr
385                 390                 395                 400

Thr Tyr Ala Phe Asn Lys Asp Ala Ser Val Asp Val Gly Val Ser Tyr
                405                 410                 415
```

```
Met His Gly Gln Ser Val Lys Ile Asn Glu Gly Pro Tyr Gln Phe Glu
            420                 425                 430

Ser Glu Gly Lys Ala Trp Leu Phe Gly Thr Asn Phe Asn Tyr Ala Phe
            435                 440                 445
```